United States Patent
Dobbins

(10) Patent No.: US 10,617,729 B2
(45) Date of Patent: Apr. 14, 2020

(54) MULTITARGETING ONOCOLYTIC ADENOVIRUS, METHODS OF USE, AND METHODS OF MAKING

(71) Applicant: THE UAB RESEARCH FOUNDATION, Birmingham, AL (US)

(72) Inventor: George Clement Dobbins, Birmingham, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 15/538,975

(22) PCT Filed: Dec. 21, 2015

(86) PCT No.: PCT/US2015/067005
§ 371 (c)(1),
(2) Date: Jun. 22, 2017

(87) PCT Pub. No.: WO2016/106178
PCT Pub. Date: Jun. 30, 2016

(65) Prior Publication Data
US 2017/0368117 A1    Dec. 28, 2017

Related U.S. Application Data

(60) Provisional application No. 62/096,611, filed on Dec. 24, 2014.

(51) Int. Cl.
| | |
|---|---|
| *A61K 35/761* | (2015.01) |
| *A61K 38/19* | (2006.01) |
| *C07K 14/005* | (2006.01) |
| *C07K 14/075* | (2006.01) |
| *C07K 14/535* | (2006.01) |
| *C12N 7/00* | (2006.01) |
| *C12N 15/861* | (2006.01) |
| *C12Q 1/6897* | (2018.01) |
| *C12N 15/86* | (2006.01) |

(52) U.S. Cl.
CPC .......... *A61K 35/761* (2013.01); *A61K 38/193* (2013.01); *C07K 14/005* (2013.01); *C07K 14/535* (2013.01); *C12N 7/00* (2013.01); *C12N 15/86* (2013.01); *C12Q 1/6897* (2013.01); *C07K 2319/33* (2013.01); *C12N 15/861* (2013.01); *C12N 2710/10022* (2013.01); *C12N 2710/10032* (2013.01); *C12N 2710/10043* (2013.01); *C12N 2710/10321* (2013.01); *C12N 2710/10322* (2013.01); *C12N 2710/10331* (2013.01); *C12N 2710/10332* (2013.01); *C12N 2710/10343* (2013.01); *C12N 2810/405* (2013.01); *C12N 2810/6018* (2013.01)

(58) Field of Classification Search
None
See application file for complete search history.

(56) References Cited

U.S. PATENT DOCUMENTS

| | | | | |
|---|---|---|---|---|
| 2006/0062764 A1* | 3/2006 | Police | ...................... | C12N 7/00 424/93.2 |
| 2007/0010016 A1* | 1/2007 | McCelland | .......... | C07K 14/535 435/456 |
| 2011/0123564 A1 | 5/2011 | Mayall et al. | | |
| 2013/0302313 A1* | 11/2013 | Yu | .......................... | C12N 15/87 424/130.1 |

FOREIGN PATENT DOCUMENTS

WO    WO 2013/076374    * 5/2013

OTHER PUBLICATIONS

Fueyo et al., Oncogene, 2000, 19:2-12. (Year: 2000).*
Ramesh et al., Clin Cancer Res, 2006, 12(1):305-313. (Year: 2006).*
International Search Report for PCT/US2015/067005 dated Mar. 17, 2016.
(Yonemura, N et al.) Donor Vector pZErOTM7ZeoGFPattB DNA, Complete Sequence. National Center for Biotechnology Information. GenBank: AB713996.1; Sep. 19, 2012 [Retrieved on Mar. 7, 2016]. Retrieved from the Internet: <URL: http://www.ncbi.nlm.nih.gov/nucleotide/401709825>.
(Choi, EW et al.) Recombination Vector pAdHTS, Complete Sequence. National Center for Biotechnology Information. GenBank: JN387044.1; May 7, 2013 [Retrieved on Mar. 7, 2016]. Retrieved from the Internet: <URL: http://www.ncbi.nlm.nih.gov/nucleotide/342159977>.
(Chroboczek, Jet al.) Mastadenovirus h5 Gene, Complete Genome. National Center for Biotechnology Information. GenBank: M73260.1; Apr. 8, 1996 [Retrieved on Mar. 7, 2016]. Retrieved from the Internet: <URL: http://www.ncbi.nlm.nih.gov/nucleotide/209842>.
Koski et al., (2015) "Biodistribution Analysis of Oncolytic Adenoviruses in Patient Autopsy Samples Reveals Vascular Transduction of Noninjected Tumors and Tissues," Mol Ther, 23: 1641-1652, (2015).
Pol et al., (2014) "Trial Watch:: Oncolytic viruses for cancer therapy," Oncoimmunology, 3: e28694.
Zheng et al., (2000) "Genomic integration and gene expression by a modified adenoviral vector," Nat Biotechnol, 18: 176-180.

(Continued)

*Primary Examiner* — Nicole Kinsey White
(74) *Attorney, Agent, or Firm* — Thomas|Horstemeyer, LLP

(57) ABSTRACT

To increase the therapeutic potential of these oncolytic viruses based on a 24 base pair deletion in the viral E1A gene (D24), a conditionally replicating adenovirus targeting multiple receptors upregulated on tumors was generated by incorporating an Ad5/3 fiber with a carboxyl terminus RGD ligand. The virus displayed full cytopathic effect in tumor lines assayed at low titers with improved cytotoxicity over Ad5-RGD D24, Ad5/3 D24 and an HSV oncolytic virus. The virus was further engineered to deliver immunotherapeutic agents such as GMCSF while maintaining enhanced heterogenic oncolysis.

36 Claims, 28 Drawing Sheets

Specification includes a Sequence Listing.

(56) References Cited

OTHER PUBLICATIONS

Fueyo et al., (2000) "A mutant oncolytic adenovirus targeting the Rb pathway produces anti-glioma effect in vivo," Oncogene, 19: 2-12.

Koski et al., "Treatment of cancer patients with a serotype 5/3 chimeric oncolytic adenovirus expressing GMCSF," Mol Ther, 18: 1874-1884.

Krasnykh et al., (1996) "Generation of recombinant adenovirus vectors with modified fibers for altering viral tropism," J Virol, 70: 6839-6846.

Suzuki et al., (2001) "A conditionally replicative adenovirus with enhanced infectivity shows improved oncolytic potency," Clin Cancer Res, 7: 120-126.

Miller et al., (1998) "Differential susceptibility of primary and established human glioma cells to adenovirus infection: targeting via the epidermal growth factor receptor achieves fiber receptor-independent gene transfer," Cancer Res, 58: 5738-5748.

Bauerschmitz et al., (2002) "Adenoviral gene therapy for cancer: from vectors to targeted and replication competent agents (review)," Int J Oncol, 21: 1161-1174.

Bergelson et al., (1997) "Isolation of a common receptor for Coxsackie B viruses and adenoviruses 2 and 5," Science, 275: 1320-1323.

Russell et al., (2012) "Oncolytic virotherapy," Nat Biotechnol, 30: 658-670.

Kanerva et al., (2002) "Targeting adenovirus to the serotype 3 receptor increases gene transfer efficiency to ovarian cancer cells," Clin Cancer Res, 8: 275-280.

Kimball et al., "A phase I study of a tropism-modified conditionally replicative adenovirus for recurrent malignant gynecologic diseases," Clin Cancer Res, 16: 5277-5287, (2010).

Liu et al., (2014) "Oncolytic vaccinia virotherapy for endometrial cancer," Gynecol Oncol, 132: 722-729.

Wang et al., (2011) "Desmoglein 2 is a receptor for adenovirus serotypes 3, 7, 11 and 14," Nat Med, 17: 96-104.

Pesonen et al., (2011) "Oncolytic adenoviruses for the treatment of human cancer: focus on translational and clinical data," Mol Pharm, 8: 12-28.

Matzinger P, (2002) "The danger model: a renewed sense of self," Science, 296: 301-305.

Gill et al., (2014) "MRI-localized biopsies reveal subtype-specific differences in molecular and cellular composition at the margins of glioblastoma," Proc Natl Acad Sci USA, 111: 12550-12555.

Heise et al., (2000) "An adenovirus E1A mutant that demonstrates potent and selective systemic anti-tumoral efficacy," Nat Med, 6: 1134-1139.

Chartier et al., (1996) "Efficient generation of recombinant adenovirus vectors by homologous recombination in *Escherichia coli*.," J Virol, 70: 4805-4810.

Ugai et al., (2007) "Thermostability/infectivity defect caused by deletion of the core protein V gene in human adenovirus type 5 is rescued by thermo-selectable mutations in the core protein X precursor," J Mol Biol, 366: 1142-1160.

Ugai et al., (2005) "Purification of infectious adenovirus in two hours by ultracentrifugation and tangential flow filtration," Biochem Biophys Res Commun, 331: 1053-1060.

Maizel et al., (1968) "The polypeptides of adenovirus. I. Evidence for multiple protein components in the virion and a comparison of types 2, 7A, and 12," Virology, 36: 115-125.

Bigner et al., (1981) "Heterogeneity of Genotypic and phenotypic characteristics of fifteen permanent cell lines derived from human gliomas," J Neuropathol Exp Neurol, 40: 201-229.

Ugai et al., (2010) "In vitro dynamic visualization analysis of fluorescently labeled minor capsid protein IX and core protein V by simultaneous detection," J Mol Biol, 395: 55-78.

Ulasov et al. (2007) "Targeting adenovirus to CD80 and CD86 receptors increases gene transfer efficiency to malignant glioma cells," J Neurosurg, 107: 617-627.

Parker et al., (2000) "Engineered herpes simplex virus expressing IL-12 in the treatment of experimental murine brain tumors," Proc Natl Acad Sci USA, 97: 2208-2213.

Megison et al. (2014) "Preclinical evaluation of engineered oncolytic herpes simplex virus for the treatment of pediatric solid tumors," PLoS One 9: e86843.

Lenaerts et al., (2008) "Clinical features and treatment of adenovirus infections," Rev Med Virol, 18: 357-374.

Meulenbroek et al., (2004) "Use of adenovirus protein IX (pIX) to display large polypeptides on the virion—generation of fluorescent virus through the incorporation of pIX-GFP," Mol Ther, 9: 617-624.

Kimball et al., (2009), "Novel infectivity-enhanced oncolytic adenovirus with a capsid-incorporated dual-imaging moiety for monitoring virotherapy in ovarian cancer," Mol Imaging, 8: 264-277.

Jiang et al., (2011) "Human adenovirus type 5 induces cell lysis through autophagy and autophagy-triggered caspase activity," J Virol, 85: 4720-4729.

Berk AJ, (1986) "Adenovirus promoters and E1A transactivation," Annu Rev Genet, 20: 45-79.

Tollefson et al., (1996) "The adenovirus death protein (E3-11.6K) is required at very late stages of infection for efficient cell lysis and release of adenovirus from infected cells," J Virol, 70: 2296-2306.

Horwitz MS, (2004) "Function of adenovirus E3 proteins and their interactions with immunoregulatory cell proteins," J Gene Med 6 Suppl, 1: S172-183.

Senzer et al., (2009) "Phase II clinical trial of a granulocyte-macrophage colony-stimulating factor-encoding, second-generation oncolytic herpesvirus in patients with unresectable metastatic melanoma," J Clin Oncol, 27: 5763-5771.

Arellano and Lonial, (2008) "Clinical uses of GM-CSF, a critical appraisal and update," Biologics, 2: 13-27.

Kim et al., (2011) "A new generation of serotype chimeric infectivity-enhanced conditionally replicative adenovirals: the safety profile of ad5/3-Delta24 in advance of a phase I clinical trial in ovarian cancer patients," Hum Gene Ther, 22: 821-828.

Tyler et al., (2006) "Enhanced transduction of malignant glioma with a double targeted Ad5/3-RGD fiber-modified adenovirus," Mol Cancer Ther, 5: 2408-2416.

Volk et al., (2003) "Enhanced adenovirus infection of melanoma cells by fiber-modification: incorporation of RGD peptide or Ad5/3 chimerism," Cancer Biol Ther, 2: 511-515.

Zhu et al., (2007) "Targeting of a conditionally replicative adenovirus agent to human squamous cell carcinomas of the head and neck," Int J Oncol, 31: 1213-1222.

Rein et al., (2006) "Current developments in adenovirus-based cancer gene therapy," Future Oncol, 2: 137-143.

Li et al., (1998) "Adenovirus endocytosis via alpha(v) integrins requires phosphoinositide-3-OH kinase," J Virol, 72: 2055-2061.

Lu et al., (2013) "Penton-dodecahedral particles trigger opening of intercellular junctions and facilitate viral spread during adenovirus serotype 3 infection of epithelial cells," PLoS Pathog, 9: e1003718.

Young et al., (2012) "Failure of translation of human adenovirus mRNA in murine cancer cells can be partially overcome by L4-100K expression in vitro and in vivo," Mol Ther, 20: 1676-1688.

Bischoff et al., (1996) "An adenovirus mutant that replicates selectively in p53-deficient human tumor cells," Science, 274(5286):373-376.

Mathis et al., (2005) "Oncolytic adenoviruses—selective retargeting to tumor cells," Oncogene, 24(52): 7775-7791.

Hemmi et al., (1998) "The presence of human coxsackievirus and adenovirus receptor is associated with efficient adenovirus-mediated transgene expression in human melanoma cell cultures." Hum Gene Ther, 9(16): 2363-2373.

Kawashima et al., (2003) "Expression of the coxsackievirus and adenovirus receptor in musculoskeletal tumors and mesenchymal tissues: efficacy ofadenoviral gene therapy for osteosarcoma," Cancer Sci, 94(1): 70-75.

Li et al., (1999) "Loss of adenoviral receptor expression in human bladder cancer cells: a potential impact on the efficacy of gene therapy," Cancer Res, 59(2): 325-330.

Qin et al., (2003) "Coxsackievirus adenovirus receptor expression predicts the efficiency of adenoviral gene transfer into non-small cell lung cancer xenografts," Clin Cancer Res, 9(13): 4992-4999.

(56) References Cited

OTHER PUBLICATIONS

Hood and Cheresh, (2002) "Role of integrins in cell invasion and migration," Nat Rev Cancer, 2(2): 91-100.
Liapis et al., (1996) "Integrin alpha V beta 3 expression by bone-residing breast cancer metastases" Diagn Mol Pathol, 5(2): 127-135.
Rolli et al., (2003) "Activated integrin alphavbeta3 cooperates with metalloproteinase MMP-9 in regulating migration of metastatic breast cancer cells," Proc Natl Acad Sci USA, 100(16): 9482-9487.
Hemminki, A, (2014) "Oncolytic Immunotherapy: Where Are We Clinically?" Scientifica (Cairo), 2014: 862925.
Heemskerk et al., (2006) "Adenovirus-specific CD4+ T cell clones recognizing endogenous antigen inhibit viral replication in vitro through cognate interaction," J Immunol, 177(12): 8851-8859.
Tam et al., (2007) "Improved in vivo whole-animal detection limits of green fluorescent protein-expressing tumor lines by spectral fluorescence imaging," Mol Imaging, 6(4): 269-276.
Borovjagin et al., (2005) "Complex mosaicism is a novel approach to infectivity enhancement of adenovirus type 5-based vectors," Cancer Gene Ther, 12(5): 475-486.
Vellinga et al., (2004) "Spacers increase the accessibility of peptide ligands linked to the carboxyl terminus of adenovirus minor capsid protein IX," J Viral, 78(7): 3470-3479.
Cerullo et al., (2010) "Oncolytic adenovirus coding for granulocyte macrophage colony-stimulating factor induces antitumoral immunity in cancer patients," Cancer Res, 70(11): 4297-4309.
Zelle-Rieser et al., (2001) "Expression and immunogenicity of oncofetal antigen-immature laminin receptor in human renal cell carcinoma," J Urol, 165(5): 1705-1709.
Thomas et al., (2006) "Syrian hamster as a permissive immunocompetent animal model for the study of oncolytic adenovirus vectors," Cancer Res, 66(3): 1270-6.
Soria et al., (2010) "Heterochromatin silencing of p53 target genes by a small viral protein," Nature, 466: 1076-1081.
Sauthoff et al., (2004) "Impact of E1a modifications on tumor-selective adenoviral replication and toxicity," Mol Ther, 10: 749-757.
Fukuda et al., (2003) "E1A, E1B double-restricted adenovirus for oncolytic gene therapy of gallbladder cancer," Cancer Res, 63: 4434-4440.

* cited by examiner

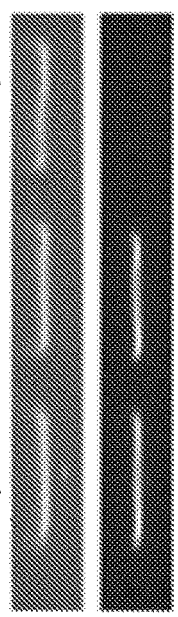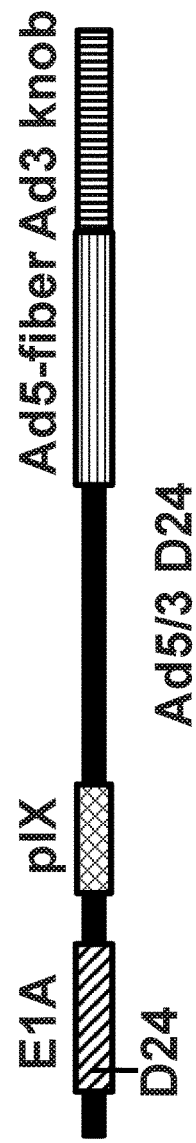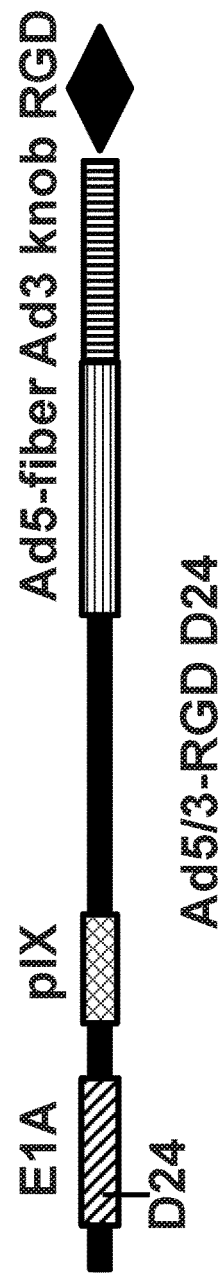
Fig. 1B  Fig. 1C

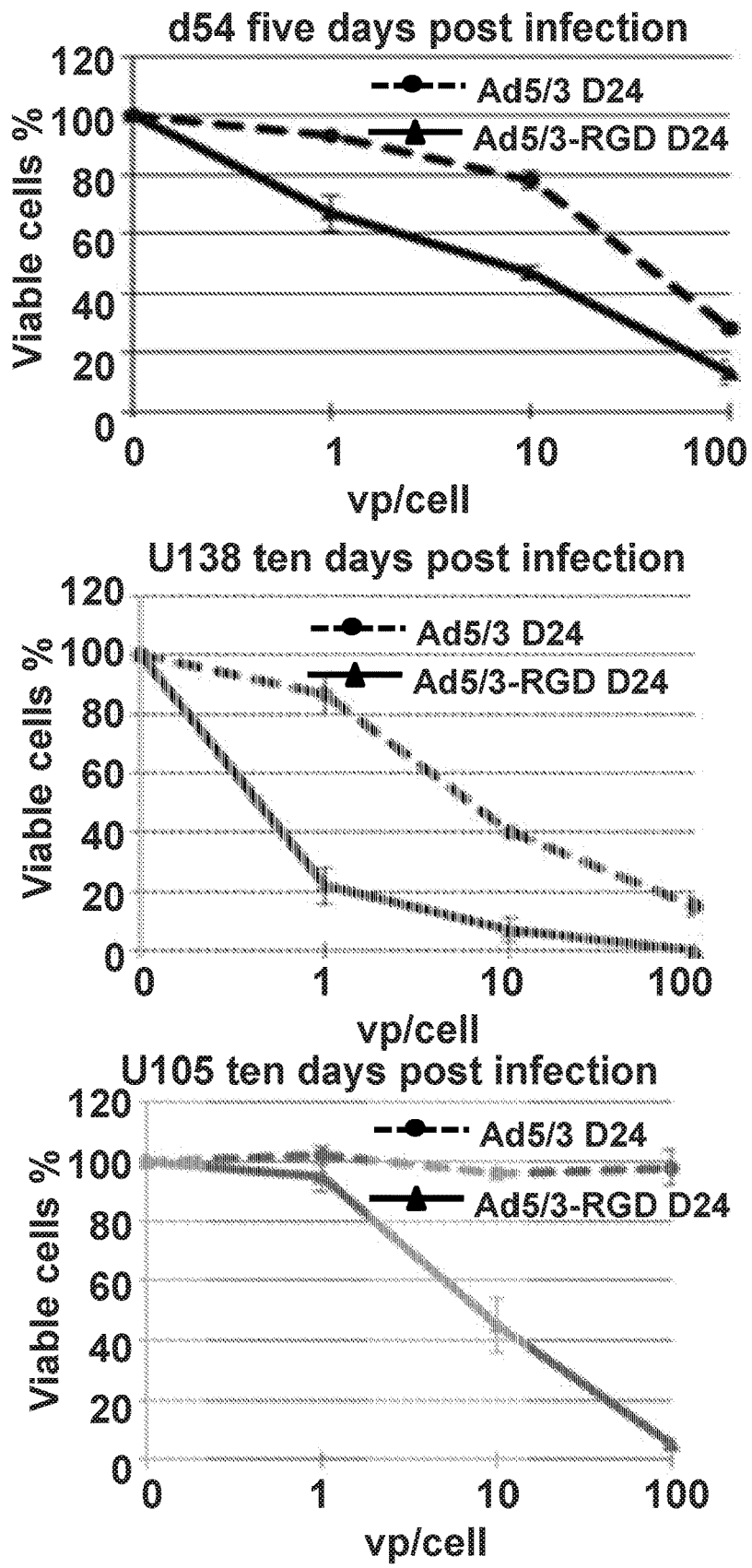
Fig. 2A-contd

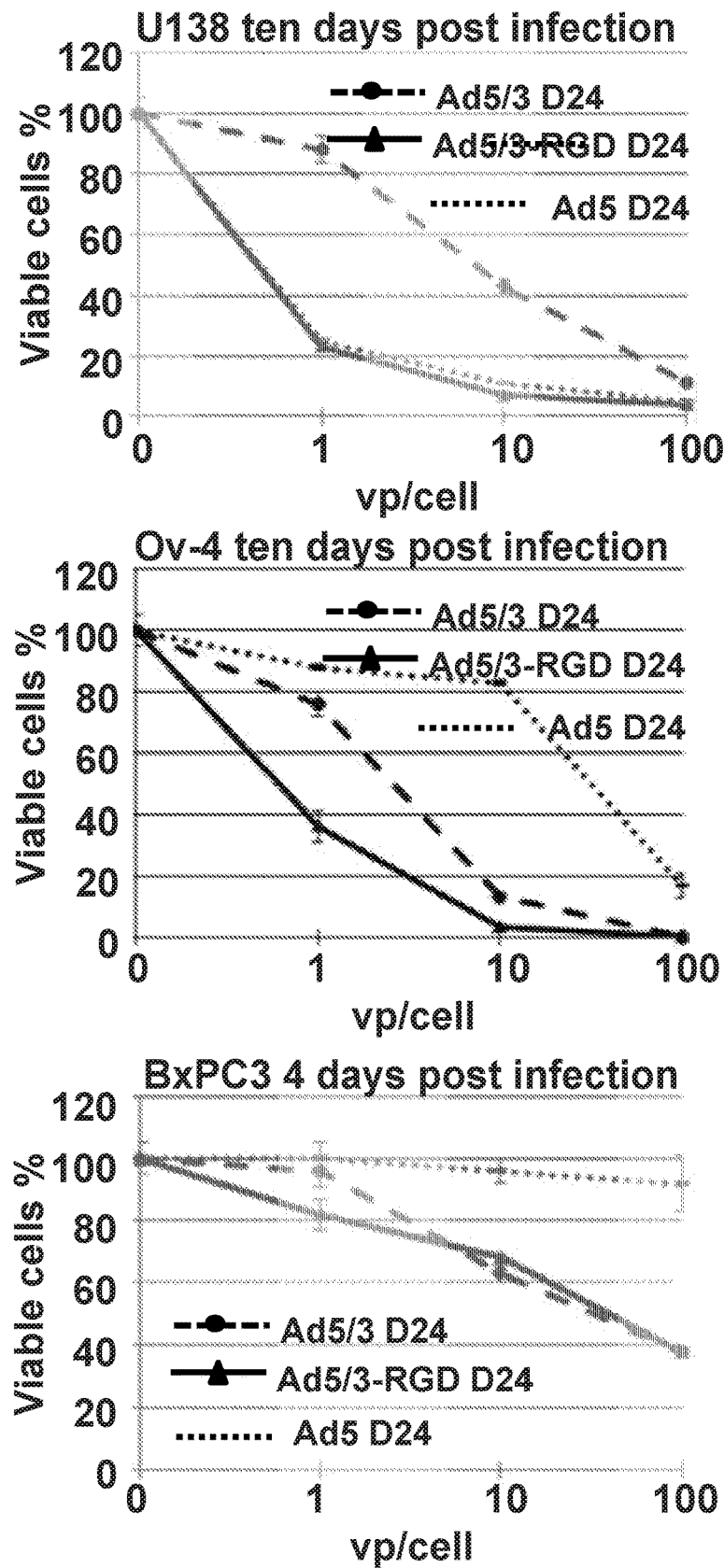
Fig. 3B-cont'd

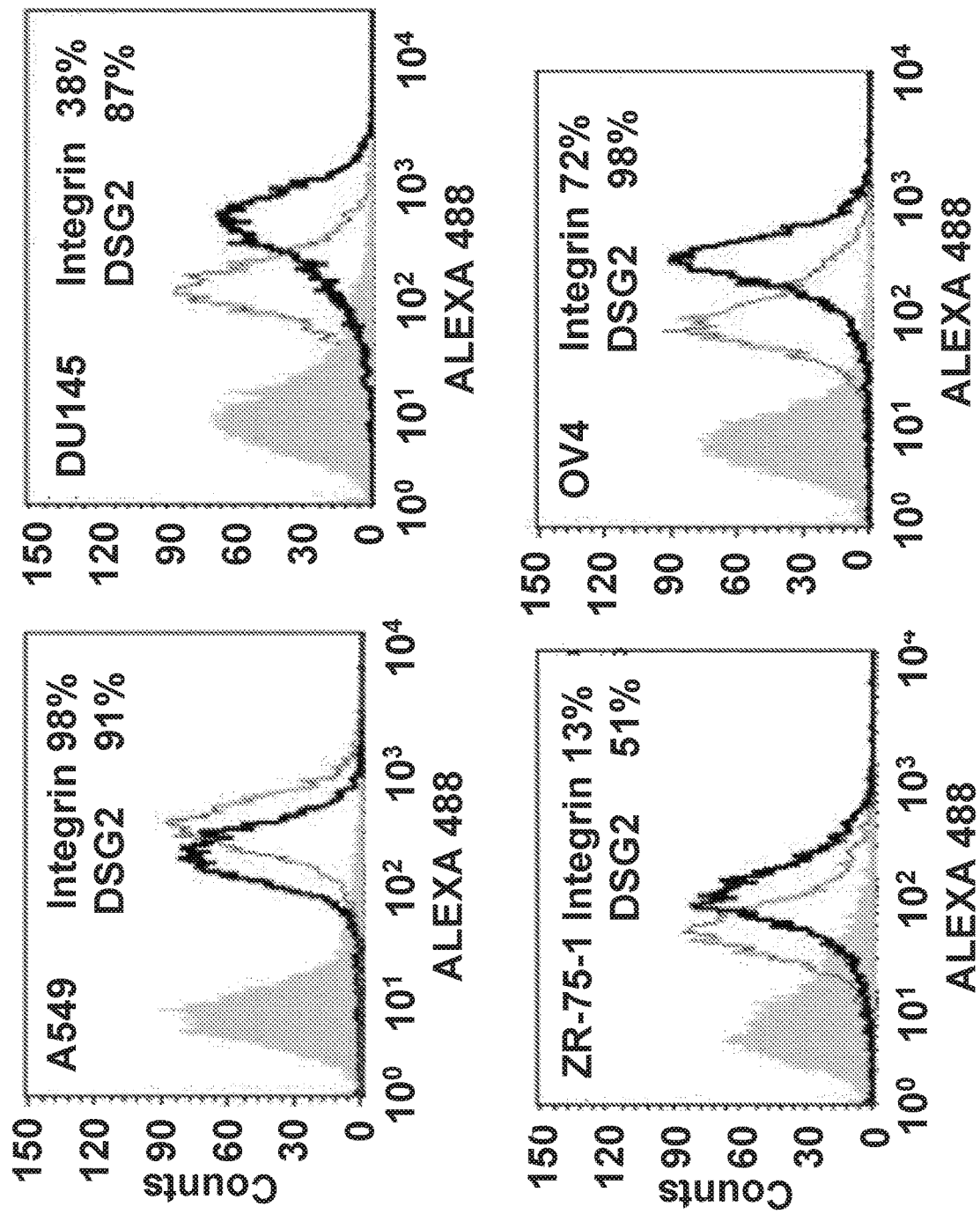
Fig. 4-cont'd

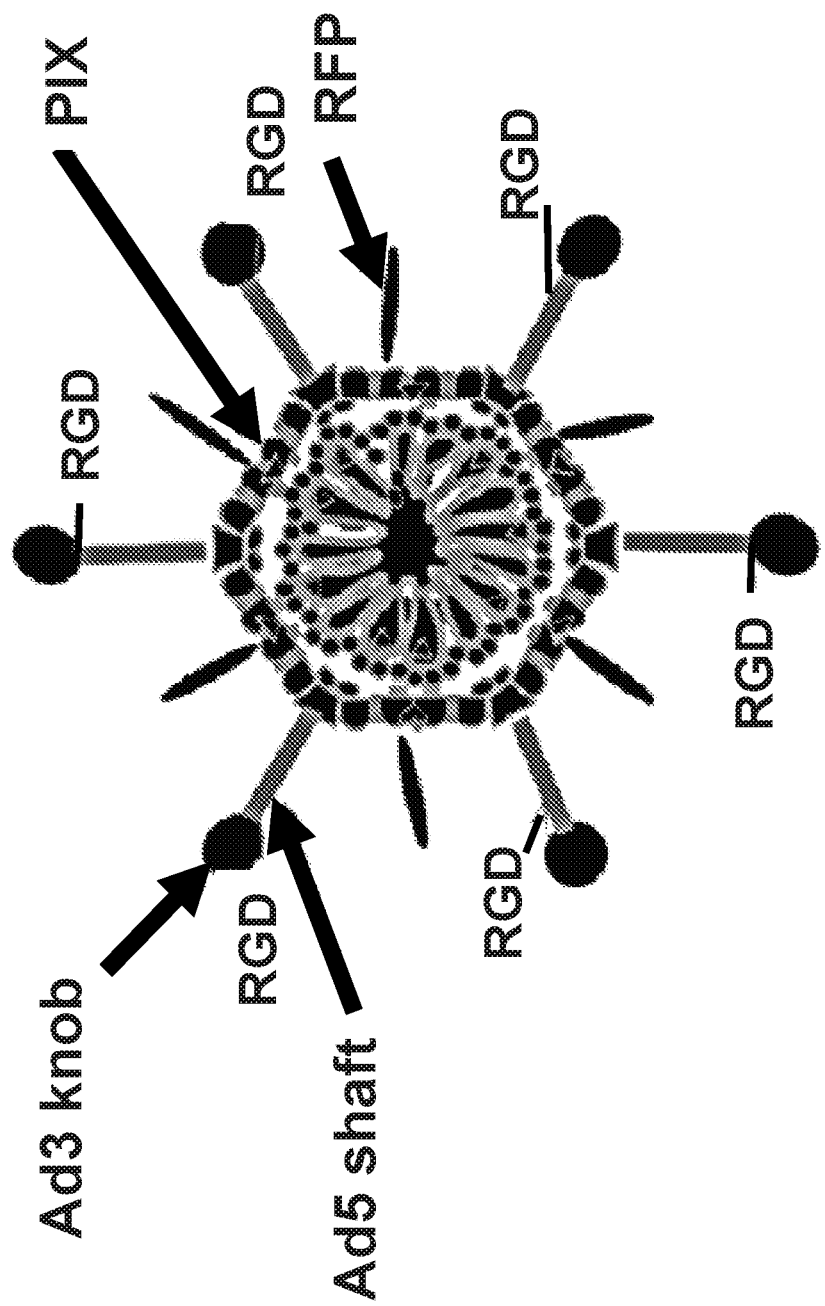

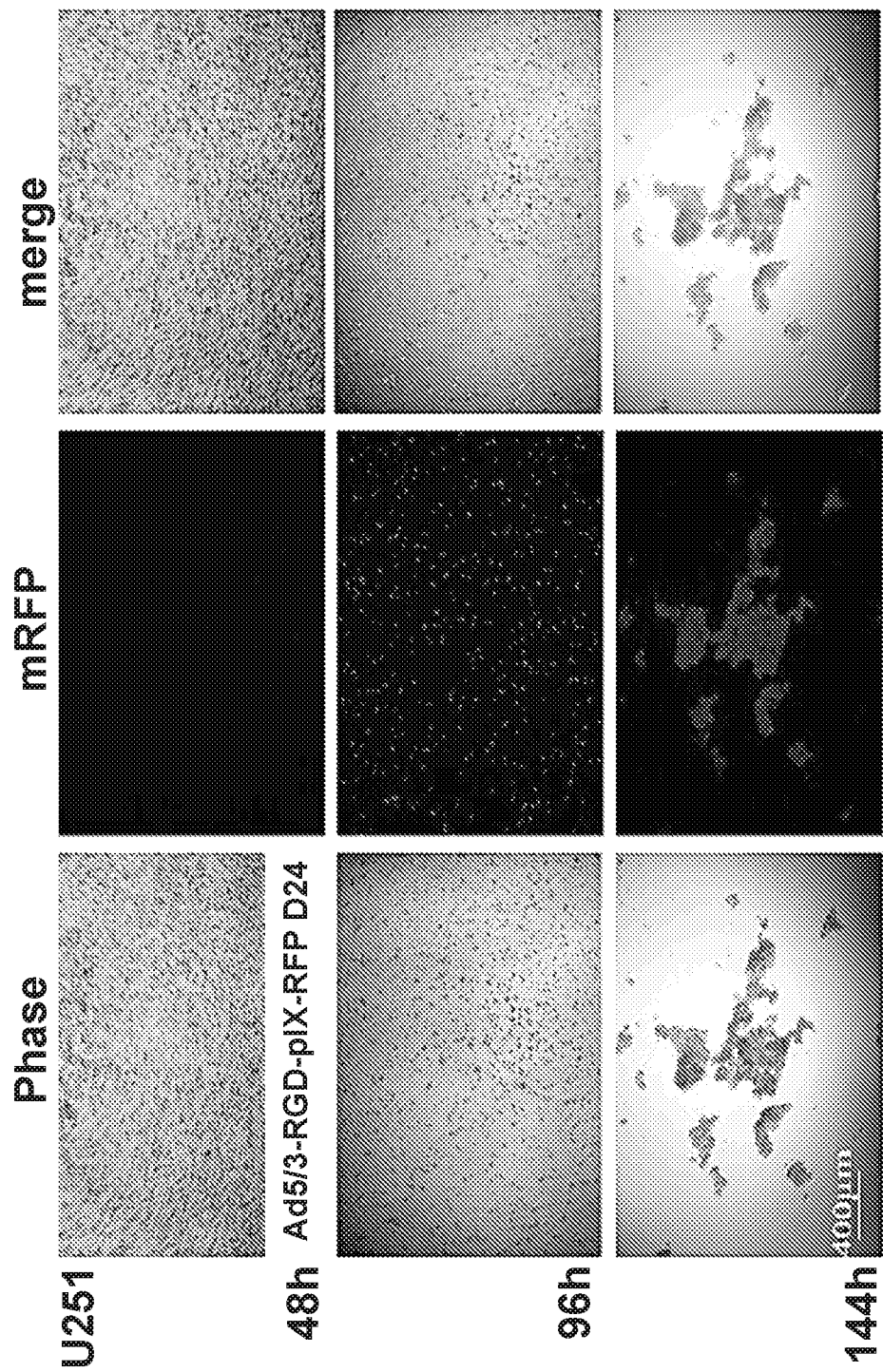

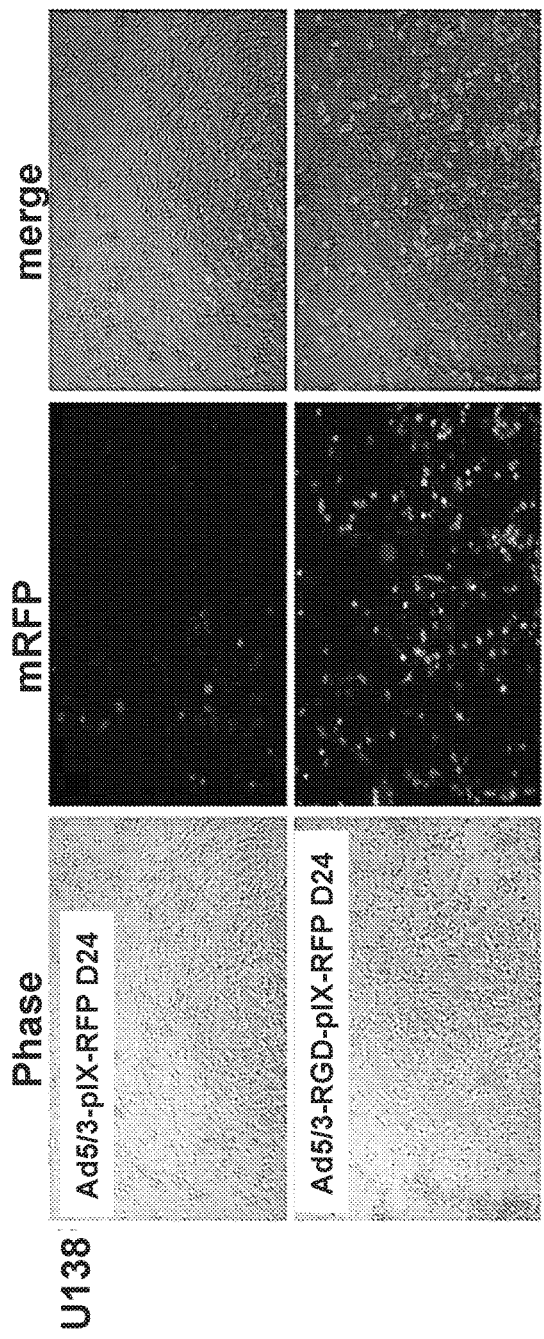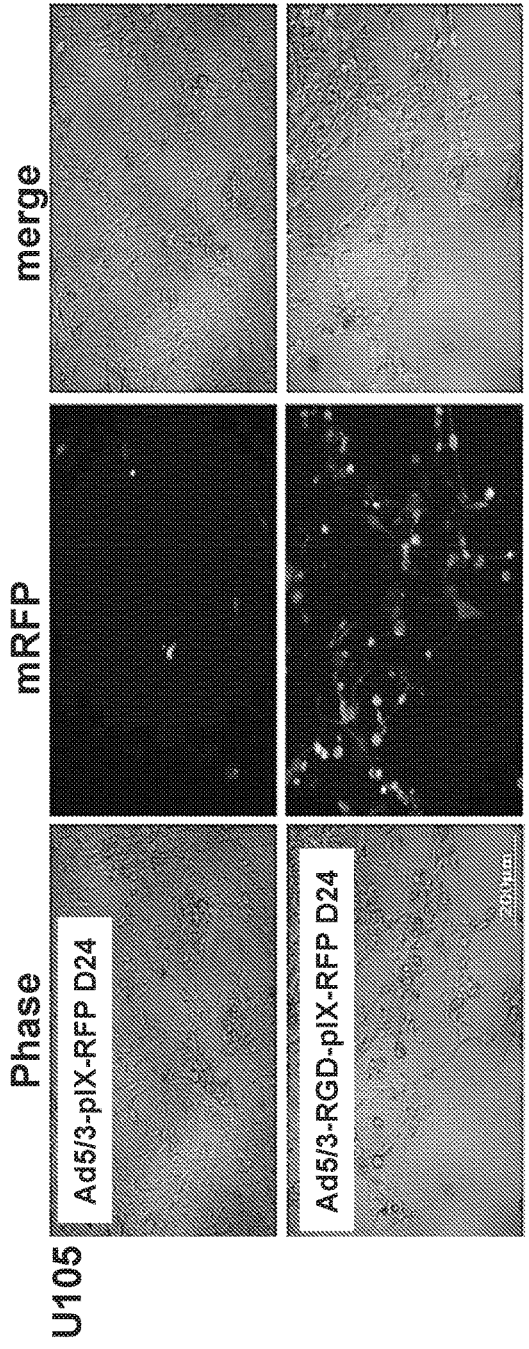

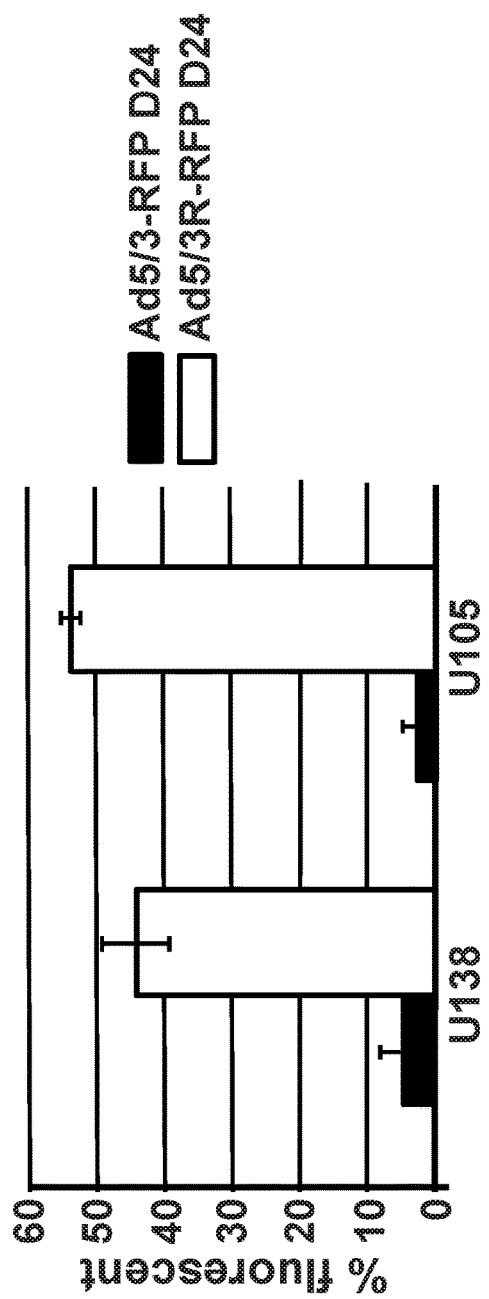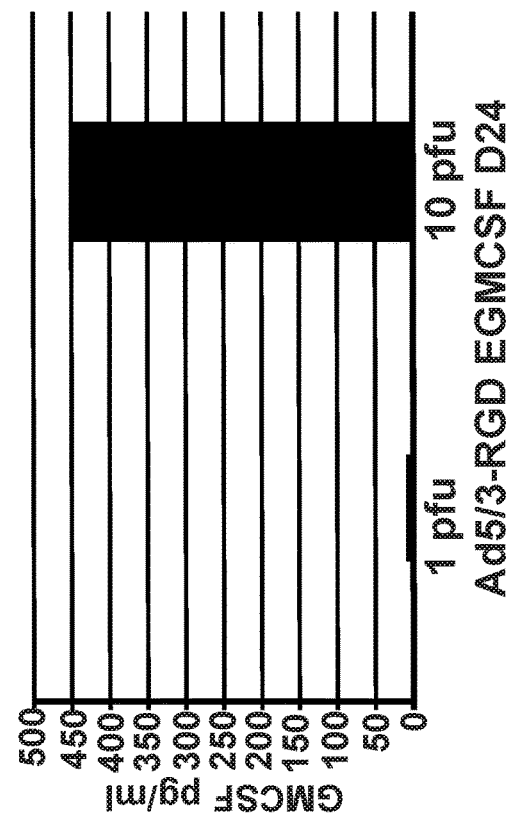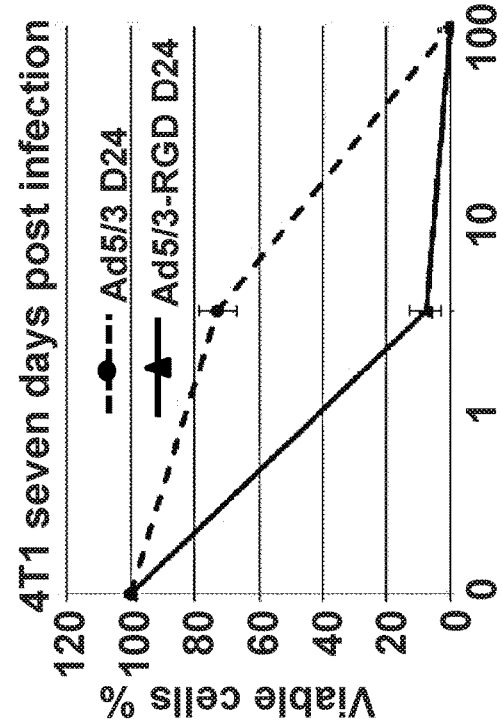
Fig. 14
Fig. 15A
Fig. 15B

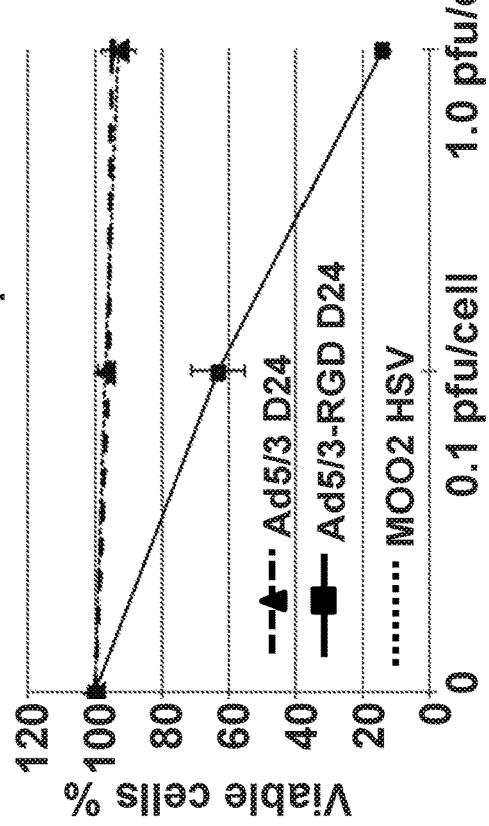
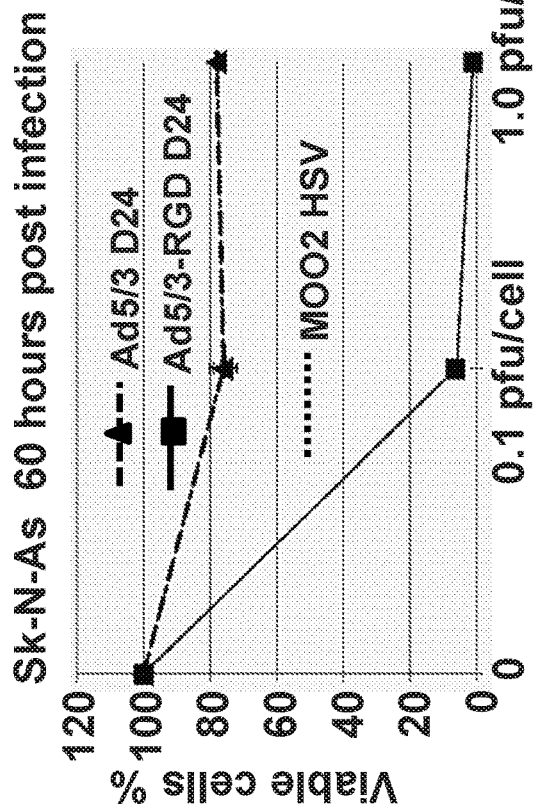
Fig. 17A
Fig. 17B

MULTITARGETING ONOCOLYTIC ADENOVIRUS, METHODS OF USE, AND METHODS OF MAKING

CROSS REFERENCE TO RELATED APPLICATIONS

This application is the 35 U.S.C. § 371 national stage application of PCT Application No. PCT/US2015/067005, filed Dec. 21, 2015, where the PCT claims priority benefit of U.S. Provisional Patent Application Ser. No. 62/096,611 filed on Dec. 24, 2014 and titled "MULTITARGETING ONOCOLYTIC ADENOVIRUS, METHODS OF USE, AND METHODS OF MAKING", both of which are herein incorporated by reference in their entireties.

STATEMENT OF GOVERNMENT SPONSORSHIP

This invention was made with government support under grant T32-NS04803 awarded by the National Institutes of Health. The government has certain rights in the invention.

FIELD OF THE DISCLOSURE

The present disclosure relates to novel oncolytic adenoviruses and to methods of their use in targeting an extended range of tumor cells and tumors.

INCORPORATION OF SEQUENCE LISTING

This application contains a sequence listing filed in electronic form as an ASCII.txt file entitled 2221042570_ST25, created on Dec. 17, 2015, and having a size of 396,541 bytes. The content of the sequence listing is incorporated herein by its entirety.

BACKGROUND

Virotherapy uses human viruses to kill infected cancer cells by targeting the virus infection and replication to different cancer types. Initially, viral therapy for cancer treatment centered on infecting a small number of target cells with a replicating virus that would replicate, amplify, and spread to adjacent cells, destroying the tumor by a lytic mechanism called oncolysis. For that purpose, adenoviruses have a number of advantages as an oncolytic virus (OV): they achieve a high rate of human cell transduction, can be grown and administered at high titers, and are clinically safe (Koski et al., (2015) *Mol. Ther.*; Pol et al., (2014) *Oncoimmunology* 3: e28694; Zheng et al., (2000) *Nat. Biotechnol.* 18: 176-180).

Oncolytic adenoviruses based on a 24-base pair deletion (D24) in the nucleotide sequence encoding the Rb-binding domain of the immediate early gene E1A, result in a virus deficient for viral replication in normal cells (Fueyo et al., (2000) *Oncogene* 19: 2-12; Koski et al., *Mol. Ther.* 18: 1874-1884; Krasnykh et al., (1996) *J. Virol.* 70: 6839-6846; Suzuki et al., (2001) *Clin. Cancer Res.* 7: 120-126). Importantly, the 24-base pair deletion does not compromise Ad replication efficiency in cancer cells or oncolytic potency (Fueyo et al., (2000) *Oncogene* 19: 2-12).

However, these first-generation conditionally replicating adenoviruses (CRAds) had limited efficacy as the therapeutics were based on the Ad5 serotype. The primary receptor for Ad5 is the Coxsackievirus B and Adenovirus Receptor (CAR) that is poorly expressed on most cancer cells (Miller et al., (1998) *Cancer Res.* 58: 5738-5748). Furthermore, CAR is highly expressed on normal lung and liver cells severely limiting the potential usefulness of the virus (Bauerschmitz et al., (2002) *Int. J. Oncol.* 21: 1161-1174; Bergelson et al., (1997) 275: 1320-1323). Although these CRAds lacked efficacy in failing to infect an adequate number of cancer cells, the therapeutics were proven safe for patient treatment (Russell et al., (2012) *Nat. Biotechnol.* 30: 658-670).

A second approach has been to construct a recombinant chimera fiber with the knob domain replaced with that from another Ad serotype. As an important region responsible for binding to cell surface receptors, the fiber knob domain represents a major determinant of Ad tropism. For example, replacing the Ad5 knob with the Ad3 knob, resulting in Ad5/3 serotype chimera, has proven successful in re-targeting the vector to cells with low levels of CAR, but high levels of the Ad3 receptor(s) that are upregulated on a number of cancer cell types (Koski et al., *Mol. Ther.* 18: 1874-1884; Krasnykh et al., (1996) *J. Virol.* 70: 6839-6846; Kanerva et al., (2002) *Clin. Cancer Res.* 8: 275-280; Kimball et al., *Clin. Cancer Res.* 16: 5277-5287).

This infectivity enhancement has become an area of research focus as Ad3 binding to the Desmoglein 2 (DSG2) receptor, a primary receptor for the Ad3 serotype, improves the tumor microenvironment for drug delivery as the interaction results in a signaling cascade that releases the tight epithelial adhesion that normally precludes white blood cell and therapeutic agent tumor penetration (Liu et al., (2014) *Gynecol. Oncol.* 132: 722-729; Wang et al., *Nat. Med.* 17: 96-104). The Ad5/3 modification serves a second important function by avoiding the coxsackievirus and adenovirus receptor that exists on many normal cells allowing improved tumor selection. Hence, the use of this virus has numerous potential therapeutic benefits. As with the Ad5-RGD D24 virus, the Ad5/3 D24 vector also exhibits a substantial improvement in the transduction efficiency of certain cancer cells (Pesonen et al., (2011) *Mol. Pharm.* 8: 12-280).

SUMMARY

One aspect of the disclosure encompasses embodiments of a nucleotide sequence encoding a genetically modified adenovirus, said nucleotide sequence comprising: a nucleotide sequence encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; a nucleotide sequence encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor.

In some embodiments of this aspect of the disclosure, the nucleotide sequence can further comprise a nucleotide sequence encoding a heterologous polypeptide desired to be expressed from the genetically modified adenovirus.

In some embodiments of this aspect of the disclosure, the nucleotide sequence encoding the heterologous polypeptide can be operably linked to a nucleotide sequence encoding an adenovirus E3 polypeptide or a fragment thereof.

In some embodiments of this aspect of the disclosure, the nucleotide sequence encoding the heterologous polypeptide can be operably linked to a nucleotide sequence of the adenovirus encoding an adenovirus pIX polypeptide.

In some embodiments of this aspect of the disclosure, the heterologous polypeptide can be a detectable fluorescent protein.

In some embodiments of this aspect of the disclosure, the heterologous polypeptide can be an immunomodulator.

In some embodiments of this aspect of the disclosure, the immunomodulator can be Granulocyte-Macrophage Colony Stimulating Factor (GMCSF).

Another aspect of the disclosure encompasses embodiments of a nucleotide sequence encoding a genetically modified shuttle adenovirus vector, wherein the nucleotide sequence is selected from the group consisting of SEQ ID NOs.:3, 6, 9, 10, 11, 12, and 13.

Another aspect of the disclosure encompasses embodiments of a genetically modified adenovirus of the Ad5 serotype, wherein said adenovirus is encoded by a nucleotide sequence comprising: a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; and a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor.

In some embodiments of this aspect of the disclosure, the nucleotide sequence can further comprise a region encoding a heterologous polypeptide desired to be expressed from the genetically modified adenovirus.

In some embodiments of this aspect of the disclosure, the heterologous polypeptide can be a detectable fluorescent protein.

In some embodiments of this aspect of the disclosure, the heterologous polypeptide can be an immunomodulator.

In some embodiments of this aspect of the disclosure, the immunomodulator can be Granulocyte-Macrophage Colony Stimulating Factor (GMCSF).

Yet another aspect of the present disclosure encompasses embodiments of a method of monitoring the progress of delivery of a genetically modified adenovirus to a tumor in a patient, said method comprising the steps of: (a) administering to the patient a pharmaceutically acceptable composition comprising a genetically modified adenovirus of the Ad5 serotype, wherein said adenovirus is encoded by a nucleotide sequence comprising: a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor; and a region encoding a reporter protein, wherein the nucleotide sequence region encoding the reporter protein is operably linked to a nucleotide sequence of the adenovirus encoding an adenovirus pIX polypeptide; and (b) detecting a signal from the reporter protein.

Yet another aspect of the present disclosure encompasses embodiments of a method of modulating an immune response to a tumor in a patient, said method comprising the steps of: (a) administering to the patient a pharmaceutically acceptable composition comprising a genetically modified adenovirus of the Ad5 serotype, wherein said adenovirus is encoded by a nucleotide sequence comprising: a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor; and a region encoding a immunomodulator protein, wherein the nucleotide sequence region encoding the reporter protein is operably linked to a nucleotide sequence encoding an adenovirus E3 polypeptide or a fragment thereof.

In some embodiments of this aspect of the disclosure, the immunomodulator protein is Granulocyte-Macrophage Colony Stimulating Factor (GMCSF).

BRIEF DESCRIPTION OF THE DRAWINGS

Many aspects of the disclosure can be better understood with reference to the following drawings.

FIGS. 1A-1C illustrate the virus constructs of the disclosure.

FIG. 1A schematically illustrates the two-step strategy employed to generate the Ad5/3-C-RGD D24 genome.

FIG. 1B illustrates a digital image of a gel analysis of a PCR amplification of the fiber region using adenoviral DNA prepared from purified virus particles. Top panel represents PCR products amplified using specific primer sets for the Ad3 knob region. Bottom panel represents PCR products amplified using specific primer sets for Ad3 knob region and RGD on the Ad3 knob C-terminus.

FIG. 1C illustrates a schematic representation of the single and multi-targeting viruses.

FIG. 2A illustrates a series of graphs where the cell-killing activities of the viral constructs Ad5/3 D24 and Ad5/3-C-RGD D24 were compared in the glioma lines U87, A172, U251, D54 U138 and U105. Cell viability was measured by MTS assay on the days indicated. All experiments were carried out in triplicate, three or more times. Error bars represent standard deviations.

FIG. 2B illustrates a series of digital phase contrast images of U105 cells treated in same conditions as MTS assays nine days post infection with Ad5/3 D24 or Ad5/3-C-RGD D24 at an MOI of 100 vp/cell (100× magnification live images in a 96 well).

FIGS. 3A-3B illustrates the results of cell-killing assays in cancer lines with a range of oncolytic viruses.

FIG. 3A is a series of graphs illustrating cell viability assays in the cancer lines A549 (lung) (left panel), DU145 (prostate) (center panel), and ZR-75-1 (breast) (right panel).

FIG. 3B is a series of graphs illustrating cancer killing in glioma (left panel), ovarian (center panel), and pancreatic (right panel) cell lines with the second-generation oncolytic viruses Ad5-RGD D24, Ad5/3 D24, and the third generation Ad5/3-C-RGD D24.

FIGS. 5A-5D illustrate the construction of the Ad5/3-C-RGD D24 immunotherapy platform of the disclosure.

FIG. 5A schematically illustrates the E3 shuttle vectors of the disclosure generated for drug delivery.

FIG. 5B schematically illustrates the two-step homologous recombination to generate the various immunotherapeutic delivery oncolytic viruses.

FIG. 5C schematically illustrates the Ad5/3-RGD-IX-RFP D24 virus.

FIG. 5D schematically illustrates the modified Ad5/3-C-RGD D24 conditionally replicating adenovirus vectors of the disclosure.

FIGS. 6A-6C are digital images illustrating capsid pIX expression in glioma cells.

FIG. 6A is a series of digital images illustrating U251 glioma cells seeded at 10,000 cells/well and infected the following day at an MOI of 1 vp/cell (Live images taken at 40× magnification at the times indicated).

FIG. 6B is a series of digital images illustrating U138 cells infected with Ad5/3-IX-RFP D24 (top panels) and Ad5/3-RGD-IX-RFP D24 (lower panels) at an MOI of 1 vp/cell for six days and at an MOI of 10 vp/cell for nine days, respectively (100× magnification live images in a 96 well).

FIG. 6C is a series of digital images illustrating U105 cells infected with Ad5/3-IX-RFP D24 (top panels) and Ad5/3-RGD-IX-RFP D24 (lower panels) at an MOI of 1 vp/cell for six days and at an MOI of 10 vp/cell for nine days, respectively (100× magnification live images in a 96 well).

FIG. 8A illustrates examples of cancer killing between the vaccine platform Ad5/3-RGD-IX-RFP D24 and the unmodified version.

FIG. 8B illustrates examples of cancer killing between the E3 modified virus with and without GM-CSF expression.

FIG. 8C illustrates GM-CSF production in A549 cells. Similar results were seen in other cell lines assayed. All experiments were carried out in triplicate, three or more times. Data presented as mean±standard deviation.

FIG. 14 is graph illustrating the enhanced protein expression by Ad5/3-C-RGD-IX-RFP D24. U138 and U105 cells were infected with Ad5/3-IX-RFP D24 and Ad5/3-RGD-IX-RFP D24 at an MOI of 1 vp/cell for six days and at an MOI of 10 vp/cell for nine days, respectively. Percentage of cells displaying fluorescence was measured in quadruplet as described by Ugai et al., *J. Mol. Biol.* 395: 55-78, incorporated herein by reference in its entirety. Data presented as mean±standard deviation.

FIGS. 15A and 15B are graphs illustrating the Fig. Ad5/3-C-RGD D24 oncolysis and GM-CSF production in a metastatic breast cancer mouse line.

FIG. 15A is graph illustrating Ad5/3 D24 and Ad5/3-C-RGD D24 compared in the mouse breast cancer cell line 4T1. Cell viability was measured by MTS assay.

FIG. 15B is graph illustrating the GM-CSF production by Ad5/3-RGD E3 GMCSF D24 in mouse cell line 4T1 seven days post infection.

FIG. 17A is a graph illustrating the cancer cell killing activity of the Ad5/3-RGD D24 carried out in comparison with the HSV virus MOO2 and the second-generation conditionally replicative adenovirus Ad5/3 D24 in the neuroblastoma line Sk-N-As.

FIG. 17B is a graph illustrating the Cancer cell killing activity of the Ad5/3-RGD D24 was carried out in comparison with the HSV virus MOO2 and the second-generation conditionally replicative adenovirus Ad5/3 D24 in the neuroblastoma line Sk-N-Be.

Figure 1A:
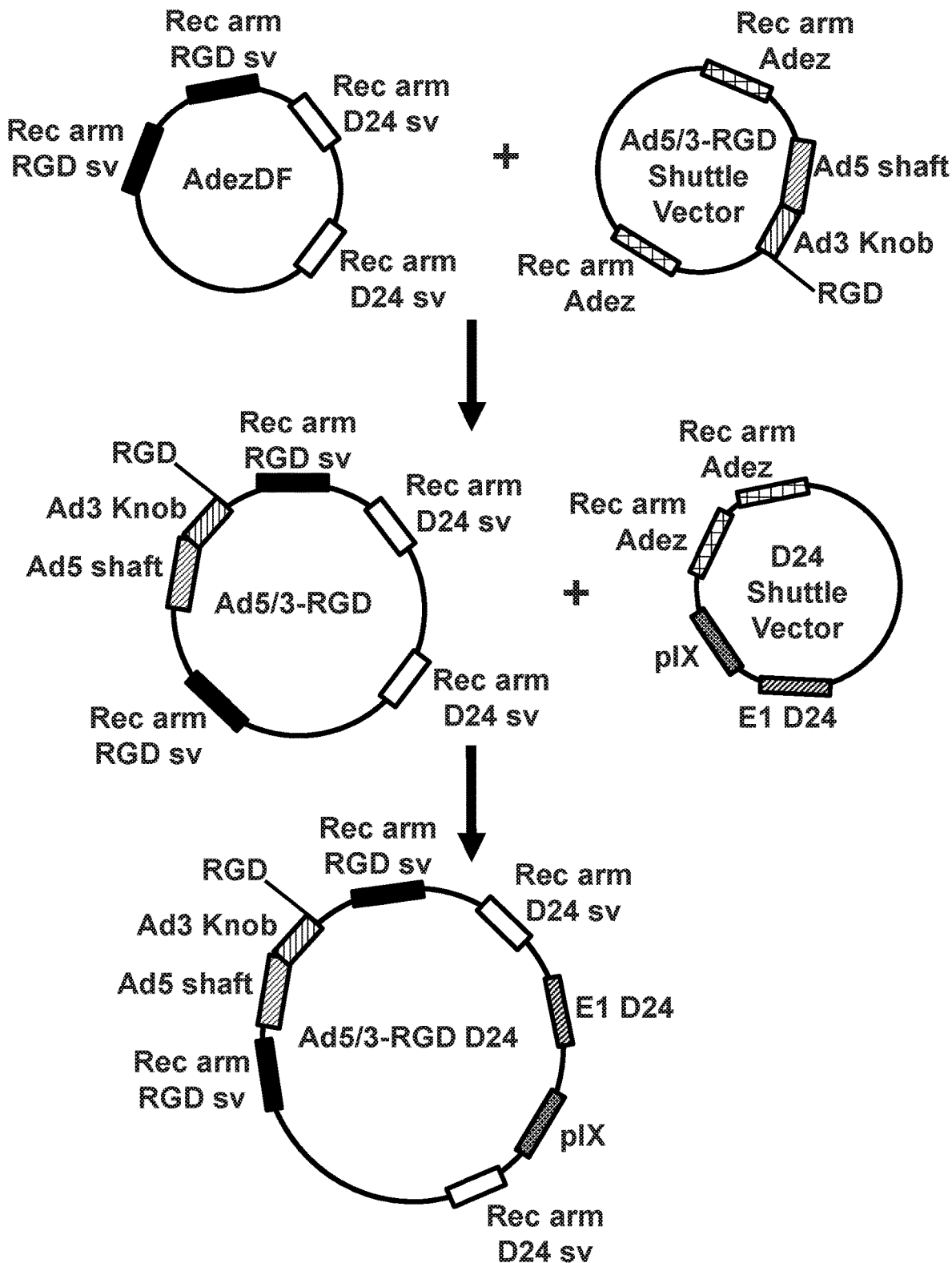

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

The term "adenoviruses" as used herein refers to a non-enveloped viruses 70-90 nm in diameter with an icosahedral capsid. Their genome is linear, double stranded DNA varying between 25-45 kilobases in size with inverted terminal repeats (ITRs) at both termini and a terminal protein attached to the 5' ends.

The icosahedral capsid is formed by three major proteins, of which the hexon trimers are most abundant. Each of the twelve vertices of the capsid also contains a pentameric protein, a penton base that is covalently attached to the fiber. The fiber is a trimeric protein that protrudes from the penton base and is a knobbed rod-like structure. Other viral proteins Ma, IVa2, VI, VIII and IX are also associated with the viral capsid. The proteins VII, small peptide mu and a terminal protein (TP) are associated with DNA. Protein V provides a structural link to the capsid via protein VI.

All human adenoviruses have similarities in their fiber architecture. Each has an N-terminal tail, a shaft with repeating sequences, and a C-terminal knob domain with a globular structure. The knob domain is principally responsible for binding the target cellular receptor and its globular structure presents a large surface for lateral and apical binding. The fiber proteins of adenoviruses from different subgroups most distinctively differ in length and ability to bend.

The fiber participates in attachment of the virus to the target cell. First, the knob domain of the fiber protein binds to the receptor of the target cell, secondly, the virus interacts with an integrin molecule, and thirdly, the virus is endocytosed into the target cell. Next, the viral genome is transported from endosomes into the nucleus and the replication of the viral genome can begin.

Adenoviruses are dependent on the cellular machinery to replicate the viral genome. They can infect quiescent cells and induce them into a cell cycle S-phase-like state enabling viral DNA replication. The adenoviral genome can be divided into immediate early (E1A), early (E1B, E2, E3, E4), intermediate (IX, Iva), and late (L1-L5) genes.

Adenoviral transcription can be described as a two-phase-event, early and late, characterized by the expression of different viral genes and separated by the onset of viral DNA replication. The first transcription unit to be expressed is the E1A. The E1A proteins stimulate the transcription of other early genes and modulate the expression of cellular genes involved in the transition into S-phase, making the cell more susceptible to viral DNA replication. The E1B proteins suppress cell death elicited in response to unregulated cell proliferation signals, including those mediated by E1A. The E2 gene products provide the replication machinery for viral gene products.

E3 gene products are not essential for virus replication in vitro, but are dedicated to the control of various host immune responses. E3-gp19K inhibits the transport of the class 1 major histocompatibility complex (MHC) from the endoplasmic reticulum (ER) to the plasma membrane, thereby preventing the presentation of peptides to T lymphocytes by MHC. Other E3 proteins inhibit apoptosis elicited by various cellular proteins such as the tumor necrosis factor .alpha. (TNFα). As an exception, E3 derived adenoviral death protein (ADP) functions late in the viral cycle to promote cell death, presumably to aid in the release of the virus after all the replicative functions have been completed. E4 gene products have been implicated in many events that occur as the late program begins. E4 proteins augment viral DNA synthesis and messenger RNA (mRNA) transport, late viral gene expression, shutoff of host protein synthesis, and production of progeny virions. The late gene transcription leads to the production of viral structural components and the encapsidation and maturation of the viral particles in the nucleus.

More than 50 different serotypes of adenoviruses have been found in humans. Serotypes are classified into six subgroups A-F and different serotypes are known to be associated with different conditions i.e. respiratory diseases, conjunctivitis and gastroenteritis. Adenovirus serotype 5 (Ad5) is known to cause respiratory diseases and it is the most common serotype studied in the field of gene therapy. In the first Ad5 vectors E1 and/or E3 regions were deleted enabling insertion of foreign DNA to the vectors. Furthermore, deletions of other regions as well as further mutations have provided extra properties to viral vectors. Indeed, various modifications of adenoviruses have been suggested for achieving efficient anti-tumor effects.

The term "immune response" as used herein refers to the development in a subject of a humoral and/or a cellular immune response to an antigen present in the composition of interest. A "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Methods of measuring cell-mediated immune response include the measurement of intracellular cytokines or cytokine secretion by T-cell populations, or by measurement of epitope specific T-cells (e.g., by the tetramer technique).

The term "reporter gene" as used herein refers to a gene, usually a foreign or modified gene, that is added to a construct and is expressed due to the promoter in the construct and the expression allows easy identification of cells or tissues that have taken up the construct. Common reporter genes include the gene that encodes jellyfish green fluorescent protein, which causes cells that express it to glow green under UV light, and the firefly luciferase gene which causes light emission when its substrate luciferin is added. Reporter genes are often placed downstream of the promoter region and in the proximity of the gene of interest to ensure that they are expressed together and not separated by cross-over events.

The term "heterologous" as used herein refers to nucleic acid sequences, amino acid sequences and antigens that are foreign and are not naturally found associated with a particular adenovirus.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands. Polypeptides that are not naturally part of a particular organism's protein, polypeptide or peptide complement are referred to as "foreign polypeptides," "heterologous polypeptide" or "exogenous polypeptide."

The terms "gene" or "genes" as used herein refer to nucleic acid sequences (including both RNA and DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes." The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The terms "expressed" or "expression" as used herein refer to the transcription from a gene to give an RNA nucleic acid molecule at least complementary in part to a region of one of the two nucleic acid strands of the gene. The terms "expressed" or "expression" as used herein also refer to the translation from said RNA nucleic acid molecule to give a protein, a polypeptide, or a portion or fragment thereof.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "expression vector" as used herein refers to a nucleic acid vector that comprises a gene expression control region operably linked to a nucleotide sequence coding at least one polypeptide. As used herein, the term "regulatory sequences" includes promoters, enhancers, and other elements that may control gene expression. Standard molecular biology textbooks (for example, Sambrook et al., eds., 1989, "Molecular Cloning: A Laboratory Manual," 2nd ed., Cold Spring Harbor Press) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "recombinant nucleic acid" and "recombinant DNA" as used herein refer to combinations of at least two nucleic acid sequences that are not naturally found in a eukaryotic or prokaryotic cell. The nucleic acid sequences include, but are not limited to, nucleic acid vectors, gene expression regulatory elements, origins of replication, suitable gene sequences that when expressed confer antibiotic resistance, protein-encoding sequences, and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The techniques used to isolate and characterize the nucleic acids and proteins of the present disclosure are well known to those of skill in the art, and standard molecular biology and biochemical manuals may be consulted to select suitable protocols without undue experimentation (see, for example, Sambrook et al., "Molecular Cloning: A Laboratory Manual," 2nd ed., 1989, Cold Spring Harbor Press; the content of which is incorporated herein by reference in its entirety).

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

"Denaturation" of a template molecule refers to the unfolding or other alteration of the structure of a template so as to make the template accessible to duplication. In the case of DNA, "denaturation" refers to the separation of the two complementary strands of the double helix, thereby creating two complementary, single stranded template molecules. "Denaturation" can be accomplished in any of a variety of ways, including by heat or by treatment of the DNA with a base or other denaturant.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR), which is defined and described in later sections below. The PCR process of Mullis is described in U.S. Pat. Nos. 4,683,195 and 4,683,202. PCR involves the use of a thermostable DNA polymerase, known sequences as primers, and heating cycles that separate the replicating deoxyribonucleic acid (DNA) strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves an enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with termini corresponding to the ends of the specific primers employed.

The term "cancer", as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

The term "nucleic acid molecule" as used herein refers to DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. An "isolated" nucleic acid molecule is one that is separated from other nucleic acid molecules that are present in the natural source of the nucleic acid. A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

The terms "nucleic acid," "nucleic acid sequence," or "oligonucleotide" also encompass a polynucleotide. A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which natural nucleotides have been partially replaced with modified nucleotides.

The term "pharmaceutically-acceptable carrier" as used herein refers to a pharmaceutically-acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "region" as used herein refers interchangeably with "domain" and refers to a functional unit of a peptide sequence.

The term "infecting" as used herein refers to exposing the recombinant adenovirus to a complementing cell line under conditions so as to facilitate the infection of the producer cell with the recombinant adenovirus. In complementing cells which have been infected by multiple copies of a given virus, the activities necessary for viral replication and virion packaging are cooperative. Conditions can be adjusted such that there is a significant probability that the cells are multiply infected with the virus. An example of a condition which enhances the production of virus in the cell is an increased virus concentration in the infection phase. Chemical agents may be employed to increase the infectivity of the cell line. Calpain inhibitor 1 has been observed to increase the infectivity of cell lines to recombinant adenovirus (see, e.g. U.S. Pat. No. 7,001,770 herein incorporated by reference in its entirety).

The term "transfection" or "transformation" as used herein refers to the introduction of a nucleic acid into a cell. A host cell that receives the introduced DNA or RNA has been "transformed" and is a "transformant" or a "clone." Examples of transformation methods which are very well known in the art include liposome delivery, electroporation, CaPO.sub.4 transformation, DEAE-Dextran transformation, microinjection and viral infection Abbreviations Ad: Adenovirus; Ad5: adenovirus serotype 5; Ad3: Adenovirus serotype 3; Ad5 D24: first generation CRAd; Ad5/3 D24: second generation CRAd; the Ad5 virus with the knob domain from the Ad3 serotype; Ad5-RGD D24: the Ad5 first generation CRAd with the RGD modification on the C terminus of the Ad5 knob serotype; Ad5/3-RGD D24: multi-targeting virus (also as Ad5/3-C-RGD D24 to denote the modification to the C terminus of the Ad3 knob; ADP: advanced death protein; APCs: antigen presenting cells; C-terminus: carboxyl terminus; CRAd: Conditionally Replicating Adenovirus incorporating D24; DSG2: Desmoglein 2; D24: 24 base pair deletion in the E1 region that renders the E1 protein unable to bind pRb; DF: deleted fiber. E1A, E2F, E4: Early transcription unit genes in Adenovirus; FCM: flow cytometery; GMCSF: Granulocyte macrophage colony-stimulating factor; HI loop: loop protein structure between beta strands H and I on the Ad5 knob; it: intratumorally; oncolytic virus: oncolytic virus; pRb: Retinoblastoma tumor suppressor protein; pIX: Adenovirus capsid protein; pKAN: shuttle vectors that contain the fiber and knob region of either Ad5 or Ad5/3 and a kanamycin resistance gene; RFP: Red Fluorescent protein; RGD: amino acids Arginine-Glycine-Aspartic acid; shuttle vector: shuttle vector; TSA(s): tumor specific antigen(s); TAA: tumor associated antigen.

Description

Part of the success of generating an immune response is dependent on killing a maximum amount of cancer cells in order to generate a debris field rich in potential new tumor specific antigens (TSAs) for processing by antigen-presenting cells (APCs) such as dendritic cells. Again, adenovirus are ideal candidates for generating such a debris field and for general cancer immunotherapy. Conditionally replicating adenoviruses (CRAds) are highly selective for cancer cells, preventing damage to normal host tissue. CRAd selectivity is based on deleting portions of the E1A gene that prevents binding of the Ad-specific regulatory protein to the tumor suppressor protein pRb, thus rendering the virus unable to induce normal cells to pass the G1/S checkpoint, thereby preventing replication in normal cells. However, as cancer cells are constantly dividing due to a variety of signaling defects, CRAds that infect the cancer retain efficient replication resulting in oncolysis. The safety of this modification has been verified in a number of clinical trials in which patients report little to no side effects from CRAd treatment Treatments based on oncolytic viruses have shown positive responses for some patients. However, evidence suggests that beneficial outcomes are most likely due to an immune response to the oncolytic virus infected cancer cells and to a lesser extent direct oncolysis by the vector. A plausible explanation is that tumor associated antigens released by oncolysis were successfully processed by antigen presenting cells (potentially induced by the inflammatory response to "danger signals" provided by the pathogenic stimuli) ((Matzinger P (2002) *Science* 296: 301-305). The outcome is that T effector cells generated to viral antigens would, through cross-epitope spreading, recognize tumor antigens, overcome the immunosuppressive signals of the cancer, resulting in cancer elimination. Hence, increasing the proportion of CRAd-infected cancer cells should enhance such an outcome, as generating a more extensive debris field in a more heterogenic number of cancer cells may increase potential tumor specific antigens (TSAs). This has become an important consideration given that multiple molecular subtypes of tumor cells can be found within any one tumor mass, confounding the ability to target a specific tumor genotype (Gill et al., (2014) *Proc. Natl. Acad. Sci. U.S.A.* 111: 12550-12555). With heterogenic oncolytic enhancement as the primary goal, this study first looked at augmenting second generation CRAds by incorporating D24, Ad5/3 serotype chimera and an RGD modified fiber into a single oncolytic virus: Ad5/3-C-RGD D24.

The compositions and methods of the present disclosure focus on overcoming low levels of specific cancer cell transduction. A number of strategies have been employed to improve first generation CRAd cancer targeting. One involves genetic incorporation of small peptide ligands with receptor targeting properties into the Ad fiber knob. Due in part to structural constraints, only a limited number of small peptide ligands can be used to produce functional fibers that enhance virus infectivity. One successful ligand is the RGD (Arg-Gly-Asp) motif which has high binding affinity to integrins such as $\alpha v\beta 3$ and $\alpha v\beta 5$, which are secondary Ad receptors that promote Ad internalization and are highly expressed on many cancer types. Importantly, incorporation of this ligand into the fiber knob did not result in loss of vector binding; and a CRAd, Ad5-RGD D24, based on this modification displayed dramatic enhancement in oncolysis of certain cancer lines with high expression of integrins. This adenovirus is currently in clinical trials (ClinicalTrials.gov identifier NCT00805376) (Russell et al., (2012) *Nat. Biotechnol.* 30: 658-670).

Accordingly, the present disclosure encompasses embodiments of a novel CRAd that incorporates multiple targeting attributes. One such modified adenovirus is Ad5/3-RGD D24 (D24 for safe cancer selectivity; RGD modified fiber for integrin targeting; and the Ad5/3 serotype chimera for decreased infection of normal cells and improved tumor penetration and oncolysis). By making a range of nucleotide changes to a variety of shuttle vectors, followed by multiple homologous recombinations, screening and bioinformatics, a combination of novel shuttle vectors were generated that were capable of forming a viable virus adept at drug and vaccine delivery. This CRAd has been assayed in over 15 different cancer lines, and has shown superior oncolysis compared to the single targeting oncolytic viruses currently in clinical trials.

The most viable option for treating metastatic cancer is for the immune system to be activated against the cancer cells. For an immune response against metastatic cancer to occur, novel TSAs must be captured and presented to T cells by APCs, resulting in the activation of effector T cells against the TSAs. For an effective result to occur the T-effector cell count must be augmented beyond the T regulatory cell level of activity responsible for tumor immune-suppression. The multi-targeting CRAd generated here is an ideal platform for such a response.

Preliminary evidence shows the Ad5/3-RGD D24 vector displays enhanced oncolysis that results in a more extensive debris field of potential TSAs. Enhanced oncolysis combined with the natural innate and adaptive response associated with Ad-infection should result in a dramatic enhancement of T effector cells to the infected tumor site.

Unlike HSV and measles virus, the Ad5/3-RGD D24 genome is more easily manipulated, the structure is stable to a range of modifications, and the genome does not undergo random mutations upon upscaling. The virus also maintains oncolysis despite temperature fluctuations and freeze thaw cycles. This makes Ad5/3-RGD D24 optimal for delivering immune-stimulatory agents, potential tumor specific antigens and is less prone to loss of function as well as more deleterious mutations.

Accordingly, Ad5/3-RGD D24 has been further engineered for the expression of heterologous polypeptide(s) to be delivered as immune-stimulatory agents and TSAs. One example, not intended to be limiting, is GMCSF cloned into the E3 region of the virus. It is contemplated that any polypeptide or peptide may be usefully expressed from the engineered adenovirus vectors of the disclosure upon their entry into a cancer cell.

The new virus, Ad5/3-RGD-GMCSF D24, elicits high doses of the heterologous polypeptide even at low viral titers. Also, as Ad-specific cytotoxic T lymphocytes (CTLs) are preferentially directed towards conserved Ad-epitopes within the Ad-capsid (Li et al., *Virology* 338: 247 (2005)), the capsid portion of the virus can be engineered to incorporate potential tumor antigens. This armed multi-targeting virus can now deliver potent immune-stimulatory agents deep within the tumor micro environment.

Embodiments of the present disclosure relate to viruses to treat cancer. More specifically, the embodiments relate to oncolytic human adenoviral vectors and pharmaceutical compositions comprising said vectors. In addition, embodiments relate to the use of said vectors for treating cancer in a patient and relates to a method of producing an adenoviral vector.

Embodiments of the present disclosure are directed towards the construction of a multi-targeting oncolytic adenovirus for enhanced cancer killing and immunotherapy via expression of biological agents and vaccine antigen delivery.

Engineered Third Generation CRAds. Ad5/3-RGD D24:

First, multi-targeting attributes and safety were combined into a single virus, Ad5/3-RGD D24. The generation of this CRAd, as shown in FIG. 1A, for example, is based on a two-step homologous recombination strategy that begins with the Adeasy (Adez) vector backbone that has been modified to allow for easy recombination with shuttle vectors (sv) that contain modified fiber domains. To aid in recombination, the Adez backbone was modified by inserting a Swa1 restriction enzyme site (AdezDF(swa1)). One shuttle vector variant contains the shaft of Ad5 serotype but the knob from Ad3 (pKANAd5/3). Importantly, a further modification of this vector was made to contain the unique restriction enzyme site BamH1 on the C-terminus for easy addition of other genes. Hence, using this site on the C-terminus of the Ad3 knob the RGD motif was cloned. For homologous recombination, this shuttle vector had been engineered to contain homologous arms with the Adez genome allowing for homologous recombination in the recombination-prone *E. coli* strain BJ5183, according to methods originally described by Chartier et al. (*J. Virol.* 70: 4805 (1996)). Following the initial homologous recombination between Adez and pKANAd5/3-RGD, the Ad5/3-RGD construct was then recombined with a delta 24 shuttle vector (D24), which contains the 24 base pair deletion in E1A as well as recombination arms with the Adez vector (FIG. 1A).

All virus genomes were then sequenced to ensure the relevant modifications were correct, as given in Table 1.

TABLE 1

Adenovirus Constructs of the Disclosure

| SEQ ID NO. | Construct |
|---|---|
| SEQ ID NO. 1 | Ad53 rgd E3 D24 |
| SEQ ID NO. 2 | Ad53 rgd E3 GMCSF D24 |
| SEQ ID NO. 3 | Ad53 rgd sv |
| SEQ ID NO. 4 | AdEz 53rgd D24 |
| SEQ ID NO. 5 | AdEz 53rgd IX rfp D24 |
| SEQ ID NO. 6 | AdEz 53rgdsv 1stHR |
| SEQ ID NO. 7 | AdEz E3 53rgd 1stHR |
| SEQ ID NO. 8 | AdEz swa1 |
| SEQ ID NO. 9 | D24 pIX frame nhe sal sv |
| SEQ ID NO. 10 | D24 pIX RFP frame sv |
| SEQ ID NO. 11 | D24 pIX stop sv |
| SEQ ID NO. 12 | E3 53rgd bst sal sv |
| SEQ ID NO. 13 | E3 gmcsf 53rgd sv |

The new viral genome was then Pac digested, purified and transfected into 293 cells. A number of clones were attempted for transfection until a viable one was found; whereby the virus was then up-scaled in A549 cells and purified by double cesium chloride density gradient centrifugation, and validated by standard molecular and biological procedures as previously described (Chartier et al., *J Virol* 70: 4805 (1996)).

As the Ad5/3 D24 virus showed promise in treating a range of cancer types (Koski et *Mol Ther* 18 (10), 1874) but also useful as a drug delivery platform (Beyer et al., *Clin Cancer Res* 18 (12), 3340; Kim et al., *Hum Gene Ther* 22 (7), 821), an analysis of cancer killing was carried out to determine if the Ad5/3-RGD D24 multi-targeting strategy improved oncolysis over the widely used second generation CRAd.

Figure 2A:
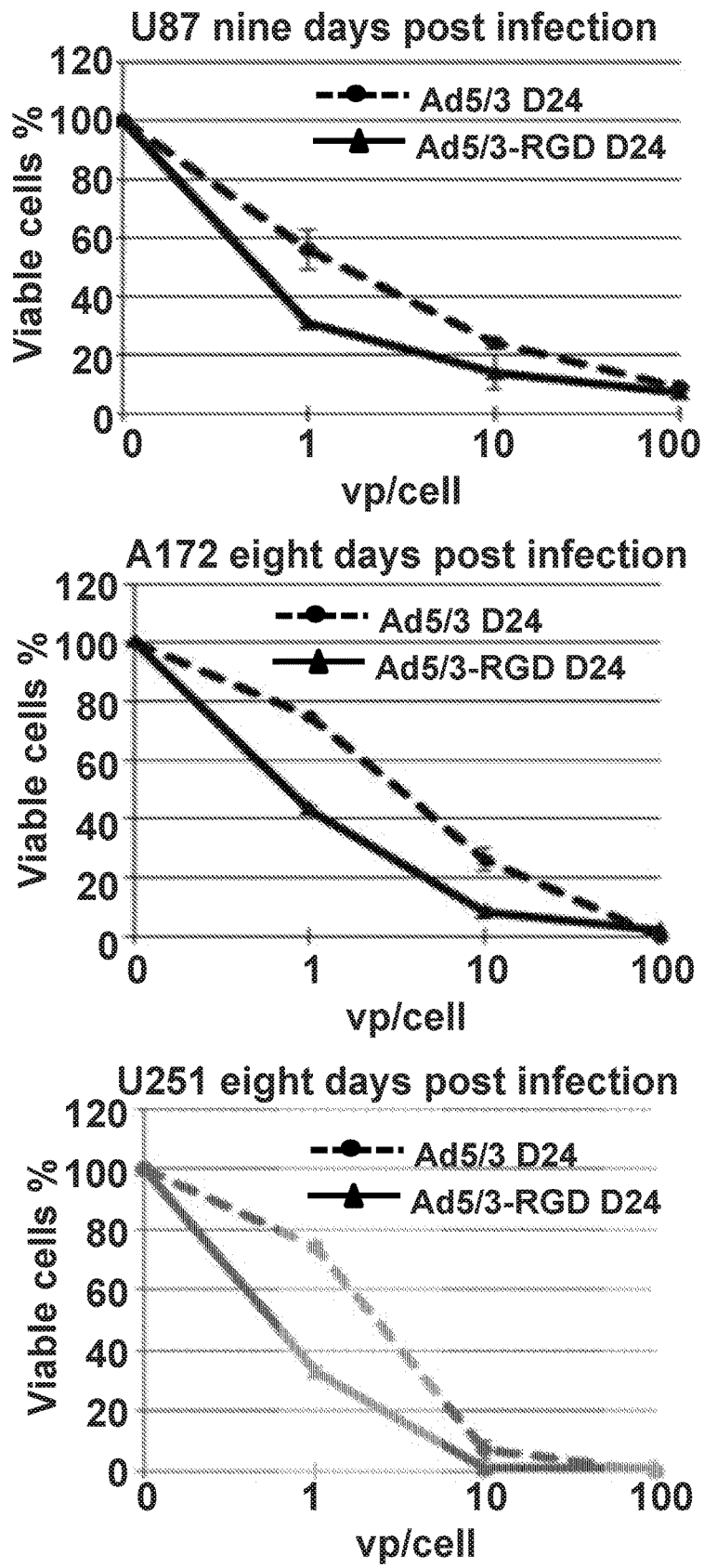
FIGS. 2A and 2B illustrate the results of cell-killing assays with glioma cell lines.
Figure 2B:
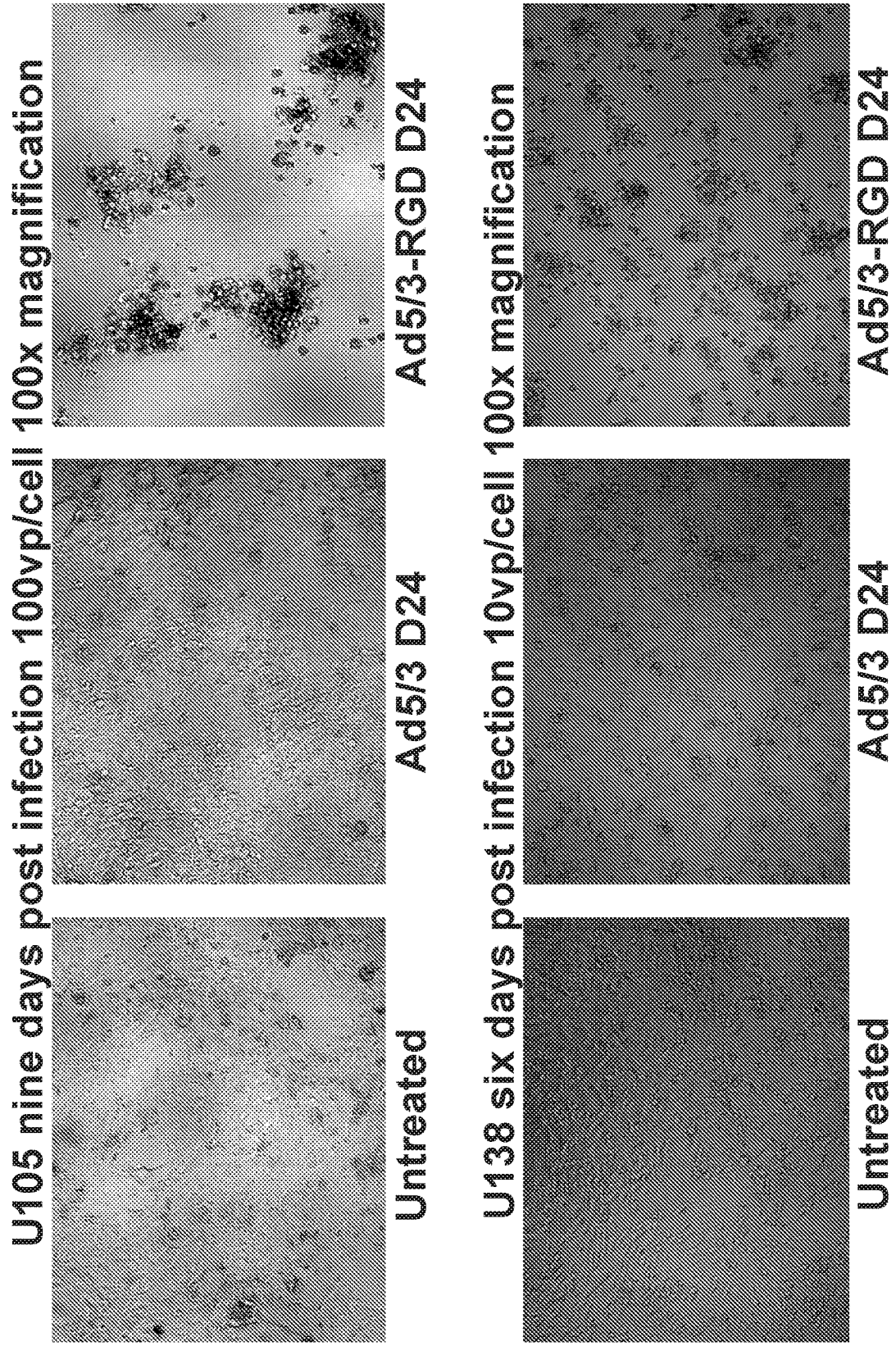

As gliomas are one of the deadliest cancers, cancer killing analysis on a range of brain cancer cell lines was performed. The Ad5/3-RGD D24 showed enhanced killing in all glioma lines assayed. In U251, A172, and U87, Ad5/3-RGD D24 showed improvement in killing potency over Ad5/3 D24 at low titer levels. Furthermore, by 10 days post infection with Ad5/3-RGD D24 (MOI 100 vp/cell) only minimal cell survival was detected. The cell lines with the greatest variability between the oncolytic viruses were the U138 and U105 cell lines, with Ad5/3 D24 displaying little to no cell killing 10 days post infection in the U105 line (FIG. 2A). Phase contrast images show a consistent monolayer of U105 and U138 cells in the Ad5/3 D24 wells similar to untreated wells at 10 days post infection compared to full cytopathic effect (CPE) seen in the Ad5/3-RGD D24 treated wells (FIG. 2B).

Given these results the viruses were assayed in three other cancer lines: lung (A549) prostate (DU145), and breast (ZR-75-1). The Ad5/3-C-RGD D24 showed similar oncolytic effect to Ad5/3 D24 in the lung and prostate lines. However, in the breast cancer line, an improvement in cell killing was again detected with the RGD modified virus (FIGS. 3A-4B).

Based on the enhancement in cancer killing with the multi-targeting approach, a comparison between the Ad5-RGD D24 and the HSV oncolytic viruses, both of which have shown potential in clinical trials, was assayed. Although not as many lines have been assayed, the Ad5/3-RGD D24 virus is clearly superior in cancer killing in the pancreatic and ovarian lines compared to the Ad 5-RGD D24 (FIGS. 3A-4B and 16).

Figure 13A:
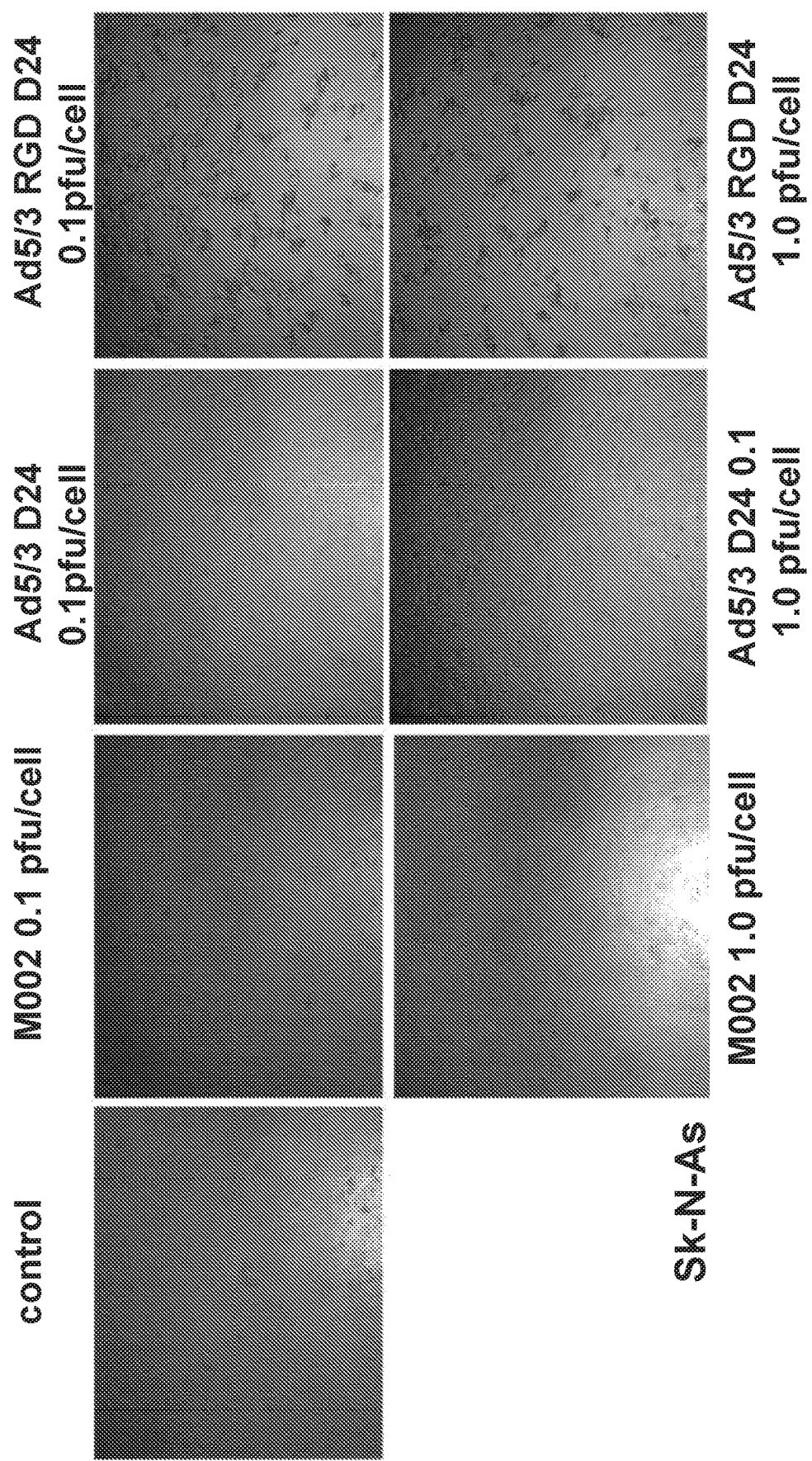
FIG. 13A is a series of digital phase contrast images of neuroblastoma cell lines treated with multiple oncolytic viruses. SK-N-As cells were infected with the indicated oncolytic viruses at an MOI of 0.1 or 1.0 PFUs/cell. Live images at 60 h post-infection in a 96 well plate prior to MTS assays (100× magnification).
Figure 13B:
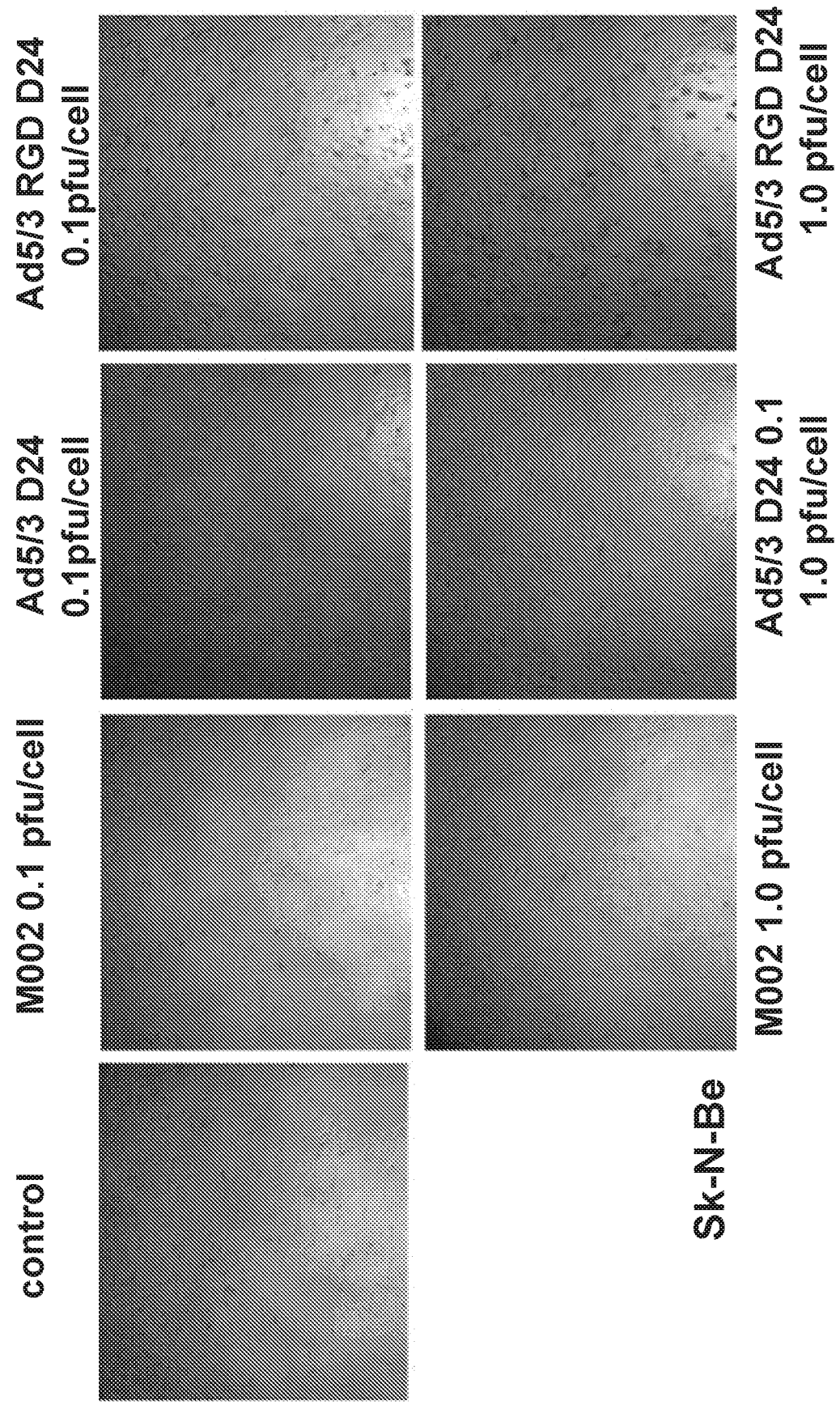
FIG. 13B is a series of digital phase contrast images of neuroblastoma lines treated with multiple oncolytic viruses. SK-N-Be cells were infected with the indicated oncolytic viruses at an MOI of 0.1 or 1.0 PFUs/cell. Live images at 60 h post-infection in a 96 well plate prior to MTS assays (100× magnification).
Figure 16:
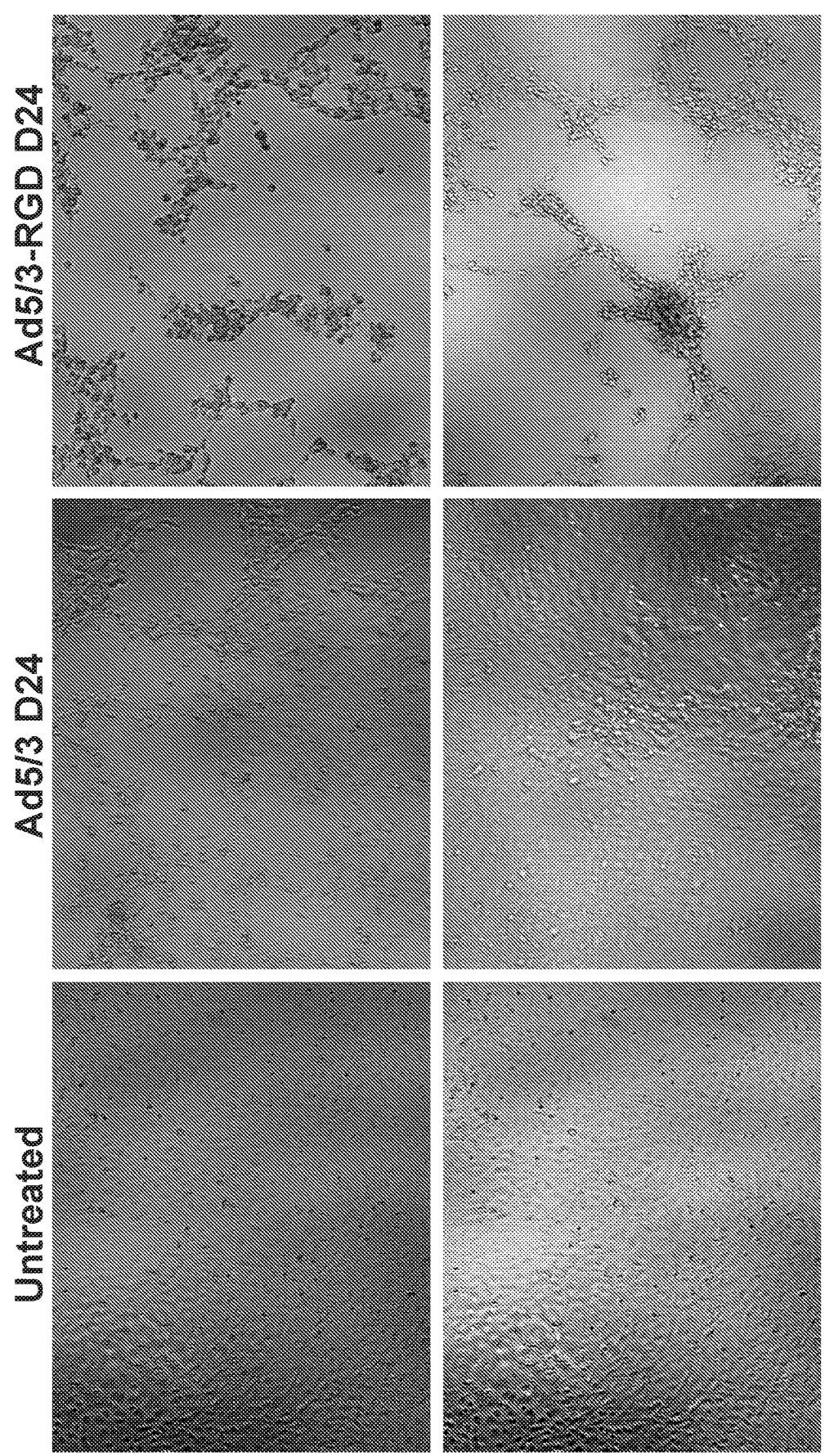
FIG. 16 is a series of digital phase contrast images showing oncolytic virus-4 cells untreated, Ad5/3 D24 and Ad5/3-RGD D24 treated at nine days post infection. 1 vp/cell top panel, and six days post infection with 10 vp/cell bottom panel (100× magnification). Full CPE is clearly seen in the Ad5/3-RGD D24 virus even at 1 vp/cell.

A similar comparison with an HSV oncolytic virus MOO2 (Parker et al., *Proc. Natl. Acad. Sci. U.S.A.* 97: 2208 (2000)) that is nearly identical to the Amgen T-vec was performed. The T-vec virus has shown over 25% complete or partial response for patients suffering from metastatic melanoma (Senzer et al., *J. Clin. Oncol.* 27: 5763 (2009)). As the MOO2 virus is also being tested for treating children with neuroblastoma (Megison et al., *PLoS One* 9 (1), e86843), the Ad5/3-RGD D24 was assayed in two neuroblastoma lines. Again the Ad5/3-RGD D24 showed vast enhancement in cancer killing 60 hours post infection at low titers over the HSV virus and Ad5/3 D24 virus (FIGS. 13A and 17A). To date, this virus has infected and killed all cancer cell lines assayed, at 1 pfu/cell or lower.

The cancer killing is related to the receptors being expressed on the cells. Flow cytometry (FCM) has been performed on a number of the cancer lines. FCM for $\alpha V\beta 3$ and $\alpha V\beta 5$ integrin (RGD receptors) expression confirmed that all glioma lines expressed integrins. Analysis of a primary receptor for Ad5/3, Desmoglein 2 (DSG2), indicated that the receptor was expressed in U87, A172, and U251 cell lines; however, little to no levels of the receptor could be detected in the U138 and U105 glioma lines (FIG. 4A). FCM analysis of the lung (A549), prostate (DU145), breast (ZR75-1) and ovarian (OV4) indicated that integrin and DSG2 were present. The Ad5/3 D24 showed similar killing to the multi-targeting virus in cells that expressed high levels of DSG2 such as the lung and prostate cancer cell lines. However, in the U138 lines and the U105 lines, DSG2 is expressed at low levels; and the virus showed little to any cell killing even at high titers. In some lines such as the breast and ovarian lines DSG2 is expressed; however, the multi-targeting virus showed superior killing especially at low titer. The improvement in cancer killing of Ad5/3-RGD D24 at low titers in these lines is most likely due to two enhancements in infection: first, the increase binding of integrin receptors which are also present and aid entry when the vp/cancer cell ratios are low; and second, the RGD modification improves infection by enhancing the signaling cascade responsible for internalizing the virus (Wickham et al., *Cell* 173 (2), 309 (1993)).

This third generation of oncolytic viruses was used, first to ascertain if a multi-targeting oncolytic virus genome would be structurally capable of forming viable viral progeny upon transfection; and second, if the virus was viable would the modification enhance cancer killing over existing second generation oncolytic viruses: Ad5/3 D24, Ad5-RGD D24 and HSV MOO2 (close to isogenic to the Amgen T-vec HSV virus). The results indicate that this is the case. The virus has been tested in over 15 different cancer lines, displaying near complete oncolysis at low titers. No current oncolytic viruses are known to show this range in cancer killing at such low titers. Moreover, as many cancers are heterogenic in nature, the Ad5/3 RGD D24 should maintain targeting regardless of the variety of cancer cells that could exist within a patient suffering from metastatic cancer.

A Fourth Generation Multi-Targeting CRAd for Immunotherapy: Drug Delivery and Vaccine: Ad5/3-RGD E3 D24, Ad5/3-RGD E3-GMCSF D24 and Ad5/3-RGD-pIX-RFP D24:

The immune system plays a key role in cancer development and progression: it can suppress tumor growth by destroying cancer cells but it can also select for tumor cells within the tumor microenvironment that facilitate tumor outgrowth. Immunotherapy has centered on augmenting the immune response in four ways: first, research has focused on the immune effector processes to bring about cancer elimination by activating T-cells and other lymphocytes as well as enhancing cytokines such as IFN gamma and TNF alpha to induce cytostatic and cytocidal effects. Second, vaccine approaches are being developed to elicit strong specific immune responses to tumor antigens. Third, researchers are using antibodies to target and eliminate tumors. Fourth, approaches are being developed that inhibit the cellular mediators that induce cancer immunosuppression (Schreiber et al., *Science* 331 (6024), 1565).

Oncolytic adenoviruses are ideal for all four approaches, as the immune system has evolved to quickly recognize certain Ads as pathogens in an innate and adaptive manner (Lenaerts et al., *Rev Med Virol* 18 (6), 357 (2008)). The innate recognition process is likely initiated by Ad DNA/capsid sensors (toll like receptor 9 (TLR9) and the inflammosome). The adaptive response results from both Ad-specific CD4+ and CD8+ T cells. Ad-specific cytotoxic T lymphocytes (CTLs) are preferentially directed towards conserved Ad-epitopes within the Ad-capsid, making the use of the capsid to incorporate tumor antigens a promising approach to initiate a cancer specific immune response and kill infected cells (Heemskerk et al., *J Immunol* 177 (12), 8851 (2006)). Ad5/3-RGD D24 can infect all tested cancer types assayed at low titer means that not only will the virus kill the infected cancer cells but more importantly the vast network of white blood cells (wbcs) will likely also target those cancer cells infected with the virus.

The key step for an immune response to metastatic cancer is that replication of the virus must result in releasing tumor-specific antigens to wbcs like dendritic cells (DCs). As the multi-targeting virus can infect cancer cells at least as low as 1 vp/cell, the Ad5/3-RGD D24 triggered immune response will be vastly enhanced over existing oncolytic viruses, thereby greatly enhancing the potential for an immune response to all the Ad infected cancer cells. Based on the enhanced oncolysis, the Ad5/3-RGD D24 virus is the optimal platform to generate both innate and adaptive immune responses as the CRAd generates a more extensive debris field then do other oncolytic viruses. Hence, the Ad5/3-RGD D24 has been engineered to augment an immune response capable of being used in all four strategies listed above: enhancing immune effector response, vaccine response via tumor antigens, delivery of agents such as antibodies and cellular mediators to inhibit immunosuppression.

Figure 5A:
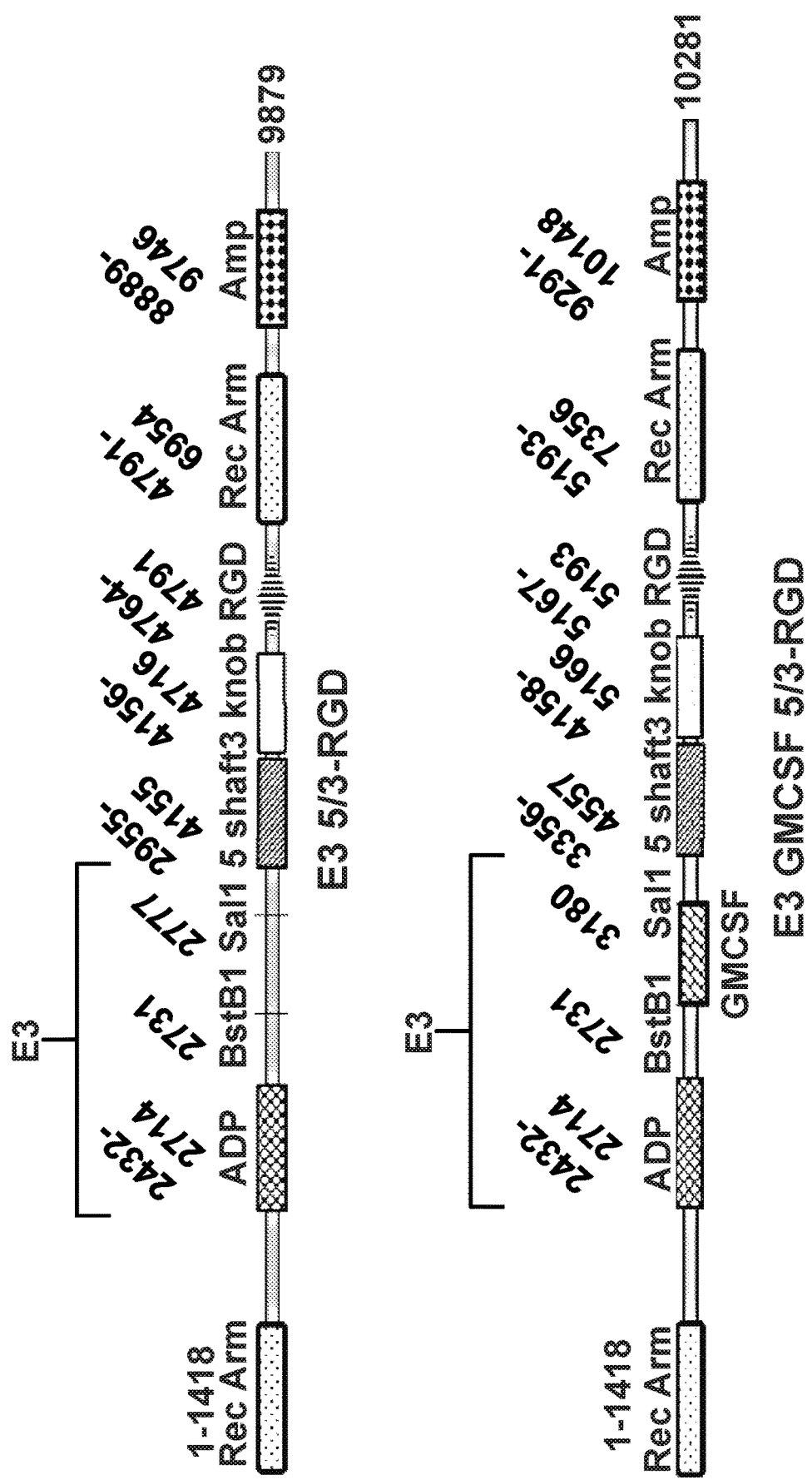
Figure 5B:
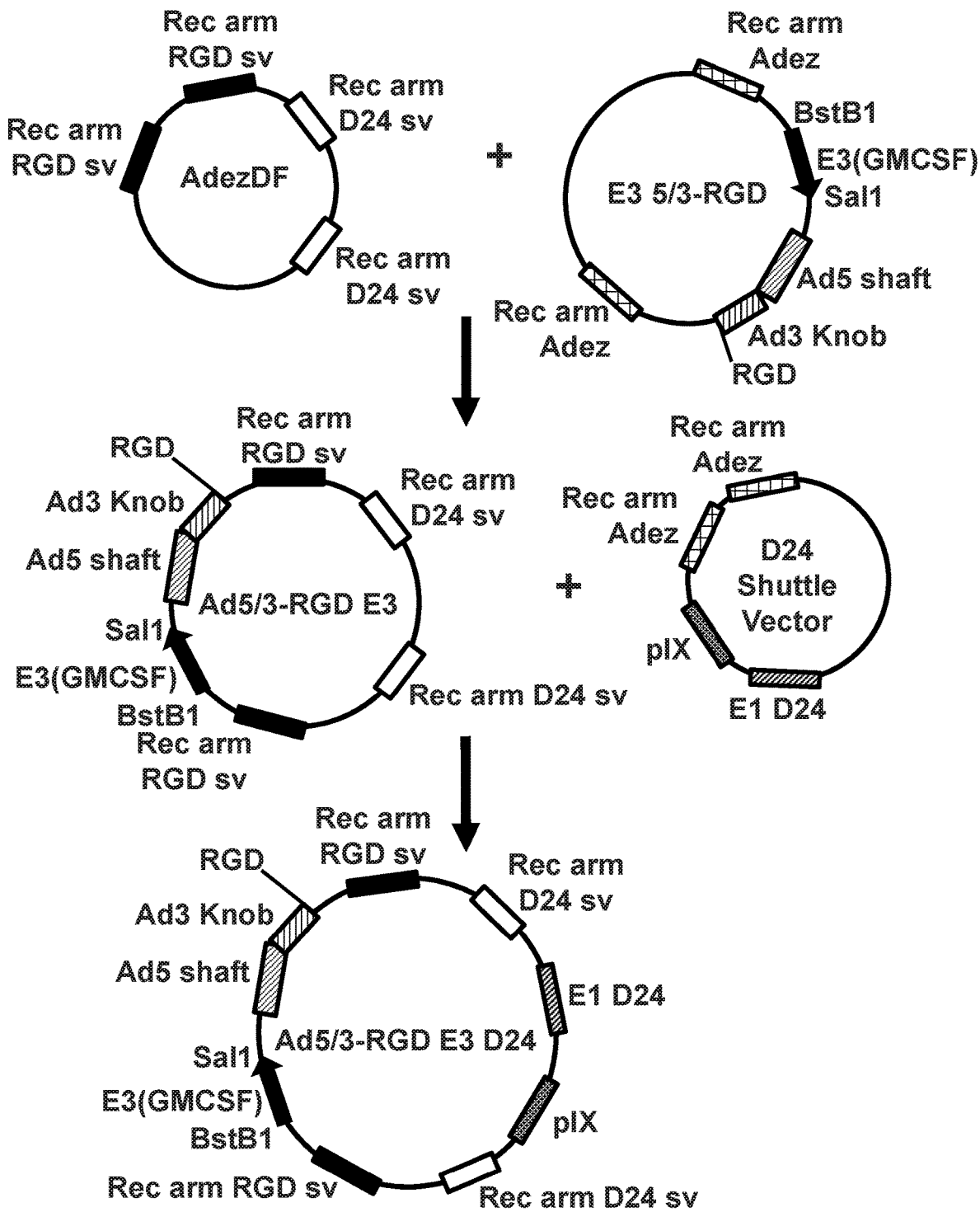

To generate the virus for enhanced immunotherapy, the virus was first engineered to be able to deliver a range of immunostimulatory agents such as antibodies and cytokines. Construction of the new virus was initiated by engineering a number of modified shuttle vectors, as schematically shown in FIGS. 5A and 5B. Similar to the one made above, these vectors contain recombination arms with AdezDF-swa1; the fiber was modified in a similar way to incorporate the Ad5 shaft with the Ad3 serotype knob followed by the RGD modification on the C-terminus. Along with adding antibiotic resistance to aid in homologous recombination, a large portion of the E3 gene was deleted and replaced with unique restriction sites BstB1 and Sal1 for cloning of immunostimulatory agents. Expression of genes cloned into this site are under E1 control which is intact in this virus genome. Importantly, the adenovirus death protein (ADP) was included in the shuttle vector as overexpression of this protein has shown enhanced oncolysis.

Furthermore, to aid in enhancing an immune response the E319k gene has been deleted. This gene serves a similar function as the ICP47 gene in HSV which was deleted in the T-vec version. The removal of this protein is thought to be a significant reason for the therapeutic robust immune response toward metastatic melanoma in a number of patients. Both of these proteins bind and retain MHC Class I proteins preventing viral antigen presentation thereby decreasing an immune response. By deleting E319k, Ad5/3-RGD D24 infected cancer cells will not suppress an immune response to those cells thereby enhancing antigen presenting cell activity and the potential for TSAs to be processed.

Due to potential problems with genome size, charge and steric hindrance, variations of the shuttle vectors were made by removing other regions of the genome until a vector was formed that proved compatible with rescuing the virus (FIG. 5A). Double homologous recombination steps were carried out as before (FIG. 5B).

Following the successful rescue of Ad5/3-RGD E3 D24, a new shuttle vector incorporating the cytokine GMCSF was generated by inserting the immunostimulant into the unique BstB1 sites and Sal 1 sites. Granulocyte-Macrophage Colony Stimulating Factor (GMCSF) is a potent inducer of antitumor immunity, activating natural killer cells, DCs and cytotoxic CD8+ T-lymphocytes (Arellano & Lonial, S., *Biologics* 2: 13 (2008)). However, when GMCSF is used systemically, the immune stimulant is compromised by toxic side effects and limited efficacy due to poor delivery to tumors. Hence, if GMCSF can be paired with an oncolytic virus that can deliver the factor deep within the microenvironment of the tumor and produce a debris field rich in tumor epitopes and costimulatory danger signals, the dual treatment can result in an immune response targeted to the tumor antigens efficacious enough to halt or eliminate the tumor.

Figure 8A:
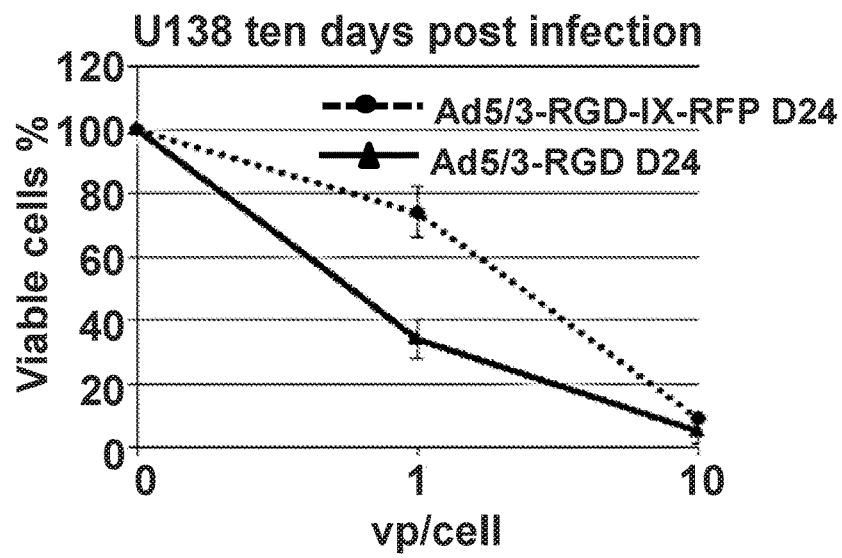
FIGS. 8A-8C are graphs illustrating oncolysis and drug delivery expression of the multi-targeting virus platform of the disclosure.
Figure 8B:
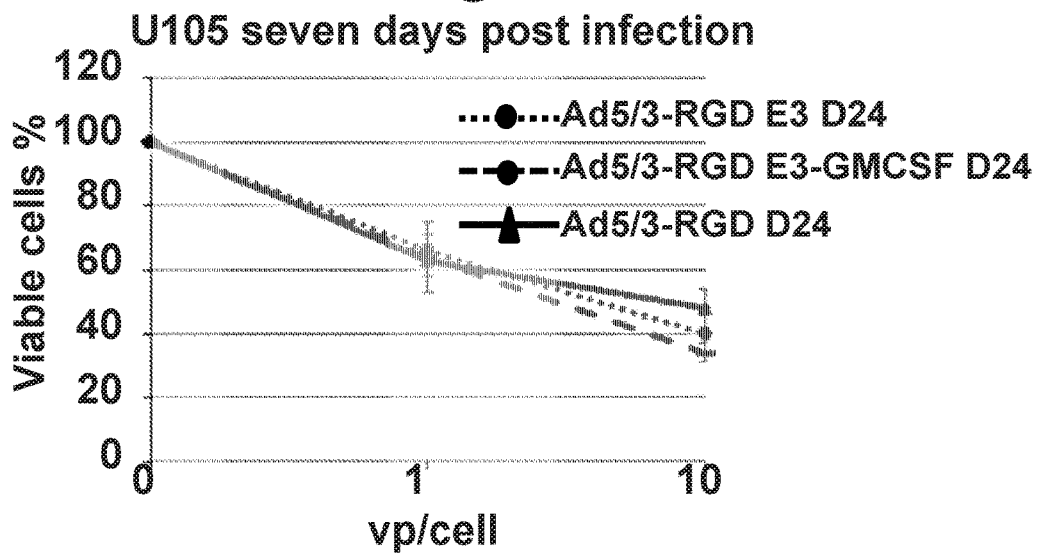
Figure 8C:
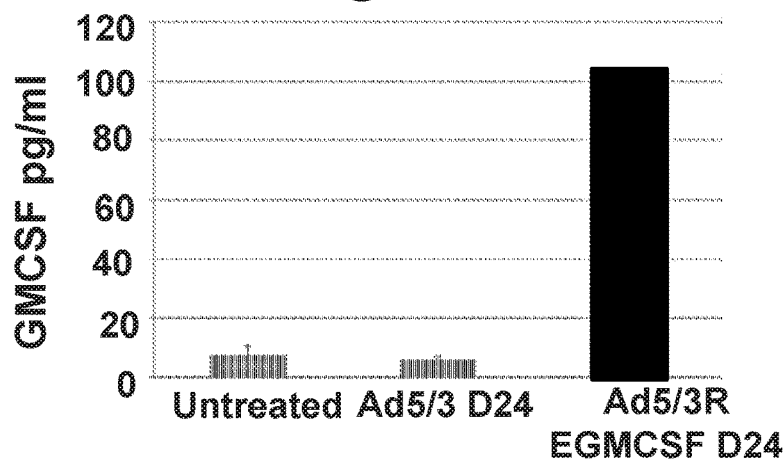

Upon successfully generating the E3 GMCSF Ad5/3-RGD shuttle vector the complete genome was homologously recombined as above (FIGS. 5A and 5B). Over 1000 pg/ml of GMCSF can be produced in a number of cancer lines at low titer (10 vp/cell) only 48 h post infection as detected by Elisa (FIG. 8C).

Finally, a better understanding of tumor immunology has led to possibilities of improving cancer vaccines. The success of these vaccines depends on appropriate tumor-rejection antigens, immune modulators and adjuvants to stimulate a potent immune response. As previously mentioned the Ad5/3-RGD D24 initiates an innate immune response due to the Ad DNA/capsid proteins as well as an adaptive response from both Ad-specific CD4+ and CD8+ T cells. Hence attaching taas and TSAs to the capsid of Ad 5/3-RGD D24 makes for a useful vaccine platform given the variety of cancer cells that Ad5/3 RGD D24 can infect at low titer.

A second variant of the D24 shuttle vector was also generated. To introduce potential TAA and TSA polypeptides onto the capsid of Ad5/3-RGD D24, the D24 shuttle vector containing the capsid protein pIX was engineered to contain unique Nhe1 and Sal1 sites on to the C-terminus of the protein allowing for the cloning of large genes into this region. A structural component of the capsid, pIX is a delayed early viral protein. Previous studies have shown that pIX can tolerate C-terminal fusions with substantially larger ligands than the fiber portion of the virus. As before the shuttle vector contains recombination arms that replaces full length E1 with an E1 containing the deleted 24 nucleotides. To assay the potential of the site suitable for expression of a heterologous polypeptide that could be used as an immunogen in a vaccine and to ensure that the modification would be compatible with the existing multi-targeting genome modifications, the red fluorescent protein (RFP) was cloned into the C-terminus of pIX. Again a number of shuttle vectors were generated and homologously recombined as above.

After screening the genome to ensure the relevant modifications were intact, the full length genomes were Pac digested and transfected into 293 cells. Upon plaque formation, fluorescence detection, viral upscale, sequence and PCR analysis to ensure the relevant modifications were intact upon viral formation, the Ad5/3-RGD-pIX-RFP D24 construct was tested in the glioma line U251 to see if it maintained cancer killing while expressing potential tumor-specific antigen proteins. Monitoring pIX-RFP expression in infected U251 glioma lines indicated that the protein increased over time in a viral DNA replication dependent manner (FIG. 6A).

Figure 7:
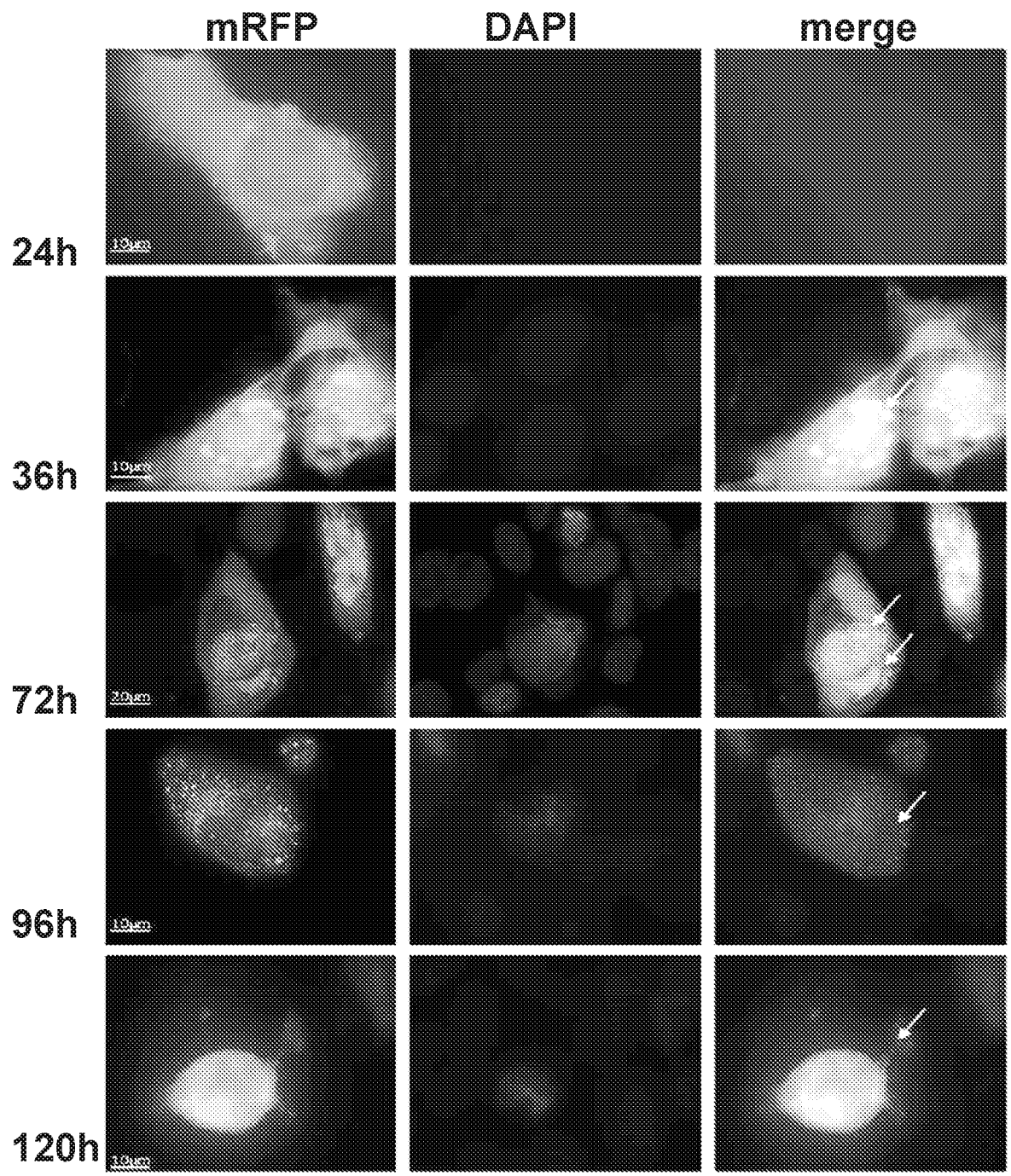
FIG. 7 is a series of digital images illustrating capsid pIX intracellular expression. U251 cells were infected at an MOI of 1 vp/cell and then fixed at the times indicated with PBS containing 10% formalin, and mounted with Vectashield with DAPI. Fluorescent signal for pIX-RFP was detected by fluorescent microscopy (all magnifications at 1,000× except 72 h at 600×). Arrows indicate virus particle sin the cytoplasm by 24 h post-infection, in the nucleus and vacuoles by 36 h post-infection; viral particles released from the nucleus into the cytoplasm by 96 h post-infection, and released from the cell by 120 h post-infection.

The RFP modification was functional, tracking both the spread of the infection as well as intracellular localization (FIG. 7). The increase in expression of RFP as the virus replicates indicates that TSA expression on pIX will be vastly enhanced as the multi-targeting virus replicates and thereby improving the potential that APCs will recognize the TSAs and launch an immune response throughout the body to remove all cells expressing the protein.

Figure 18A:
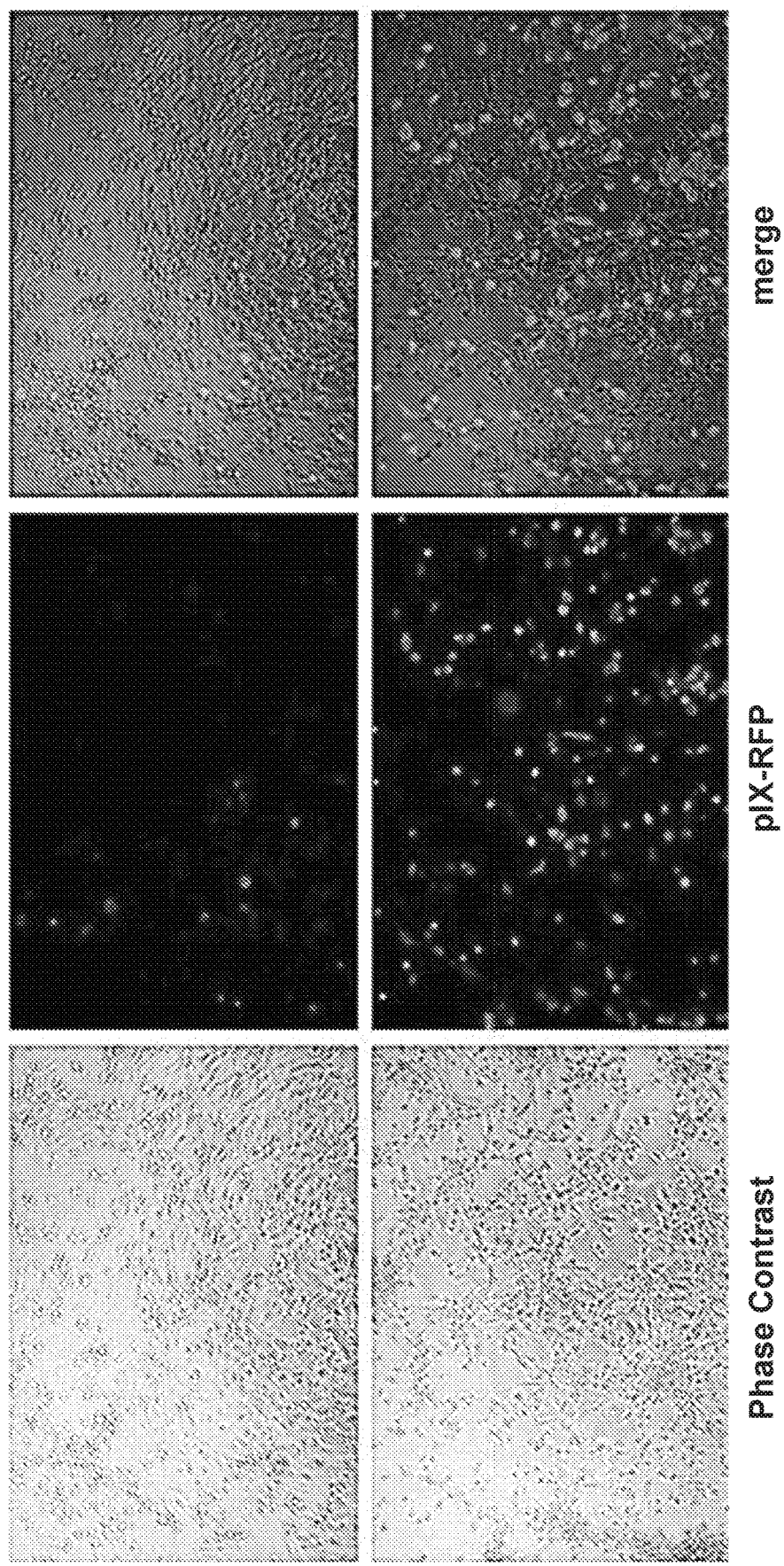
FIG. 18A is a series of digital images illustrating U138 cells infected with Ad5/3-pIX-RFP D24 (top panels) and Ad5/3-RGD-pIX-RFP D24 (lower panels) at an MOI of 1 vp/cell for six days and at an MOI of 10 vp/cell for nine days, respectively (100× magnification live images in a 96 well).
Figure 18B:
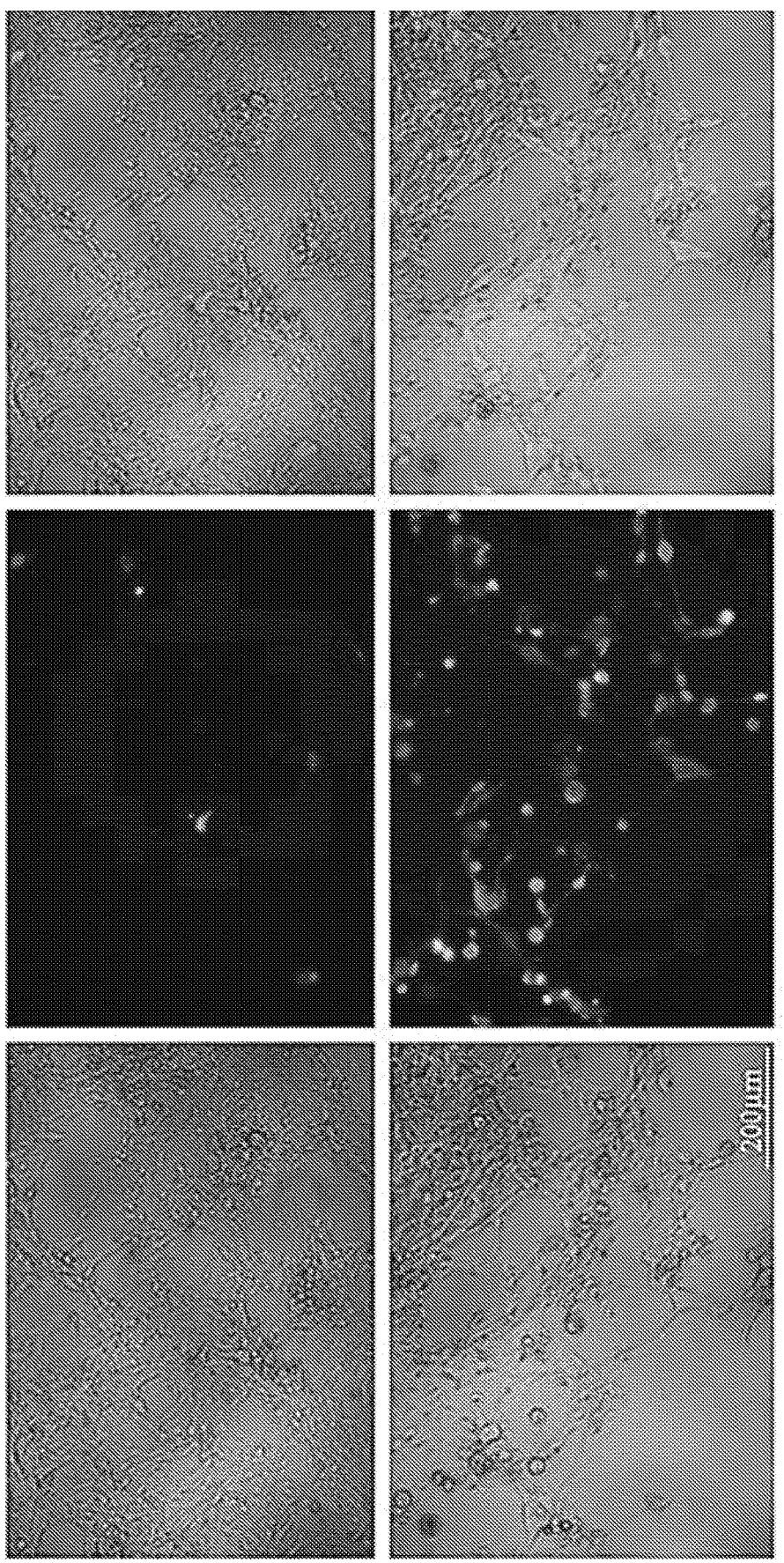
FIG. 18B is a series of digital images illustrating U105 cells were infected with Ad5/3-pIX-RFP D24 (top panels) and Ad5/3-RGD-pIX-RFP D24 (lower panels) at an MOI of 1 vp/cell for six days and at an MOI of 10 vp/cell for nine days, respectively (100× magnification live images in a 96 well).

Similar to the improvement in oncolysis seen by the Ad5/3-RGD D24 over the unmodified Ad5/3 D24, an increase in the number of fluorescent cells was also detected in the RGD modified fluorescent oncolytic virus. At 1 vp/cell, 51% of U138 cells treated with Ad5/3-RGD-pIX-RFP D24 showed fluorescence versus 15% treated with Ad5/3-pIX-RFP D24. Similarly, in the U105 glioma line, 62% of the cells infected with Ad5/3-RGD-pIX-RFP D24 at an MOI of 10 vp/cell displayed fluorescence versus 3% treated with the Ad5/3-pIX-RFP D24 (FIGS. 18A-18B).

The functional Ad5/3-RGD pIX-RFP D24 virus also serves a second function in that genetic labeling of Ad particles provide visualization of the replicating viral mass as a readout of viral replication and accumulation in tumors; the labeling also serves as a control for delivery of the agents immediately or shortly after administration, i.e. prior to the onset of reporter gene expression and CRAd replication. Employment of new spectral imaging technology for tracking CRAd replication and spread in tumors can allow overcoming the high level of autofluorescence in mammalian tissues. The spectral imaging approach is based upon analysis of spectral profiles of the original digital image, and can distinguish the specific fluorescence of the imaging reporter from the background autofluorescence. The special image processing software can identify the specific signals within each pixel of an image by their spectral signatures and extract those from the total signal, thereby disentangling the reporter fluorescence from the background autofluorescence (Tang et al., *Virology* 377: 391 (2008)).

Hence, the data demonstrates that the large globular protein RFP is functional at this site, evidence that this capsid protein can be used for the attachment of TSAs. Also the Ad5/3-RGD pIX-RFP D24 will provide key imaging data for tracking virus, tumor spread and eventually aiding surgical resection.

This virus of the disclosure has now been assayed in a metastatic breast cancer mouse cell line. The lack of in vivo mouse models has been a major hindrance to CRAd research. As adenoviruses are attenuated in mouse cells due to a deficiency in protein translation, first- and second-generation viruses displayed only weak oncolysis in most mouse cancer lines (Young et al., *Mol Ther* 20 (9), 1676). Based on the enhanced infection and killing of the Ad5/3-RGD D24, the virus was assayed in the mouse metastatic breast cancer cell line 4T1 (Pulaski & Ostrand-Rosenberg *Curr Protoc Immunol*). Although the virus showed a decrease in efficiency in cancer killing compared to human cancer cells, the enhanced infection and oncolysis of the virus nonetheless produced full CPE and copious GMCSF production at 1 and 10 pfu/cell respectively seven days post infection (FIGS. 15A-15B). Accordingly, this oncolytic virus can be used in a metastatic mouse models that closely resembles breast cancer in humans, greatly aiding the generation of key immunocompetent in vivo data. The most likely explanation for mouse cancer cell killing is that the multi-targeting nature of the virus simple results in enhanced infection of the cells. Although Ad protein translation is attenuated, infection augmentation by the multi-targeting virus results in replication to a level adequate for drug delivery expression, cancer killing and potentially an immune response.

There has been some concern in the past that certain oncolytic viruses may kill non-cancerous cells. Although these infections may occur in some limited way, all the clinical trials to date with the D24 modification have proven safe. Furthermore, although the viruses generated here are more efficacious in cancer killing than those in clinical trials, they are still based on the D24 modification.

For example, the Ad5 D24, proven safe in clinical trials, has the highest tropism for the sensitive cells of the lung and the liver. Although this tropism is one of the reasons the virus was ineffective at stimulating an efficacious response, it nonetheless did not replicate or damage these cells in any significant way as the patients reported no serious side effects: only a few patients reported mild flu like symptoms. Hence, not only is oncolysis based on D24 vectors suitable for ensuring selective replication in cancer cells, the side effects are minute in comparison to those of chemo and radiation therapy, further justifying the benefits of a CRAd strategy. Also the in vivo results mentioned above indicate that the Ad5/3-RGD D24 multi-targeting virus of the disclosure can be injected directly into mouse brains with no adverse symptoms detected.

Figure 5D:
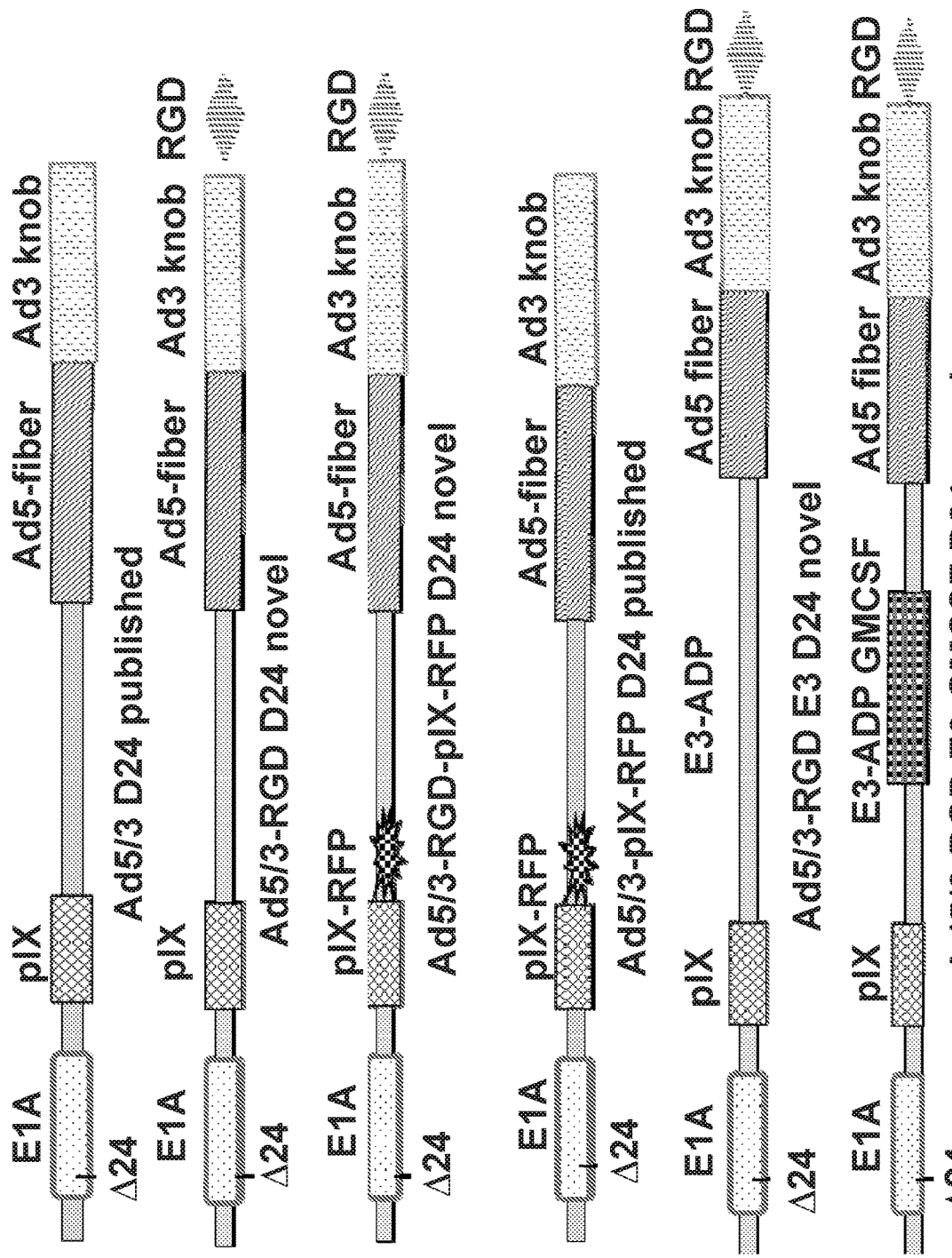

Accordingly, a range of new oncolytic viruses have been generated (FIG. 5D) that show improved cancer killing compared to those that are currently in clinical trials. Importantly the viruses of the disclosure have the ability to infect and kill all cancer lines tested to date. Although a non-replicating version of this virus rescued and showed enhanced infectivity, it has not previously been shown to be possible to rescue a replicating one based on the D24 modification which is known to be safe for patients. Herein is outlined the first such virus. Importantly components of the virus have been modified to incorporate TSAs and drug delivery expression both of which are functional and have the potential to increase a robust immune response to the cancer.

The protocols for using the viruses described in this disclosure in the treatment of cancer can follow the same procedures as those used in the fields of virotherapy with adenoviruses and gene therapy with adenoviruses. There is wide experience in the use of non-replicative and replicative adenoviruses in the field of gene therapy. In particular, adenoviruses with selective-replication methods other than that proposed in this disclosure have been used to treat cancer. There are numerous publications dealing with treatment of tumor cells in cultivation, animal models and clinical trials with human patients. For the treatment of cells in in vitro cultures, the purified adenovirus in any of the forms described above can be added to the culture medium for the infection of tumoral cells. To treat tumors in animal models or in human patients, the adenovirus can be administered locoregionally by injection in the tumor or in a body cavity where the tumor is located, or even systematically by injection into the bloodstream. Adenovirus replications can be administered loco-regionally by injection in the tumor or in a body cavity where the tumor is located, or systemically by injection in the bloodstream. The treatment of tumors with the adenoviruses described that are the subject of this disclosure can be combined with other methods of treatment such as chemotherapy or radiotherapy.

When used in vivo for therapy, the adenovirus of the present disclosure can be administered to the patient or an animal in therapeutically effective amounts, i.e., amounts that eliminate or reduce the tumor burden. A person having ordinary skill in this art would readily be able to determine, without undue experimentation, the appropriate dosages and routes of administration of this adenovirus of the present invention. It may be administered parenterally, e.g. intravenously, but other routes of administration will be used as appropriate. The dose and dosage regimen will depend upon the nature of the cancer (primary or metastatic) and its population, the characteristics of the particular immunotoxin, e.g., its therapeutic index, the patient, the patients history and other factors. The amount of adenovirus administered will typically be in the range of about 1010 to about 1011 viral particles per patient. The schedule will be continued to optimize effectiveness while balanced against negative effects of treatment. See Remington's Pharmaceutical Science, 17th Ed. (1990) Mark Publishing Co., Easton, Pa.; and Goodman and Gilman's: The Pharmacological Basis of Therapeutics 8th Ed (1990) Pergamon Press; which are incorporated herein by reference.

One aspect of the disclosure encompasses embodiments of a nucleotide sequence encoding a genetically modified adenovirus, said nucleotide sequence comprising: a nucleotide sequence encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; a nucleotide sequence encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor.

In some embodiments of this aspect of the disclosure, the adenovirus can be of the Ad5 serotype.

In embodiments of this aspect of the disclosure, the adenovirus can selectively kill a cancer cell of a cancer selected from the group consisting of: acoustic neuroma, brain cancer, bone cancer, cancer of unknown primary site, carcinoid, carcinoid of gastrointestinal cervical cancer, colorectal cancer, oral cancer, liver cancer, pancreatic cancer, nasopharyngeal cancer, synovial cancer, hepatocellular cancer, renal cancer, cancer of connective tissues, melanoma, lung cancer, bowel cancer, colon cancer, rectal cancer, colorectal cancer, Kaposi's sarcoma, prostate cancer, lung cancer, testicular cancer, Hodgkin's disease, non-Hodgkin's lymphoma, gastrinoma, pheochromocytoma, prolactinoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, fibrosarcoma, breast cancer, Paget's disease, esophagus cancer, gall bladder cancer, head cancer, eye cancer, neck cancer, kidney cancer, liver cancer, skin cancer, mesothelioma, parotid gland cancer, peritoneum cancer, pharynx cancer, pleural cancer, salivary gland cancer, tongue cancer and tonsil cancer multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, mycosis fungoides, insulinoma, rectal cancer, tractchorio carcinoma, somatostatinoma, throat cancer, gum cancer, heart cancer, lip cancer, meninges cancer, mouth cancer, nerve cancer, palate cancer, T-cell leukemia/lymphoma, and Wilms' tumor.

In some embodiments of this aspect of the disclosure, the nucleotide sequence can further comprises a nucleotide sequence encoding a heterologous polypeptide desired to be expressed from the genetically modified adenovirus.

In some embodiments of this aspect of the disclosure, the nucleotide sequence encoding the heterologous polypeptide can be operably linked to a nucleotide sequence encoding an adenovirus E3 polypeptide or a fragment thereof.

In some embodiments of this aspect of the disclosure, the nucleotide sequence encoding the heterologous polypeptide can be operably linked to a nucleotide sequence of the adenovirus encoding an adenovirus pIX polypeptide.

In some embodiments of this aspect of the disclosure, the heterologous polypeptide can be a reporter gene.

In some embodiments of this aspect of the disclosure, the heterologous polypeptide can be a detectable fluorescent protein.

In some embodiments of this aspect of the disclosure, the heterologous polypeptide can be an immunomodulator.

In some embodiments of this aspect of the disclosure, the immunomodulator can be Granulocyte-Macrophage Colony Stimulating Factor (GMCSF).

In some embodiments of this aspect of the disclosure, the nucleotide sequence is selected from the group consisting of SEQ ID NOs.: 1, 2, 4, 5, 7, and 8.

In some embodiments of this aspect of the disclosure, the nucleotide sequence is according to SEQ ID NO.: 2.

In some embodiments of this aspect of the disclosure, the nucleotide sequence is according to SEQ ID NO.: 10.

In some embodiments of this aspect of the disclosure, the nucleotide sequence is within an isolated eukaryotic cell.

Another aspect of the disclosure encompasses embodiments of a nucleotide sequence encoding a genetically modified shuttle adenovirus vector, wherein the nucleotide sequence is selected from the group consisting of SEQ ID NOs.:3, 6, 9, 10, 11, 12, and 13.

Another aspect of the disclosure encompasses embodiments of a genetically modified adenovirus of the Ad5 serotype, wherein said adenovirus is encoded by a nucleotide sequence comprising: a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; and a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor.

In some embodiments of this aspect of the disclosure, the nucleotide sequence can further comprise a region encoding a heterologous polypeptide desired to be expressed from the genetically modified adenovirus.

In some embodiments of this aspect of the disclosure, the nucleotide sequence encoding the heterologous polypeptide can be operably linked to a nucleotide sequence encoding an adenovirus E3 polypeptide or a fragment thereof.

In some embodiments of this aspect of the disclosure, the nucleotide sequence encoding the heterologous polypeptide can be operably linked to a nucleotide sequence of the adenovirus encoding an adenovirus pIX polypeptide.

In some embodiments of this aspect of the disclosure, the heterologous polypeptide can be a reporter protein.

In some embodiments of this aspect of the disclosure, the heterologous polypeptide can be a detectable fluorescent protein.

In some embodiments of this aspect of the disclosure, the heterologous polypeptide can be an immunomodulator.

In some embodiments of this aspect of the disclosure, the immunomodulator can be Granulocyte-Macrophage Colony Stimulating Factor (GMCSF).

In some embodiments of this aspect of the disclosure, the nucleotide sequence is selected from the group consisting of SEQ ID NOs.: 1, 2, 4, 5, 7, and 8.

In some embodiments of this aspect of the disclosure, the adenovirus replicates selectively in a cancer cell and has a reduced cell toxic effect on a non-cancer cell.

In some embodiments of this aspect of the disclosure, the cancer cell is of a cancer selected from the group consisting of: acoustic neuroma, brain cancer, bone cancer, cancer of unknown primary site, carcinoid, carcinoid of gastrointestinal cervical cancer, colorectal cancer, oral cancer, liver cancer, pancreatic cancer, nasopharyngeal cancer, synovial cancer, hepatocellular cancer, renal cancer, cancer of connective tissues, melanoma, lung cancer, bowel cancer, colon cancer, rectal cancer, colorectal cancer, Kaposi's sarcoma, prostate cancer, lung cancer, testicular cancer, Hodgkin's disease, non-Hodgkin's lymphoma, gastrinoma, pheochromocytoma, prolactinoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, fibrosarcoma, breast cancer, Paget's disease, esophagus cancer, gall bladder cancer, head cancer, eye cancer, neck cancer, kidney cancer, liver cancer, skin cancer, mesothelioma, parotid gland cancer, peritoneum cancer, pharynx cancer, pleural cancer, salivary gland cancer, tongue cancer and tonsil cancer multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, mycosis fungoides, insulinoma, rectal cancer, tractchorio carcinoma, somatostatinoma, throat cancer, gum cancer, heart cancer, lip cancer, meninges cancer, mouth cancer, nerve cancer, palate cancer, T-cell leukemia/lymphoma, and Wilms' tumor.

In some embodiments of this aspect of the disclosure, the adenovirus is within an isolated eukaryotic cell.

In some embodiments of this aspect of the disclosure, the adenovirus is admixed with a pharmaceutically acceptable carrier.

Yet another aspect of the present disclosure encompasses embodiments of a method of monitoring the progress of delivery of a genetically modified adenovirus to a tumor in a patient, said method comprising the steps of: (a) administering to the patient a pharmaceutically acceptable composition comprising a genetically modified adenovirus of the Ad5 serotype, wherein said adenovirus is encoded by a nucleotide sequence comprising: a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor; and a region encoding a reporter protein, wherein the nucleotide sequence region encoding the reporter protein is operably linked to a nucleotide sequence of the adenovirus encoding an adenovirus pIX polypeptide; and (b) detecting a signal from the reporter protein.

In some embodiments of this aspect of the disclosure, the reporter protein is a detectable fluorescent protein.

In some embodiments of this aspect of the disclosure, the nucleotide sequence encoding the genetically modified adenovirus is according to SEQ ID NO.: 5.

Yet another aspect of the present disclosure encompasses embodiments of a method of modulating an immune response to a tumor in a patient, said method comprising the steps of: (a) administering to the patient a pharmaceutically acceptable composition comprising a genetically modified adenovirus of the Ad5 serotype, wherein said adenovirus is encoded by a nucleotide sequence comprising: a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor; and a region encoding a immunomodulator protein, wherein the nucleotide sequence region encoding the reporter protein is operably linked to a nucleotide sequence encoding an adenovirus E3 polypeptide or a fragment thereof.

In some embodiments of this aspect of the disclosure, the immunomodulator protein is Granulocyte-Macrophage Colony Stimulating Factor (GMCSF).

In some embodiments of this aspect of the disclosure, the nucleotide sequence encoding the genetically modified adenovirus is according to SEQ ID NO.: 2.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

EXAMPLE

Example 1

Construction of the Multi-Targeting Adenoviral Plasmid DNAs:

To generate the virus genomes a double homologous recombination strategy was employed between a modified AdEasy-1 (AdEz)-derived backbone vector and various shuttle vectors. The Ad5 vector, with deleted E1 and E3 regions of the Ad5 genome (AdEz), was modified by inserting a SwaI restriction enzyme site in place of the deleted fiber gene to yield AdEzDF, aiding recombination with shuttle vectors incorporating further changes in the Ad genome.

The shuttle vectors were of two variants: one contained the tail and shaft of the Ad5 serotype but the knob from Ad3. This vector has been further modified to contain the unique restriction enzyme sites BamH1 and MfeI on the Carboxyl terminus (C-terminus) of the Ad3 knob domain for easy addition of motifs such as the 27 nucleotide (nt) long oligonucleotide duplex encoding CDCRGDCFC peptide (RGD) (Ad5/3-C-RGD) shuttle vector. These shuttle vectors have been engineered with flanking regions that contain homologous recombination (homologous recombination) arms with the AdEzDF genome. The second shuttle vector variant employed was the delta 24 E1 shuttle vector (D24), containing the 24 base pair deletion in the E1A gene (Heise et al., (2000) *Nat. Med.* 6: 1134-1139).

The first homologous recombination was carried out between the AdEzDF and the Ad5/3-C-RGD shuttle vector in the recombination-prone *Escherichia coli* (*E. coli*) strain BJ5183 (Chartier et al., (1996) *J. Virol.* 70: 4805-4810). This Ad5/3-C-RGD construct was then recombined with the D24 shuttle (FIG. 1). The isogenic control Ad5/3 D24 was generated by recombining the AdEzDF with the unmodified Ad5/3 shuttle vector followed by recombination with the D24 shuttle vector. PCR and nucleotide sequencing were carried out on the viral particle genomes to ensure they were isogenic and that the relevant modifications were intact.

Example 2

Ad5/3-C-RGD D24 Engineered for Drug Delivery:

As a tumor associated antigen (TAA) or tumor specific antigen (TSA), a second variant of the D24 shuttle vector was generated. To clone potential TSAs onto the capsid of Ad5/3-RGD D24, the D24 shuttle vector containing the capsid protein pIX was engineered to contain unique Nhe1 and Sal1 sites on to the C-terminus of the protein allowing for the cloning of large genes into this region. As before the shuttle vector contains recombination arms that replaces full length E1 with an E1 containing the deleted 24 nucleotides. To ensure that the modification would be compatible with the existing multi-targeting genome modifications, the monomeric red fluorescent protein (RFP) was cloned into the C-terminus of pIX and homologously recombined as above. After screening the genome to ensure the relevant modifications were intact, the full length genomes were Pac1 digested and transfected into 293 cells.

To further test the ability of the multi-targeting oncolytic virus to deliver immunotherapeutic agents, a new virus was engineered to deliver heterologous polypeptides useful as immunostimulatory agents including but not limited to as antibodies and cytokines. Construction of the new virus was initiated by engineering a number of modified shuttle vectors (SV). Similar to the one made above, these vectors contain recombination arms with AdezDF-swa1; and the fiber was modified in a similar way to incorporate the Ad5 shaft with the Ad3 serotype knob followed by the RGD modification on the C-terminus. A large portion of the E3 gene was deleted and replaced with unique restriction sites BstBI and SalI for cloning of immunostimulatory agents. The adenovirus death protein (ADP) was included in the shuttle vector N-terminus of the cloning. Other genes known to decrease the immune response were removed.

A number of shuttle vector modifications were tried until one was found that proved compatible with rescuing the virus. Double homologous recombination steps were carried out as before. Following the successful rescue of Ad5/3-RGD E3 D24, a new shuttle vector incorporating human GM-CSF was generated by amplifying the cytokine from pORF-hGMCSF (Invivogen, San Diego Calif.) and subcloning the immunostimulant into the unique BstBI and SalI sites, then recombined as above. (FIGS. 5A-5B)

Example 3

Generation, Propagation, Purification, and Titration of Adenoviruses:

Following molecular validation, adenoviral plasmid DNAs were digested with PacI and transfected into 293 cells, using Lipofectamine LTX (Invitrogen; Carlsbad, Calif.). The cells were harvested 2 weeks later when cytopathic effect (CPE) was observed and disrupted by four freeze/thaw cycles. Cell lysates were used to upscale the virus in A549 cells. The viruses were then purified by double cesium chloride (CsCl) density gradient centrifugation, dialyzed and stored at −80° C., as previously described (Ugai et al., (2007) *J. Mol. Biol.* 366: 1142-1160). DNA was extracted from purified virus particles using Qiagen QIAmp DNA mini kit (Qiagen, Valencia, Calif.); PCR and sequencing were used to verify that the relevant modifications were present. The infectious titer (plaque forming units [PFU]/ml) of the purified Ad vectors were determined by 50% Tissue Culture Infective Dose ($TCID_{50}$) assay using A549 cells, as previously described ((Ugai et al., (2005) *Biochem. Biophys. Res. Commun.* 331: 1053-1060). The physical particle titer (vp/ml) was calculated based on the protein amount of the purified adenovirus determined at an absorbance of 260 nm (OD260) as described previously by Maizel et al., ((1968) *Virology* 36: 115-125).

Example 4

Cell Lines:

Human glioma U87, human lung epithelial A549, human breast epithelial ZR-75-1, human prostate epithelial DU145 and human foreskin fibroblast HFF cell lines were obtained from the American Type Culture Collection (ATCC; Manassas, Va.). The human glioma lines A172, U105, U138 and U251 were from Dr. Darell D. Bigner ((Bigner et al., (1981) *J. Neuropathol. Exp. Neurol.* 40: 201-229) (Duke University Medical School; Durham, N.C.). The ovarian carcinoma line, oncolytic virus-4 (ATCC), was from Dr. Timothy J. Eberlein (Brigham and Women's Hospital, Harvard Medical School, Boston, Mass.). The metastatic mouse breast cancer cell line 4T1 (ATCC) and pancreatic cell line BxPC3 (ATCC) were from Dr. Donald Buchsbaum (UAB); and the neuroblastoma cell lines SK-N-As (ATCC) and SK-N-Be (ATCC) were from Dr. Elizabeth Beierle (UAB). All lines were cultured in Dulbecco's Modified Eagle's Medium/Ham's Nutrient Mixture F-12, (DMEM/F12; Sigma-Aldrich; St. Louis, Mo.) containing 10% fetal bovine serum, (FBS; Hyclone; Logan, Utah), 2 mM L-glutamine, 100 U/ml penicillin (Mediatech, Inc., Herndon, Va.).

Example 5

Flow Cytometry:

Cell lines were detached from a 75-cm² tissue culture flask by treatment with cell stripper (Cellgro; Manassas, Va.). Cells were counted, blocked and aliquots of $1.5 \times 10^6$ cells were incubated with 1.5 µg of anti-$\alpha V \beta 3$ and anti-$\alpha V \beta 5$ integrin antibodies (Millipore; Temecula, Calif.), 1.5 µg of mouse monoclonal antibody Desmoglein 2 (DSG2) (clone AH12.2, Santa Cruz Biotechnology Inc, Santa Cruz, Calif.) or untreated (control). Following primary antibody incubation, the cells were washed and incubated with Alexa fluor 488-conjugated goat anti-mouse immunoglobulin G (Invitrogen) diluted in PBS with 0.1% BSA. Cells were then diluted in PBS and a cytometric analysis of 10,000 events per sample was conducted using FACScan with CellQuest software (Becton Dickinson, Mountain View, Calif.).

Example 6

Cell Viability Assays:

Cells were plated at $10^4$ cells per well on 96-well plates and infected the following day with viruses at 1-100 viral particles (VP)/cell or 0.1-1 PFU/cell in triplicate. Infections were carried out in 2% FBS. Two to ten days post infection, depending on when full CPE was first visually detected, cell viability was analyzed via MTS assay (Cell Titer 96 AQueous One Solution Cell Proliferation Assay, Promega; Madison, Wis.). Cell killing activity was measured relative to percentage of uninfected cells. Data are presented as mean±standard deviation. The titers for the oncolytic viruses used in the study are in Tables 2 and 3.

TABLE 2

| Oncolytic adenovirus | vp/ml |
| --- | --- |
| Ad5-RGD D24 | $1.5 \times 10^{12}$ |
| Ad5/3 D24 | $2.4 \times 10^{11}$ |
| Ad5/3-C-RGD D24* | $4.8 \times 10^{11}$ |
| Ad5/3-IX-RFP D24 | $3.4 \times 10^{12}$ |
| Ad5/3-RGD-IX-RFP D24* | $6.8 \times 10^{11}$ |
| Ad5/3-RGD E3 D24* | $1.5 \times 10^{11}$ |
| Ad5/3-RGD E3-GMCSF D24* | $4.4 \times 10^{11}$ |

TABLE 3

| Oncolytic virus | pfu/ml |
| --- | --- |
| Ad5/3 D24 | $1.5 \times 10^{9}$ |
| Ad5/3-C-RGD D24* | $3.0 \times 10^{8}$ |
| HSV MOO2 | $3.0 \times 10^{11}$ |

Comparisons between Ad viruses were based on physical particle titer (vp/cell) as the measurement is more consistent between laboratories (Maize) et al., (1968) *Virology* 36: 115-125) and includes total viral particles which may be clinically relevant. Infectious titer (PFU/cell) was used for comparisons with the HSV virus; as an enveloped virus, $OD_{260}$ measurements are not reliable.

Example 7

Visualization and Expression:

For phase contrast and fluorescent live images, cells were grown and infected as in the viability assays and imaged with a Nikon inverted microscope equipped with a Nikon DS FI1 camera (Nikon Instruments Inc., Melville, N.Y.) and analyzed as previously described ((Ugai et al., J. Mol. Biol. 395: 55-78). For high magnification images, cells were grown in Lab Tek II chamber slides (Nunc; Rochester, N.Y.) in the same conditions as viability assays. On the indicated days, cells were fixed with 4% formaldehyde, washed with PBS and mounted using Vectashield mounting medium containing DAPI (Vector Laboratories; Burlingame, Calif.). Images were overlaid with NIS-Element AR™ software.

For measuring GM-CSF production, cells were grown as for the MTS assays and infected with virus at the indicated titers. Medium was harvested on the indicated days and measured via ELISA (Biolegend; San Diego, Calif.).

Example 8

Multi-Step Curve Analysis:

Sk N-As and Sk N-Be cell lines were grown as above in 6 well plates and infected with adenovirus at an MOI of 1 PFU/cell. Culture medium containing the virus released from the infected cells was harvested at 24, 48, 72 and 96 h post infection. Infectious titers from the medium were measured via TCID50 on 549 cells.

Example 9

Third Generation Multi-Targeting CRAd Construction and Generation:

Construction of the multi-targeting virus was carried out using standard cloning techniques described in the Materials and Methods section. A schematic representation of plasmid DNAs, genome construction and the oncolytic adenoviruses generated are shown in FIG. 1. Ad5/3-C-RGD D24 (Ad5/3-RGD D24) and an isogenic Ad5/3 D24 control were rescued, grown to large scale, and purified by ultracentrifugation. DNA from purified virus particles was amplified by PCR using specific primer sets to confirm RGD insertion in the carboxy terminus of the Ad3 knob (FIG. 1B). Subsequently, the nucleotide sequence of the Ad3 knob region and the D24 region for each virus was verified by sequencing.

Figure 9:
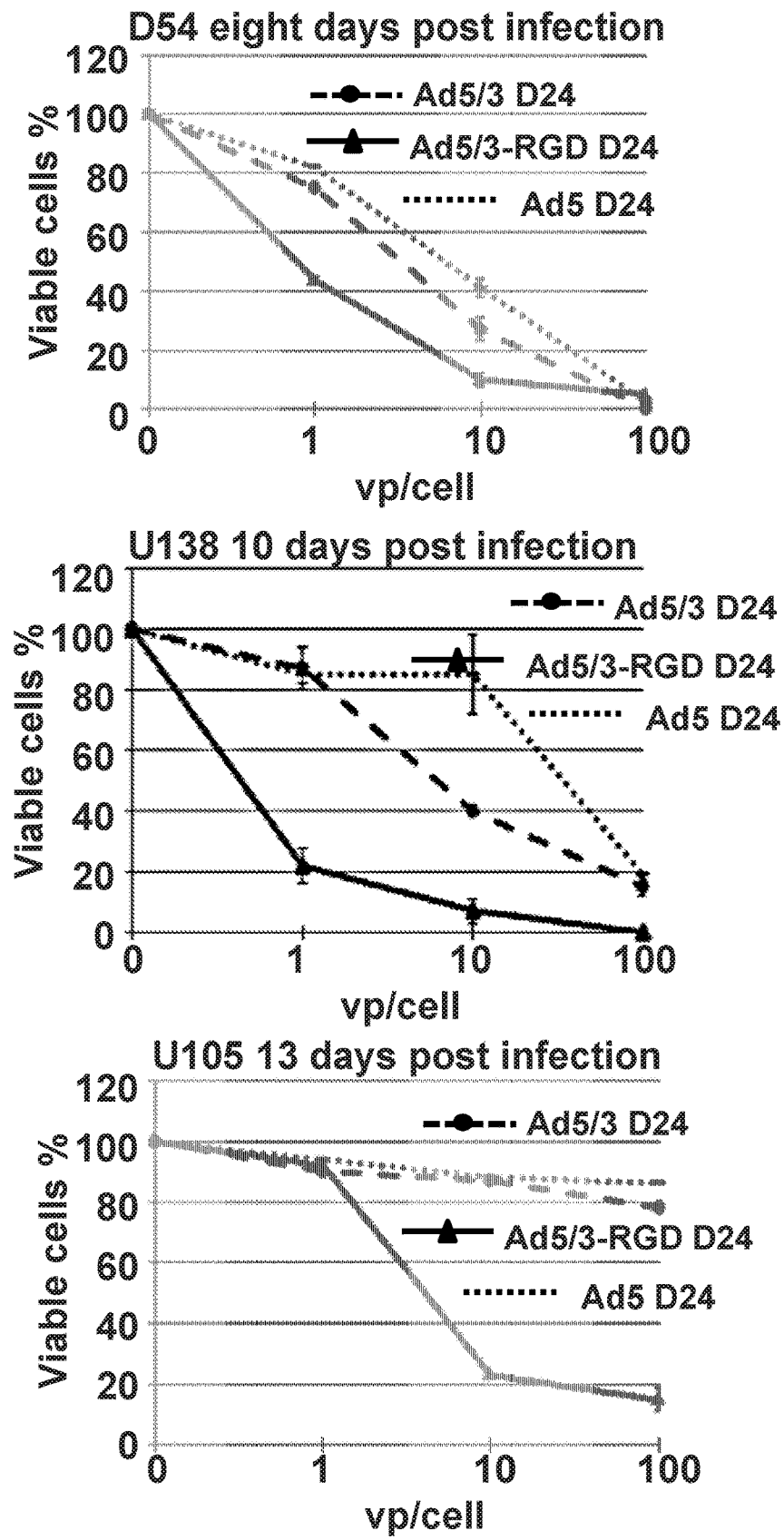
FIG. 9 is a series of graphs illustrating cell killing assays in glioma cell lines D54, U138 and U105. Ad5 D24, Ad5/3 D24 and Ad5/3-C-RGD D24 were compared in the glioma lines D54, U138 and U105. Cell viability was measured by MTS assay on the days indicated as previously described. Data presented as mean±standard deviation.

Incorporation of an RGD Motif in the C-Terminus of the Ad3 Knob Domain Enhances Oncolysis:

Considering that Ad5/3 D24 virus shows promise in treating a range of cancer types and has potential for drug delivery (Pesonen et al., (2011) Mol Pharm 8: 12-28), an analysis of infection and oncolysis was carried out to determine if the Ad5/3-C-RGD D24 multi-targeting strategy improved oncolysis over the second generation CRAd. Work first began on analyzing CPE of the oncolytic viruses in glioma lines, as these tumors are one of the deadliest cancers, are known to have reduced CAR expression (Miller et al., (1998) *Cancer Res.* 58: 5738-5748), and a number of oncolytic viruses have been tested for treatment of the disease. Similar to previous reports (Ulasov et al., (2007) *J. Neurosurg.* 107: 617-627), initial studies showed that the Ad5/3 component enhanced cancer killing over the first generation Ad5 D24 virus (FIG. 9).

The Ad5/3-C-RGD D24 showed enhancement in glioma killing in all lines assayed. In U251, A172, and U87, Ad5/3-C-RGD D24 showed improvement in killing potency over Ad5/3 D24 at low titer levels. By 10 days post infection with Ad5/3-C-RGD D24 (MOI 100 vp/cell) only minimal cell survival was detected. The cell lines with the greatest variability between the oncolytic viruses were the U138 and U105 cell lines, with Ad5/3 D24 displaying little to no cell killing 10 days post infection in the U105 line (FIG. 2A). Phase contrast images show a consistent monolayer of U105 and U138 cells in the Ad5/3 D24 wells similar to untreated wells at 10 days post infection compared to full cytopathic effect seen in the Ad5/3-C-RGD D24 treated wells (FIG. 2B).

Figure 10A:
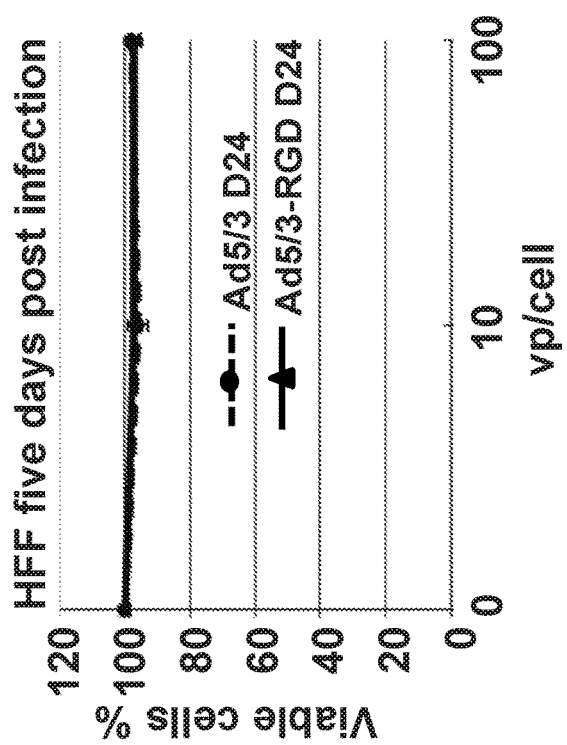
FIG. 10A is graph illustrating cell killing assays in human fibroblast (HFF) cells. Ad5/3 D24 and Ad5/3-C-RGD D24 were compared in the normal cell line HFF. Cell viability was measured by MTS assay five days post infection. Error bars represent standard deviations.
Figure 10B:
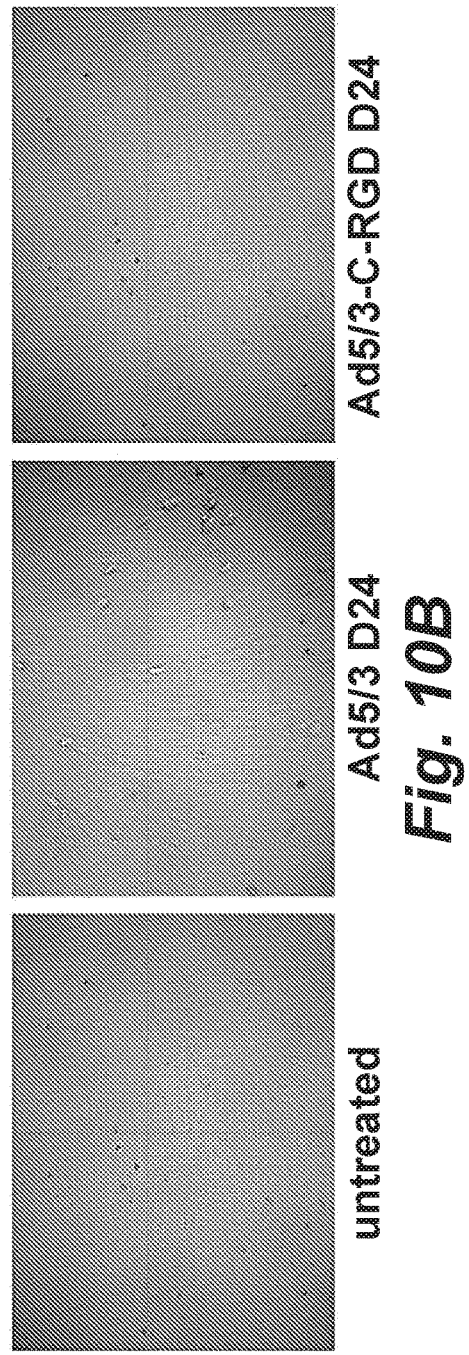
FIG. 10B illustrate cell killing assays in human fibroblast (HFF) cells. Live images in a 96 well plate prior to MTS assays shown in FIG. 10A (100× magnification).

Although D24 viruses are safe in patients, there is evidence of limited replication in normal cells (Fukuda et al., (2003) *Cancer Res.* 63: 4434-4440; Sauthoff et al., (2004) *Mol. Ther.* 10: 749-757; Soria et al., (2010) *Nature* 466: 1076-1081). However, the multi-targeting modifications did not result in an increase in cell killing over the Ad5/3 D24 virus in a normal cell line (FIGS. 10A and 10B).

Figure 3A:
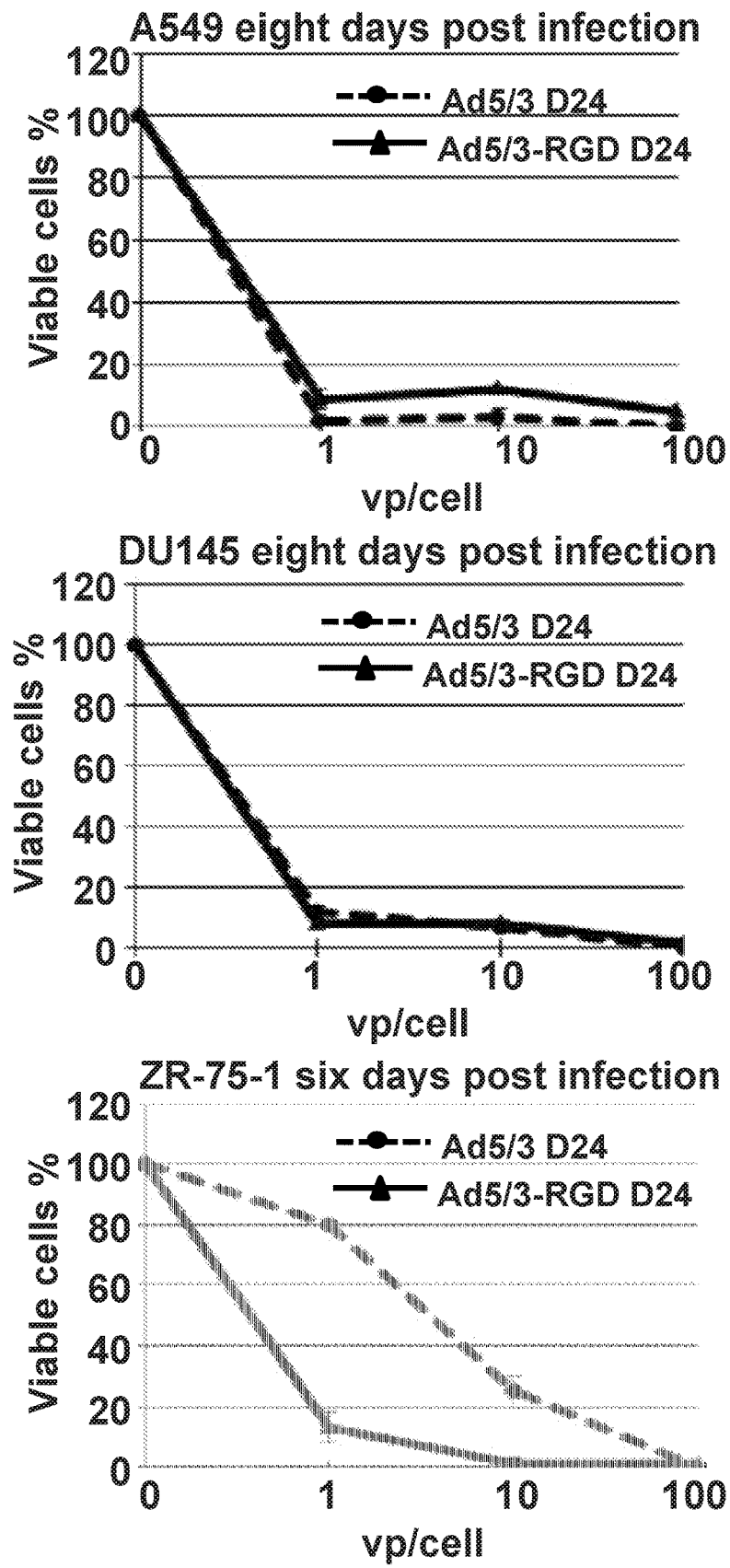
Figure 4:
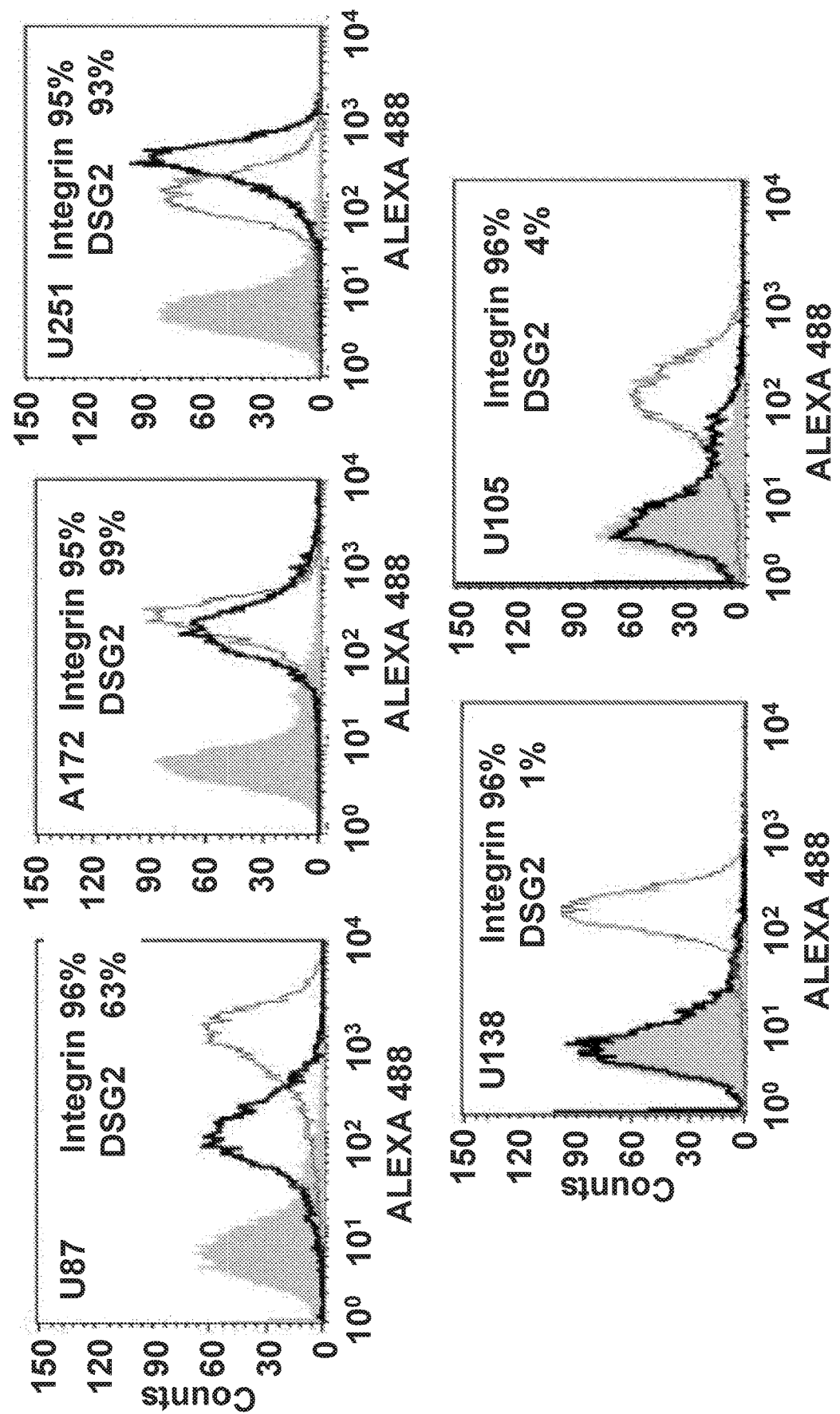
FIG. 4 illustrates the analysis of integrin and DSG2 expression carried out via flow cytometry in the indicated glioma lines. Filled grey histograms indicate unstained control cells; open black histograms indicate DSG2-positive cells; open grey histograms indicate integrin-positive stained cells. Percentages of positively-stained cells are also illustrated.
Figure 11:
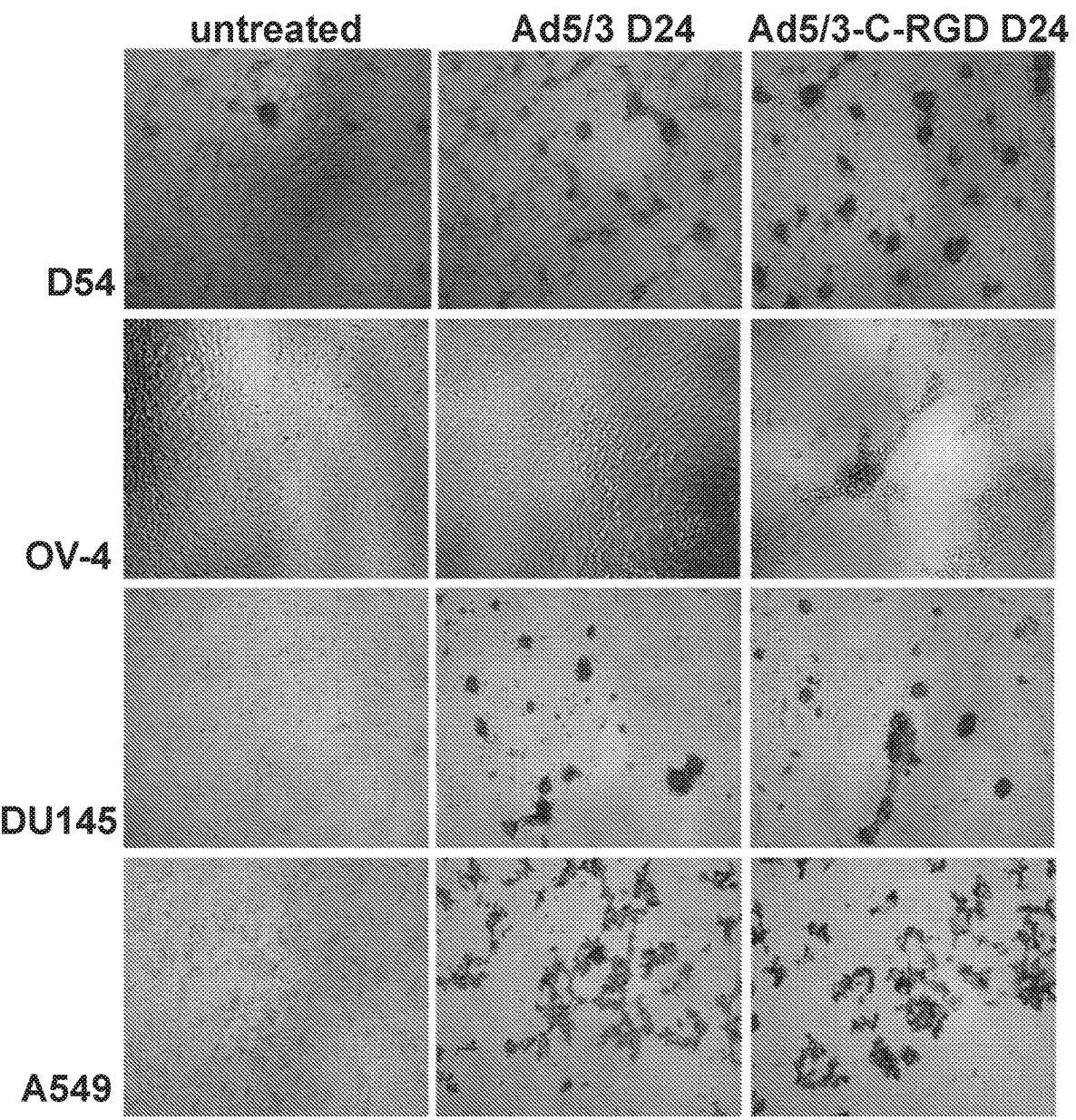
FIG. 11 is a series of digital phase contrast images of Ad5/3 D24 and Ad5/3-C-RGD D24 in D54-MG (glioma) six days post infection; oncolytic virus-4 (ovarian) nine days post infection; DU145 (prostate) and A549 (lung) six days post-infection (All at an MOI of 1 vp/cell and 100× magnification live images in a well of a 96 well plate).

Given the enhancement in cytotoxicity in the glioma lines, the viruses were assayed in three other cancer lines: lung (A549), prostate (DU145), and breast (ZR-75-1). The Ad5/3-C-RGD D24 showed similar oncolytic effect to Ad5/3 D24 in the lung and prostate lines. However, in the breast cancer line, an improvement in cell killing was again detected with the RGD modified virus (FIG. 3A and FIG. 11).

Figures 12A, 12B:
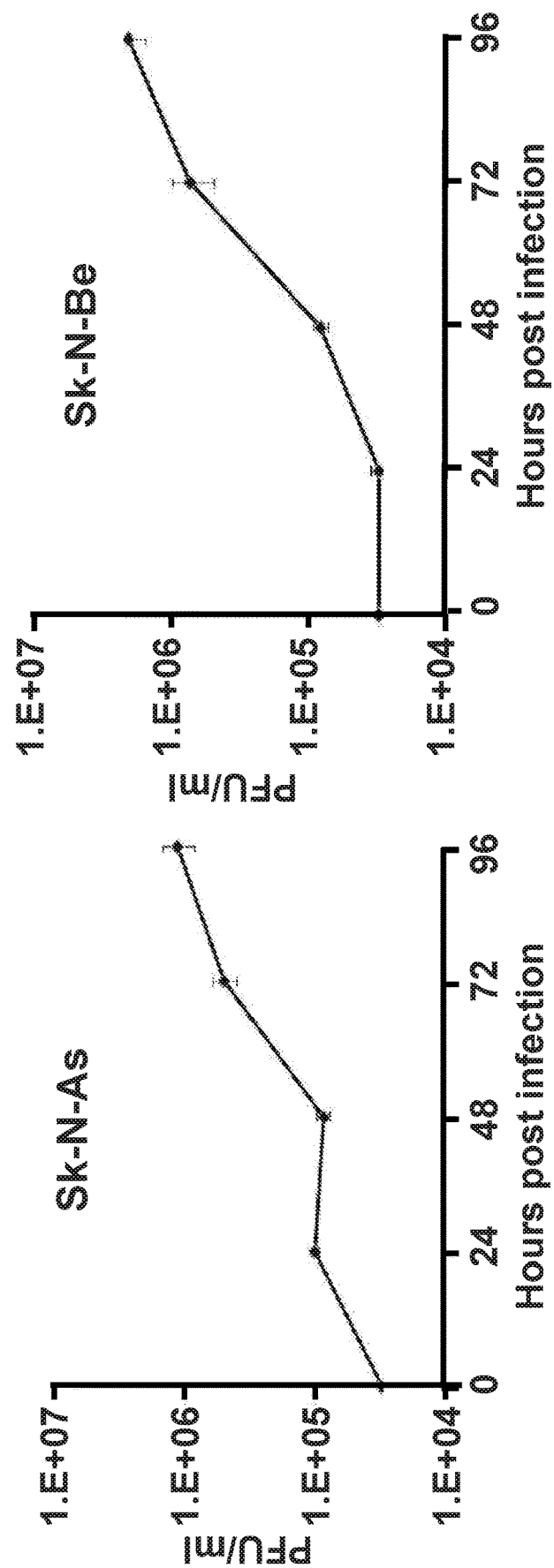
FIG. 12A is graph illustrating the release of Ad5/3-C-RGD D24 from infected cells to culture medium. SK-N-As cells were infected with Ad5/3-C-RGD D24 at an MOI of 1 PFU/cell. Culture medium containing released virus particles from the infected cells was harvested at the indicated time points. Infectious titers from each time point were measured by TCID50 on 549 cells. Error bars represent standard deviations.
FIG. 12B is graph illustrating the release of Ad5/3-C-RGD D24 from infected cells to culture medium. SK-N-Be cells were infected with Ad5/3-C-RGD D24 at an MOI of 1 PFU/cell. Culture medium containing released virus particles from the infected cells was harvested at the indicated time points. Infectious titers from each time point were measured by TCID50 on 549 cells. Error bars represent standard deviations.

Based on the improvement in cancer killing with the multi-targeting approach, analysis has begun on a comparison with other promising oncolytic viruses, the Ad5-RGD D24 (Suzuki et al., (2001) *Clin. Cancer Res.* 7: 120-126) and a herpes simplex virus (HSV) oncolytic virus (Parker et al., (2000) *Proc. Natl. Acad. Sci. U.S.A.* 97: 2208-2213). Although no enhancement was seen in the glioma lines over Ad5-RGD D24, the multi-targeting virus was enhanced in the pancreatic and ovarian lines (FIG. 3B). A comparison with the HSV oncolytic virus M002 was carried out as well. As the M002 virus is effective in animal models of neuroblastoma (Megison et al., (2014) *PLoS One* 9: e86843), the Ad5/3-C-RGD D24 was assayed in two neuroblastoma lines. In both lines the multi-targeting CRAd displayed efficient release into the culture medium as determined by TCID50 (FIGS. 12A and 12B). Moreover, Ad5/3-C-RGD D24 showed enhancement in tumor cell killing 60 hours post infection over the HSV virus and Ad5/3 D24 virus (FIGS. 13A, 13B, 17A, and 17B). Further analysis comparing the third-generation Ad5/3-C-RGD D24 virus to the second-generation oncolytic viruses is continuing; however, the evidence is strong that the multi-targeting strategy is equal or superior at tumor cell killing in vitro. To date, this virus has infected and killed all cancer cell lines assayed at 1 PFU/cell or lower.

As expected the enhanced oncolysis is related to the receptors being expressed on the cells. Flow cytometry (FCM) has been performed on a number of the cancer lines. FCM for $\alpha V\beta 3$ and $\alpha V\beta 5$ integrin (RGD receptors) expression confirmed that all glioma lines expressed integrins. Analysis of a primary receptor for Ad5/3, Desmoglein 2 (DSG2), indicated that the receptor was expressed in U87, A172, and U251 cell lines; however, little to no levels of the receptor could be detected in the U138 and U105 glioma lines (FIG. 4A). FCM analysis of the lung (A549), prostate (DU145), breast (ZR75-1) and ovarian (OV4) indicated that integrin and DSG2 were present (FIG. 4B). The Ad5/3 D24 showed similar killing to the multi-targeting virus in cells that expressed high levels of DSG2 such as the lung and prostate cancer cell lines. However, in the U138 lines and the U105 lines, DSG2 is expressed at low levels; and the virus showed attenuated cell killing compared to the multi-targeting virus. Interestingly, in some lines such as the breast and ovarian lines DSG2 is expressed; however, Ad5/3-C-RGD D24 showed superior killing at low titers.

Ad5/3-C-RGD D24 Engineered for Immunotherapy:

To further evaluate Ad5/3-C-RGD D24 as an immunotherapeutic platform, the virus was first tested for potential delivery of neoantigens in a vaccine strategy. With the advent of inexpensive next generation sequencing and other techniques, there is now the possibility of isolating mutations in the exome of a tumor, potentially predicting TSAs that could be used as a future vaccine. The success of a vaccine depends on not just tumor-rejection antigens, but also immune modulators and adjuvants to stimulate a potent immune response. Inherently, adenoviruses are both strong immune modulators and adjuvants as the virus initiates an innate immune response via Ad DNA/capsid proteins as well as an adaptive response from both Ad-specific CD4+ and CD8+ T cells (Lenaerts et al., (2008) *Rev. Med. Virol.* 18: 357-374). Hence, capsid proteins such as pIX are promising regions in which to clone specific tumor antigens. Previous studies have shown that pIX can tolerate C-terminal fusions with substantially larger ligands than the fiber portion of the virus (Meulenbroek et al., (2004) *Mol. Ther.* 9: 617-624). Given that Ad5/3-C-RGD D24 can infect a wide array of cancer cells at low titers the capsid of the virus is a promising platform to attach neoantigens.

A second variant of the D24 shuttle vector was generated containing the unique Nhe1 and Sal1 sites on to the C-terminus of the protein allowing for the cloning of large genes into this region. As before the shuttle vector contained recombination arms that replaces full length E1 with an E1 containing the deleted 24 nucleotides. To ensure that the modification would be compatible with the existing multi-targeting genome modifications, the monomeric red fluorescent protein (RFP) was cloned onto the C-terminus of pIX. Shuttle vectors were then generated and recombined as above (FIG. 5). After screening the genome to ensure the relevant modifications were intact, the full length genomes were PacI digested and transfected into 293 cells. Upon plaque formation and fluorescence detection, the Ad5/3-RGD-IX-RFP D24 virus was upscaled, analyzed via PCR and sequenced as before to ensure the relevant modifications were intact upon viral formation.

The new CRAd, Ad5/3-RGD-IX-RFP D24, was tested in the glioma line U251 to see if it maintained CPE while expressing pIX incorporated proteins. Monitoring pIX-RFP expression in infected U251 glioma lines indicated that the protein increased over time in a viral DNA replication dependent manner (FIG. 6A).

To ensure the virus maintained enhanced targeting and oncolysis, Ad5/3-RGD-IX-RFP D24 was compared with a previously generated Ad5/3-IX-RFP D24 (Kimball et al., (2009) *Mol. Imaging* 8: 264-277). Similar to the improvement in oncolysis by the Ad5/3-C-RGD D24 over the unmodified Ad5/3 D24, an increase in the number of fluorescent cells was detected in the RGD modified fluorescent oncolytic virus (FIGS. 6B, 6C, and 14). The fluorescent labeling technique also allowed accurate observation of unique aspects of viral replication and the fate of pIX expressed proteins. Importantly, analysis of viral and protein intracellular trafficking indicates that both the multi-targeting modifications and pIX protein expression did not adversely affect viral infection, trafficking or release as the time course were similar to reports from first and second generation viruses: preferential localization in the cytoplasm at 24 hours post-infection (hpi) and nuclear localization by 36 hours, indicative of the necessity of the protein in virus particle assembly (Ugai et al., *J. Mol. Biol.* 395: 55-78). Large vacuoles, characteristic of autophagy, could be seen in the infected cells by 72 hpi similar to reports from other D24 virus infected cells (Jiang et al., *J. Virol.* 85: 4720-4729). Nuclear membrane integrity appeared fragile with virus release from the nucleus by 96 hpi followed by release from the cell by 120 hpi (FIG. 7). The increase in expression of RFP as the virus replicates is an important observation suggesting that any neoantigen expression will be enhanced as the multi-targeting virus replicates improving the potential that antigen presenting cells (APC) will recognize the TSAs.

Hence, the data demonstrates that the large globular protein RFP is functional at this site while the virus maintains enhanced oncolysis over the Ad5/3-RFP D24. The data further suggests that this capsid protein can be used for the attachment of TSAs and that the expression of these antigens can be enhanced as seen in the enhancement of RFP signals over the second generation CRAd. Furthermore, the Ad5/3-RGD-IX-RFP D24 can provide important imaging data for detecting, tracking and monitoring both the spread of the virus and infected tumor cells.

E3 Expression of Heterologous Polypeptides:

oncolytic virus delivery of immunotherapeutic drugs such as cytokines, checkpoint inhibitors, and prodrugs is an ideal way to induce sustained expression of the agents safely to local tumor tissue. Hence, Ad5/3-C-RGD D24 was engineered to ascertain if the virus could express polypeptides that could aid an immunotherapeutic response while maintaining enhanced heterogenic oncolysis. Construction of the new virus was initiated by engineering a number of modified shuttle vectors (SV). Similar to the one made above, these vectors contain recombination arms with AdezDF-swa1; and the fiber was modified to incorporate the 5 shaft with the Ad3 serotype knob followed by the RGD modification on the C-terminus. Along with adding antibiotic resistance to aid in homologous recombination, a large portion of the E3 gene was deleted and replaced with unique restriction sites BstBI and SalI for cloning of immunostimulatory agents. Expression of genes cloned into this site are under control of the immediate early gene E1A (Berk A J (1986) *Ann. Rev. Genet.* 20: 45-79). Importantly, the adenovirus death protein was included in the shuttle vector as overexpression of this protein has shown enhanced oncolysis and viral spread (Tollefson et al., (1996) *J. Virol.* 70: 2296-2306). Furthermore, to aid an immune response a number of genes that down regulate the immune response such as E319k have been deleted. This gene serves a similar function as the ICP47 gene in HSV which was deleted in T-Vec. Both of these proteins bind and retain MHC Class I proteins preventing viral antigen presentation (Horwitz M S (2004) *J. Gene Med.* 6 Suppl. 1: S172-183; Senzer et al., (2009) *J. Clin. Oncol.* 27: 5763-5771). Hence, by deleting these regions, Ad5/3-C-RGD D24 infected cancer cells may be less likely to suppress an immune response to those cells potentially enhancing APC activity and TSA processing.

A number of variations of the shuttle vectors were made until a successful vector was formed that proved compatible with rescuing the virus while maintaining the enhancement in cytotoxicity. Double homologous recombination steps were carried out as before (FIG. 5).

Following the successful rescue of Ad5/3-RGD E3 D24, a new shuttle vector incorporating the cytokine GM-CSF was generated by inserting the immunostimulant into the unique BstBI and SalI sites generated during the construction of the above shuttle vectors.

Upon successfully generating the E3-GMCSF 5/3-RGD shuttle vector the complete genome was homologous recombined, rescued and upscaled as above (FIG. 5). The new virus showed similar oncolysis as the non-drug delivery viruses and produced over 1000 pg/ml of GM-CSF at low titer (10 vp/cell) only 48 hpi as detected by ELISA (FIG. 8).

Oncolytic viruses show therapeutic potential in treating a range of cancers. In this study the promising Ad5/3 D24 oncolytic adenovirus (Koski et al., *Mol. Ther.* 18: 1874-1884; Kanerva et al., (2002) *Clin. Cancer Res.* 8: 275-280; Ulasov et al., (2007) *J. Neurosurg.* 107: 617-627; Kim et al., *Hum. Gene Ther.* 22: 821-828; Tyler et al., (2006) *Mol. Cancer Ther.* 5: 2408-2416; Volk et al., (2003) *Cancer Biol. Ther.* 2: 511-515; Zhu et al., (2007) *Int. J. Oncol.* 31: 1213-1222) has been further modified by incorporating an RGD motif onto the C-terminus of the Ad3 knob. The modification resulted in equal to, or improved in vitro cell killing in all cancer lines assayed when compared to the cytotoxicities of Ad5 D24, Ad5-RGD D24, Ad5/3 D24 or the HSV M002 viruses. The enhancement was most pronounced at low titers.

The Ad5/3-C-RGD D24 virus targets multiple receptors upregulated on cancer cells: integrins and the receptors for Ad3. All cell lines tested were positive for $\alpha v\beta 3$, $\alpha v\beta 5$ integrins or DSG2 a primary receptor for Ad3. Hence, this multi-targeting CRAd may have potential to target a wide range of cancers as full CPE has been detected in all cancer lines assayed to date including glioma, ovarian, breast, pancreatic, prostate, lung and neuroblastomas.

The first focus of this study was to improve oncolysis of the Ad5/3 D24 CRAd. The Ad5/3 component of this virus has numerous therapeutic benefits: first, the modification redirects targeting to receptors up regulated on a number of cancers and away from CAR, the primary receptor for Ad5, which is down regulated on many tumor types while being expressed on normal cells like those of the liver and lung (Rein et al., (2006) *Future Oncol.* 2: 137-143). Also DSG2, a primary receptor for Ad5/3, is a component of the epithelial cell-cell adhesion structure (Liu et al., (2014) *Gynecol. Oncol.* 132: 722-729; Wang et al., *Nat. Med.* 17: 96-104); hence, directing oncolytic viruses to this receptor may greatly aid drug delivery, as binding of the virus to DSG2 triggers the opening of tight junctions. By improving the targeting capacity of Ad5/3 with the RGD modification, the opening of tight junctions may further enhance access to other cancer receptors allowing improved delivery of the virus, and therapeutic agents expressed by the virus, deep into the tumor. This enhancement in oncolysis and delivery should improve the interaction of immune-related inflammatory cells with TSAs generated in the debris field of infected cancer cells. Furthermore, such a modification may enhance conventional radiation and chemotherapy treatments when paired with the virus, as the Ad5/3 component of the virus has shown to improve access to the tumor microenvironment.

Previous reports indicate that the receptors for Ad3 are up-regulated on a number of cancer lines, whether these receptors consist of DSG2 or other receptors is unclear. The analysis here provides evidence of the importance of DSG2 in Ad5/3 oncolysis: the glioma lines U105 and U138 expressed little to no DSG2. In the U105 line, the result was little to no oncolysis for Ad5/3 D24 while the multi-targeting CRAd showed full CPE. Full CPE was also seen in U138 cell lines treated with Ad5/3-C-RGD D24. Interestingly, given the lack of DSG2, Ad5/3 D24 though attenuated did result in full CPE at the higher titers in the U138 line suggesting the virus may be accessing other receptors besides DSG2 that are not present on the U105 cell line.

Regardless, the data here indicate that Ad5/3 D24 has limited infectivity in a number of cancer lines at low titers (e.g. 1 vp/cell): glioma, breast, ovarian and neuroblastoma lines. The same lack of infection of certain cancer cells can be seen with the Ad5-RGD D24 and the HSV oncolytic viruses. However, by targeting multiple receptors, a synergistic effect seems to occur in which the multi-targeting virus displays enhanced oncolysis even if integrins and/or DSG2 are not expressed or weakly expressed.

The improved cytotoxicity may simply be due to an increase in the number and variety of receptors accessible, aiding infection most when the vp/cell ratio is low. A synergistic effect could also be the result of the increase in the RGD-integrin interaction combined with the activation of DSG2. The former has been shown to improve infection by enhancing the signaling cascade responsible for internalizing the virus ((Li et al., (1998) *J. Virol.* 72: 2055-2061) while the later opens tight junctions improving access to other receptors on tumor cells aiding oncolysis and viral spread (Lu et al., (2013) *PLoS Pathog.* 9: e1003718). Future work will look into these possibilities and how the multi-targeting strategy is resulting in such a synergistic enhancement in oncolysis. Nonetheless, given that tumors are extremely heterogenic and the obvious need to target as many cancer cells as possible with the fewest virus particles prior to Ad clearance, the Ad5/3-C-RGD D24 should produce a marked therapeutic improvement.

Recent clinical data indicates that successful oncolytic virus treatment for cancer patients depends on triggering systemic antitumor immune responses. The immune system plays a key role in cancer development and progression: it can suppress tumor growth but it can also select for tumor cells facilitating tumor outgrowth. Immunotherapy centers on augmenting the immune response in four ways: first, enhancing the immune effector process against cancer by activating lymphocytes and cytokines; second, developing vaccines to elicit specific immune responses to tumor antigens; third, using antibodies to target and eliminate tumors; fourth, inhibiting cellular mediators that induce cancer immunosuppression. Ad5/3-C-RGD D24 has potential to be used in all four approaches. Adenovirus infected cancer cells trigger both an innate and adaptive immune response. Also, the Ad5/3-C-RGD D24 is able to infect and kill all cancer lines assayed to date at low titers, which should create a larger debris field of potential TAAs, danger signals and cytokines in a more diverse population of cancer cells. Despite the heterogenic oncolytic enhancement, to generate a consistent complete response in cancer patients, the virus will most likely need to be timed with existing therapies and deliver therapeutic agents to optimize the immune response, as there is no certainty that adequate TSAs will be released and or the danger signals may lack robust efficacy to circumvent immunosuppression regardless of the larger debris field.

To further optimize the therapeutic treatment of the virus, Ad5/3-C-RGD D24 was engineered to deliver both potential TSAs and immunotherapeutic drugs. As deep sequencing combined with other techniques are discovering immunogenic mutant peptides that can serve as T-cell epitopes, Ad5/3-C-RGD D24 was first tested to determine if the capsid could be a site for attachment for such TSAs in a future oncolytic virus vaccine strategy. For proof of principle, RFP was successfully cloned onto the capsid protein pIX. The data demonstrates that the large globular protein is functional at this site. Ad5/3-RGD IX-RFP D24 not only displayed enhanced cancer killing but also expressed more potential antigens over the second generation CRAd.

The Ad5/3-RGD-IX-RFP D24 virus will also serve as a readout of viral replication and accumulation in tumors, as well as a control for delivery of the agents immediately or shortly after administration, i.e. prior to the onset of reporter gene expression and CRAd replication. Of note, the pIX RFP modified virus did show a decrease in oncolysis compared to the unmodified Ad5/3-C-RGD D24. The most likely explanation for this is that the infectious titer was carried out via vp/ml, which underestimates the RFP virus as the RFP protein skews the OD260 reading. In other words, the OD260 measures RFP as virus particles (Ugai et al., *J. Mol. Biol.* 395: 55-78); hence, fewer virus particles were added.

Next, to aid delivery of immunotherapeutic agents, a number of novel shuttle vectors were engineered and through an extensive trial and error process various modifications were made to the vectors until viable viruses were generated that were capable of drug delivery while maintaining the improved oncolysis. The adenovirus death protein was incorporated into this genome while a number of genes that down regulate the immune system have been removed to maximize both oncolysis and an immune response. Importantly, no decrease in cancer killing has been detected in the drug delivery E3 modified viruses with similar CPE seen in all cancer lines assayed along with GM-CSF production. With this platform, new armed Ad5/3-C-RGD D24 viruses can be made, upscaled and ready for use in as little as three months, raising the possibility of enhanced heterogenic oncolysis while delivering TSAs, monoclonal antibodies, checkpoint inhibitors, cytokines, and other agents tailored to specific patient cancer types with the goal of augmenting an immune response capable of halting or eliminating the cancer.

What is claimed:

1. A nucleotide sequence encoding a genetically modified adenovirus, said nucleotide sequence comprising:
   a nucleotide sequence encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; and
   a nucleotide sequence encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor, and wherein the adenovirus E1A gene encoding the E1A polypeptide is operably linked to an adenovirus E1A promoter.

2. The nucleotide sequence of claim 1, wherein the adenovirus is of the Ad5 serotype.

3. The nucleotide sequence of claim 1, wherein the adenovirus selectively kills a cancer cell of a cancer selected from the group consisting of: acoustic neuroma, brain cancer, bone cancer, cancer of unknown primary site, carcinoid, carcinoid of gastrointestinal cervical cancer, colorectal cancer, oral cancer, liver cancer, pancreatic cancer, nasopharyngeal cancer, synovial cancer, hepatocellular cancer, renal cancer, cancer of connective tissues, melanoma, lung cancer, bowel cancer, colon cancer, rectal cancer, colorectal cancer, Kaposi's sarcoma, prostate cancer, lung cancer, testicular cancer, Hodgkin's disease, non-Hodgkin's lymphoma, gastrinoma, pheochromocytoma, prolactinoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, fibrosarcoma, breast cancer, Paget's disease, esophagus cancer, gall bladder cancer, head cancer, eye cancer, neck cancer, kidney cancer, liver cancer, skin cancer, mesothelioma, parotid gland cancer, peritoneum cancer, pharynx cancer, pleural cancer, salivary gland cancer, tongue cancer and tonsil cancer multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, mycosis fungoides, insulinoma, rectal cancer, tractchorio carcinoma, somatostatinoma, throat cancer, gum cancer, heart cancer, lip cancer, meninges cancer, mouth cancer, nerve cancer, palate cancer, T-cell leukemia/lymphoma, and Wilms' tumor.

4. The nucleotide sequence of claim 1, further comprising a nucleotide sequence encoding a heterologous polypeptide desired to be expressed from the genetically modified adenovirus.

5. The nucleotide sequence of claim 4, wherein the nucleotide sequence encoding the heterologous polypeptide is operably linked to a nucleotide sequence encoding an adenovirus E3 polypeptide or a fragment thereof.

6. The nucleotide sequence of claim 4, wherein the nucleotide sequence encoding the heterologous polypeptide is operably linked to a nucleotide sequence of the adenovirus encoding an adenovirus pIX polypeptide.

7. The nucleotide sequence of claim 4, wherein the heterologous polypeptide is a reporter gene.

8. The nucleotide sequence of claim 7, wherein the heterologous polypeptide is a detectable fluorescent protein.

9. The nucleotide sequence of claim 6, wherein the heterologous polypeptide is an immunomodulator.

10. The nucleotide sequence of claim 9, wherein the immunomodulator is Granulocyte-Macrophage Colony Stimulating Factor (GMCSF).

11. The nucleotide sequence of claim 7, wherein the nucleotide sequence is according to SEQ ID NO.: 5.

12. The nucleotide sequence of claim 10, wherein the nucleotide sequence is according to SEQ ID NO.: 2.

13. The nucleotide sequence of claim 1, wherein the nucleotide sequence is within an isolated eukaryotic cell.

14. A nucleotide sequence encoding a genetically modified shuttle adenovirus vector, wherein the nucleotide sequence is selected from the group consisting of SEQ ID NOs.: 3, 6, 9, 10, 11, 12, and 13.

15. A genetically modified adenovirus of the Ad5 serotype, wherein said adenovirus comprises a nucleotide sequence, wherein the nucleotide sequence encodes the adenovirus and comprises:
   a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; and
   a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor, and wherein the adenovirus E1A gene encoding the E1A polypeptide is operably linked to an adenovirus E1A promoter.

16. The genetically modified adenovirus of claim 15, wherein the nucleotide sequence further comprises a region encoding a heterologous polypeptide desired to be expressed from the genetically modified adenovirus.

17. The genetically modified adenovirus of claim 16, wherein the nucleotide sequence encoding the heterologous polypeptide is operably linked to a nucleotide sequence encoding an adenovirus E3 polypeptide or a fragment thereof.

18. The genetically modified adenovirus of claim 16, wherein the nucleotide sequence encoding the heterologous polypeptide is operably linked to a nucleotide sequence of the adenovirus encoding an adenovirus pIX polypeptide.

19. The genetically modified adenovirus of claim 16, wherein the heterologous polypeptide is a reporter protein.

20. The genetically modified adenovirus of claim 16, wherein the heterologous polypeptide is a detectable fluorescent protein.

21. The genetically modified adenovirus of claim 16, wherein the heterologous polypeptide is an immunomodulator.

22. The genetically modified adenovirus of claim 21, wherein the immunomodulator is Granulocyte-Macrophage Colony Stimulating Factor (GMCSF).

23. The genetically modified adenovirus of claim 22, wherein the nucleotide sequence encoding the genetically modified adenovirus is according to SEQ ID NO.: 2.

24. The genetically modified adenovirus of claim 15, where the adenovirus replicates selectively in a cancer cell and has a reduced cell toxic effect on a non-cancer cell.

25. The genetically modified adenovirus of claim 24, wherein the cancer cell is of a cancer selected from the group consisting of: acoustic neuroma, brain cancer, bone cancer, cancer of unknown primary site, carcinoid, carcinoid of gastrointestinal cervical cancer, colorectal cancer, oral cancer, liver cancer, pancreatic cancer, nasopharyngeal cancer, synovial cancer, hepatocellular cancer, renal cancer, cancer of connective tissues, melanoma, lung cancer, bowel cancer, colon cancer, rectal cancer, colorectal cancer, Kaposi's sarcoma, prostate cancer, lung cancer, testicular cancer, Hodgkin's disease, non-Hodgkin's lymphoma, gastrinoma, pheochromocytoma, prolactinoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, fibrosarcoma, breast cancer, Paget's disease, esophagus cancer, gall bladder cancer, head cancer, eye cancer, neck cancer, kidney cancer, liver cancer, skin cancer, mesothelioma, parotid gland cancer, peritoneum cancer, pharynx cancer, pleural cancer, salivary gland cancer, tongue cancer and tonsil cancer multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, mycosis fungoides, insulinoma, rectal cancer, tractchorio carcinoma, somatostatinoma, throat cancer, gum cancer, heart cancer, lip cancer, meninges cancer, mouth cancer, nerve cancer, palate cancer, T-cell leukemia/lymphoma, and Wilms' tumor.

26. The genetically modified adenovirus of claim 22, wherein the adenovirus is encoded by the nucleotide sequence according to SEQ ID NOs.: 2.

27. The genetically modified adenovirus of claim 15, wherein the adenovirus is within an isolated eukaryotic cell.

28. The genetically modified adenovirus of claim 15, wherein the adenovirus is admixed with a pharmaceutically acceptable carrier.

29. A method of monitoring the progress of delivery of a genetically modified adenovirus to a tumor in a patient, said method comprising the steps of:
(a) administering to the patient a pharmaceutically acceptable composition comprising a genetically modified adenovirus of the Ad5 serotype, wherein said adenovirus is encoded by a nucleotide sequence comprising:
a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob;
a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor, and wherein the adenovirus E1A gene encoding the E1A polypeptide is operably linked to an adenovirus E1A promoter; and
a region encoding a reporter protein,
wherein the nucleotide sequence region encoding the reporter protein is operably linked to a nucleotide sequence of the adenovirus encoding an adenovirus pIX polypeptide; and
(b) detecting a signal from the reporter protein, wherein the detected signal indicates the presence of the genetically modified adenovirus in cells of a tumor in the patient.

30. The method of claim 29, wherein the reporter protein is a detectable fluorescent protein.

31. The method of claim 30, wherein the nucleotide sequence encoding the genetically modified adenovirus is according to SEQ ID NO.: 5.

32. A method of modulating an immune response to a tumor in a patient, said method comprising:
administering to the patient a pharmaceutically acceptable composition comprising a genetically modified adenovirus of the Ad5 serotype, wherein said adenovirus is encoded by a nucleotide sequence comprising:
a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob;
a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor, and wherein the adenovirus E1A gene encoding the E1A polypeptide is operably linked to an adenovirus E1A promoter; and
a region encoding a immunomodulator protein,
wherein the nucleotide sequence region encoding the reporter protein is operably linked to a nucleotide sequence encoding an adenovirus E3 polypeptide or a fragment thereof.

33. The method of claim 29, wherein the immunomodulator protein is Granulocyte-Macrophage Colony Stimulating Factor (GMCSF).

34. The method of claim 32, wherein the nucleotide sequence encoding the genetically modified adenovirus is according to SEQ ID NO.: 2.

35. A nucleotide sequence encoding a genetically modified adenovirus, said nucleotide sequence comprising:
   a nucleotide sequence encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; and
   a nucleotide sequence encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor, wherein the nucleotide sequence is SEQ ID NO: 1.

36. A genetically modified adenovirus of the Ad5 serotype, wherein said adenovirus is encoded by a nucleotide sequence comprising:
   a region encoding an amino acid sequence comprising an N-terminal Ad5 serotype fiber shaft domain, a Ad3 serotype fiber knob domain, and an arginine-glycine-aspartate (RGD) peptide wherein the peptide RGD is at the C-terminus of the Ad3 serotype fiber knob; and
   a region encoding an adenovirus E1A polypeptide having a 24 base pair deletion compared to a wild-type E1A polypeptide, wherein the 24 base pair deletion in E1A-encoding nucleotide sequence renders the expressed E1A polypeptide unable to bind a pRb transcription factor, wherein the nucleotide sequence is SEQ ID NO: 1.

* * * * *

SEQUENCE LISTING

```
<160> NUMBER OF SEQ ID NOS: 13

<210> SEQ ID NO 1
<211> LENGTH: 36780
<212> TYPE: DNA
<213> ORGANISM: Artificial sequence
<220> FEATURE:
<223> OTHER INFORMATION: Recombinant adenovirus Ad5/5-RGD E3 D24,
      n=A,C,G,T
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (36771)..(36775)
<223> OTHER INFORMATION: n is a, c, g, or t

<400> SEQUENCE: 1
nnnttaatta aggatccnnn cggtgtgaaa taccgcacag atgcgtaagg agaaaatacc      60
gcatcaggcg ctcttccgct tcctcgctca ctgactcgct gcgctcggtc gttcggctgc     120
ggcgagcggt atcagctcac tcaaaggcgg taatacggtt atccacagaa tcagggata     180 acgcaggaaa gaacatgtga gcaaaaggcc agcaaaaggc caggaaccgt aaaaaggccg     240
cgttgctggc gtttttccat aggctccgcc cccctgacga gcatcacaaa aatcgacgct     300
caagtcagag gtggcgaaac ccgacaggac tataaagata ccaggcgttt ccccctggaa     360
gctccctcgt gcgctctcct gttccgaccc tgccgcttac cggatacctg tccgcctttc     420
```

```
tcccttcggg aagcgtggcg ctttctcata gctcacgctg taggtatctc agttcggtgt    480
aggtcgttcg ctccaagctg ggctgtgtgc acgaaccccc cgttcagccc gaccgctgcg    540
ccttatccgg taactatcgt cttgagtcca acccggtaag acacgactta tcgccactgg    600
cagcagccac tggtaacagg attagcagag cgaggtatgt aggcggtgct acagagttct    660
tgaagtggtg cctaactacg gctacacta gaaggacagt atttggtatc tgcgctctgc     720
tgaagccagt taccttcgga aaaagagttg gtagctcttg atccggcaaa caaaccaccg    780
ctggtagcgg tggttttttt gtttgcaagc agcagattac gcgcagaaaa aaggatctc     840
aagaagatcc tttgatcttt tctacggggt ctgacgctca gtggaacgaa aactcacgtt    900
aagggatttt ggtcatgaga ttatcaaaaa ggatcttcac ctagatcctt ttaaattaaa    960
aatgaagttt taaatcaatc taagtatat atgagtaaac ttggtctgac agttaccaat    1020
gcttaatcag tgaggcacct atctcagcga tctgtctatt tcgttcatcc atagttgcct   1080
gactccccgt cgtgtagata actacgatac gggagggctt accatctggc cccagtgctg   1140
caatgatacc gcgagaccca cgctcaccgg ctccagattt atcagcaata aaccagccag   1200
ccggaagggc cgagcgcaga agtggtcctg caactttatc cgcctccatc cagtctatta   1260
attgttgccg ggaagctaga gtaagtagtt cgccagttaa tagtttgcgc aacgttgttg   1320
ccattgctgc agccatgaga ttatcaaaaa ggatcttcac ctagatcctt ttcacgtaga   1380
aagccagtcc gcagaaacgg tgctgacccc ggatgaatgt cagctactgg gctatctgga   1440
caagggaaaa cgcaagcgca aagagaaagc aggtagcttg cagtgggctt acatggcgat   1500
agctagactg ggcggtttta tggacagcaa gcgaaccgga attgccagct ggggcgccct   1560
ctggtaaggt tgggaagccc tgcaaagtaa actggatggc tttctcgccg ccaaggatct   1620
gatggcgcag gggatcaagc tctgatcaag agacaggatg aggatcgttt cgcatgattg   1680
aacaagatgg attgcacgca ggttctccgg ccgcttgggt ggagaggcta ttcggctatg   1740
actgggcaca acagacaatc ggctgctctg atgccgccgt gttccggctg tcagcgcagg   1800
ggcgcccggt tctttttgtc aagaccgacc tgtccggtgc cctgaatgaa ctgcaagacg   1860
aggcagcgcg gctatcgtgg ctggccacga cgggcgttcc ttgcgcagct gtgctcgacg   1920
ttgtcactga agcgggaagg gactggctgc tattgggcga agtgccgggg caggatctcc   1980
tgtcatctca ccttgctcct gccgagaaag tatccatcat ggctgatgca atgcggcggc   2040
tgcatacgct tgatccggct acctgcccat tcgaccacca agcgaaacat cgcatcgagc   2100
gagcacgtac tcggatggaa gccggtcttg tcgatcagga tgatctggac gaagagcatc   2160
aggggctcgc gccagccgaa ctgttcgcca ggctcaaggc gagcatgccc gacggcgagg   2220
atctcgtcgt gacccatggc gatgcctgct tgccgaatat catggtggaa aatggccgct   2280
tttctggatt catcgactgt ggccggctgg gtgtggcgga ccgctatcag gacatagcgt   2340
tggctacccg tgatattgct gaagagcttg gcggcgaatg ggctgaccgc ttcctcgtgc   2400
tttacggtat cgccgctccc gattcgcagc gcatcgcctt ctatcgcctt cttgacgagt   2460
tcttctgaat tttgttaaaa ttttttgttaa atcagctcat ttttaacca ataggccgaa   2520
atcggcaaca tcccttataa atcaaaagaa tagaccgcga tagggttgag tgttgttcca   2580
gtttggaaca agagtccact attaaagaac gtggactcca acgtcaaagg gcgaaaaacc   2640
gtctatcagg gcgatggccc actacgtgaa ccatcaccca aatcaagttt ttgcggtcg    2700
aggtgccgta aagctctaaa tcggaacccct aaagggagcc cccgatttag agcttgacgg   2760
ggaaagccgg cgaacgtggc gagaaaggaa gggaagaaag cgaaaggagc gggcgctagg   2820
```

```
gcgctggcaa gtgtagcggt cacgctgcgc gtaaccacca cacccgcgcg cttaatgcgc    2880
cgctacaggg cgcgtccatt cgccattcag gatcgaatta attcttaatt aacatcatca    2940
ataatatacc ttattttgga ttgaagccaa tatgataatg aggggggtgga gtttgtgacg    3000 tggcgcgggg cgtgggaacg gggcgggtga cgtagtagtg tggcggaagt gtgatgttgc    3060
aagtgtggcg gaacacatgt aagcgacgga tgtggcaaaa gtgacgtttt tggtgtgcgc    3120
cggtgtacac aggaagtgac aattttcgcg cggttttagg cggatgttgt agtaaatttg    3180
ggcgtaaccg agtaagattt ggccattttc gcgggaaaac tgaataagag gaagtgaaat    3240
ctgaataatt ttgtgttact catagcgcgt aatatttgtc tagggccgcg gggactttga    3300
ccgtttacgt ggagactcgc ccaggtgttt ttctcaggtg ttttccgcgt tccgggtcaa    3360
agttggcgtt ttattattat agtcagctga cgtgtagtgt atttataccc ggtgagttcc    3420
tcaagaggcc actcttgagt gccagcgagt agagttttct cctccgagcc gctccgacac    3480
cgggactgaa aatgagacat attatctgcc acggaggtgt tattaccgaa gaaatggccg    3540
ccagtctttt ggaccagctg atcgaagagg tactggctga taatcttcca cctcctagcc    3600
attttgaacc acctacccct cacgaactgt atgatttaga cgtgacggcc cccgaagatc    3660
ccaacgagga ggcggtttcg cagatttttc ccgactctgt aatgttggcg gtgcaggaag    3720
ggattgactt actcactttt ccgccggcgc ccggttctcc ggagccgcct cacctttccc    3780
ggcagcccga gcagccggag cagagagcct tgggtccggt ttctatgcca aaccttgtac    3840
cggaggtgat cgatccaccc agtgacgacg aggatgaaga gggtgaggag tttgtgttag    3900
attatgtgga gcacccccggg cacggttgca ggtcttgtca ttatcaccgg aggaatacgg    3960
gggacccaga tattatgtgt tcgctttgct atatgaggac ctgtggcatg tttgtctaca    4020
gtaagtgaaa attatgggca gtgggtgata gagtggtggg tttggtgtgg taatttttttt    4080 tttaattttt acagttttgt ggtttaaaga attttgtatt gtgatttttt taaaaggtcc    4140
tgtgtctgaa cctgagcctg agcccgagcc agaaccggag cctgcaagac ctacccgccg    4200
tcctaaaatg gcgcctgcta tcctgagacg cccgacatca cctgtgtcta gagaatgcaa    4260
tagtagtacg gatagctgtg actccggtcc ttctaacaca cctcctgaga tacacccggt    4320
ggtcccgctg tgcccccatta aaccagttgc cgtgagagtt ggtgggcgtc gccaggctgt    4380
ggaatgtatc gaggacttgc ttaacgagcc tgggcaacct ttggacttga gctgtaaacg    4440
ccccaggcca taaggtgtaa acctgtgatt gcgtgtgtgg ttaacgcctt tgtttgctga    4500
atgagttgat gtaagtttaa taagggtgat taagtgttt aacttgcatg gcgtgttaaa    4560
tggggcgggg cttaaagggt atataatgcg ccgtgggcta atcttggtta catctgacct    4620
catgagggct tgggagtgtt tggaagattt ttctgctgtg cgtaacttgc tggaacagag    4680
ctctaacagt acctcttggt tttggaggtt tctgtggggc tcatcccagg caaagttagt    4740
ctgcagaatt aaggaggatt acaagtggga atttgaagag cttttgaaat cctgtggtga    4800
gctgtttgat tctttgaatc tgggtcacca ggcgcttttc caagagaagg tcatcaagac    4860
tttggatttt tccacaccgg ggcgcgctgc ggctgctgtt gcttttttga gttttataaa    4920
ggataaatgg agcgaagaaa cccatctgag cgggggggtac ctgctggatt ttctggccat    4980
gcatctgtgg agagcggttg tgagacacaa gaatcgcctg ctactgttgt cttccgtccg    5040
cccggcgata ataccgacgg aggagcagca gcagcagcag gaggaagcca ggcggcggcg    5100
gcaggagcag agcccatgga acccgagagc cggcctggac cctcgggaat gaatgttgta    5160
```

```
caggtggctg aactgtatcc agaactgaga cgcatttga caattacaga ggatgggcag    5220
gggctaaagg gggtaaagag ggagcggggg gcttgtgagg ctacagagga ggctaggaat    5280
ctagctttta gcttaatgac cagacaccgt cctgagtgta ttacttttca acagatcaag    5340
gataattgcg ctaatgagct tgatctgctg gcgcagaagt attccataga gcagctgacc    5400
acttactggc tgcagccagg ggatgatttt gaggaggcta ttagggtata tgcaaaggtg    5460
gcacttaggc cagattgcaa gtacaagatc agcaaacttg taaatatcag gaattgttgc    5520
tacatttctg ggaacggggc cgaggtggag atagatacgg aggatagggt ggcctttaga    5580
tgtagcatga taaatatgtg gccgggggtg cttggcatgg acggggtggt tattatgaat    5640
gtaaggttta ctggccccaa ttttagcggt acggttttcc tggccaatac caaccttatc    5700
ctacacggtg taagcttcta tgggtttaac aatacctgtg tggaagcctg gaccgatgta    5760
agggttcggg gctgtgcctt ttactgctgc tggaagggg tggtgtgtcg ccccaaaagc    5820
agggcttcaa ttaagaaatg cctctttgaa aggtgtacct tgggtatcct gtctgagggt    5880
aactccaggg tgcgccacaa tgtggcctcc gactgtggtt gcttcatgct agtgaaaagc    5940
gtggctgtga ttaagcataa catggtatgt gcaactgcg aggacagggc ctctcagatg    6000
ctgacctgct cggacggcaa ctgtcacctg ctgaagacca ttcacgtagc cagccactct    6060
cgcaaggcct ggccagtgtt tgagcataac atactgaccc gctgttcctt gcatttgggt    6120
aacaggaggg gggtgttcct accttaccaa tgcaatttga gtcacactaa gatattgctt    6180
gagcccgaga gcatgtccaa ggtgaacctg aacggggtgt ttgacatgac catgaagatc    6240
tggaaggtgc tgaggtacga tgagacccgc accaggtgca gaccctgcga gtgtggcggt    6300
aaacatatta ggaaccagcc tgtgatgctg gatgtgaccg aggagctgag gcccgatcac    6360
ttggtgctgg cctgcacccg cgctgagttt ggctctagcg atgaagatac agattgaggt    6420
actgaaatgt gtgggcgtgg cttaagggtg ggaaagaata tataaggtgg gggtcttatg    6480
tagttttgta tctgttttgc agcagccgcc gccgccatga gcaccaactc gtttgatgga    6540
agcattgtga gctcatattt gacaacgcgc atgcccccat gggccggggt gcgtcagaat    6600
gtgatgggct ccagcattga tggtcgcccc gtcctgcccg caaactctac taccttgacc    6660
tacgagaccg tgtctggaac gccgttggag actgcagcct ccgccgccgc ttcagccgct    6720
gcagccaccg cccgcgggat tgtgactgac tttgcttttcc tgagcccgct tgcaagcagt    6780
gcagcttccc gttcatccgc ccgcgatgac aagttgacgg ctcttttggc acaattggat    6840
tctttgaccc gggaacttaa tgtcgttttct cagcagctgt tggatctgcg ccagcaggtt    6900
tctgccctga aggcttcctc ccctcccaat gcggttttaaa acataaataa aaaaccagac    6960
tctgtttgga tttggatcaa gcaagtgtct tgctgtcttt atttaggggt tttgcgcgcg    7020
cggtaggccc gggaccagcg gtctcggtcg ttgagggtcc tgtgtatttt ttccaggacg    7080
tggtaaaggt gactctggat gttcagatac atgggcataa gcccgtctct ggggtggagg    7140
tagcaccact gcagagcttc atgctgcggg gtggtgttgt agatgatcca gtcgtagcag    7200
gagcgctggg cgtggtgcct aaaaatgtct ttcagtagca agctgattgc caggggcagg    7260
cccttggtgt aagtgtttac aaagcggtta agctgggatg ggtgcatacg tggggatatg    7320
agatgcatct tggactgtat ttttaggttg gctatgttcc cagccatatc cctccgggga    7380
ttcatgttgt gcagaaccac cagcacagtg tatccggtgc acttgggaaa tttgtcatgt    7440
agcttagaag gaaatgcgtg gaagaacttg gagacgccct tgtgacctcc aagattttcc    7500
atgcattcgt ccataatgat ggcaatgggc ccacgggcgg cggcctgggc gaagatattt    7560
```

```
ctgggatcac taacgtcata gttgtgttcc aggatgagat cgtcataggc cattttaca    7620 aagcgcgggc ggagggtgcc agactgcggt ataatggttc catccggccc aggggcgtag    7680
ttaccctcac agatttgcat ttcccacgct ttgagttcag atggggggat catgtctacc    7740 tgcgggggcga tgaagaaaac ggtttccggg gtaggggaga tcagctggga agaaagcagg    7800
ttcctgagca gctgcgactt accgcagccg gtgggcccgt aaatcacacc tattaccggg    7860
tgcaactggt agttaagaga gctgcagctg ccgtcatccc tgagcagggg ggccacttcg    7920
ttaagcatgt ccctgactcg catgttttcc ctgaccaaat ccgcagaag gcgctcgccg     7980 cccagcgata gcagttcttg caaggaagca aagttttca acggtttgag accgtccgcc    8040
gtaggcatgc ttttgagcgt ttgaccaagc agttccaggc ggtcccacag ctcggtcacc    8100
tgctctacgg catctcgatc cagcatatct cctcgtttcg cggttgggg cggctttcgc     8160 tgtacggcag tagtcggtgc tcgtccagac gggccagggt catgtctttc cacgggcgca    8220
gggtcctcgt cagcgtagtc tgggtcacgg tgaaggggtg cgctccggc tgcgcgctgg     8280 ccagggtgcg cttgaggctg gtcctgctgg tgctgaagcg ctgccggtct tcgccctgcg    8340
cgtcggccag gtagcatttg accatggtgt catagtccag cccctccgcg gcgtggccct    8400
tggcgcgcag cttgcccttg gaggaggcgc cgcacgaggg gcagtgcaga cttttgaggg    8460
cgtagagctt gggcgcgaga aataccgatt ccggggagta ggcatccgcg ccgcaggccc    8520
cgcagacggt ctcgcattcc acgagccagg tgagctctgg ccgttcgggg tcaaaaacca    8580
ggtttccccc atgcttttg atgcgttct tacctctggt ttccatgagc cggtgtccac      8640
gctcggtgac gaaaaggctg tccgtgtccc cgtatacaga cttgagaggc ctgtcctcga    8700
gcggtgttcc gcggtcctcc tcgtatagaa actcggacca ctctgagaca aaggctcgcg    8760
tccaggccag cacgaaggag gctaagtggg aggggtagcg gtcgttgtcc actaggggt      8820 ccactcgctc cagggtgtga agacacatgt cgccctcttc ggcatcaagg aaggtgattg    8880
gtttgtaggt gtaggccacg tgaccgggtg ttcctgaagg ggggctataa aaggggtgg     8940 gggcgcgttc gtcctcactc tcttccgcat cgctgtctgc gagggccagc tgttggggtg    9000
agtactccct ctgaaaagcg ggcatgactt ctgcgctaag attgtcagtt ccaaaaacg     9060 aggaggattt gatattcacc tggcccgcgg tgatgccttt gagggtggcc gcatccatct    9120
ggtcagaaaa gacaatcttt tgttgtcaa gcttggtggc aaacgacccg tagagggcgt     9180
tggacagcaa cttggcgatg gagcgcaggg tttggttttt gtcgcgatcg gcgcgctcct    9240
tggccgcgat gtttagctgc acgtattcgc gcgcaacgca ccgccattcg ggaaagacgg    9300
tggtgcgctc gtcgggcacc aggtgcacgc gccaaccgcg gttgtgcagg gtgacaaggt    9360
caacgctggt ggctacctct ccgcgtaggc gctcgttggt ccagcagagg cggccgccct    9420
tgcgcgagca gaatggcggt aggggggtcta gctgcgtctc gtccgggggg tctgcgtcca    9480
cggtaaagac cccgggcagc aggcgcgcgt cgaagtagtc tatcttgcat ccttgcaagt    9540
ctagcgcctg ctgccatgcg cgggcggcaa gcgcgcgctc gtatggttg agtgggggac     9600 cccatggcat ggggtgggtg agcgcggagg cgtacatgcc gcaaatgtcg taaacgtaga    9660
ggggctctct gagtattcca agatatgtag ggtagcatct tccaccgcgg atgctggcgc    9720
gcacgtaatc gtatagttcg tgcgagggag cgaggaggtc gggaccgagg ttgctacggg    9780
cgggctgctc tgctcggaag actatctgcc tgaagatggc atgtgagttg gatgatatgg    9840
ttggacgctg gaagacgttg aagctggcgt ctgtgagacc taccgcgtca cgcacgaagg    9900
```

```
aggcgtagga gtcgcgcagc ttgttgacca gctcggcggt gacctgcacg tctagggcgc    9960
agtagtccag ggtttccttg atgatgtcat acttatcctg tccctttttt ttccacagct   10020
cgcggttgag gacaaactct tcgcggtctt tccagtactc ttggatcgga aacccgtcgg   10080
cctccgaacg gtaagagcct agcatgtaga actggttgac ggcctggtag gcgcagcatc   10140
ccttttctac gggtagcgcg tatgcctgcg cggccttccg gagcgaggtg tgggtgagcg   10200
caaaggtgtc cctgaccatg actttgaggt actggtattt gaagtcagtg tcgtcgcatc   10260
cgccctgctc ccagagcaaa aagtccgtgc gcttttgga acgcggattt ggcagggcga    10320
aggtgacatc gttgaagagt atctttcccg cgcgaggcat aaagttgcgt gtgatgcgga   10380
agggtcccgg cacctcggaa cggttgttaa ttacctgggc ggcgagcacg atctcgtcaa   10440
agccgttgat gttgtggccc acaatgtaaa gttccaagaa gcgcgggatg cccttgatgg   10500
aaggcaattt tttaagttcc tcgtaggtga gctcttcagg ggagctgagc ccgtgctctg   10560
aaagggccca gtctgcaaga tgaggggttgg aagcgacgaa tgagctccac aggtcacggg   10620
ccattagcat ttgcaggtgg tcgcgaaagg tcctaaactg gcgacctatg gccattttt    10680 ctggggtgat gcagtagaag gtaagcgggt cttgttccca gcggtcccat ccaaggttcg   10740
cggctaggtc tcgcgcggca gtcactagag gctcatctcc gccgaacttc atgaccagca   10800
tgaagggcac gagctgcttc ccaaaggccc ccatccaagt ataggtctct acatcgtagg   10860
tgacaaagag acgctcggtg cgaggatgcg agccgatcgg gaagaactgg atctcccgcc   10920
accaattgga ggagtggcta ttgatgtggt gaaagtagaa gtccctgcga cgggccgaac   10980
actcgtgctg gcttttgtaa aaacgtgcgc agtactggca gcggtgcacg ggctgtacat   11040
cctgcacgag gttgacctga cgaccgcgca caaggaagca gagtgggaat ttgagcccct   11100
cgcctggcgg gtttggctgg tggtcttcta cttcggctgc ttgtccttga ccgtctggct   11160
gctcgagggg agttacggtg gatcggacca ccacgccgcg cgagcccaaa gtccagatgt   11220
ccgcgcgcgc cggtcggagc ttgatgacaa catcgcgcag atgggagctg tccatggtct   11280
ggagctcccg cggcgtcagg tcaggcggga gctcctgcag gtttacctcg catagacggg   11340
tcagggcgcg ggctagatcc aggtgatacc taatttccag gggctggttg gtggcggcgt   11400
cgatggcttg caagaggccg catccccgcg gcgcgactac ggtaccgcgc ggcgggcggt   11460
gggccgcggg ggtgtccttg gatgatgcat ctaaaagcgg tgacgcgggc gagccccgg    11520 aggtaggggg ggctccggac ccgccgggag agggggcagg ggcacgtcgg cgccgcgcgc   11580
gggcaggagc tggtgctgcg cgcgtaggtt gctggcgaac gcgacgacgc ggcggttgat   11640
ctcctgaatc tggcgcctct gcgtgaagac gacgggcccg gtgagcttga gcctgaaaga   11700
gagttcgaca gaatcaattt cggtgtcgtt gacggcggcc tggcgcaaaa tctcctgcac   11760
gtctcctgag ttgtcttgat aggcgatctc ggccatgaac tgctcgatct cttcctcctg   11820
gagatctccg cgtccggctc gctccacggt ggcggcgagg tcgttggaaa tgcgggccat   11880
gagctgcgag aaggcgttga ggcctccctc gttccagacg cggctgtaga ccacgccccc   11940
ttcggcatcg cgggcgcgca tgaccacctg cgcgagattg agctccacgt gccgggcgaa   12000
gacggcgtag tttcgcaggc gctgaaagag gtagttgagg gtggtggcgg tgtgttctgc   12060
cacgaagaag tacataaccc agcgtcgcaa cgtggattcg ttgatatccc ccaaggcctc   12120
aaggcgctcc atggcctcgt agaagtccac ggcgaagttg aaaaactggg agttgcgcgc   12180
cgacacggtt aactcctcct ccagaagacg gatgagctcg gcgacagtgt cgcgcacctc   12240
gcgctcaaag gctacagggg cctcttcttc ttcttcaatc tcctcttcca taagggcctc   12300
```

```
cccttcttct tcttctggcg gcggtggggg aggggggaca cggcggcgac gacggcgcac   12360
cgggaggcgg tcgacaaagc gctcgatcat ctccccgcgg cgacggcgca tggtctcggt   12420
gacggcgcgg ccgttctcgc gggggcgcag ttggaagacg ccgcccgtca tgtcccggtt   12480
atgggttggc gggggggctgc catgcggcag ggatacggcg ctaacgatgc atctcaacaa   12540
ttgttgtgta ggtactccgc cgccgaggga cctgagcgag tccgcatcga ccggatcgga   12600
aaacctctcg agaaaggcgt ctaaccagtc acagtcgcaa ggtaggctga gcaccgtggc   12660
gggcggcagc gggcggcggt cggggttgtt tctggcggag gtgctgctga tgatgtaatt   12720
aaagtaggcg gtcttgagac ggcggatggt cgacagaagc accatgtcct tgggtccggc   12780
ctgctgaatg cgcaggcggt cggccatgcc ccaggcttcg ttttgacatc ggcgcaggtc   12840
tttgtagtag tcttgcatga gcctttctac cggcacttct tcttctcctt cctcttgtcc   12900
tgcatctctt gcatctatcg ctgcggcggc ggcggagttt ggccgtaggt ggcgccctct   12960
tcctcccatg cgtgtgaccc cgaagcccct catcggctga agcagggcta ggtcggcgac   13020
aacgcgctcg gctaatatgg cctgctgcac ctgcgtgagg gtagactgga agtcatccat   13080
gtccacaaag cggtggtatg cgcccgtgtt gatggtgtaa gtgcagttgg ccataacgga   13140
ccagttaacg gtctggtgac ccggctgcga gagctcggtg tacctgagac gcgagtaagc   13200
cctcgagtca aatacgtagt cgttgcaagt ccgcaccagg tactggtatc ccaccaaaaa   13260
gtgcggcggc ggctggcggt agaggggcca gcgtagggtg gccggggctc cggggcgag   13320 atcttccaac ataaggcgat gatatccgta gatgtacctg gacatccagg tgatgccggc   13380
ggcggtggtg gaggcgcgcg gaaagtcgcg gacgcggttc cagatgttgc gcagcggcaa   13440
aaagtgctcc atggtcggga cgctctggcc ggtcaggcgc gcgcaatcgt tgacgctcta   13500
ccgtgcaaaa ggagagcctg taagcgggca ctcttccgtg gtctggtgga taaattcgca   13560
agggtatcat ggcggacgac cggggttcga gccccgtatc cggccgtccg ccgtgatcca   13620
tgcggttacc gcccgcgtgt cgaacccagg tgtgcgacgt cagacaacgg gggagtgctc   13680
cttttggctt ccttccaggc gcggcggctg ctgcgctagc ttttttggcc actggccgcg   13740
cgcagcgtaa gcggttaggc tggaaagcga aagcattaag tggctcgctc cctgtagccg   13800
gagggttatt ttccaagggt tgagtcgcgg gaccccggt tcgagtctcg gaccggccgg   13860
actgcggcga acgggggttt gcctcccgt catgcaagac cccgcttgca aattcctccg   13920
gaaacaggga cgagccccctt ttttgctttt cccagatgca tccggtgctg cggcagatgc   13980 gccccctcc tcagcagcgg caagagcaag agcagcggca gacatgcagg gcaccctccc   14040
ctcctcctac cgcgtcagga ggggcgacat ccgcggttga cgcggcagca gatggtgatt   14100
acgaaccccc gcggcgccgg gcccggcact acctggactt ggaggagggc gagggcctgg   14160
cgcggctagg agcgcccctct cctgagcggt acccaagggt gcagctgaag cgtgatacgc   14220
gtgaggcgta cgtgccgcgg cagaacctgt ttcgcgaccg cgaggagag gagcccgagg   14280 agatgcggga tcgaaagttc cacgcagggc gcgagctgcg gcatggcctg aatcgcgagc   14340
ggttgctgcg cgaggaggac tttgagcccg acgcgcgaac cgggattagt cccgcgcgcg   14400
cacacgtggg ggccgccgac ctggtaaccg catacgagca gacggtgaac caggagatta   14460
actttcaaaa aagctttaac aaccacgtgc gtacgcttgt ggcgcgcgag gaggtggcta   14520
taggactgat gcatctgtgg gactttgtaa gcgcgctgga gcaaaaccca aatagcaagc   14580
cgctcatggc gcagctgttc cttatagtgc agcacagcag ggacaacgag gcattcaggg   14640
```

```
atgcgctgct aaacatagta gagcccgagg gccgctggct gctcgatttg ataaacatcc   14700
tgcagagcat agtggtgcag gagcgcagct tgagcctggc tgacaaggtg gccgccatca   14760
actattccat gcttagcctg ggcaagtttt acgcccgcaa gatataccat accccttacg   14820
ttcccataga caaggaggta aagatcgagg ggttctacat gcgcatggcg ctgaaggtgc   14880
ttaccttgag cgacgacctg ggcgtttatc gcaacgagcg catccacaag gccgtgagcg   14940
tgagccggcg gcgcgagctc agcgaccgcg agctgatgca cagcctgcaa agggccctgg   15000
ctggcacggg cagcggcgat agagaggccg agtcctactt tgacgcgggc gctgacctgc   15060
gctgggcccc aagccgacgc gccctggagg cagctgggc cggacctggg ctggcggtgg    15120 caccccgcgcg cgctggcaac gtcggcggcg tggaggaata tgacgaggac gatgagtacg   15180
agccagagga cggcgagtac taagcggtga tgtttctgat cagatgatgc aagacgcaac   15240
ggacccggcg gtgcgggcgg cgctgcagag ccagccgtcc ggccttaact ccacggacga   15300
ctggcgccag gtcatggacc gcatcatgtc gctgactgcg cgcaatcctg acgcgttccg   15360
gcagcagccg caggccaacc ggctctccgc aattctggaa gcgtggtcc cggcgcgcgc     15420 aaacccccacg cacgagaagg tgctggcgat cgtaaacgcg ctggccgaaa cagggccat    15480 ccggcccgac gaggccggcc tggtctacga cgcgctgctt cagcgcgtgg ctcgttacaa   15540
cagcggcaac gtgcagacca acctggaccg gctggtgggg gatgtgcgcg aggccgtggc   15600
gcagcgtgag cgcgcgcagc agcagggcaa cctgggctcc atggttgcac taaacgcctt   15660
cctgagtaca cagcccgcca acgtgccgcg gggacaggag gactacacca actttgtgag   15720
cgcactgcgg ctaatggtga ctgagacacc gcaaagtgag gtgtaccagt ctgggccaga   15780 ctatttttc cagaccagta gacaaggcct gcagaccgta aacctgagcc aggctttcaa    15840
aaacttgcag gggctgtggg gggtgcgggc tcccacaggc gaccgcgcga ccgtgtctag   15900
cttgctgacg cccaactcgc gcctgttgct gctgctaata gcgcccttca cggacagtgg   15960
cagcgtgtcc cggacacat acctaggtca cttgctgaca ctgtaccgcg aggccatagg    16020
tcaggcgcat gtggacgagc atactttcca ggagattaca agtgtcagcc gcgcgctggg   16080
gcaggaggac acgggcagcc tggaggcaac cctaaactac ctgctgacca accggcggca   16140
gaagatcccc tcgttgcaca gtttaaacag cgaggaggag cgcattttgc gctacgtgca   16200
gcagagcgtg agccttaacc tgatgcgcga cggggtaacg cccagcgtgg cgctggacat   16260
gaccgcgcgc aacatggaac cgggcatgta tgcctcaaac cggccgttta tcaaccgcct   16320
aatggactac ttgcatcgcg cggccgccgt gaaccccgag tatttcacca atgccatctt   16380
gaacccgcac tggctaccgc ccctggtttt ctacaccggg ggattcgagg tgcccgaggg   16440
taacgatgga ttcctctggg acgacataga cgacagcgtg ttttcccgc aaccgcagac    16500 cctgctagag ttgcaacagc gcgagcaggc agaggcggcg ctgcgaaagg aaagcttccg   16560
caggccaagc agcttgtccg atctaggcgc tgcggcccg cggtcagatg ctagtagccc    16620
atttccaagc ttgatagggt ctcttaccag cactcgcacc acccgcccgc gcctgctggg   16680
cgaggaggag tacctaaaca actcgctgct gcagccgcag cgcgaaaaaa acctgcctcc   16740
ggcatttccc aacaacggga tagagagcct agtggacaag atgagtagat ggaagacgta   16800
cgcgcaggag cacgggacg tgccaggccc cgcgcccgcc accgtcgtc aaaggcacga     16860 ccgtcagcgg ggtctggtgt gggaggacga tgactcggca gacgacagca gcgtcctgga   16920
tttgggaggg agtggcaacc cgtttgcgca ccttcgcccc aggctgggga gaatgtttta   16980
aaaaaaaaaa agcatgatgc aaaataaaaa actcaccaag gccatggcac cgagcgttgg   17040
```

```
ttttcttgta ttccccttag tatgcggcgc gcggcgatgt atgaggaagg tcctcctccc   17100
tcctacgaga gtgtggtgag cgcggcgcca gtggcggcgg cgctgggttc tcccttcgat   17160
gctcccctgg acccgccgtt tgtgcctccg cggtacctgc ggcctaccgg ggggagaaac   17220
agcatccgtt actctgagtt ggcaccccta ttcgacacca cccgtgtgta cctggtggac   17280
aacaagtcaa cggatgtggc atccctgaac taccagaacg accacagcaa ctttctgacc   17340
acggtcattc aaaacaatga ctacagcccg ggggaggcaa gcacacagac catcaatctt   17400
gacgaccggt cgcactgggg cggcgacctg aaaaccatcc tgcataccaa catgccaaat   17460
gtgaacgagt tcatgtttac caataagttt aaggcgcggg tgatggtgtc gcgcttgcct   17520
actaaggaca atcaggtgga gctgaaatac gagtgggtgg agttcacgct gcccgagggc   17580
aactactccg agaccatgac catagacctt atgaacaacg cgatcgtgga gcactacttg   17640
aaagtgggca gacagaacgg ggttctggaa agcgacatcg gggtaaagtt tgacacccgc   17700
aacttcagac tggggtttga ccccgtcact ggtcttgtca tgcctggggt atatacaaac   17760
gaagccttcc atccagacat catttttgctg ccaggatgcg gggtggactt cacccacagc   17820
cgcctgagca acttgttggg catccgcaag cggcaaccct tccaggaggg ctttaggatc   17880
acctacgatg atctggaggg tggtaacatt cccgcactgt tggatgtgga cgcctaccag   17940
gcgagcttga aagatgacac cgaacagggc ggggtggcg caggcggcag caacagcagt   18000
ggcagcggcg cggaagagaa ctccaacgcg gcagccgcgg caatgcagcc ggtggaggac   18060
atgaacgatc atgccattcg cggcgacacc tttgccacac gggctgagga gaagcgcgct   18120
gaggccgaag cagcggccga agctgccgcc cccgctgcgc aacccgaggt cgagaagcct   18180
cagaagaaac cggtgatcaa acccctgaca gaggacagca agaaacgcag ttacaaccta   18240
ataagcaatg acagcacctt cacccagtac cgcagctggt accttgcata caactacggc   18300
gaccctcaga ccggaatccg ctcatgggcc ctgctttgca ctcctgacgt aacctgcggc   18360
tcggagcagg tctactggtc gttgccagac atgatgcaag accccgtgac cttccgctcc   18420
acgcgccaga tcagcaactt tccggtggtg ggcgccgagc tgttgcccgt gcactccaag   18480
agcttctaca cgaccaggc cgtctactcc caactcatcc gccagtttac ctctctgacc   18540
cacgtgttca atcgctttcc cgagaaccag attttggcgc gccgccagc ccccaccatc   18600 accaccgtca gtgaaaacgt tcctgctctc acagatcacg ggacgctacc gctgcgcaac   18660
agcatcggag gagtccagcg agtgaccatt actgacgcca gacgccgcac ctgcccctac   18720
gtttacaagg ccctgggcat agtctcgccg cgcgtcctat cgagccgcac ttttttgagca   18780 agcatgtcca tccttatatc gcccagcaat aacacaggct ggggcctgcg cttcccaagc   18840
aagatgtttg gcggggccaa gaagcgctcc gaccaacacc cagtgcgcgt gcgcgggcac   18900
taccgcgcgc cctggggcgc gcacaaacgc ggccgcactg ggcgcaccac cgtcgatgac   18960
gccatcgacg cggtggtgga ggaggcgcgc aactacacgc ccacgccgcc accagtgtcc   19020
acagtggacg cggccattca gaccgtggtg cgcggagccc ggcgctatgc taaaatgaag   19080
agacggcgga ggcgcgtagc acgtcgccac cgccgccgac ccggcactgc cgcccaacgc   19140
gcggcggcgg ccctgcttaa ccgcgcacgt cgcaccggcc gacgggcggc catgcgggcc   19200
gctcgaaggc tggccgcggg tattgtcact gtgccccca ggtccaggcg acgagcggcc   19260
gccgcagcag ccgcggccat tagtgctatg actcagggtc gcaggggcaa cgtgtattgg   19320
gtgcgcgact cggttagcgg cctgcgcgtg cccgtgcgca cccgccccc gcgcaactag   19380
```

```
attgcaagaa aaaactactt agactcgtac tgttgtatgt atccagcggc ggcggcgcgc   19440
aacgaagcta tgtccaagcg caaaatcaaa gaagagatgc tccaggtcat cgcgccggag   19500
atctatggcc ccccgaagaa ggaagagcag gattacaagc cccgaaagct aaagcgggtc   19560
aaaaagaaaa agaaagatga tgatgatgaa cttgacgacg aggtggaact gctgcacgct   19620
accgcgccca ggcgacgggt acagtggaaa ggtcgacgcg taaaacgtgt tttgcgaccc   19680
ggcaccaccg tagtctttac gcccggtgag cgctccaccc gcacctacaa gcgcgtgtat   19740
gatgaggtgt acggcgacga ggacctgctt gagcaggcca acgagcgcct cggggagttt   19800
gcctacggaa agcggcataa ggacatgctg gcgttgccgc tggacgaggg caacccaaca   19860
cctagcctaa agcccgtaac actgcagcag gtgctgcccg cgcttgcacc gtccgaagaa   19920
aagcgcggcc taaagcgcga gtctggtgac ttggcaccca ccgtgcagct gatggtaccc   19980
aagcgccagc gactggaaga tgtcttggaa aaaatgaccg tggaacctgg gctggagccc   20040
gaggtccgcg tgcggccaat caagcaggtg gcgccgggac tgggcgtgca gaccgtggac   20100
gttcagatac ccactaccag tagcaccagt attgccaccg ccacagaggg catggagaca   20160
caaacgtccc cggttgcctc agcggtggcg gatgccgcgg tgcaggcggt cgctgcggcc   20220
gcgtccaaga cctctacgga ggtgcaaacg gacccgtgga tgtttcgcgt ttcagccccc   20280
cggcgcccgc gcggttcgag gaagtacggc gccgcagcg cgctactgcc cgaatatgcc   20340
ctacatcctt ccattgcgcc taccccggc tatcgtggct acacctaccg ccccagaaga   20400
cgagcaacta cccgacgccg aaccaccact ggaacccgcc gccgccgtcg ccgtcgccag   20460
cccgtgctgg ccccgatttc cgtgcgcagg gtggctcgcg aaggaggcag gaccctggtg   20520
ctgccaacag cgcgctacca ccccagcatc gtttaaaagc cggtctttgt ggttcttgca   20580
gatatggccc tcacctgccg cctccgtttc ccggtgccgg gattccgagg aagaatgcac   20640
cgtaggaggg gcatggccgg ccacggcctg acgggcggca tgcgtcgtgc gcaccaccgg   20700
cggcggcgcg cgtcgcaccg tcgcatgcgc ggcggtatcc tgcccctcct tattccactg   20760
atcgccgcgg cgattggcgc cgtgcccgga attgcatccg tggccttgca ggcgcagaga   20820
cactgattaa aaacaagttg catgtggaaa aatcaaaata aaaagtctgg actctcacgc   20880
tcgcttggtc ctgtaactat tttgtagaat ggaagacatc aactttgcgt ctctggcccc   20940
gcgacacggc tcgcgcccgt tcatgggaaa ctggcaagat atcggcacca gcaatatgag   21000
cggtggcgcc ttcagctggg gctcgctgtg gagcggcatt aaaaatttcg gttccaccgt   21060
taagaactat ggcagcaagg cctggaacag cagcacaggc cagatgctga gggataagtt   21120
gaaagagcaa aatttccaac aaaaggtggt agatggcctg gcctctggca ttagcggggt   21180
ggtggacctg gccaaccagg cagtgcaaaa taagattaac agtaagcttg atccccgccc   21240
tcccgtagag gagcctccac cggccgtgga gacagtgtct ccagaggggc gtggcgaaaa   21300
gcgtccgcgc cccgacaggg aagaaactct ggtgacgcaa atagacgagc tccctcgta   21360
cgaggaggca ctaaagcaag gcctgcccac caccccgtccc atcgcgccca tggctaccgg   21420
agtgctgggc cagcacacac ccgtaacgct ggacctgcct cccccgccg acacccagca   21480
gaaacctgtg ctgccaggcc cgaccgccgt tgttgtaacc cgtcctagcc gcgcgtccct   21540
gcgccgcgcc gccagcggtc cgcgatcgtt gcggcccgta gccagtggca actggcaaag   21600
cacactgaac agcatcgtgg gtctgggggt gcaatccctg aagcgccgac gatgcttctg   21660
aatagctaac gtgtcgtatg tgtgtcatgt atgcgtccat gtcgccgcca gaggagctgc   21720
tgagccgccg cgcgcccgct ttccaagatg gctaccccct cgatgatgcc gcagtggtct   21780
```

```
tacatgcaca tctcgggcca ggacgcctcg gagtacctga gccccgggct ggtgcagttt    21840
gcccgcgcca ccgagacgta cttcagcctg aataacaagt ttagaaaccc cacggtggcg    21900
cctacgcacg acgtgaccac agaccggtcc cagcgtttga cgctgcggtt catccctgtg    21960
gaccgtgagg atactgcgta ctcgtacaag gcgcggttca ccctagctgt gggtgataac    22020
cgtgtgctgg acatggcttc cacgtacttt gacatccgcg gcgtgctgga caggggccct    22080
acttttaagc cctactctgg cactgcctac aacgccctgg ctcccaaggg tgccccaaat    22140
ccttgcgaat gggatgaagc tgctactgct cttgaaataa acctagaaga agaggacgat    22200
gacaacgaag acgaagtaga cgagcaagct gagcagcaaa aaactcacgt atttgggcag    22260
gcgccttatt ctggtataaa tattacaaag gagggtattc aaataggtgt cgaaggtcaa    22320
acacctaaat atgccgataa acatttcaa cctgaacctc aaataggaga atctcagtgg    22380
tacgaaactg aaattaatca tgcagctggg agagtcctta aaaagactac cccaatgaaa    22440
ccatgttacg gttcatatgc aaaacccaca atgaaaatg gagggcaagg cattcttgta    22500
aagcaacaaa atggaaagct agaaagtcaa gtggaaatgc aattttctc aactactgag    22560 gcgaccgcag gcaatggtga taacttgact cctaaagtgg tattgtacag tgaagatgta    22620
gatatagaaa ccccagacac tcatatttct tacatgccca ctattaagga aggtaactca    22680
cgagaactaa tgggccaaca atctatgccc aacaggccta attacattgc ttttagggac    22740 aatttttattg gtctaatgta ttacaacagc acgggtaata tgggtgttct ggcgggccaa    22800
gcatcgcagt tgaatgctgt tgtagatttg caagacagaa acacagagct ttcataccag    22860
cttttgcttg attccattgg tgatagaacc aggtactttt ctatgtggaa tcaggctgtt    22920
gacagctatg atccagatgt tagaattatt gaaaatcatg gaactgaaga tgaacttcca    22980
aattactgct ttccactggg aggtgtgatt aatacagaga ctcttaccaa ggtaaaacct    23040
aaaacaggtc aggaaaatgg atgggaaaaa gatgctacag aattttcaga taaaaatgaa    23100
ataagagttg gaaataattt tgccatggaa atcaatctaa atgccaacct gtggagaaat    23160
ttcctgtact ccaacatagc gctgtatttg cccgacaagc taaagtacag tccttccaac    23220
gtaaaaattt ctgataaccc aaacacctac gactacatga caagcgagt ggtggctccc    23280 gggttagtgg actgctacat taaccttgga gcacgctggt cccttgacta tatggacaac    23340
gtcaacccat ttaaccacca ccgcaatgct ggcctgcgct accgctcaat gttgctgggc    23400
aatggtcgct atgtgccctt ccacatccag gtgcctcaga gttctttgc cattaaaaac    23460 ctccttctcc tgccgggctc atacacctac gagtggaact tcaggaagga tgttaacatg    23520
gttctgcaga gctccctagg aaatgaccta agggttgacg gagccagcat taagtttgat    23580
agcatttgcc tttacgccac cttcttcccc atggcccaca caccgcctc cacgcttgag    23640 gccatgctta gaaacgacac caacgaccag tcctttaacg actatctctc cgccgccaac    23700
atgctctacc ctatcccgc caacgctacc aacgtgccca tatccatccc ctcccgcaac    23760
tgggcggctt tccgcggctg ggccttcacg cgccttaaga ctaaggaaac cccatcactg    23820
ggctcgggct acgacccta ttacacctac tctggctcta taccctacct agatggaacc    23880
ttttacctca accacacctt taagaaggtg gccattacct ttgactcttc tgtcagctgg    23940
cctggcaatg accgcctgct tacccccaac gagtttgaaa ttaagcgctc agttgacggg    24000
gagggttaca acgttgccca gtgtaacatg accaaagact ggttcctggt acaaatgcta    24060
gctaactaca acattggcta ccagggcttc tatatcccag agagctacaa ggaccgcatg    24120
```

```
tactccttct ttagaaactt ccagcccatg agccgtcagg tggtggatga tactaaatac   24180
aaggactacc aacaggtggg catcctacac caacacaaca actctggatt tgttggctac   24240
cttgccccca ccatgcgcga aggacaggcc taccctgcta acttccccta tccgcttata   24300
ggcaagaccg cagttgacag cattacccag aaaaagtttc tttgcgatcg caccctttgg   24360
cgcatcccat tctccagtaa ctttatgtcc atgggcgcac tcacagacct gggccaaaac   24420
cttctctacg ccaactccgc ccacgcgcta gacatgactt tgaggtgga tcccatggac    24480 gagcccaccc ttctttatgt tttgtttgaa gtctttgacg tggtccgtgt gcaccggccg   24540
caccgcggcg tcatcgaaac cgtgtacctg cgcacgccct tctcggccgg caacgccaca   24600
acataaagaa gcaagcaaca tcaacaacag ctgccgccat gggctccagt gagcaggaac   24660
tgaaagccat tgtcaaagat cttggttgtg ggccatattt ttgggcacc tatgacaagc    24720 gctttccagg cttttgtttct ccacacaagc tcgcctgcgc catagtcaat acggccggtc  24780
gcgagactgg gggcgtacac tggatggcct ttgcctggaa cccgcactca aaaacatgct   24840
acctctttga gcccttttggc ttttctgacc agcgactcaa gcaggtttac cagttttgagt 24900 acgagtcact cctgcgccgt agcgccattg cttcttcccc cgaccgctgt ataacgctgg   24960
aaaagtccac ccaaagcgta caggggccca actcggccgc ctgtggacta ttctgctgca   25020
tgtttctcca cgccttttgcc aactggcccc aaactcccat ggatcacaac cccaccatga   25080
accttattac cgggtaccc aactccatgc tcaacagtcc ccaggtacag cccacccctgc   25140 gtcgcaacca ggaacagctc tacagcttcc tggagcgcca ctcgccctac ttccgcagcc   25200
acagtgcgca gattaggagc gccacttctt tttgtcactt gaaaaacatg taaaaataat    25260
gtactagaga cactttcaat aaaggcaaat gcttttattt gtacactctc gggtgattat   25320 ttaccccccac ccttgccgtc tgccgcgttt aaaaatcaaa ggggttctgc cgcgcatcgc   25380
tatgcgccac tggcagggac acgttgcgat actggtgttt agtgctccac ttaaactcag   25440
gcacaaccat ccgcggcagc tcggtgaagt tttcactcca caggctgcgc accatcacca   25500
acgcgtttag caggtcgggc gccgatatct tgaagtcgca gttggggcct ccgccctgcg   25560
cgcgcgagtt gcgatacaca gggttgcagc actggaacac tatcagcgcc gggtggtgca   25620
cgctggccag cacgctcttg tcggagatca gatccgcgtc caggtcctcc gcgttgctca   25680
gggcgaacgg agtcaacttt ggtagctgcc ttcccaaaaa gggcgcgtgc ccaggctttg   25740
agttgcactc gcaccgtagt ggcatcaaaa ggtgaccgtg cccggtctgg gcgttaggat   25800
acagcgcctg cataaaagcc ttgatctgct taaaagccac ctgagccttt gcgccttcag   25860
agaagaacat gccgcaagac ttgccggaaa actgattggc cggacaggcc gcgtcgtgca   25920
cgcagcacct tgcgtcggtg ttggagatct gcaccacatt tcggcccac cggttcttca   25980 cgatcttggc cttgctagac tgctccttca gcgcgcgctg cccgttttcg ctcgtcacat   26040
ccatttcaat cacgtgctcc ttatttatca taatgcttcc gtgtagacac ttaagctcgc   26100
cttcgatctc agcgcagcgg tgcagccaca acgcgcagcc cgtgggctcg tgatgcttgt   26160
aggtcacctc tgcaaacgac tgcaggtacg cctgcaggaa tcgccccatc atcgtcacaa   26220
aggtcttgtt gctggtgaag gtcagctgca acccgcggtg ctcctcgttc agccaggtct   26280
tgcatacggc cgccagagct tccacttggt caggcagtag tttgaagttc gcctttagat   26340
cgttatccac gtggtacttg tccatcagcg cgcgcgcagc ctccatgccc ttctcccacg   26400
cagacacgat cggcacactc agcggggttca tcaccgtaat ttcactttcc gcttcgctgg   26460
gctcttcctc ttcctcttgc gtccgcatac cacgcgccac tgggtcgtct tcattcagcc   26520
```

```
gccgcactgt gcgcttacct cctttgccat gcttgattag caccggtggg ttgctgaaac  26580
ccaccatttg tagcgccaca tcttctcttt cttcctcgct gtccacgatt acctctggtg  26640
atggcgggcg ctcgggcttg ggagaagggc gcttcttttt cttcttgggc gcaatggcca  26700
aatccgccgc cgaggtcgat ggccgcgggc tgggtgtgcg cggcaccagc gcgtcttgtg  26760
atgagtcttc ctcgtcctcg gactcgatac gccgcctcat ccgcttttt gggggcgccc  26820 ggggaggcgg cggcgacggg gacggggacg acacgtcctc catggttggg ggacgtcgcg  26880
ccgcaccgcg tccgcgctcg ggggtggttt cgcgctgctc ctcttcccga ctggccattt  26940
ccttctccta taggcagaaa aagatcatgg agtcagtcga gaagaaggac agcctaaccg  27000 cccctctga gttcgccacc accgcctcca ccgatgccgc caacgcgcct accaccttcc  27060
ccgtcgaggc accccgctt gaggaggagg aagtgattat cgagcaggac ccaggttttg  27120
taagcgaaga cgacgaggac cgctcagtac caacagagga taaaaagcaa gaccaggaca  27180
acgcagaggc aaacgaggaa caagtcgggc gggggacga aaggcatggc gactacctag  27240
atgtgggaga cgacgtgctg ttgaagcatc tgcagcgcca gtgcgccatt atctgcgacg  27300
cgttgcaaga gcgcagcgat gtgcccctcg ccatagcgga tgtcagcctt gcctacgaac  27360
gccacctatt ctcaccgcgc gtaccccca aacgccaaga aaacggcaca tgcgagccca  27420
acccgcgcct caacttctac cccgtatttg ccgtgccaga ggtgcttgcc acctatcaca  27480 tcttttttcca aaactgcaag ataccctat cctgccgtgc caaccgcagc cgagcggaca  27540
agcagctggc cttgcggcag ggcgctgtca tacctgatat cgcctcgctc aacgaagtgc  27600
caaaaatctt tgagggtctt ggacgcgacg agaagcgcgc ggcaaacgct ctgcaacagg  27660
aaaacagcga aaatgaaagt cactctggag tgttggtgga actcgagggt gacaacgcgc  27720
gcctagccgt actaaaacgc agcatcgagg tcacccactt tgcctacccg gcacttaacc  27780 tacccccaa ggtcatgagc acagtcatga gtgagctgat cgtgcgccgt gcgcagcccc  27840
tggagaggga tgcaaatttg caagaacaaa cagaggaggg cctacccgca gttggcgacg  27900
agcagctagc gcgctggctt caaacgcgcg agcctgccga cttggaggag cgacgcaaac  27960
taatgatggc cgcagtgctc gttaccgtgg agcttgagtg catgcagcgg ttctttgctg  28020
acccggagat gcagcgcaag ctagaggaaa cattgcacta cacctttcga cagggctacg  28080
tacgccaggc ctgcaagatc tccaacgtgg agctctgcaa cctggtctcc tacctttggaa  28140 ttttgcacga aaaccgcctt gggcaaaacg tgcttcattc cacgctcaag ggcgaggcgc  28200
gccgcgacta cgtccgcgac tgcgtttact tatttctatg ctacacctgg cagacggcca  28260
tgggcgtttg gcagcagtgc ttggaggagt gcaacctcaa ggagctgcag aaactgctaa  28320
agcaaaactt gaaggaccta tggacggcct tcaacgagcg ctccgtggcc gcgcacctgg  28380
cggacatcat tttccccgaa cgcctgctta aaaccctgca cagggtctg ccagacttca  28440 ccagtcaaag catgttgcag aactttagga actttatcct agagcgctca ggaatcttgc  28500
ccgccacctg ctgtgcactt cctagcgact tgtgcccat taagtaccgc gaatgccctc  28560
cgccgctttg ggccactgc taccttctgc agctagccaa ctaccttgcc taccactctg  28620
acataatgga agacgtgagc ggtgacggtc tactggagtg tcactgtcgc tgcaacctat  28680
gcaccccgca ccgctccctg gtttgcaatt cgcagctgct taacgaaagt caaattatcg  28740 gtaccttga gctgcagggt ccctcgcctg acgaaaagtc cgcggctccg gggttgaaac  28800
tcactccggg gctgtggacg tcggcttacc ttcgcaaatt tgtacctgag gactaccacg  28860
```

```
cccacgagat taggttctac gaagaccaat cccgcccgcc aaatgcggag cttaccgcct    28920
gcgtcattac ccagggccac attcttggcc aattgcaagc catcaacaaa gcccgccaag    28980
agtttctgct acgaaaggga cgggggggttt acttggaccc ccagtccggc gaggagctca    29040
acccaatccc cccgccgccg cagccctatc agcagcagcc gcgggcccct tgcttcccagg    29100 atggcaccca aaagaagct gcagctgccg ccgccaccca cggacgagga ggaatactgg    29160
gacagtcagg cagaggaggt tttggacgag gaggaggagg acatgatgga agactgggag    29220
agcctagacg aggaagcttc cgaggtcgaa gaggtgtcag acgaaacacc gtcaccctcg    29280
gtcgcattcc cctcgccggc gccccagaaa tcggcaaccg gttccagcat ggctacaacc    29340
tccgctcctc aggcgccgcc ggcactgccc gttcgccgac ccaaccgtag atgggacacc    29400
actggaacca gggccggtaa gtccaagcag ccgccgccgt tagcccaaga gcaacaacag    29460
cgccaaggct accgctcatg gcgcgggcac aagaacgcca tagttgcttg cttgcaagac    29520
tgtgggggca acatctcctt cgcccgccgc tttcttctct accatcacgg cgtggccttc    29580
ccccgtaaca tcctgcatta ctaccgtcat ctctacagcc catactgcac cggcggcagc    29640
ggcagcggca gcaacagcag cggccacaca gaagcaaagg cgaccggata gcaagactct    29700
gacaaagccc aagaaatcca cagcggcggc agcagcagga ggaggagcgc tgcgtctggc    29760
gcccaacgaa cccgtatcga cccgcgagct tagaaacagg attttcccca ctctgtatgc    29820
tatatttcaa cagagcaggg gccaagaaca agagctgaaa ataaaaaaca ggtctctgcg    29880
atccctcacc cgcagctgcc tgtatcacaa aagcgaagat cagcttcggc gcacgctgga    29940
agacgcggag gctctcttca gtaaatactg cgcgctgact cttaaggact agtttcgcgc    30000
cctttctcaa atttaagcgc gaaaactacg tcatctccag cggccacacc cggcgccagc    30060
acctgtcgtc agcgccatta tgagcaagga aattcccacg ccctacatgt ggagttacca    30120
gccacaaatg ggacttgcgg ctggagctgc ccaagactac tcaacccgaa taaactacat    30180
gagcgcggga ccccacatga tatcccgggt caacggaatc cgcgcccacc gaaaccgaat    30240
tctcttggaa caggcggcta ttaccaccac acctcgtaat aaccttaatc cccgtagttg    30300
gcccgctgcc ctggtgtacc aggaaagtcc cgctcccacc actgtggtac ttcccagaga    30360
cgcccaggcc gaagttcaga tgactaactc aggggcgcag cttgcgggcg gctttcgtca    30420
cagggtgcgg tcgcccgggc agggtataac tcacctgaca atcagagggc gaggtattca    30480
gctcaacgac gagtcggtga gctcctcgct tggtctccgt ccggacggga catttcagat    30540
cggcggcgcg ggccgtcctt cattcacgcc tcgtcaggca atcctaactc tgcagacctc    30600
gtcctctgag ccgcgctctg gaggcattgg aactctgcaa tttattgagg agtttgtgcc    30660
atcggtctac tttaacccct ctcgggaccc tccggccac tatccggatc aatttattcc    30720
taactttgac gcggtaaagg actcggcgga cggctacgac tgattattaa gtggagaggc    30780
agagcaactg cgcctgaaac acctggtcca ctgtcgccgc cacaagtgct ttgcccgcga    30840
ctccggtgag ttttgctact ttgaattgcc cgaggatcat atcgaggatc tttgttgcca    30900
tctctgtgct gagtataata aatacagaaa ttaaaatata ctgggctcc tatcgccatc    30960 ctgtaaacgc caccgtcttc acccgcccaa gcaaaccaag gcgaacctta cctggtactt    31020
ttaacatctc tccctctgtg atttacaaca gtttcaaccc agacggagtg agtctacgag    31080
agaacctctc cgagctcagc tactccatca gaaaaacac cacccctcctt acctgccggg    31140 aacgtaccct tatataaaag tcaggcttcc tggatgtcag catctgactt tggccagcac    31200
ctgtcccgcg gatttgttcc agtccaacta cagcgaccca ccctaacaga gatgaccaac    31260
```

```
acaaccaacg cggccgccgc taccggactt acatctacca caaatacacc ccaagtttct    31320
gcctttgtca ataactggga taacttgggc atgtggtggt tctccatagc gcttatgttt    31380
gtatgcctta ttattatgtg gctcatctgc tgcctaaagc gcaaacgcgc ccgaccaccc    31440
atctatagtc ccatcattgt gctacaccca aacaatgatg gaatccatag attggacgga    31500
ctgaaacaca tgttcttttc tcttacagta tgattaaatg agaattttaa ttcgaattta    31560
aatgaattcg agctcggtac ccggggatcc tctagagtcg acctgcagga aatgcaattt    31620
ctgtccagtt tattcagcag cacctccttg ccctcctccc agctctggta ttgcagcttc    31680
ctcctggctg caaactttct ccacaatcta aatggaatgt cagtttcctc ctgttcctgt    31740
ccatccgcac ccactatctt catgttgttg cagatgaagc gcgcaagacc gtctgaagat    31800
accttcaacc ccgtgtatcc atatgacacg gaaaccggtc ctccaactgt gccttttctt    31860
actcctccct ttgtatcccc caatgggttt caagagagtc cccctggggt actctctttg    31920
cgcctatccg aacctctagt tacctccaat ggcatgcttg cgctcaaaat gggcaacggc    31980
ctctctctgg acgaggccgg caaccttacc tcccaaaatg taaccactgt gagcccacct    32040
ctcaaaaaaa ccaagtcaaa cataaacctg gaaatatctg caccccctcac agttacctca    32100 gaagccctaa ctgtggctgc cgccgcacct ctaatggtcg cgggcaacac actcaccatg    32160
caatcacagg ccccgctaac cgtgcacgac tccaaactta gcattgccac ccaaggaccc    32220
ctcacagtgt cagaaggaaa gctagccctg caaacatcag gcccctcac caccaccgat    32280 agcagtaccc ttactatcac tgcctcaccc cctctaacta ctgccactgg tagcttgggc    32340
attgacttga aagagcccat ttatacacaa aatggaaaac taggactaaa gtacggggct    32400
cctttgcatg taacagacga cctaaacact ttgaccgtag caactggtcc aggtgtgact    32460
attaataata cttccttgca aactaaagtt actggagcct tgggttttga ttcacaaggc    32520
aatatgcaac ttaatgtagc aggaggacta aggattgatt ctcaaaacag acgccttata    32580
cttgatgtta gttatccgtt tgatgctcaa aaccaactaa atctaagact aggacagggc    32640
cctcttttta taaactcagc ccacaacttg gatattaact acaacaaagg cctttacttg    32700
tttacagctt caaacaattc caaaaagctt gaggttaacc taagcactgc caaggggttg    32760
atgtttgacg ctacagccat agccattaat gcaggagatg ggcttgaatt tggttcacct    32820
aatgcaccaa acacaaatcc cctcaaaaca aaaattggcc atggcctaga atttgattca    32880
aacaaggcta tggttcctaa actaggaact ggccttagtt ttgacagcac aggtgccatt    32940
acagtaggaa acaaaaataa tgataagcta acccctatgga caggtccaaa accagaagcc    33000
aactgcataa ttgaatacgg gaaagaaaac ccagatagca aactaacttt aatccttgta    33060
aaaaatggag gaattgttaa tggatatgta acgctaatgg gagcctcaga ctatgttaac    33120 accttatttta aaaacaaaaa tgtctccatt aatgtagaat tatactttga tgccactggt    33180
catatattac cagacttatc ttctcttaaa acagatctag aactaaaata caagcaaacc    33240
actcacttta gtgcaagagg ttttatgcca agtactacag cgtatccatt tgtccttcct    33300
aatgcgggaa cagataatga aaattatatt tttggtcaat gctactacaa agcaagcgat    33360
ggcgcccttt ttccgttgga agttactgtt acgcttaata aacgcctgcc agatagtcgc    33420
acatcctatg ttatgacttt tttatggtcc ttgaatgctg gtctagctcc agaaactact    33480
caggcaaccc tcataacctc cccatttacc ttttcctata ttagagaaga tgactgacg    33540 tggaggcggt tcaggcggag gtggctctgg cggtggcgga tcctgtgact gccgcggaga    33600
```

```
ctgtttctgc taataaactc taaagaatcg tttgtgttat gtttcaacgt gtttattttt   33660
caattgcaga aaatttcaag tcattttca ttcagtagta tagccccacc accacatagc    33720
ttatacagat caccgtacct taatcaaact cacagaaccc tagtattcaa cctgccacct   33780
ccctcccaac acacagagta cacagtcctt tctccccggc tggccttaaa aagcatcata   33840
tcatgggtaa cagacatatt cttaggtgtt atattccaca cggtttcctg tcgagccaaa   33900
cgctcatcag tgatattaat aaactccccg ggcagctcac ttaagttcat gtcgctgtcc   33960
agctgctgag ccacaggctg ctgtccaact tgcggttgct taacgggcgg cgaaggagaa   34020
gtccacgcct acatggggt agagtcataa tcgtgcatca ggatagggcg gtggtgctgc    34080
agcagcgcgc gaataaactg ctgccgccgc cgctccgtcc tgcaggaata caacatggca   34140
gtggtctcct cagcgatgat tcgcaccgcc cgcagcataa ggcgccttgt cctccgggca   34200
cagcagcgca ccctgatctc acttaaatca gcacagtaac tgcagcacag caccacaata   34260
ttgttcaaaa tcccacagtg caaggcgctg tatccaaagc tcatggcggg gaccacagaa   34320
cccacgtggc catcatacca caagcgcagg tagattaagt ggcgacccct cataaacacg   34380
ctggacataa acattacctc ttttggcatg ttgtaattca ccacctcccg gtaccatata   34440
aacctctgat taaacatggc gccatccacc accatcctaa accagctggc caaaacctgc   34500
ccgccggcta tacactgcag ggaaccggga ctggaacaat gacagtggag agcccaggac   34560
tcgtaaccat ggatcatcat gctcgtcatg atatcaatgt tggcacaaca caggcacacg   34620
tgcatacact tcctcaggat tacaagctcc tcccgcgtta gaaccatatc ccagggaaca   34680
acccattcct gaatcagcgt aaatcccaca ctgcagggaa gacctcgcac gtaactcacg   34740
ttgtgcattg tcaaagtgtt acattcgggc agcagcggat gatcctccag tatggtagcg   34800
cgggtttctg tctcaaaagg aggtagacga tccctactgt acggagtgcg ccgagacaac   34860
cgagatcgtg ttggtcgtag tgtcatgcca aatggaacgc cggacgtagt catatttcct   34920
gaagcaaaac caggtgcggg cgtgacaaac agatctgcgt ctccggtctc gccgcttaga   34980
tcgctctgtg tagtagttgt agtatatcca ctctctcaaa gcatccaggc gcccctggc    35040
ttcgggttct atgtaaactc cttcatgcgc cgctgccctg ataacatcca ccaccgcaga   35100
ataagccaca cccagccaac ctacacattc gttctgcgag tcacacacgg gaggagcggg   35160
aagagctgga agaaccatgt tttttttttt attccaaaag attatccaaa acctcaaaat   35220
gaagatctat taagtgaacg cgctcccctc cggtggcgtg gtcaaactct acagccaaag   35280
aacagataat ggcatttgta agatgttgca caatggcttc caaaaggcaa acggccctca   35340
cgtccaagtg gacgtaaagg ctaaacccctt cagggtgaat ctcctctata aacattccag   35400
caccttcaac catgcccaaa taattctcat ctcgccacct tctcaatata tctctaagca   35460
aatcccgaat attaagtccg gccattgtaa aaatctgctc cagagcgccc tccaccttca   35520
gcctcaagca gcgaatcatg attgcaaaaa ttcaggttcc tcacagacct gtataagatt   35580
caaaagcgga acattaacaa aaataccgcg atcccgtagg tcccttcgca gggccagctg   35640
aacataatcg tgcaggtctg cacggaccag cgcggccact tccccgccag gaaccatgac   35700
aaaagaaccc acactgatta tgacacgcat actcggagct atgctaacca gcgtagcccc   35760
gatgtaagct ttgttgcatg ggcggcgata taaaatgcaa ggtgctgctc aaaaaatcag   35820
gcaaagcctc gcgcaaaaaa gaaagcacat cgtagtcatg ctcatgcaga taaaggcagg   35880
taagctccgg aaccaccaca gaaaaagaca ccattttttct ctcaaacatg tctgcgggtt   35940
tctgcataaa cacaaaataa aataacaaaa aaacatttaa acattagaag cctgtcttac   36000
```

-continued

| | | | |
|---|---|---|---|
| aacaggaaaa | acaaccctta | taagcataag | acggactacg gccatgccgg cgtgaccgta | 36060 |
| aaaaaactgg | tcaccgtgat | taaaaagcac | caccgacagc tcctcggtca tgtccggagt | 36120 |
| cataatgtaa | gactcggtaa | acacatcagg | ttgattcatc ggtcagtgct aaaaagcgac | 36180 |
| cgaaatagcc | cgggggaata | catacccgca | ggcgtagaga caacattaca gcccccatag | 36240 |
| gaggtataac | aaaattaata | ggagagaaaa | acacataaac acctgaaaaa ccctcctgcc | 36300 |
| taggcaaaat | agcaccctcc | cgctccagaa | caacatacag cgcttcacag cggcagccta | 36360 |
| acagtcagcc | ttaccagtaa | aaaagaaaac | ctattaaaaa aacaccactc gacacggcac | 36420 |
| cagctcaatc | agtcacagtg | taaaaaaggg | ccaagtgcag agcgagtata tataggacta | 36480 |
| aaaaatgacg | taacggttaa | agtccacaaa | aaacacccag aaaaccgcac gcgaacctac | 36540 |
| gcccagaaac | gaaagccaaa | aaacccacaa | cttcctcaaa tcgtcacttc cgttttccca | 36600 |
| cgttacgtaa | cttcccattt | taagaaaact | acaattccca acacatacaa gttactccgc | 36660 |
| cctaaaacct | acgtcacccg | ccccgttccc | acgccccgcg ccacgtcaca aactccaccc | 36720 |
| cctcattatc | atattggctt | caatccaaaa | taaggtatat tattgatgat nnnnnttaat | 36780 |

<210> SEQ ID NO 2
<211> LENGTH: 38828
<212> TYPE: DNA
<213> ORGANISM: Artificial sequence
<220> FEATURE:
<223> OTHER INFORMATION: Recombinant adenovirus Ad5/3-RGD E3 GMCSF D24,
      n=A,C,G,T
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (38819)..(38823)
<223> OTHER INFORMATION: n is a, c, g, or t

<400> SEQUENCE: 2

| | | | |
|---|---|---|---|
| taaggatccn | nncctgtcct | cgaccgatgc | ccttgagagc cttcaaccca gtcagctcct | 60 |
| tccggtgggc | gcggggcatg | actatcgtcg | ccgcacttat gactgtcttc tttatcatgc | 120 |
| aactcgtagg | acaggtgccg | gcagcgctct | gggtcatttt cggcgaggac cgctttcgct | 180 |
| ggagcgcgac | gatgatcggc | ctgtcgcttg | cggtattcgg aatcttgcac gccctcgctc | 240 |
| aagccttcgt | cactggtccc | gccaccaaac | gtttcggcga agcaggcc attatcgccg | 300 |
| gcatggcggc | cgacgcgctg | ggctacgtct | tgctggcgtt cgcgacgcga ggctggatgg | 360 |
| ccttccccat | tatgattctt | ctcgcttccg | gcggcatcgg gatgcccgcg ttgcaggcca | 420 |
| tgctgtccag | gcaggtagat | gacgaccatc | agggacagct tcaaggatcg ctcgcggctc | 480 |
| ttaccagcct | aacttcgatc | actggaccgc | tgatcgtcac ggcgatttat gccgcctcgg | 540 |
| cgagcacatg | gaacgggttg | gcatggattg | taggcgccgc cctataccct tgtctgcctcc | 600 |
| ccgcgttgcg | tcgcggtgca | tggagccggg | ccacctcgac ctgaatggaa gccggcggca | 660 |
| cctcgctaac | ggattcacca | ctccaagaat | tggagccaat caattcttgc ggagaactgt | 720 |
| gaatgcgcaa | accaaccctt | ggcagaacat | atccatcgcg tccgccatct ccagcagccg | 780 |
| cacgcggcgc | atctcgggca | gcgttgggtc | ctggccacgg gtgcgcatga tcgtgctcct | 840 |
| gtcgttgagg | acccggctag | gctggcgggg | ttgccttact ggttagcaga atgaatcacc | 900 |
| gatacgcgag | cgaacgtgaa | gcgactgctg | ctgcaaaacg tctgcgacct gagcaacaac | 960 |
| atgaatggtc | ttcggtttcc | gtgtttcgta | aagtctggaa acgcggaagt cagcgccctg | 1020 |

```
caccattatg ttccggatct gcatcgcagg atgctgctgg ctaccctgtg aacacctac    1080
atctgtatta acgaagcgct ggcattgacc ctgagtgatt tttctctggt cccgccgcat   1140
ccataccgcc agttgtttac cctcacaacg ttccagtaac cgggcatgtt catcatcagt   1200
aacccgtatc gtgagcatcc tctctcgttt catcggtatc attccccca tgaacagaaa    1260
ttccccctta cacggaggca tcaagtgacc aaacaggaaa aaaccgccct taacatggcc   1320
cgctttatca gaagccagac attaacgctt ctggagaaac tcaacgagct ggacgcggat   1380
gaacaggcag acatctgtga atcgcttcac gaccacgctg atgagcttta ccgcagctgc   1440
ctcgcgcgtt tcggtgatga cggtgaaaac ctctgacaca tgcagctccc ggagacggtc   1500
acagcttgtc tgtaagcgga tgccgggagc agacaagccc gtcagggcgc gtcagcgggt   1560
gttggcgggt gtcggggcgc agccatgacc cagtcacgta gcgatagcgg agtgtatact   1620
ggcttaacta tgcggcatca gagcagattg tactgagagt gcaccatatg cggtgtgaaa   1680
taccgcacag atgcgtaagg agaaaatacc gcatcaggcg ctcttccgct tcctcgctca   1740
ctgactcgct gcgctcggtc gttcggctgc ggcgagcggt atcagctcac tcaaaggcgg   1800
taatacggtt atccacagaa tcaggggata acgcaggaaa gaacatgtga gcaaaaggcc   1860
agcaaaaggc caggaaccgt aaaaaggccg cgttgctggc gtttttccat aggctccgcc   1920
cccctgacga gcatcacaaa aatcgacgct caagtcagag gtggcgaaac ccgacaggac   1980
tataaagata ccaggcgttt ccccctggaa gctccctcgt gcgctctcct gttccgaccc   2040
tgccgcttac cggatacctg tccgcctttc tcccttcggg aagcgtggcg ctttctcata   2100
gctcacgctg taggtatctc agttcggtgt aggtcgttcg ctccaagctg gctgtgtgc    2160
acgaacccc cgttcagccc gaccgctgcg ccttatccgg taactatcgt cttgagtcca    2220
acccggtaag acacgactta tcgccactgg cagcagccac tggtaacagg attagcagag    2280
cgaggtatgt aggcggtgct acagagttct tgaagtggtg gcctaactac ggctacacta    2340
gaaggacagt atttggtatc tgcgctctgc tgaagccagt taccttcgga aaaagagttg    2400
gtagctcttg atccgcaaa caaccaccg ctggtagcgg tggttttttt gtttgcaagc     2460
agcagattac gcgcagaaaa aaaggatctc aagaagatcc tttgatcttt tctacggggt    2520
ctgacgctca gtggaacgaa aactcacgtt aagggatttt ggtcatgaga ttatcaaaaa    2580
ggatcttcac ctagatcctt ttaaattaaa aatgaagttt aaatcaatc taagtatat      2640
atgagtaaac ttggtctgac agttaccaat gcttaatcag tgaggcacct atctcagcga    2700
tctgtctatt tcgttcatcc atagttgcct gactccccgt cgtgtagata actacgatac    2760
gggagggctt accatctggc cccagtgctg caatgatacc gcgagaccca cgctcaccgg    2820
ctccagattt atcagcaata accagccag ccggaagggc cgagcgcaga agtggtcctg     2880
caactttatc cgcctccatc cagtctatta attgttgccg ggaagctaga gtaagtagtt    2940
cgccagttaa tagtttgcgc aacgttgttg ccattgctgc agccatgaga ttatcaaaaa    3000
ggatcttcac ctagatcctt ttcacgtaga aagccagtcc gcagaaacgg tgctgacccc    3060
ggatgaatgt cagctactgg gctatctgga caagggaaaa cgcaagcgca aagaaaagc     3120
aggtagcttg cagtgggctt acatggcgat agctagactg gcggtttta tggacagcaa    3180
gcgaaccgga attgccagct ggggcgccct ctggtaaggt tgggaagccc tgcaaagtaa    3240
actggatggc tttctcgccg ccaaggatct gatggcgcag gggatcaagc tctgatcaag   3300
agacaggatg aggatcgttt cgcatgattg aacaagatgg attgcacgca ggttctccgg   3360
```

```
ccgcttgggt ggagaggcta ttcggctatg actgggcaca acagacaatc ggctgctctg    3420
atgccgccgt gttccggctg tcagcgcagg ggcgcccggt tcttttgtc aagaccgacc      3480 tgtccggtgc cctgaatgaa ctgcaagacg aggcagcgcg gctatcgtgg ctggccacga    3540
cgggcgttcc ttgcgcagct gtgctcgacg ttgtcactga agcgggaagg gactggctgc    3600
tattgggcga agtgccgggg caggatctcc tgtcatctca ccttgctcct gccgagaaag    3660
tatccatcat ggctgatgca atgcggcggc tgcatacgct tgatccggct acctgcccat    3720
tcgaccacca agcgaaacat cgcatcgagc gagcacgtac tcggatggaa gccggtcttg    3780
tcgatcagga tgatctggac gaagagcatc aggggctcgc gccagccgaa ctgttcgcca    3840
ggctcaaggc gagcatgccc gacggcgagg atctcgtcgt gacccatggc gatgcctgct    3900
tgccgaatat catggtggaa aatggccgct tttctggatt catcgactgt ggccggctgg    3960
gtgtggcgga ccgctatcag gacatagcgt tggctacccg tgatattgct gaagagcttg    4020
gcggcgaatg ggctgaccgc ttcctcgtgc tttacggtat cgccgctccc gattcgcagc    4080
gcatcgcctt ctatcgcctt cttgacgagt tcttctgaat tttgttaaaa tttttgttaa     4140
atcagctcat tttttaacca ataggccgaa atcggcaaca tcccttataa atcaaaagaa     4200
tagaccgcga taggggttgag tgttgttcca gtttggaaca agagtccact attaaagaac    4260
gtggactcca acgtcaaagg gcgaaaaacc gtctatcagg gcgatggccc actacgtgaa     4320
ccatcaccca aatcaagttt tttgcggtcg aggtgccgta aagctctaaa tcggaaccct     4380
aaagggagcc cccgatttag agcttgacgg ggaaagccgg cgaacgtggc gagaaaggaa     4440
gggaagaaag cgaaaggagc gggcgctagg gcgctggcaa gtgtagcggt cacgctgcgc    4500
gtaaccacca cacccgcgcg cttaatgcgc cgctacaggg cgcgtccatt cgccattcag    4560
gatcgaatta attcttaatt aacatcatca ataatatacc ttattttgga ttgaagccaa     4620
tatgataatg aggggggtgga gtttgtgacg tggcgcgggg cgtgggaacg ggcgggtga    4680 cgtagtagtg tggcggaagt gtgatgttgc aagtgtggcg gaacacatgt aagcgacgga    4740
tgtggcaaaa gtgacgttt tggtgtgcgc cggtgtacac aggaagtgac aattttcgcg     4800
cggttttagg cggatgttgt agtaaatttg ggcgtaaccg agtaagattt ggccatttcc    4860
gcgggaaaac tgaataagag gaagtgaaat ctgaataatt ttgtgttact catagcgcgt     4920
aatatttgtc tagggccgcg gggactttga ccgtttacgt ggagactcgc ccaggtgttt    4980
ttctcaggtg ttttccgcgt tccgggtcaa agttggcgtt ttattattat agtcagctga    5040
cgtgtagtgt atttatacccc ggtgagttcc tcaagaggcc actcttgagt gccagcgagt   5100
agagttttct cctccgagcc gctccgacac cgggactgaa aatgagacat attatctgcc    5160
acggaggtgt tattaccgaa gaaatggccg ccagtctttt ggaccagctg atcgaagagg    5220
tactggctga taatcttcca cctcctagcc attttgaacc cctacccctt cacgaactgt    5280
atgatttaga cgtgacggcc cccgaagatc ccaacgagga ggcggtttcg cagattttc    5340 ccgactctgt aatgttggcg gtgcaggaag ggattgactt actcactttt ccgccggcgc    5400
ccggttctcc ggagccgcct caccttttccc ggcagcccga gcagccggag cagagagcct    5460
tgggtccggt ttctatgcca aaccttgtac cggaggtgat cgatccaccc agtgacgacg    5520
aggatgaaga gggtgaggag tttgtgttag attatgtgga gcaccccggg cacggttgca    5580
ggtcttgtca ttatcaccgg aggaaatacgg gggacccaga tattatgtgt tcgctttgct    5640
atatgaggac ctgtggcatg tttgtctaca gtaagtgaaa attatgggca gtgggtgata    5700
gagtggtggg tttggtgtgg taatttttt tttaattttt acagttttgt ggttttaaaga    5760
```

```
attttgtatt gtgatttttt taaaaggtcc tgtgtctgaa cctgagcctg agcccgagcc   5820
agaaccggag cctgcaagac ctacccgccg tcctaaaatg gcgcctgcta tcctgagacg   5880
cccgacatca cctgtgtcta gagaatgcaa tagtagtacg gatagctgtg actccggtcc   5940
ttctaacaca cctcctgaga tacaccggt ggtcccgctg tgccccatta aaccagttgc    6000
cgtgagagtt ggtgggcgtc gccaggctgt ggaatgtatc gaggacttgc ttaacgagcc   6060
tgggcaacct ttggacttga gctgtaaacg ccccaggcca taaggtgtaa acctgtgatt   6120
gcgtgtgtgg ttaacgcctt tgtttgctga atgagttgat gtaagtttaa taaagggtga   6180
gataatgttt aacttgcatg gcgtgttaaa tggggcgggg cttaaagggt atataatgcg   6240
ccgtgggcta atcttggtta catctgacct catggaggct tgggagtgtt tggaagatt t   6300
ttctgctgtg cgtaacttgc tggaacagag ctctaacagt acctcttggt tttgaggtt    6360
tctgtggggc tcatcccagg caaagttagt ctgcagaatt aaggaggatt acaagtggga   6420
atttgaagag cttttgaaat cctgtggtga gctgtttgat tctttgaatc tgggtcacca   6480
ggcgcttttc caagagaagg tcatcaagac tttggatttt tccacaccgg ggcgcgctgc   6540
ggctgctgtt gctttttttga gttttataaa ggataaatgg agcgaagaaa cccatctgag  6600
cgggggggtac ctgctggatt ttctggccat gcatctgtgg agagcggttg tgagacacaa  6660
gaatcgcctg ctactgttgt cttccgtccg cccggcgata ataccgacgg aggagcagca   6720
gcagcagcag gaggaagcca ggcggcggcg gcaggagcag agcccatgga acccgagagc   6780
cggcctggac cctcgggaat gaatgttgta caggtggctg aactgtatcc agaactgaga   6840
cgcattttga caattacaga ggatgggcag gggctaaagg gggtaaagag ggagcggggg   6900
gcttgtgagg ctacagagga ggctaggaat ctagctttta gcttaatgac cagacaccgt   6960
cctgagtgta ttacttttca acagatcaag gataattgcg ctaatgagct tgatctgctg   7020
gcgcagaagt attccataga gcagctgacc acttactggc tgcagccagg ggatgatttt   7080
gaggaggcta ttagggtata tgcaaaggtg gcacttaggc cagattgcaa gtacaagatc   7140
agcaaacttg taaatatcag gaattgttgc tacatttctg ggaacggggc cgaggtggag   7200
atagatacgg aggatagggt ggcctttaga tgtagcatga taaatatgtg gccgggggtg   7260
cttggcatgg acggggtggt tattatgaat gtaaggttta ctggccccaa ttttagcggt   7320
acggttttcc tggccaatac caaccttatc ctacacggtg taagcttcta tgggtttaac   7380
aatacctgtg tggaagcctg gaccgatgta agggttcggg gctgtgcctt ttactgctgc   7440
tggaaggggg tggtgtgtcg ccccaaaagc agggcttcaa ttaagaaatg cctctttgaa   7500
aggtgtacct tgggtatcct gtctgagggt aactccaggg tgcgccacaa tgtggcctcc   7560
gactgtggtt gcttcatgct agtgaaaagc gtggctgtga ttaagcataa catggtatgt   7620
ggcaactgcg aggacagggc ctctcagatg ctgacctgct cggacggcaa ctgtcacctg   7680
ctgaagacca ttcacgtagc cagccactct cgcaaggcct ggccagtgtt tgagcataac   7740
atactgaccc gctgttcctt gcatttgggt aacaggaggg gggtgttcct accttaccaa   7800
tgcaatttga gtcacactaa gatattgctt gagcccgaga gcatgtccaa ggtgaacctg   7860
aacgggtgt  ttgacatgac catgaagatc tggaaggtgc tgaggtacga tgagacccgc   7920
accaggtgca gaccctgcga gtgtggcggt aaacatatta ggaaccagcc tgtgatgctg   7980
gatgtgaccg aggagctgag gcccgatcac ttggtgctgg cctgcacccg cgctgagttt   8040
ggctctagcg atgaagatac agattgaggt actgaaatgt gtgggcgtgg cttaagggtg   8100
```

```
ggaaagaata tataaggtgg gggtcttatg tagttttgta tctgttttgc agcagccgcc   8160
gccgccatga gcaccaactc gtttgatgga agcattgtga gctcatattt gacaacgcgc   8220
atgcccccat gggccggggt gcgtcagaat gtgatgggct ccagcattga tggtcgcccc   8280
gtcctgcccg caaactctac taccttgacc tacgagaccg tgtctggaac gccgttggag   8340
actgcagcct ccgccgccgc ttcagccgct gcagccaccg cccgcgggat tgtgactgac   8400
tttgctttcc tgagcccgct tgcaagcagt gcagcttccc gttcatccgc ccgcgatgac   8460
aagttgacgg ctcttttggc acaattggat tctttgaccc gggaacttaa tgtcgtttct   8520
cagcagctgt tggatctgcg ccagcaggtt tctgccctga aggcttcctc ccctcccaat   8580
gcggtttaaa acataaataa aaaaccagac tctgtttgga tttggatcaa gcaagtgtct   8640
tgctgtcttt atttaggggt tttgcgcgcg cggtaggccc gggaccagcg gtctcggtcg   8700
ttgagggtcc tgtgtatttt ttccaggacg tggtaaaggt gactctggat gttcagatac   8760
atgggcataa gcccgtctct ggggtggagg tagcaccact gcagagcttc atgctgcggg   8820
gtggtgttgt agatgatcca gtcgtagcag gagcgctggg cgtggtgcct aaaaatgtct   8880
ttcagtagca agctgattgc caggggcagg cccttggtgt aagtgtttac aaagcggtta   8940
agctgggatg ggtgcatacg tggggatatg agatgcatct tggactgtat ttttaggttg   9000
gctatgttcc cagccatatc cctccgggga ttcatgttgt gcagaaccac cagcacagtg   9060
tatccggtgc acttgggaaa tttgtcatgt agcttagaag gaaatgcgtg gaagaacttg   9120
gagacgccct tgtgacctcc aagattttcc atgcattcgt ccataatgat ggcaatgggc   9180
ccacgggcgg cggcctgggc gaagatattt ctgggatcac taacgtcata gttgtgttcc   9240
aggatgagat cgtcataggc catttttaca aagcgcgggc ggagggtgcc agactgcggt   9300
ataatggttc catccggccc aggggcgtag ttaccctcac agatttgcat ttcccacgct   9360
ttgagttcag atgggggat catgtctacc tgcggggcga tgaagaaaac ggtttccggg   9420
gtaggggaga tcagctggga agaaagcagg ttcctgagca gctgcgactt accgcagccg   9480
gtgggcccgt aaatcacacc tattaccggg tgcaactggt agttaagaga gctgcagctg   9540
ccgtcatccc tgagcagggg ggccacttcg ttaagcatgt ccctgactcg catgttttcc   9600
ctgaccaaat ccgccagaag gcgctcgccg cccagcgata gcagttcttg caaggaagca   9660 aagttttttca acggtttgag accgtccgcc gtaggcatgc ttttgagcgt ttgaccaagc   9720
agttccaggc ggtcccacag ctcggtcacc tgctctacgg catctcgatc cagcatatct   9780
cctcgtttcg cggttgggg cggctttcgc tgtacggcag tagtcggtgc tcgtccagac   9840
gggccagggt catgtctttc cacgggcgca gggtcctcgt cagcgtagtc tgggtcacgg   9900
tgaaggggtg cgctccgggc tgcgcgctgg ccagggtgcg cttgaggctg gtcctgctgg   9960
tgctgaagcg ctgccggtct tcgccctgcg cgtcggccag gtagcatttg accatggtgt  10020
catagtccag cccctccgcg gcgtggccct tggcgcgcag cttgcccttg gaggaggcgc  10080
cgcacgaggg gcagtgcaga cttttgaggg cgtagagctt gggcgcgaga aataccgatt  10140
ccggggagta ggcatccgcg ccgcaggccc cgcagacggt ctcgcattcc acgagccagg  10200
tgagctctgg ccgttcgggg tcaaaaacca ggtttccccc atgcttttg atgcgttct    10260 tacctctggt ttccatgagc cggtgtccac gctcggtgac gaaaaggctg tccgtgtccc  10320
cgtatacaga cttgagaggc ctgtcctcga gcggtgttcc gcggtcctcc tcgtatagaa  10380
actcggacca ctctgagaca aaggctcgcg tccaggccag cacgaaggag gctaagtggg  10440
aggggtagcg gtcgttgtcc actaggggt ccactcgctc cagggtgtga agacacatgt   10500
```

```
cgccctcttc ggcatcaagg aaggtgattg gtttgtaggt gtaggccacg tgaccgggtg    10560
ttcctgaagg ggggctataa aagggggtgg gggcgcgttc gtcctcactc tcttccgcat    10620
cgctgtctgc gagggccagc tgttggggtg agtactccct ctgaaaagcg ggcatgactt    10680
ctgcgctaag attgtcagtt tccaaaaacg aggaggattt gatattcacc tggcccgcgg    10740
tgatgccttt gagggtggcc gcatccatct ggtcagaaaa gacaatcttt tgttgtcaa     10800 gcttggtggc aaacgacccg tagagggcgt tggacagcaa cttggcgatg gagcgcaggg    10860
tttggttttt gtcgcgatcg gcgcgctcct tggccgcgat gtttagctgc acgtattcgc    10920
gcgcaacgca ccgccattcg ggaaagacgg tggtgcgctc gtcgggcacc aggtgcacgc    10980
gccaaccgcg gttgtgcagg gtgacaaggt caacgctggt ggctacctct ccgcgtaggc    11040
gctcgttggt ccagcagagg cggccgcsct tgcgcgagca gaatggcggt aggggtctca   11100
gctgcgtctc gtccgggggg tctgcgtcca cggtaaagac cccgggcagc aggcgcgcgt    11160
cgaagtagtc tatcttgcat ccttgcaagt ctagcgcctg ctgccatgcg cgggcggcaa    11220
gcgcgcgctc gtatgggttg agtgggggac cccatggcat ggggtgggtg agcgcggagg    11280
cgtacatgcc gcaaatgtcg taaacgtaga ggggctctct gagtattcca agatatgtag    11340
ggtagcatct tccaccgcgg atgctggcgc gcacgtaatc gtatagttcg tgcgagggag    11400
cgaggaggtc gggaccgagg ttgctacggg cgggctgctc tgctcggaag actatctgcc    11460
tgaagatggc atgtgagttg gatgatatgg ttggacgctg gaagacgttg aagctggcgt    11520
ctgtgagacc taccgcgtca cgcacgaagg aggcgtagga gtcgcgcagc ttgttgacca    11580
gctcggcggt gacctgcacg tctagggcgc agtagtccag ggtttccttg atgatgtcat    11640
acttatcctg tccctttttt ttccacagct cgcggttgag acaaactct tcgcggtctt     11700 tccagtactc ttggatcgga aacccgtcgg cctccgaacg gtaagagcct agcatgtaga    11760
actggttgac ggcctggtag gcgcagcatc ccttttctac gggtagcgcg tatgcctgcg    11820
cggccttccg gagcgaggtg tgggtgagcg caaaggtgtc cctgaccatg actttgaggt    11880
actggtattt gaagtcagtg tcgtcgcatc cgccctgctc ccagagcaaa aagtccgtgc    11940 gcttttttgga acgcggattt ggcagggcga aggtgacatc gttgaagagt atctttcccg   12000
cgcgaggcat aaagttgcgt gtgatgcgga agggtcccgg cacctcggaa cggttgttaa    12060
ttacctgggc ggcgagcacg atctcgtcaa agccgttgat gttgtggccc acaatgtaaa    12120
gttccaagaa gcgcgggatg cccttgatgg aaggcaattt tttaagttcc tcgtaggtga    12180
gctcttcagg ggagctgagc ccgtgctctg aaagggccca gtctgcaaga tgagggttgg    12240
aagcgacgaa tgagctccac aggtcacggg ccattagcat ttgcaggtgg tcgcgaaagg    12300
tcctaaactg gcgacctatg gccattttt ctggggtgat gcagtagaag gtaagcgggt     12360
cttgttccca gcggtcccat ccaaggttcg cggctaggtc tcgcgcggca gtcactagag    12420
gctcatctcc gccgaacttc atgaccagca tgaagggcac gagctgcttc ccaaaggccc    12480
ccatccaagt ataggtctct acatcgtagg tgacaaagag acgctcggtg cgaggatgcg    12540
agccgatcgg gaagaactgg atctcccgcc accaattgga ggagtggcta ttgatgtggt    12600
gaaagtagaa gtccctgcga cgggccgaac actcgtgctg gcttttgtaa aaacgtgcgc    12660
agtactggca gcggtgcacg ggctgtacat cctgcacgag gttgacctga cgaccgcgca    12720
caaggaagca gagtgggaat ttgagcccct cgcctggcgg gtttggctgg tggtcttcta    12780
cttcggctgc ttgtccttga ccgtctggct gctcgagggg agttacggtg gatcggacca    12840
```

```
ccacgccgcg cgagcccaaa gtccagatgt ccgcgcgcgg cggtcggagc ttgatgacaa    12900
catcgcgcag atgggagctg tccatggtct ggagctcccg cggcgtcagg tcaggcggga    12960
gctcctgcag gtttacctcg catagacggg tcagggcgcg ggctagatcc aggtgatacc    13020
taatttccag gggctggttg gtggcggcgt cgatggcttg caagaggccg catcccgcg     13080
gcgcgactac ggtaccgcgc ggcgggcggt gggccgcggg ggtgtccttg gatgatgcat    13140
ctaaaagcgg tgacgcgggc gagcccccgg aggtaggggg ggctccggac ccgccgggag    13200
aggggggcagg ggcacgtcgg cgccgcgcgc gggcaggagc tggtgctgcg cgcgtaggtt   13260
gctggcgaac gcgacgacgc ggcggttgat ctcctgaatc tggcgcctct gcgtgaagac    13320
gacgggcccg gtgagcttga gcctgaaaga gagttcgaca gaatcaattt cggtgtcgtt    13380
gacggcggcc tggcgcaaaa tctcctgcac gtctcctgag ttgtcttgat aggcgatctc    13440
ggccatgaac tgctcgatct cttcctcctg gagatctccg cgtccggctc gctccacggt    13500
ggcggcgagg tcgttggaaa tgcgggccat gagctgcgag aaggcgttga ggcctccctc    13560
gttccagacg cggctgtaga ccacgccccc ttcggcatcg cgggcgcgca tgaccacctg    13620
cgcgagattg agctccacgt gccgggcgaa gacggcgtag tttcgcaggc gctgaaagag    13680
gtagttgagg gtggtggcgg tgtgttctgc cacgaagaag tacataaccc agcgtcgcaa    13740
cgtggattcg ttgatatccc ccaaggcctc aaggcgctcc atggcctcgt agaagtccac    13800
ggcgaagttg aaaaactggg agttgcgcgc cgacacggtt aactcctcct ccagaagacg    13860
gatgagctcg gcgacagtgt cgcgcacctc gcgctcaaag gctacagggg cctcttcttc    13920
ttcttcaatc tcctcttcca taagggcctc cccttcttct tcttctggcg gcggtggggg    13980
agggggggaca cggcggcgac gacggcgcac cgggaggcgg tcgacaaagc gctcgatcat    14040
ctccccgcgg cgacgcgca tggtctcggt gacggcgcgg ccgttctcgc gggggcgcag     14100
ttggaagacg ccgcccgtca tgtcccggtt atgggttggc ggggggctgc catgcggcag    14160
ggatacggcc taacgatgc atctcaacaa ttgttgtgta ggtactccgc cgccgaggga     14220
cctgagcgag tccgcatcga ccggatcgga aaacctctcg agaaaggcgt ctaaccagtc    14280
acagtcgcaa ggtaggctga gcaccgtggc gggcggcagc gggcggcggt cggggttgtt    14340
tctggcggag gtgctgctga tgatgtaatt aaagtaggcg gtcttgagac ggcggatggt    14400
cgacagaagc accatgtcct ggggtccggc ctgctgaatg cgcaggcggt cggccatgcc    14460
ccaggcttcg ttttgacatc ggcgcaggtc tttgtagtag tcttgcatga gccttttctac   14520
cggcacttct tcttctcctt cctcttgtcc tgcatctctt gcatctatcg ctgcggcggc    14580
ggcggagttt ggccgtaggt ggcgccctct tcctcccatg cgtgtgaccc cgaagcccct    14640
catcggctga agcagggcta ggtcggcgac aacgcgctcg gctaatatgg cctgctgcac    14700
ctgcgtgagg gtagactgga agtcatccat gtccacaaag cggtggtatg cgcccgtgtt    14760
gatggtgtaa gtgcagttgg ccataacgga ccagttaacg gtctggtgac ccggctgcga    14820
gagctcggtg tacctgagac gcgagtaagc cctcgagtca aatacgtagt cgttgcaagt    14880
ccgcaccagg tactggtatc ccaccaaaaa gtgcggcggc ggctggcggt agagggggcca   14940
gcgtaggggtg gccggggctc cgggggcgag atcttccaac ataaggcgat gatatccgta   15000
gatgtacctg gacatccagg tgatgccggc ggcggtggtg gaggcgcgcg gaaagtcgcg    15060
gacgcggttc cagatgttgc gcagcggcaa aaagtgctcc atggtcggga cgctctggcc    15120
ggtcaggcgc gcgcaatcgt tgacgctcta ccgtgcaaaa ggagagcctg taagcgggca    15180
ctcttccgtg gtctggtgga taaattcgca agggtatcat ggcggacgac cggggttcga    15240
```

```
gccccgtatc cggccgtccg ccgtgatcca tgcggttacc gcccgcgtgt cgaacccagg    15300
tgtgcgacgt cagacaacgg gggagtgctc cttttggctt ccttccaggc gcggcggctg    15360
ctgcgctagc ttttttggcc actggccgcg cgcagcgtaa gcggttaggc tggaaagcga    15420
aagcattaag tggctcgctc cctgtagccg gagggttatt ttccaagggt tgagtcgcgg    15480 gaccccggt  tcgagtctcg gaccggccgg actgcggcga acgggggttt gcctccccgt     15540
catgcaagac cccgcttgca aattcctccg gaaacaggga cgagcccctt ttttgctttt    15600
cccagatgca tccggtgctg cggcagatgc gccccctcc tcagcagcgg caagagcaag     15660
agcagcggca gacatgcagg gcaccctccc ctcctcctac cgcgtcagga ggggcgacat    15720
ccgcggttga cgcggcagca gatggtgatt acgaaccccc gcggcgccgg gcccggcact    15780
acctggactt ggaggagggc gagggcctgg cgcggctagg agcgccctct cctgagcggt    15840
acccaagggt gcagctgaag cgtgatacgc gtgaggcgta cgtgccgcgg cagaacctgt    15900
ttcgcgaccg cgagggagag gagcccgagg agatgcggga tcgaaagttc cacgcagggc    15960
gcgagctgcg gcatggcctg aatcgcgagc ggttgctgcg cgaggaggac tttgagcccg    16020
acgcgcgaac cggggattagt cccgcgcgcg cacacgtggc ggccgccgac ctggtaaccg    16080
catacgagca gacggtgaac caggagatta actttcaaaa aagctttaac aaccacgtgc    16140
gtacgcttgt ggcgcgcgag gaggtggcta taggactgat gcatctgtgg gactttgtaa    16200
gcgcgctgga gcaaaaccca aatagcaagc cgctcatggc gcagctgttc cttatagtgc    16260
agcacagcag ggacaacgag gcattcaggg atgcgctgct aaacatagta gagcccgagg    16320
gccgctggct gctcgatttg ataaacatcc tgcagagcat agtggtgcag gagcgcagct    16380
tgagcctggc tgacaaggtg gccgccatca actattccat gcttagcctg gcaagttttt    16440
acgcccgcaa gatataccat accccttacg ttcccataga caaggaggta aagatcgagg    16500
ggttctacat gcgcatggcg ctgaaggtgc ttaccttgag cgacgacctg ggcgtttatc    16560
gcaacgagcg catccacaag gccgtgagcg tgagccggcg gcgcgagctc agcgaccgcg    16620
agctgatgca cagcctgcaa agggccctgg ctggacgggg cagcggcgat agagaggccg    16680
agtcctactt tgacgcgggc gctgacctgc gctgggcccc aagccgacgc gccctggagg    16740
cagctggggc cggacctggg ctggcggtgg cacccgcgcg cgctggcaac gtcggcggcg    16800
tggaggaata tgacgaggac gatgagtacg agccagagga cggcgagtac taagcggtga    16860
tgtttctgat cagatgatgc aagacgcaac ggacccggcg gtgcgggcgg cgctgcagag    16920
ccagccgtcc ggccttaact ccacggacga ctggcgccag gtcatggacc gcatcatgtc    16980
gctgactgcg cgcaatcctg acgcgttccg gcagcagccg caggccaacc ggctctccgc    17040
aattctggaa gcggtggtcc cggcgcgcgc aaacccacg cacgagaagg tgctggcgat     17100
cgtaaacgcg ctggccgaaa acagggccat ccggcccgac gaggccggcc tggtctacga    17160
cgcgctgctt cagcgcgtgg ctcgttacaa cagcggcaac gtgcagacca acctggaccg    17220
gctggtgggg gatgtgcgcg aggccgtggc gcagcgtgag cgcgcgcagc agcagggcaa    17280
cctgggctcc atggttgcac taaacgcctt cctgagtaca cagcccgcca acgtgccgcg    17340
gggacaggag gactacacca actttgtgag cgcactgcgg ctaatggtga ctgagacacc    17400
gcaaagtgag gtgtaccagt ctgggccaga ctatttttc cagaccagta gacaaggcct     17460
gcagaccgta aacctgagcc aggctttcaa aaacttgcag gggctgtggg gggtgcgggc    17520
tcccacaggc gaccgcgcga ccgtgtctag cttgctgacg cccaactcgc gcctgttgct    17580
```

```
gctgctaata gcgcccttca cggacagtgg cagcgtgtcc cgggacacat acctaggtca    17640
cttgctgaca ctgtaccgcg aggccatagg tcaggcgcat gtggacgagc atactttcca    17700
ggagattaca agtgtcagcc gcgcgctggg gcaggaggac acgggcagcc tggaggcaac    17760
cctaaactac ctgctgacca accggcggca gaagatcccc tcgttgcaca gtttaaacag    17820
cgaggaggag cgcattttgc gctacgtgca gcagagcgtg agccttaacc tgatgcgcga    17880
cggggtaacg cccagcgtgg cgctggacat gaccgcgcgc aacatggaac cgggcatgta    17940
tgcctcaaac cggccgttta tcaaccgcct aatggactac ttgcatcgcg cggccgccgt    18000
gaaccccgag tatttcacca atgccatctt gaacccgcac tggctaccgc cccctggttt    18060
ctacaccggg ggattcgagg tgcccgaggg taacgatgga ttcctctggg acgacataga    18120
cgacagcgtg ttttcccgc aaccgcagac cctgctagag ttgcaacagc gcagcaggc     18180 agaggcggcg ctgcgaaagg aaagcttccg caggccaagc agcttgtccg atctaggcgc    18240
tgcggccccg cggtcagatg ctagtagccc atttccaagc ttgatagggt ctcttaccag    18300
cactcgcacc acccgcccgc gcctgctggg cgaggaggag tacctaaaca actcgctgct    18360
gcagccgcag cgcgaaaaaa acctgcctcc ggcatttccc aacaacggga tagagagcct    18420
agtggacaag atgagtagat ggaagacgta cgcgcaggag cacagggacg tgccaggccc    18480
gcgcccgccc acccgtcgtc aaaggcacga ccgtcagcgg ggtctggtgt gggaggacga    18540
tgactcggca gacgacagca gcgtcctgga tttgggaggg agtggcaacc cgtttgcgca    18600
ccttcgcccc aggctgggga gaatgttta aaaaaaaaa agcatgatgc aaaataaaaa      18660
actcaccaag gccatggcac cgagcgttgg ttttcttgta ttccccttag tatgcggcgc    18720
gcggcgatgt atgaggaagg tcctcctccc tcctacgaga gtgtggtgag cgcggcgcca    18780
gtggcggcgg cgctgggttc tcccttcgat gctcccctgg accgccgtt tgtgcctccg     18840 cggtacctgc ggcctaccgg ggggagaaac agcatccgtt actctgagtt ggcacccta    18900 ttcgacacca cccgtgtgta cctggtggac aacaagtcaa cggatgtggc atccctgaac    18960
taccagaacg accacagcaa ctttctgacc acggtcattc aaaacaatga ctacagcccg    19020
ggggaggcaa gcacacagac catcaatctt gacgaccggt cgcactgggg cggcgacctg    19080
aaaaccatcc tgcataccaa catgccaaat gtgaacgagt tcatgtttac caataagttt    19140
aaggcgcggg tgatggtgtc gcgcttgcct actaaggaca atcaggtgga gctgaaatac    19200
gagtgggtgg agttcacgct gcccgagggc aactactccg agaccatgac catagacctt    19260
atgaacaacg cgatcgtgga gcactacttg aaagtgggca gacagaacgg ggttctggaa    19320
agcgacatcg gggtaaagtt tgacacccgc aacttcagac tggggtttga ccccgtcact    19380
ggtcttgtca tgcctggggt atatacaaac gaagccttcc atccagacat catttttgctg    19440 ccaggatgcg gggtggactt cacccacagc cgcctgagca acttgttggg catccgcaag    19500
cggcaaccct tccaggaggg ctttaggatc acctacgatg atctggaggg tggtaacatt    19560
cccgcactgt tggatgtgga cgcctaccag gcgagcttga agatgacac cgaacagggc    19620 gggggtggcg caggcggcag caacagcagt ggcagcggcg cggaagagaa ctccaacgcg    19680
gcagccgcgg caatgcagcc ggtggaggac atgaacgatc atgccattcg cggcgacacc    19740
tttgccacac gggctgagga aagcgcgct gaggccgaag cagcggccga agctgccgcc    19800
cccgctgcgc aacccgaggt cgagaagcct cagaagaaac cggtgatcaa accctgaca     19860 gaggacagca agaaacgcag ttacaaccta ataagcaatg acagcacctt cacccagtac    19920
cgcagctggt accttgcata caactacggc gaccctcaga ccggaatccg ctcatggacc    19980
```

```
ctgctttgca ctcctgacgt aacctgcggc tcggagcagg tctactggtc gttgccagac    20040
atgatgcaag accccgtgac cttccgctcc acgcgccaga tcagcaactt tccggtggtg    20100
ggcgccgagc tgttgcccgt gcactccaag agcttctaca cgaccaggc cgtctactcc     20160 caactcatcc gccagtttac ctctctgacc cacgtgttca atcgctttcc cgagaaccag    20220
attttggcgc gcccgccagc ccccaccatc accaccgtca gtgaaaacgt tcctgctctc    20280
acagatcacg ggacgctacc gctgcgcaac agcatcggag gagtccagcg agtgaccatt    20340
actgacgcca gacgccgcac ctgcccctac gtttacaagg ccctgggcat agtctcgccg    20400
cgcgtcctat cgagccgcac tttttgagca agcatgtcca tccttatatc gcccagcaat    20460
aacacaggct ggggcctgcg cttcccaagc aagatgtttg gcggggccaa gaagcgctcc    20520
gaccaacacc cagtgcgcgt gcgcgggcac taccgcgcgc cctggggcgc gcacaaacgc    20580
ggccgcactg ggcgcaccac cgtcgatgac gccatcgacg cggtggtgga ggaggcgcgc    20640
aactacacgc ccacgccgcc accagtgtcc acagtggacg cggccattca gaccgtggtg    20700
cgcggagccc ggcgctatgc taaaatgaag agacggcgga ggcgcgtagc acgtcgccac    20760
cgccgccgac ccggcactgc cgcccaacgc gcggcggcgg ccctgcttaa ccgcgcacgt    20820
cgcaccggcc gacgggcggc catgcgggcc gctcgaaggc tggccgcggg tattgtcact    20880
gtgcccccca ggtccaggcg acgagcggcc gccgcagcag ccgcggccat tagtgctatg    20940
actcagggtc gcaggggcaa cgtgtattgg gtgcgcgact cggttagcgg cctgcgcgtg    21000
cccgtgcgca cccgccccccc gcgcaactag attgcaagaa aaaactactt agactcgtac    21060
tgttgtatgt atccagcggc ggcggcgcgc aacgaagcta tgtccaagcg caaaatcaaa    21120
gaagagatgc tccaggtcat cgcgccgag atctatggcc cccgaagaa ggaagagcag      21180 gattacaagc cccgaaagct aaagcgggtc aaaaagaaaa agaaagatga tgatgatgaa    21240
cttgacgacg aggtggaact gctgcacgct accgcgccca ggcgacgggt acagtggaaa    21300
ggtcgacgcg taaaacgtgt tttgcgaccc ggcaccaccg tagtctttac gcccggtgag    21360
cgctccaccc gcacctacaa gcgcgtgtat gatgaggtgt acggcgacga ggacctgctt    21420
gagcaggcca acgagcgcct cggggagttt gcctacggaa agcggcataa ggacatgctg    21480
gcgttgccgc tggacgaggg caacccaaca cctagcctaa agcccgtaac actgcagcag    21540
gtgctgcccg cgcttgcacc gtccgaagaa aagcgcggcc taaagcgcga gtctggtgac    21600
ttggcaccca ccgtgcagct gatggtaccc aagcgccagc gactggaaga tgtcttggaa    21660
aaaatgaccg tggaacctgg gctggagccc gaggtccgcg tgcggccaat caagcaggtg    21720
gcgccgggac tgggcgtgca gaccgtggac gttcagatac ccactaccag tagcaccagt    21780
attgccaccg ccacagaggg catggagaca caaacgtccc cggttgcctc agcggtggcg    21840
gatgccgcgg tgcaggcggt cgctgcggcc gcgtccaaga cctctacgga ggtgcaaacg    21900
gacccgtgga tgtttcgcgt ttcagcccccc ggcgcccgc gcggttcgag gaagtacggc    21960
gccgccagcg cgctactgcc cgaatatgcc ctacatcctt ccattgcgcc taccccggc     22020 tatcgtggct acacctaccg ccccagaaga cgagcaacta cccgacgccg aaccaccact    22080
ggaacccgcc gccgccgtcg ccgtcgccag cccgtgctgg ccccgatttc cgtgcgcagg    22140
gtggctcgcg aaggaggcag gaccctggtg ctgccaacag cgcgctacca ccccagcatc    22200
gtttaaaagc cggtctttgt ggttcttgca gatatggccc tcacctgccg cctccgtttc    22260
ccggtgccgg gattccgagg aagaatgcac cgtaggaggg gcatggccgg ccacggcctg    22320
```

```
acgggcggca tgcgtcgtgc gcaccaccgg cggcggcgcg cgtcgcaccg tcgcatgcgc   22380
ggcggtatcc tgcccctcct tattccactg atcgccgcgg cgattggcgc cgtgcccgga   22440
attgcatccg tggccttgca ggcgcagaga cactgattaa aaacaagttg catgtggaaa   22500
aatcaaaata aaaagtctgg actctcacgc tcgcttggtc ctgtaactat tttgtagaat   22560
ggaagacatc aactttgcgt ctctggcccc gcgacacggc tcgcgcccgt tcatgggaaa   22620
ctggcaagat atcggcacca gcaatatgag cggtggcgcc ttcagctggg gctcgctgtg   22680
gagcggcatt aaaaatttcg gttccaccgt taagaactat ggcagcaagg cctggaacag   22740
cagcacaggc cagatgctga gggataagtt gaaagagcaa aatttccaac aaaaggtggt   22800
agatggcctg gcctctggca ttagcggggt ggtggacctg gccaaccagg cagtgcaaaa   22860
taagattaac agtaagcttg atccccgccc tcccgtagag gagcctccac cggccgtgga   22920
gacagtgtct ccagaggggc gtggcgaaaa gcgtccgcgc cccgacaggg aagaaactct   22980
ggtgacgcaa atagacgagc ctccctcgta cgaggaggca ctaaagcaag gcctgcccac   23040
cacccgtccc atcgcgccca tggctaccgg agtgctgggc cagcacacac ccgtaacgct   23100
ggacctgcct cccccgccg acacccagca gaaacctgtg ctgccaggcc cgaccgccgt   23160
tgttgtaacc cgtcctagcc gcgcgtccct gcgccgcgcc gccagcggtc cgcgatcgtt   23220
gcggcccgta gccagtggca actggcaaag cacactgaac agcatcgtgg gtctgggggt   23280
gcaatccctg aagcgccgac gatgcttctg aatagctaac gtgtcgtatg tgtgtcatgt   23340
atgcgtccat gtcgccgcca gaggagctgc tgagccgccg cgcgcccgct ttccaagatg   23400
gctacccctt cgatgatgcc gcagtggtct tacatgcaca tctcgggcca ggacgcctcg   23460
gagtacctga gccccgggct ggtgcagttt gcccgcgcca ccgagacgta cttcagcctg   23520
aataacaagt ttagaaaccc cacggtggcg cctacgcacg acgtgaccac agaccggtcc   23580
cagcgtttga cgctgcggtt catccctgtg gaccgtgagg atactgcgta ctcgtacaag   23640
gcgcggttca ccctagctgt gggtgataac cgtgtgctgg acatggcttc cacgtacttt   23700
gacatccgcg gcgtgctgga caggggccct acttttaagc cctactctgg cactgcctac   23760
aacgccctgg ctcccaaggg tgccccaaat ccttgcgaat gggatgaagc tgctactgct   23820
cttgaaataa acctagaaga agaggacgat gacaacgaag acgaagtaga cgagcaagct   23880
gagcagcaaa aaactcacgt atttgggcag gcgccttatt ctggtataaa tattacaaag   23940
gagggtattc aaataggtgt cgaaggtcaa acacctaaat atgccgataa acatttcaa    24000 cctgaacctc aaataggaga atctcagtgg tacgaaactg aaattaatca tgcagctggg   24060
agagtcctta aaaagactac cccaatgaaa ccatgttacg gttcatatgc aaaacccaca   24120
aatgaaaatg gagggcaagg cattcttgta aagcaacaaa atggaaagct agaaagtcaa   24180
gtggaaatgc aattttctc aactactgag gcgaccgcag gcaatggtga acttgact     24240 cctaaagtgg tattgtacag tgaagatgta gatatagaaa ccccagacac tcatatttct   24300
tacatgccca ctattaagga aggtaactca cgagaactaa tgggccaaca atctatgccc   24360
aacaggccta attacattgc ttttagggac aatttttattg gtctaatgta ttacaacagc   24420
acgggtaata tgggtgttct ggcgggccaa gcatcgcagt tgaatgctgt tgtagatttg   24480
caagacagaa acacagagct ttcataccag cttttgcttg attccattgg tgatagaacc   24540
aggtactttt ctatgtggaa tcaggctgtt gacagctatg atccagatgt tagaattatt   24600
gaaaatcatg gaactgaaga tgaacttcca aattactgct ttcccactgg gaggtgtgatt   24660 aatacagaga ctcttaccaa ggtaaaacct aaaacaggtc aggaaaatgg atgggaaaaa   24720
```

```
gatgctacag aattttcaga taaaaatgaa ataagagttg gaaataattt tgccatggaa   24780
atcaatctaa atgccaacct gtggagaaat ttcctgtact ccaacatagc gctgtatttg   24840
cccgacaagc taaagtacag tccttccaac gtaaaaattt ctgataaccc aaacacctac   24900
gactacatga acaagcgagt ggtggctccc gggttagtgg actgctacat taaccttgga   24960
gcacgctggt cccttgacta tatggacaac gtcaacccat ttaaccacca ccgcaatgct   25020
ggcctgcgct accgctcaat gttgctgggc aatggtcgct atgtgccctt ccacatccag   25080
gtgcctcaga agttctttgc cattaaaaac ctccttctcc tgccgggctc atacacctac   25140
gagtggaact tcaggaagga tgttaacatg gttctgcaga gctccctagg aaatgaccta   25200
agggttgacg gagccagcat taagtttgat agcatttgcc tttacgccac cttcttcccc   25260
atggcccaca acaccgcctc cacgcttgag gccatgctta gaaacgacac caacgaccag   25320
tcctttaacg actatctctc cgccgccaac atgctctacc ctatacccgc caacgctacc   25380
aacgtgccca tatccatccc ctcccgcaac tgggcggctt ccgcggctg ggccttcacg    25440 cgccttaaga ctaaggaaac cccatcactg ggctcgggct acgaccctta ttacacctac   25500
tctggctcta taccctacct agatggaacc ttttacctca accacacctt taagaaggtg   25560
gccattacct ttgactcttc tgtcagctgg cctggcaatg accgcctgct tacccccaac   25620
gagtttgaaa ttaagcgctc agttgacggg gagggttaca acgttgccca gtgtaacatg   25680
accaaagact ggttcctggt acaaatgcta gctaactaca acattggcta ccagggcttc   25740
tatatcccag agagctacaa ggaccgcatg tactccttct ttagaaactt ccagcccatg   25800
agccgtcagg tggtggatga tactaaatac aaggactacc aacaggtggg catcctacac   25860
caacacaaca actctggatt tgttggctac cttgccccca ccatgcgcga aggacaggcc   25920
taccctgcta acttccccta tccgcttata ggcaagaccg cagttgacag cattacccag   25980
aaaaagtttc tttgcgatcg caccctttgg cgcatcccat tctccagtaa ctttatgtcc   26040
atgggcgcac tcacagacct gggccaaaac cttctctacg ccaactccgc ccacgcgcta   26100
gacatgactt ttgaggtgga tcccatggac gagcccaccc ttctttatgt tttgtttgaa   26160
gtctttgacg tggtccgtgt gcaccggccg caccgcggcg tcatcgaaac cgtgtacctg   26220
cgcacgccct tctcggccgg caacgccaca acataaagaa gcaagcaaca tcaacaacag   26280
ctgccgccat gggctccagt gagcaggaac tgaaagccat tgtcaaagat cttggttgtg   26340
ggccatattt ttttgggcacc tatgacaagc gctttccagg ctttgtttct ccacacaagc   26400
tcgcctgcgc catagtcaat acggccggtc gcgagactgg gggcgtacac tggatggcct   26460
ttgcctggaa cccgcactca aaaacatgct acctctttga gccctttggc ttttctgacc   26520
agcgactcaa gcaggtttac cagtttgagt acgagtcact cctgcgccgt agcgccattg   26580
cttcttcccc cgaccgctgt ataacgctgg aaaagtccac ccaaagcgta caggggccca   26640
actcggccgc ctgtggacta ttctgctgca tgtttctcca cgcctttgcc aactggcccc   26700
aaactcccat ggatcacaac cccaccatga accttattac cggggtaccc aactccatgc   26760
tcaacagtcc ccaggtacag cccacccctgc gtcgcaacca ggaacagctc tacagcttcc   26820
tggagcgcca ctcgccctac ttccgcagcc acagtgcgca gattaggagc gccacttctt   26880
tttgtcactt gaaaaacatg taaaaataat gtactagaga cactttcaat aaaggcaaat   26940
gcttttattt gtacactctc gggtgattat ttacccccac ccttgccgtc tgcgccgttt   27000
aaaaatcaaa gggggttctgc cgcgcatcgc tatgcgccac tggcagggac acgttgcgat   27060
```

```
actggtgttt agtgctccac ttaaactcag gcacaaccat ccgcggcagc tcggtgaagt    27120
tttcactcca caggctgcgc accatcacca acgcgtttag caggtcgggc gccgatatct    27180
tgaagtcgca gttggggcct ccgccctgcg cgcgcgagtt gcgatacaca gggttgcagc    27240
actggaacac tatcagcgcc gggtggtgca cgctggccag cacgctcttg tcggagatca    27300
gatccgcgtc caggtcctcc gcgttgctca gggcgaacgg agtcaacttt ggtagctgcc    27360
ttcccaaaaa gggcgcgtgc ccaggctttg agttgcactc gcaccgtagt ggcatcaaaa    27420
ggtgaccgtg cccggtctgg gcgttaggat acagcgcctg cataaaagcc ttgatctgct    27480
taaaagccac ctgagccttt gcgccttcag agaagaacat gccgcaagac ttgccggaaa    27540
actgattggc cggacaggcc gcgtcgtgca cgcagcacct tgcgtcggtg tttggagatct    27600 gcaccacatt tcggcccac cggttcttca cgatcttggc cttgctagac tgctccttca    27660
gcgcgcgctg cccgttttcg ctcgtcacat ccatttcaat cacgtgctcc ttatttatca    27720
taatgcttcc gtgtagacac ttaagctcgc cttcgatctc agcgcagcgg tgcagccaca    27780
acgcgcagcc cgtgggctcg tgatgcttgt aggtcacctc tgcaaacgac tgcaggtacg    27840
cctgcaggaa tcgccccatc atcgtcacaa aggtcttgtt gctggtgaag gtcagctgca    27900
acccgcggtg ctcctcgttc agccaggtct tgcatacggc cgccagagct tccacttggt    27960
caggcagtag tttgaagttc gcctttagat cgttatccac gtggtacttg tccatcagcg    28020
cgcgcgcagc ctccatgccc ttctcccacg cagacacgat cggcacactc agcgggttca    28080
tcaccgtaat ttcactttcc gcttcgctgg gctcttcctc ttcctcttgc gtccgcatac    28140
cacgcgccac tgggtcgtct tcattcagcc gccgcactgt gcgcttacct cctttgccat    28200
gcttgattag caccggtggg ttgctgaaac ccaccatttg tagcgccaca tcttctcttt    28260
cttcctcgct gtccacgatt acctctggtg atggcgggcg ctcgggcttg ggagaagggc    28320
gcttcttttt cttcttgggc gcaatggcca aatccgccgc cgaggtcgat ggccgcgggc    28380
tgggtgtgcg cggcaccagc gcgtcttgtg atgagtcttc ctcgtcctcg gactcgatac    28440
gccgcctcat ccgcttttt gggggcgccc ggggaggcgg cggcgacggg gacggggacg    28500
acacgtcctc catggttggg ggacgtcgcg ccgcaccgcg tccgcgctcg ggggtggttt    28560
cgcgctgctc ctcttcccga ctggccattt ccttctccta taggcagaaa aagatcatgg    28620
agtcagtcga gaagaaggac agcctaaccg cccctctga gttcgccacc accgcctcca    28680
ccgatgccgc caacgcgcct accaccttcc ccgtcgaggc accccgctt gaggaggagg    28740 aagtgattat cgagcaggac ccaggttttg taagcgaaga cgacgaggac cgctcagtac    28800
caacagagga taaaaagcaa gaccaggaca acgcagaggc aaacgaggaa caagtcgggc    28860 gggggacga aaggcatggc gactacctag atgtgggaga cgacgtgctg ttgaagcatc    28920
tgcagcgcca gtgcgccatt atctgcgacg cgttgcaaga gcgcagcgat gtgccctcg    28980 ccatagcgga tgtcagcctt gcctacgaac gccacctatt ctcaccgcgc gtaccccca    29040 aacgccaaga aaacggcaca tgcgagccca acccgcgcct caacttctac cccgtatttg    29100
ccgtgccaga ggtgcttgcc acctatcaca tcttttttcca aaactgcaag ataccctat    29160 cctgccgtgc caaccgcagc cgagcggaca agcagctggc cttgcggcag ggcgctgtca    29220
tacctgatat cgcctcgctc aacgaagtgc caaaaatctt tgagggtctt ggacgcgacg    29280
agaagcgcgc ggcaaacgct ctgcaacagg aaaacagcga aaatgaaagt cactctggag    29340
tgttggtgga actcgagggt gacaacgcgc gcctagccgt actaaaacgc agcatcgagg    29400
tcacccactt tgcctacccg gcacttaacc tacccccaa ggtcatgagc acagtcatga    29460
```

```
gtgagctgat cgtgcgccgt gcgcagcccc tggagaggga tgcaaatttg caagaacaaa   29520
cagaggaggg cctacccgca gttggcgacg agcagctagc gcgctggctt caaacgcgcg   29580
agcctgccga cttggaggag cgacgcaaac taatgatggc cgcagtgctc gttaccgtgg   29640
agcttgagtg catgcagcgg ttctttgctg acccggagat gcagcgcaag ctagaggaaa   29700
cattgcacta cacctttcga cagggctacg tacgccaggc ctgcaagatc tccaacgtgg   29760
agctctgcaa cctggtctcc taccttggaa ttttgcacga aaaccgcctt gggcaaaacg   29820
tgcttcattc cacgctcaag ggcgaggcgc gccgcgacta cgtccgcgac tgcgtttact   29880
tatttctatg ctacacctgg cagacggcca tgggcgtttg gcagcagtgc ttggaggagt   29940
gcaacctcaa ggagctgcag aaactgctaa agcaaaactt gaaggaccta tggacggcct   30000
tcaacgagcg ctccgtggcc gcgcacctgg cggacatcat tttccccgaa cgcctgctta   30060
aaaccctgca acagggtctg ccagacttca ccagtcaaag catgttgcag aactttagga   30120
actttatcct agagcgctca ggaatcttgc ccgccacctg ctgtgcactt cctagcgact   30180
ttgtgcccat taagtaccgc gaatgccctc cgccgctttg gggccactgc taccttctgc   30240
agctagccaa ctaccttgcc taccactctg acataatgga agacgtgagc ggtgacggtc   30300
tactggagtg tcactgtcgc tgcaacctat gcaccccgca ccgctccctg gtttgcaatt   30360
cgcagctgct taacgaaagt caaattatcg gtacctttga gctgcagggt ccctcgcctg   30420
acgaaaagtc cgcggctccg gggttgaaac tcactccggg gctgtggacg tcggcttacc   30480
ttcgcaaatt tgtacctgag gactaccacg cccacgagat taggttctac gaagaccaat   30540
cccgcccgcc aaatgcggag cttaccgcct gcgtcattac ccagggccac attcttggcc   30600
aattgcaagc catcaacaaa gcccgccaag agtttctgct acgaaaggga cgggggggttt   30660 acttggaccc ccagtccggc gaggagctca acccaatccc ccgccgccg cagccctatc   30720 agcagcagcc gcgggccctt gcttccagg atggcaccca aaagaagct gcagctgccg   30780 ccgccaccca cggacgagga ggaatactgg gacagtcagg cagaggaggt tttggacgag   30840
gaggaggagg acatgatgga agactgggag agcctagacg aggaagcttc cgaggtcgaa   30900
gaggtgtcag acgaaacacc gtcaccctcg gtcgcattcc cctcgccggc gccccagaaa   30960
tcggcaaccg gttccagcat ggctacaacc tccgctcctc aggcgccgcc ggcactgccc   31020
gttcgccgac ccaaccgtag atgggacacc actggaacca gggccggtaa gtccaagcag   31080
ccgccgccgt tagcccaaga gcaacaacag cgccaaggct accgctcatg gcgcgggcac   31140
aagaacgcca tagttgcttg cttgcaagac tgtgggggca acatctcctt cgcccgccgc   31200
tttcttctct accatcacgg cgtggccttc ccccgtaaca tcctgcatta ctaccgtcat   31260
ctctacagcc catactgcac cggcggcagc ggcagcggca gcaacagcag cggccacaca   31320
gaagcaaagg cgaccggata gcaagactct gacaaagccc aagaaatcca cagcggcggc   31380
agcagcagga ggaggagcgc tgcgtctggc gccaacgaa cccgtatcga cccgcgagct   31440
tagaaacagg attttttccca ctctgtatgc tatatttcaa cagagcaggg gccaagaaca   31500
agagctgaaa ataaaaaaca ggtctctgcg atccctcacc cgcagctgcc tgtatcacaa   31560
aagcgaagat cagcttcggc gcacgctgga agacgcggag gctctcttca gtaaatactg   31620
cgcgctgact cttaaggact agtttcgcgc ccttctcaa atttaagcgc gaaaactacg   31680
tcatctccag cggccacacc cggcgccagc acctgtcgtc agcgccatta tgagcaagga   31740
aattcccacg ccctacatgt ggagttacca gccacaaatg ggacttgcgg ctggagctgc   31800
```

```
ccaagactac tcaacccgaa taaactacat gagcgcggga ccccacatga tatcccgggt   31860
caacggaatc cgcgcccacc gaaaccgaat tctcttggaa caggcggcta ttaccaccac   31920
acctcgtaat aaccttaatc cccgtagttg gcccgctgcc ctggtgtacc aggaaagtcc   31980
cgctcccacc actgtggtac ttcccagaga cgcccaggcc gaagttcaga tgactaactc   32040
aggggcgcag cttgcgggcg gctttcgtca cagggtgcgg tcgcccgggc agggtataac   32100
tcacctgaca atcagagggc gaggtattca gctcaacgac gagtcggtga gctcctcgct   32160
tggtctccgt ccggacggga catttcagat cggcggcgcc ggccgtcctt cattcacgcc   32220
tcgtcaggca atcctaactc tgcagacctc gtcctctgag ccgcgctctg gaggcattgg   32280
aactctgcaa tttattgagg agtttgtgcc atcggtctac tttaacccct tctcgggacc   32340
tcccggccac tatccggatc aatttattcc taactttgac gcggtaaagg actcggcgga   32400
cggctacgac tgattattaa gtggagaggc agagcaactg cgcctgaaac acctggtcca   32460
ctgtcgccgc cacaagtgct ttgcccgcga ctccggtgag ttttgctact ttgaattgcc   32520
cgaggatcat atcgaggatc tttgttgcca tctctgtgct gagtataata aatacagaaa   32580
ttaaaatata ctggggctcc tatcgccatc ctgtaaacgc caccgtcttc acccgcccaa   32640
gcaaaccaag gcgaacctta cctggtactt ttaacatctc tccctctgtg atttacaaca   32700
gtttcaaccc agacggagtg agtctacgag agaacctctc cgagctcagc tactccatca   32760
gaaaaaacac caccctcctt acctgccggg aacgtaccct tatataaaag tcaggcttcc   32820
tggatgtcag catctgactt tggccagcac ctgtcccgcg gatttgttcc agtccaacta   32880
cagcgaccca ccctaacaga gatgaccaac acaaccaacg cggccgccgc taccggactt   32940
acatctacca caaatacacc ccaagtttct gcctttgtca ataactggga taacttgggc   33000
atgtggtggt tctccatagc gcttatgttt gtatgcctta ttattatgtg gctcatctgc   33060
tgcctaaagc gcaaacgcgc ccgaccaccc atctatagtc ccatcattgt gctacaccca   33120
aacaatgatg gaatccatag attggacgga ctgaaacaca tgttcttttc tcttacagta   33180
tgattaaatg agaattttaa ttcgaatacc atgtggctgc agagcctgct gctcttgggc   33240
actgtgcct gcagcatctc tgcacccgcc cgctcgccca gccccagcac gcagccctgg   33300
gagcatgtga atgccatcca ggaggcccgg cgtctcctga acctgagtag agacactgct   33360
gctgagatga atgaaacagt agaagtcatc tcagaaatgt ttgacctcca ggagccgacc   33420
tgcctacaga cccgcctgga gctgtacaag cagggcctgc ggggcagcct caccaagctc   33480
aagggcccct tgaccatgat ggccagccac tacaagcagc actgccctcc aaccccggaa   33540
acttcctgtg caacccagac tatcaccttt gaaagtttca agagaacct gaaggacttt   33600
ctgcttgtca tccccttga ctgctgggag ccagtccagg agtgaattgt cgacctgcag   33660
gaaatggaat ttctgtccag tttattcagc agcacctcct tgccctcctc ccagctctgg   33720
tattgcagct tcctcctggc tgcaaacttt ctccacaatc taaatggaat gtcagtttcc   33780
tcctgttcct gtccatccgc acccactatc ttcatgttgt tgcagatgaa gcgcgcaaga   33840
ccgtctgaag ataccttcaa ccccgtgtat ccatatgaca cggaaaccgg tcctccaact   33900
gtgccttttc ttactcctcc cttttgtatcc cccaatgggt ttcaagagag tcccctggg   33960
gtactctctt tgcgcctatc cgaacctcta gttacctcca atggcatgct tgcgctcaaa   34020
atgggcaacg gcctctctct ggacgaggcc ggcaacctta cctcccaaaa tgtaaccact   34080
gtgagccac ctctcaaaaa aaccaagtca aacataaacc tggaaatatc tgcacccctc   34140
acagttacct cagaagccct aactgtggct gccgccgcac ctctaatggt cgcgggcaac   34200
```

```
acactcacca tgcaatcaca ggccccgcta accgtgcacg actccaaact tagcattgcc    34260
acccaaggac ccctcacagt gtcagaagga aagctagccc tgcaaacatc aggcccccta    34320
accaccaccg atagcagtac ccttactatc actgcctcac cccctctaac tactgccact    34380
ggtagcttgg gcattgactt gaaagagccc atttatacac aaaatggaaa actaggacta    34440
aagtacgggg ctcctttgca tgtaacagac gacctaaaca ctttgaccgt agcaactggt    34500
ccaggtgtga ctattaataa tacttccttg caaactaaag ttactggagc cttgggtttt    34560
gattcacaag gcaatatgca acttaatgta gcaggaggac taaggattga ttctcaaaac    34620
agacgcctta tacttgatgt tagttatccg tttgatgctc aaaaccaact aaatctaaga    34680
ctaggacagg gccctctttt tataaactca gcccacaact tggatattaa ctacaacaaa    34740
ggcctttact tgtttacagc ttcaaacaat tccaaaaagc ttgaggttaa cctaagcact    34800
gccaaggggt tgatgtttga cgctacagcc atagccatta atgcaggaga tgggcttgaa    34860
tttggttcac ctaatgcacc aaacacaaat cccctcaaaa caaaaattgg ccatggccta    34920
gaatttgatt caaacaaggc tatggttcct aaactaggaa ctggccttag ttttgacagc    34980
acaggtgcca ttacagtagg aaacaaaaat aatgataagc taccctatg acaggtcca      35040 aaaccagaag ccaactgcat aattgaatac gggaaacaaa acccagatag caaactaact    35100
ttaatccttg taaaaatgg aggaattgtt aatggatatg taacgctaat gggagcctca    35160
gactacgtta acaccttatt taaaaacaaa aatgtctcca ttaatgtaga actatacttt    35220
gatgccactg gtcatatatt accagactca tcttctctta aaacagatct agaactaaaa    35280
tacaagcaaa ccgctgactt tagtgcaaga ggttttatgc caagtactac agcgtatcca    35340
tttgtccttc ctaatgcggg aacacataat gaaaattata ttttggtca atgctactac    35400 aaagcaagcg atggtgccct ttttccgttg gaagttactg ttatgcttaa taaacgcctg    35460
ccagatagtc gcacatccta tgttatgact tttttatggt ccttgaatgc tggtctagct    35520
ccagaaacta ctcaggcaac cctcataacc tccccattta cctttcctta tattagagaa    35580
gatgacggtg gaggcggttc aggcggaggt ggctctggcg gtggcggatc ctgtgactgc    35640
cgcggagact gtttctgcta ataaactcta aagaatcgtt tgtgttatgt ttcaacgtgt    35700
ttatttttca attgcagaaa atttcaagtc attttttcatt cagtagtata gccccaccac    35760
cacatagctt atacagatca ccgtaccttta atcaaactca cagaacccta gtattcaacc    35820
tgccacctcc ctcccaacac acagagtaca cagtcctttc tccccggctg gccttaaaaa    35880
gcatcatatc atgggtaaca gacatattct taggtgttat attccacacg gtttcctgtc    35940
gagccaaacg ctcatcagtg atattaataa actccccggg cagctcactt aagttcatgt    36000
cgctgtccag ctgctgagcc acaggctgct gtccaacttg cggttgctta acgggcggcg    36060
aaggagaagt ccacgcctac atgggggtag agtcataatc gtgcatcagg atagggcggt    36120
ggtgctgcag cagcgcgcga ataaactgct gccgccgccg ctccgtcctg caggaataca    36180
acatggcagt ggtctcctca gcgatgattc gcaccgcccg cagcataagg cgccttgtcc    36240
tccgggcaca gcagcgcacc ctgatctcac ttaaatcagc acagtaactg cagcacagca    36300
ccacaatatt gttcaaaatc ccacagtgca aggcgctgta tccaaagctc atggcgggga    36360
ccacagaacc cacgtggcca tcataccaca agcgcaggta gattaagtgg cgaccctca    36420 taaacacgct ggacataaac attacctctt ttggcatgtt gtaattcacc acctcccggt    36480
accatataaa cctctgatta aacatggcgc catccaccac catcctaaac cagctggcca    36540
```

```
aaacctgccc gccggctata cactgcaggg aaccgggact ggaacaatga cagtggagag    36600
cccaggactc gtaaccatgg atcatcatgc tcgtcatgat atcaatgttg gcacaacaca    36660
ggcacacgtg catacacttc ctcaggatta caagctcctc ccgcgttaga accatatccc    36720
agggaacaac ccattcctga atcagcgtaa atcccacact gcagggaaga cctcgcacgt    36780
aactcacgtt gtgcattgtc aaagtgttac attcgggcag cagcggatga tcctccagta    36840
tggtagcgcg ggtttctgtc tcaaaaggag gtagacgatc cctactgtac ggagtgcgcc    36900
gagacaaccg agatcgtgtt ggtcgtagtg tcatgccaaa tggaacgccg gacgtagtca    36960
tatttcctga agcaaaacca ggtgcgggcg tgacaaacag atctgcgtct ccggtctcgc    37020
cgcttagatc gctctgtgta gtagttgtag tatatccact ctctcaaagc atccaggcgc    37080
cccctggctt cgggttctat gtaaactcct tcatgcgccg ctgccctgat aacatccacc    37140
accgcagaat aagccacacc cagccaacct acacattcgt tctgcgagtc acacacggga    37200
ggagcgggaa gagctggaag aaccatgttt tttttttttat tccaaaagat tatccaaaac    37260
ctcaaaatga agatctatta agtgaacgcg ctcccctccg gtggcgtggt caaactctac    37320
agccaaagaa cagataatgg catttgtaag atgttgcaca atggcttcca aaaggcaaac    37380
ggccctcacg tccaagtgga cgtaaaggct aaacccttca gggtgaatct cctctataaa    37440
cattccagca ccttcaacca tgcccaaata attctcatct cgccaccttc tcaatatatc    37500
tctaagcaaa tcccgaatat taagtccggc cattgtaaaa atctgctcca gagcgccctc    37560
caccttcagc ctcaagcagc gaatcatgat tgcaaaaatt caggttcctc acagacctgt    37620
ataagattca aaagcggaac attaacaaaa ataccgcgat cccgtaggtc ccttcgcagg    37680
gccagctgaa cataatcgtg caggtctgca cggaccagcg cggccacttc cccgccagga    37740
accatgacaa agaacccac actgattatg acacgcatac tcggagctat gctaaccagc    37800
gtagccccga tgtaagcttt gttgcatggg cggcgatata aaatgcaagg tgctgctcaa    37860
aaaatcaggc aaagcctcgc gcaaaaaaga aagcacatcg tagtcatgct catgcagata    37920
aaggcaggta agctccggaa ccaccacaga aaaagacacc attttttctct caaacatgtc    37980
tgcgggtttc tgcataaaca caaaataaaa taacaaaaaa acatttaaac attagaagcc    38040
tgtcttacaa caggaaaaac aacccttata agcataagac ggactacggc catgccggcg    38100
tgaccgtaaa aaaactggtc accgtgatta aaaagcacca ccgacagctc ctcggtcatg    38160
tccggagtca taatgtaaga ctcggtaaac acatcaggtt gattcatcgg tcagtgctaa    38220
aaagcgaccg aaatagcccg ggggaataca tacccgcagg cgtagagaca acattacagc    38280
ccccatagga ggtataacaa aattaatagg agagaaaaac acataaacac ctgaaaaacc    38340
ctcctgccta ggcaaaatag cacctcccg ctccagaaca acatacagcg cttcacagcg    38400
gcagcctaac agtcagcctt accagtaaaa aagaaaacct attaaaaaa caccactcga    38460
cacggcacca gctcaatcag tcacagtgta aaaaagggcc aagtgcagag cgagtatata    38520
taggactaaa aaatgacgta acggttaaag tccacaaaaa acacccagaa aaccgcacgc    38580
gaacctacgc ccagaaacga aagccaaaaa acccacaact tcctcaaatc gtcacttccg    38640
ttttcccacg ttacgtaact tcccatttta agaaaactac aattcccaac acatacaagt    38700
tactccgccc taaaacctac gtcacccgcc ccgttccac gccccgcgcc acgtcacaaa    38760
ctccaccccc tcattatcat attggcttca atccaaaata aggtatatta ttgatgatnn    38820
nnnttaat                                                             38828
```

<210> SEQ ID NO 3
<211> LENGTH: 5110
<212> TYPE: DNA
<213> ORGANISM: Artificial sequence
<220> FEATURE:
<223> OTHER INFORMATION: Shuttle virus Ad5/3 rgd

<400> SEQUENCE: 3

| | | | | | |
|---|---|---|---|---|---|
| aaacagtcga | ctctagaaat | ggacggaatt | attacagagc | agcgcctgct | agaaagacgc | 60 |
| agggcagcgg | ccgagcaaca | gcgcatgaat | caagagctcc | aagacatggt | taacttgcac | 120 |
| cagtgcaaaa | ggggtatctt | ttgtctggta | aagcaggcca | aagtcaccta | cgacagtaat | 180 |
| accaccggac | accgccttag | ctacaagttg | ccaaccaagc | gtcagaaatt | ggtggtcatg | 240 |
| gtgggagaaa | agcccattac | cataactcag | cactcggtag | aaaccgaagg | ctgcattcac | 300 |
| tcaccttgtc | aaggacctga | ggatctctgc | acccttatta | agaccctgtg | cggtctcaaa | 360 |
| gatcttattc | cctttaacta | taaaaaaaa | ataataaagc | atcacttact | taaaatcagt | 420 |
| tagcaaattt | ctgtccagtt | tattcagcag | cacctccttg | ccctcctccc | agctctggta | 480 |
| ttgcagcttc | ctcctggctg | caaactttct | ccacaatcta | aatggaatgt | cagtttcctc | 540 |
| ctgttcctgt | ccatccgcac | ccactatctt | catgttgttg | cagatgaagc | gcgcaagacc | 600 |
| gtctgaagat | accttcaacc | ccgtgtatcc | atatgacacg | gaaaccggtc | ctccaactgt | 660 |
| gccttttctt | actcctccct | ttgtatcccc | aatgggttt | caagagagtc | ccctggggt | 720 |
| actctctttg | cgcctatccg | aacctctagt | tacctccaat | ggcatgcttg | cgctcaaaat | 780 |
| gggcaacggc | ctctctctgg | acgaggccgg | caaccttacc | tcccaaaatg | taaccactgt | 840 |
| gagcccacct | ctcaaaaaaa | ccaagtcaaa | cataaacctg | gaaatatctg | caccccctcac | 900 |
| agttacctca | gaagccctaa | ctgtggctgc | cgccgcacct | ctaatggtcg | cgggcaacac | 960 |
| actcaccatg | caatcacagg | ccccgctaac | cgtgcacgac | tccaaactta | gcattgccac | 1020 |
| ccaaggaccc | ctcacagtgt | cagaaggaaa | gctagccctg | caaacatcag | gccccctcac | 1080 |
| caccaccgat | agcagtaccc | ttactatcac | tgcctcaccc | cctctaacta | ctgccactgg | 1140 |
| tagcttgggc | attgacttga | agagccat | ttatacacaa | aatggaaaac | taggactaaa | 1200 |
| gtacggggct | cctttgcatg | taacagacga | cctaaacact | ttgaccgtag | caactggtcc | 1260 |
| aggtgtgact | attaataata | cttccttgca | aactaaagtt | actggagcct | tgggttttga | 1320 |
| ttcacaaggc | aatatgcaac | ttaatgtagc | aggaggacta | aggattgatt | ctcaaaacag | 1380 |
| acgccttata | cttgatgtta | gttatccgtt | tgatgctcaa | aaccaactaa | atctaagact | 1440 |
| aggacagggc | cctctttta | taaactcagc | ccacaacttg | gatattaact | acaacaaagg | 1500 |
| cctttacttg | tttacagctt | caacaattc | caaaagctt | gaggttaacc | taagcactgc | 1560 |
| caaggggttg | atgtttgacg | ctacagccat | agccattaat | gcaggagatg | gcttgaattt | 1620 |
| tggttcacct | aatgcaccaa | acacaaatcc | cctcaaaaca | aaaattggcc | atggcctaga | 1680 |
| atttgattca | aacaaggcta | tggttcctaa | actaggaact | ggccttagtt | ttgacagcac | 1740 |
| aggtgccatt | acagtaggaa | acaaaaataa | tgataagcta | accctatgga | caggtccaaa | 1800 |
| accagaagcc | aactgcataa | ttgaatacgg | gaaacaaaac | ccagatagca | aactaactt | 1860 |
| aatccttgta | aaaaatggag | gaattgttaa | tggatatgta | acgctaatgg | gagcctcaga | 1920 |
| ctacgttaac | accttatta | aaaacaaaaa | tgtctccatt | aatgtagaac | tatactttga | 1980 |
| tgccactggt | catatattac | cagactcatc | ttctcttaaa | acagatcag | aactaaaata | 2040 |
| caagcaaacc | gctgactta | gtgcaagagg | ttttatgcca | agtactacag | cgtatccatt | 2100 |

```
tgtccttcct aatgcgggaa cacataatga aaattatatt tttggtcaat gctactacaa    2160
agcaagcgat ggtgccctttt ttccgttgga agttactgtt atgcttaata aacgcctgcc    2220
agatagtcgc acatcctatg ttatgacttt tttatggtcc ttgaatgctg gtctagctcc    2280
agaaactact caggcaaccc tcataacctc cccatttacc ttttcctata ttagagaaga    2340
tgacggtgga ggcggttcag gcggaggtgg ctctggcggt ggcggatcct gtgactgccg    2400
cggagactgt ttctgctaat aaactctaaa gaatcgtttg tgttatgttt caacgtgttt    2460
atttttcaat tgcagaaaat ttcaagtcat ttttcattca gtagtatagc cccaccacca    2520
catagcttat acagatcacc gtaccttaat caaactcaca gaaccctagt attcaacctg    2580
ccacctccct cccaacacac agagtacaca gtcctttctc cccggctggc cttaaaaagc    2640
atcatatcat gggtaacaga catattctta ggtgttatat tccacacggt ttcctgtcga    2700
gccaaacgct catcagtgat attaataaac tccccgggca gctcacttaa gttcatgtcg    2760
ctgtccagct gctgagccac aggctgctgt ccaacttgcg gttgcttaac gggcggcgaa    2820
ggagaagtcc acgcctacat gggggtagag tcataatcgt gcatcaggat agggcggtgg    2880
tgctgcagca gcgcgcgaat aaactgctgc cgccgccgct ccgtcctgca ggaatacaac    2940
atggcagtgg tctcctcagc gatgattcgc accgccgca gcataaggcg ccttgtcctc    3000
cgggcacagc agcgcaccct gatctcactt aaatcagcac agtaactgca gcacagcacc    3060
acaatattgt tcaaaatccc acagtgcaag gcgctgtatc caaagctcat ggcggggacc    3120
acagaaccca cgtggccatc ataccacaag cgcaggtaga ttaagtggcg acccctcata    3180
aacacgctgg acataaacat tacctctttt ggcatgttgt aattcaccac ctcccggtac    3240
cgagctcgaa ttctagtgag caaaaggcca gcaaaagccc aggaaccgta aaaaggccgc    3300
gttgctggcg ttttttccata ggctccgccc ccctgacgag catcacaaaa atcgacgctc    3360
aagtcagagg tggcgaaacc cgacaggact ataaagatac caggcgtttc cccctggaag    3420
ctccctcgtg cgctctcctg ttccgaccct gccgcttacc ggatacctgt ccgcctttct    3480
cccttcggga agcgtggcgc tttctcatag ctcacgctgt aggtatctca gttcggtgta    3540
ggtcgttcgc tccaagctgg gctgtgtgca cgaaccccc gttcagcccg accgctgcgc    3600
cttatccggt aactatcgtc ttgagtccaa cccggtaaga cacgacttat cgccactggc    3660
agcagccact ggtaacagga ttagcagagc gaggtatgta ggcggtgcta cagagttctt    3720
gaagtggtgg cctaactacg gctacactag aaggacagta tttggtatct gcgctctgct    3780
gaagccagtt accttcggaa aaagagttgg tagctcttga tccggcaaac aaaccaccgc    3840
tggtagcggt ggttttttttg tttgcaagca gcagattacg cgcagaaaaa aaggatctca    3900
agaagatcct ttgatctttt ctacgggtc tgacgctcag tggaacgaaa actcacgtta    3960
agggattttg gtcatgagat tatcaaaaag gatcttcacc tagatccttt tcacgtagaa    4020
agccagtccg cagaaacggt gctgaccccg gatgaatgtc agctactggg ctatctggac    4080
aagggaaaac gcaagcgcaa agagaaagca ggtagcttgc agtgggctta catggcgata    4140
gctagactgg gcggttttat ggacagcaag cgaaccggaa ttgccagctg gggcgccctc    4200
tggtaaggtt gggaagccct gcaaagtaaa ctggatggct ttctcgccgc caaggatctg    4260
atggcgcagg ggatcaagat ctgatcaaga acaggatga ggatcgtttc gcatgattga    4320
acaagatgga ttgcacgcag gttctccggc cgcttgggtg gagaggctat tcggctatga    4380
ctgggcacaa cagacaatcg gctgctctga tgccgccgtg ttccggctgt cagcgcaggg    4440
gcgcccggtt ctttttgtca agaccgacct gtccggtgcc ctgaatgaac tgcaagacga    4500
```

```
ggcagcgcgg ctatcgtggc tggccacgac gggcgttcct tgcgcagctg tgctcgacgt    4560
tgtcactgaa gcgggaaggg actggctgct attgggcgaa gtgccggggc aggatctcct    4620
gtcatctcac cttgctcctg ccgagaaagt atccatcatg gctgatgcaa tgcggcggct    4680
gcatacgctt gatccggcta cctgcccatt cgaccaccaa gcgaaacatc gcatcgagcg    4740
agcacgtact cggatggaag ccggtcttgt cgatcaggat gatctggacg aagagcatca    4800
ggggctcgcg ccagccgaac tgttcgccag gctcaaggcg agcatgcccg acggcgagga    4860
tctcgtcgtg acccatggcg atgcctgctt gccgaatatc atggtggaaa atggccgctt    4920
ttctggattc atcgactgtg gccggctggg tgtggcggac cgctatcagg acatagcgtt    4980
ggctacccgt gatattgctg aagagcttgg cggcgaatgg gctgaccgct tcctcgtgct    5040
ttacggtatc gccgctcccg attcgcagcg catcgccttc tatcgccttc ttgacgagtt    5100
cttctgaatt                                                           5110

<210> SEQ ID NO 4
<211> LENGTH: 33541
<212> TYPE: DNA
<213> ORGANISM: Artificial sequence
<220> FEATURE:
<223> OTHER INFORMATION: Recombinant adenvirus AdEz5/3-RGD D24,
      n=A,C,G,T
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (3655)..(3657)
<223> OTHER INFORMATION: n is a, c, g, or t
<220> FEATURE:
<221> NAME/KEY: misc_feature
<222> LOCATION: (3684)..(3686)
<223> OTHER INFORMATION: n is a, c, g, or t
<220> FEATURE:
<221> NAME/KEY: misc_feature
<222> LOCATION: (33532)..(33536)
<223> OTHER INFORMATION: n is a, c, g, or t

<400> SEQUENCE: 4
taaggatccn nncctgtcct cgaccgatgc ccttgagagc cttcaaccca gtcagctcct     60
tccggtgggc gcggggcatg actatcgtcg ccgcacttat gactgtcttc tttatcatgc    120
aactcgtagg acaggtgccg gcagcgctct gggtcatttt cggcgaggac cgctttcgct    180
ggagcgcgac gatgatcggc ctgtcgcttg cggtattcgg aatcttgcac gccctcgctc    240
aagccttcgt cactggtccc gccaccaaac gtttcggcga agcaggcc attatcgccg    300 gcatggcggc cgacgcgctg ggctacgtct tgctggcgtt cgcgacgcga ggctggatgg    360
ccttccccat tatgattctt ctcgcttccg gcggcatcgg gatgcccgcg ttgcaggcca    420
tgctgtccag gcaggtagat gacgaccatc agggacagct tcaaggatcg ctcgcggctc    480
ttaccagcct aacttcgatc actggaccgc tgatcgtcac ggcgatttat gccgcctcgg    540
cgagcacatg gaacgggttg gcatggattg taggcgccgc cctataccgg tgtctgcctcc     600 ccgcgttgcg tcgcggtgca tggagccggg ccacctcgac ctgaatggaa gccggcggca    660
cctcgctaac ggattcacca ctccaagaat tggagccaat caattcttgc ggagaactgt    720
gaatgcgcaa accaacccct tggcagaaca tatccatcgcg tccgccatct ccagcagccg    780
cacgcggcgc atctcgggca gcgttgggtc ctggccacgg gtgcgcatga tcgtgctcct    840
gtcgttgagg acccggctag gctggcgggg ttgccttact ggttagcaga atgaatcacc    900
```

-continued

```
gatacgcgag cgaacgtgaa gcgactgctg ctgcaaaacg tctgcgacct gagcaacaac     960
atgaatggtc ttcggtttcc gtgtttcgta aagtctggaa acgcggaagt cagcgccctg    1020
caccattatg ttccggatct gcatcgcagg atgctgctgg ctaccctgtg aacacctac     1080
atctgtatta cgaagcgct ggcattgacc ctgagtgatt tttctctggt cccgccgcat     1140
ccataccgcc agttgtttac cctcacaacg ttccagtaac cgggcatgtt catcatcagt    1200
aacccgtatc gtgagcatcc tctctcgttt catcggtatc attcccca tgaacagaaa      1260
ttccccctta cacggaggca tcaagtgacc aaacaggaaa aaaccgccct taacatggcc    1320
cgctttatca gaagccagac attaacgctt ctggagaaac tcaacgagct ggacgcggat    1380
gaacaggcag acatctgtga atcgcttcac gaccacgctg atgagcttta ccgcagctgc    1440
ctcgcgcgtt tcggtgatga cggtgaaaac ctctgacaca tgcagctccc ggagacggtc    1500
acagcttgtc tgtaagcgga tgccgggagc agacaagccc gtcagggcgc gtcagcgggt    1560
gttggcgggt gtcggggcgc agccatgacc cagtcacgta gcgatagcgg agtgtatact    1620
ggcttaacta tgcggcatca gagcagattg tactgagagt gcaccatatg cggtgtgaaa    1680
taccgcacag atgcgtaagg agaaaatacc gcatcaggcg ctcttccgct tcctcgctca    1740
ctgactcgct gcgctcggtc gttcggctgc ggcgagcggt atcagctcac tcaaaggcgg    1800
taatacggtt atccacagaa tcaggggata acgcaggaaa gaacatgtga gcaaaaggcc    1860
agcaaaaggc caggaaccgt aaaaaggccg cgttgctggc gttttccat aggctccgcc     1920
cccctgacga gcatcacaaa aatcgacgct caagtcagag gtggcgaaac ccgacaggac    1980
tataaagata ccaggcgttt ccccctggaa gctccctcgt gcgctctcct gttccgaccc    2040
tgccgcttac cggatacctg tccgcctttc tcccttcggg aagcgtggcg ctttctcaat    2100
gctcacgctg taggtatctc agttcggtgt aggtcgttcg ctccaagctg ggctgtgtgc    2160
acgaaccccc cgttcagccc gaccgctgcg ccttatccgg taactatcgt cttgagtcca    2220
acccggtaag acacgactta cgccactgg cagcagccac tggtaacagg attagcagag     2280
cgaggtatgt aggcggtgct acagagttct tgaagtggtg gcctaactac ggctacacta    2340
gaaggacagt atttggtatc tgcgctctgc tgaagccagt taccttcgga aaaagagttg    2400
gtagctcttg atccggcaaa caaaccaccg ctggtagcgg tggtttttt gtttgcaagc     2460
agcagattac gcgcagaaaa aaaggatctc aagaagatcc tttgatcttt tctacggggt    2520
ctgacgctca gtggaacgaa aactcacgtt aagggatttt ggtcatgaga ttatcaaaaa    2580
ggatcttcac ctagatcctt ttaaattaaa aatgaagttt aaatcaatc taaagtatat     2640
atgagtaaac ttggtctgac agttaccaat gcttaatcag tgaggcacct atctcagcga    2700
tctgtctatt tcgttcatcc atagttgcct gactccccgt cgtgtagata actacgatac    2760
gggagggctt accatctggc cccagtgctg caatgatacc gcgagaccca cgctcaccgg    2820
ctccagattt atcagcaata aaccagccag ccggaagggc cgagcgcaga agtggtcctg    2880
caactttatc cgcctccatc cagtctatta attgttgccg ggaagctaga gtaagtagtt    2940
cgccagttaa tagtttgcgc aacgttgttg ccattgctgc aggcatcgtg gtgtcacgct    3000
cgtcgtttgg tatggcttca ttcagctccg gttcccaacg atcaaggcga gttacatgat    3060
cccccatgtt gtgcaaaaaa gcggttagct ccttcggtcc tccgatcgtt gtcagaagta    3120
agttggccgc agtgttatca ctcatggtta tggcagcact gcataattct cttactgtca    3180
tgccatccgt aagatgcttt tctgtgactg gtgagtactc aaccaagtca ttctgagaat    3240
```

```
agtgtatgcg gcgaccgagt tgctcttgcc cggcgtcaac acgggataat accgcgccac    3300
atagcagaac tttaaaagtg ctcatcattg gaaaacgttc ttcggggcga aaactctcaa    3360
ggatcttacc gctgttgaga tccagttcga tgtaacccac tcgtgcaccc aactgatctt    3420
cagcatcttt tactttcacc agcgtttctg ggtgagcaaa acaggaagg caaaatgccg     3480
caaaaaggg aataagggcg cacggaaat gttgaatact catactcttc cttttcaat       3540
attattgaag catttatcag ggttattgtc tcatgagcgg atacatattt gaatgtattt    3600
agaaaaataa acaaataggg gttccgcgca catttccccg aaaagtgcca cctgnnngaa    3660
ttcgaatcta gtatcgattc gaannnctta agggtgggaa agaatatata aggtgggggt    3720
cttatgtagt tttgtatctg ttttgcagca gccgccgccg ccatgagcac caactcgttt    3780
gatggaagca ttgtgagctc atatttgaca acgcgcatgc ccccatgggc cggggtgcgt    3840
cagaatgtga tgggctccag cattgatggt cgccccgtcc tgcccgcaaa ctctactacc    3900
ttgacctacg agaccgtgtc tggaacgccg ttggagactg cagcctccgc cgccgcttca    3960
gccgctgcag ccaccgcccg cgggattgtg actgactttg ctttcctgag cccgcttgca    4020
agcagtgcag cttcccgttc atccgcccgc gatgacaagt tgacggctct tttggcacaa    4080
ttggattctt tgacccggga acttaatgtc gtttctcagc agctgttgga tctgcgccag    4140
caggtttctg ccctgaaggc ttcctcccct cccaatgcgg tttaaaacat aaataaaaaa    4200
ccagactctg tttggatttg gatcaagcaa gtgtcttgct gtctttattt aggggttttg    4260
cgcgcgcggt aggcccggga ccagcggtct cggtcgttga gggtcctgtg tattttttcc    4320
aggacgtggt aaaggtgact ctggatgttc agatacatgg gcataagccc gtctctgggg    4380
tggaggtagc accactgcag agcttcatgc tgcggggtgg tgttgtagat gatccagtcg    4440
tagcaggagc gctgggcgtg gtgcctaaaa atgtctttca gtagcaagct gattgccagg    4500
ggcaggccct tggtgtaagt gtttacaaag cggttaagct gggatgggtg catacgtggg    4560
gatatgagat gcatcttgga ctgtattttt aggttggcta tgttcccagc catatccctc    4620
cggggattca tgttgtgcag aaccaccagc acagtgtatc cggtgcactt gggaaatttg    4680
tcatgtagct tagaaggaaa tgcgtggaag aacttggaga cgcccttgtg acctccaaga    4740
ttttccatgc attcgtccat aatgatggca atgggcccac gggcggcggc ctgggcgaag    4800
atatttctgg gatcactaac gtcatagttg tgttccagga tgagatcgtc ataggccatt    4860
tttacaaagc gcgggcggag ggtgccagac tgcggtataa tggttccatc cggcccaggg    4920
gcgtagttac cctcacagat ttgcatttcc cacgctttga gttcagatgg ggggatcatg    4980
tctacctgcg gggcgatgaa gaaaacggtt tccggggtag gggagatcag ctgggaagaa    5040
agcaggttcc tgagcagctg cgacttaccg cagccggtgg gccgtaaat cacacctatt     5100
accgggtgca actggtagtt aagagagctg cagctgccgt catccctgag caggggggcc    5160
acttcgttaa gcatgtccct gactcgcatg ttttccctga ccaaatccgc cagaaggcgc    5220
tcgccgccca gcgatagcag ttcttgcaag gaagcaaagt ttttcaacgg tttgagaccg    5280
tccgccgtag gcatgctttt gagcgtttga ccaagcagtt ccaggcggtc ccacagctcg    5340
gtcacctgct ctacgcatc tcgatccagc atatctcctc gtttcgcggg ttggggcggc     5400
tttcgctgta cggcagtagt cggtgctcgt ccagacgggc cagggtcatg tctttccacg    5460
ggcgcagggt cctcgtcagc gtagtctggg tcacggtgaa ggggtgcgct ccgggctgcg    5520
cgctggccag ggtgcgcttg aggctggtcc tgctggtgct gaagcgctgc cggtcttcgc    5580
cctgcgcgtc ggccaggtag catttgacca tggtgtcata gtccagcccc tccgcggcgt    5640
```

```
ggcccttggc gcgcagcttg cccttggagg aggcgccgca cgaggggcag tgcagacttt    5700
tgagggcgta gagcttgggc gcgagaaata ccgattccgg ggagtaggca tccgcgccgc    5760 aggcccccgca gacggtctcg cattccacga gccaggtgag ctctggccgt tcggggtcaa   5820
aaaccaggtt tcccccatgc ttttgatgc gtttcttacc tctggtttcc atgagccggt     5880
gtccacgctc ggtgacgaaa aggctgtccg tgtccccgta tacagacttg agaggcctgt    5940
cctcgagcgg tgttccgcgg tcctcctcgt atagaaactc ggaccactct gagacaaagg    6000
ctcgcgtcca ggccagcacg aaggaggcta agtgggaggg gtagcggtcg ttgtccacta    6060
gggggtccac tcgctccagg gtgtgaagac acatgtcgcc ctcttcggca tcaaggaagg    6120
tgattggttt gtaggtgtag gccacgtgac cgggtgttcc tgaaggggg ctataaaagg     6180 gggtgggggc gcgttcgtcc tcactctctt ccgcatcgct gtctgcgagg ccagctgtt     6240 ggggtgagta ctccctctga aaagcgggca tgacttctgc gctaagattg tcagtttcca   6300
aaaacgagga ggatttgata ttcacctggc ccgcggtgat gcctttgagg gtggccgcat    6360
ccatctggtc agaaaagaca atcttttttgt tgtcaagctt ggtggcaaac gacccgtaga  6420
gggcgttgga cagcaacttg gcgatggagc gcagggtttg gttttttgtcg cgatcggcgc   6480 gctccttggc cgcgatgttt agctgcacgt attcgcgcgc aacgcaccgc cattcgggaa    6540
agacggtggt gcgctcgtcg ggaccaggt gcacgcgcca accgcggttg tgcagggtga    6600
caaggtcaac gctggtggct acctctccgc gtaggcgctc gttggtccag cagaggcggc    6660
cgcccttgcg cgagcagaat ggcggtaggg ggtctagctg cgtctcgtcc gggggtctg     6720 cgtccacggt aaagaccccg ggcagcaggc gcgcgtcgaa gtagtctatc ttgcatcctt    6780
gcaagtctag cgcctgctgc catgcgcggg cggcaagcgc gcgctcgtat gggttgagtg    6840
ggggacccca tggcatgggg tgggtgagcg cggaggcgta catgccgcaa atgtcgtaaa    6900
cgtagagggg ctctctgagt attccaagat atgtagggta gcatcttcca ccgcggatgc    6960
tggcgcgcac gtaatcgtat agttcgtgcg agggagcgag gaggtcggga ccgaggttgc    7020
tacgggcggg ctgctctgct cggaagacta tctgcctgaa gatggcatgt gagttggatg    7080
atatggttgg acgctggaag acgttgaagc tggcgtctgt gagacctacc gcgtcacgca    7140
cgaaggaggc gtaggagtcg cgcagcttgt tgaccagctc ggcggtgacc tgcacgtcta    7200
gggcgcagta gtccagggtt tccttgatga tgtcatactt atcctgtccc ttttttttcc    7260
acagctcgcg gttgaggaca aactcttcgc ggtctttcca gtactcttgg atcggaaacc    7320
cgtcggcctc cgaacggtaa gagcctagca tgtagaactg gttgacgcc tggtaggcgc     7380 agcatccctt ttctacgggt agcgcgtatg cctgcgcggc cttccggagc gaggtgtggg    7440
tgagcgcaaa ggtgtccctg accatgactt tgaggtactg gtatttgaag tcagtgtcgt    7500
cgcatccgcc ctgctcccag agcaaaaagt ccgtgcgctt tttggaacgc ggatttggca    7560
gggcgaaggt gacatcgttg aagagtatct ttccgcgcg aggcataaag ttgcgtgtga    7620
tgcggaaggg tcccggcacc tcggaacggt tgttaattac ctgggcggcg agcacgatct    7680
cgtcaaagcc gttgatgttg tggcccacaa tgtaaagttc caagaagcgc gggatgccct    7740
tgatggaagg caattttttta agttcctcgt aggtgagctc ttcaggggag ctgagcccgt    7800
gctctgaaag ggcccagtct gcaagatgag ggttggaagc gacgaatgag ctccacaggt    7860
cacgggccat tagcatttgc aggtggtcgc gaaaggtcct aaactggcga cctatggcca    7920
ttttttctgg ggtgatgcag tagaaggtaa gcgggtcttg ttcccagcgg tcccatccaa    7980
```

```
ggttcgcggc taggtctcgc gcggcagtca ctagaggctc atctccgccg aacttcatga    8040
ccagcatgaa gggcacgagc tgcttcccaa aggcccccat ccaagtatag gtctctacat    8100
cgtaggtgac aaagagacgc tcggtgcgag gatgcgagcc gatcgggaag aactggatct    8160
cccgccacca attggaggag tggctattga tgtggtgaaa gtagaagtcc ctgcgacggg    8220
ccgaacactc gtgctggctt ttgtaaaaac gtgcgcagta ctggcagcgg tgcacgggct    8280
gtacatcctg cacgaggttg acctgacgac cgcgcacaag gaagcagagt gggaatttga    8340
gcccctcgcc tggcgggttt ggctggtggt cttctacttc ggctgcttgt ccttgaccgt    8400
ctggctgctc gaggggagtt acggtggatc ggaccaccac gccgcgcgag cccaaaagtcc   8460 agatgtccgc gcgcggcggt cggagcttga tgacaacatc gcgcagatgg gagctgtcca    8520
tggtctggag ctcccgcggc gtcaggtcag gcgggagctc ctgcaggttt acctcgcata    8580
gacgggtcag ggcgcgggct agatccaggt gataccfaat ttccaggggc tggttggtgg    8640
cggcgtcgat ggcttgcaag aggccgcatc cccgcggcgc gactacggta ccgcgcggcg    8700
ggcggtgggc cgcgggggtg tccttggatg atgcatctaa aagcggtgac gcgggcgagc    8760
ccccggaggt aggggggggct ccggacccgc cgggagaggg ggcaggggca cgtcggcgcc    8820
gcgcgcgggc aggagctggt gctgcgcgcg taggttgctg cgaacgcga cgacgcggcg     8880 gttgatctcc tgaatctggc gcctctgcgt gaagacgacg ggcccggtga gcttgagcct    8940
gaaagagagt tcgacagaat caatttcggt gtcgttgacg gcggcctggc gcaaaatctc    9000
ctgcacgtct cctgagttgt cttgataggc gatctcggcc atgaactgct cgatctcttc    9060
ctcctggaga tctccgcgtc cggctcgctc acggtggcg gcgaggtcgt tggaaatgcg     9120
ggccatgagc tgcgagaagg cgttgaggcc tccctcgttc cagacgcggc tgtagaccac    9180 gccccttcg gcatcgcggg cgcgcatgac cacctgcgcg agattgagct ccacgtgccg     9240
ggcgaagacg gcgtagtttc gcaggcgctg aaagaggtag ttgagggtgg tggcggtgtg    9300
ttctgccacg aagaagtaca taacccagcg tcgcaacgtg gattcgttga tatcccccaa    9360
ggcctcaagg cgctccatgg cctcgtagaa gtccacggcg aagttgaaaa actgggagtt    9420
gcgcgccgac acggttaact cctcctccag aagacggatg agctcggcga cagtgtcgcg    9480
cacctcgcgc tcaaaggcta caggggcctc ttcttcttct tcaatctcct cttccataag    9540
ggcctcccct tcttcttctt ctggcggcgg tgggggaggg gggacacggc ggcgacgacg    9600
gcgcaccggg aggcggtcga caaagcgctc gatcatctcc ccgcggcgac ggcgcatggt    9660
ctcggtgacg gcgcggccgt tctcgcgggg gcgcagttgg aagacgccgc ccgtcatgtc    9720
ccggttatgg gttggcgggg ggctgccatg cggcagggat acggcgctaa cgatgcatct    9780
caacaattgt tgtgtaggta ctccgccgcc gagggacctg agcgagtccg catcgaccgg    9840
atcggaaaac ctctcgagaa aggcgtctaa ccagtcacag tcgcaaggta ggctgagcac    9900
cgtggcgggc ggcagcgggc ggcggtcggg gttgtttctg gcggaggtgc tgctgatgat    9960
gtaattaaag taggcggtct tgagacggcg gatggtcgac agaagcacca tgtccttggg    10020
tccggcctgc tgaatgcgca ggcggtcggc catgcccag gcttcgtttt gacatcggcg     10080
caggtctttg tagtagtctt gcatgagcct ttctaccggc acttcttctt ctccttcctc    10140
ttgtcctgca tctcttgcat ctatcgctgc ggcggcggcg gagtttggcc gtaggtggcg    10200
ccctcttcct cccatgcgtg tgaccccgaa gccctcatc ggctgaagca gggctaggtc     10260
ggcgacaacg cgctcggcta atatggcctg ctgcacctgc gtgagggtag actggaagtc    10320
atccatgtcc acaaagcggt ggtatgcgcc cgtgttgatg gtgtaagtgc agttggccat    10380
```

```
aacggaccag ttaacggtct ggtgacccgg ctgcgagagc tcggtgtacc tgagacgcga   10440
gtaagccctc gagtcaaata cgtagtcgtt gcaagtccgc accaggtact ggtatcccac   10500
caaaaagtgc ggcggcggct ggcggtagag gggccagcgt agggtggccg gggctccggg   10560
ggcgagatct tccaacataa ggcgatgata tccgtagatg tacctggaca tccaggtgat   10620
gccggcggcg gtggtggagg cgcgcggaaa gtcgcggacg cggttccaga tgttgcgcag   10680
cggcaaaaag tgctccatgg tcgggacgct ctggccggtc aggcgcgcgc aatcgttgac   10740
gctctaccgt gcaaaggag agcctgtaag cgggcactct tccgtggtct ggtggataaa   10800
ttcgcaaggg tatcatggcg gacgaccggg gttcgagccc cgtatccggc cgtccgccgt   10860
gatccatgcg gttaccgccc gcgtgtcgaa cccaggtgtg cgacgtcaga caacggggga   10920
gtgctccttt tggcttcctt ccaggcgcgg cggctgctgc gctagctttt ttggccactg   10980
gccgcgcgca gcgtaagcgg ttaggctgga aagcgaaagc attaagtggc tcgctccctg   11040
tagccggagg gttattttcc aagggttgag tcgcgggacc cccggttcga gtctcggacc   11100
ggccggactg cggcgaacgg gggtttgcct ccccgtcatg caagaccccg cttgcaaatt   11160
cctccggaaa cagggacgag ccccttttt gcttttccca gatgcatccg gtgctgcggc   11220
agatgcgccc ccctcctcag cagcggcaag agcaagagca gcggcagaca tgcagggcac   11280
cctcccctcc tcctaccgcg tcaggagggg cgacatccgc ggttgacgcg gcagcagatg   11340
gtgattacga accccgcgg cgccgggccc ggcactacct ggacttggag gagggcgagg   11400
gcctggcgcg gctaggagcg ccctctcctg agcggtaccc aagggtgcag ctgaagcgtg   11460
atacgcgtga ggcgtacgtg ccgcggcaga acctgtttcg cgaccgcgag ggagaggagc   11520
ccgaggagat gcgggatcga aagttccacg cagggcgcga gctgcggcat ggcctgaatc   11580
gcgagcggtt gctgcgcgag gaggactttg agcccgacgc gcgaaccggg attagtcccg   11640
cgcgcgcaca cgtggcggcc gccgacctgg taaccgcata cgagcagacg gtgaaccagg   11700
agattaactt tcaaaaaagc tttaacaacc acgtgcgtac gcttgtggcg cgcgaggagg   11760
tggctatagg actgatgcat ctgtgggact ttgtaagcgc gctggagcaa aacccaaata   11820
gcaagccgct catggcgcag ctgttcctta tagtgcagca cagcagggac aacgaggcat   11880
tcagggatgc gctgctaaac atagtagagc ccgagggccg ctggctgctc gatttgataa   11940
acatcctgca gagcatagtg gtgcaggagc gcagcttgag cctggctgac aaggtggccg   12000
ccatcaacta ttccatgctt agcctgggca agttttacgc ccgcaagata taccatcccc   12060
cttacgttcc catagacaag gaggtaaaga tcgaggggtt ctacatgcgc atggcgctga   12120
aggtgcttac cttgagcgac gacctgggcg tttatcgcaa cgagcgcatc cacaaggccg   12180
tgagcgtgag ccggcggcgc gagctcagcg accgcgagct gatgcacagc ctgcaaaggg   12240
ccctggctgg cacgggcagc ggcgatagag aggccgagtc ctactttgac gcgggcgctg   12300
acctgcgctg gcccaagc cgacgcgccc tggaggcagc tggggccgga cctgggctgg   12360
cggtggcacc cgcgcgcgct ggcaacgtcg gcggcgtgga ggaatatgac gaggacgatg   12420
agtacgagcc agaggacggc gagtactaag cggtgatgtt tctgatcaga tgatgcaaga   12480
cgcaacggac ccggcggtgc gggcggcgct gcagagccag ccgtccggcc ttaactccac   12540
ggacgactgg cgccaggtca tggaccgcat catgtcgctg actgcgcgca atcctgacgc   12600
gttccggcag cagccgcagg ccaaccggct ctccgcaatt ctggaagcgg tggtcccggc   12660
gcgcgcaaac cccacgcacg agaaggtgct ggcgatcgta aacgcgctgg ccgaaaacag   12720
```

```
ggccatccgg cccgacgagg ccggcctggt ctacgacgcg ctgcttcagc gcgtggctcg    12780
ttacaacagc ggcaacgtgc agaccaacct ggaccggctg gtgggggatg tgcgcgaggc    12840
cgtggcgcag cgtgagcgcg cgcagcagca gggcaacctg ggctccatgg ttgcactaaa    12900
cgccttcctg agtacacagc ccgccaacgt gccgcgggga caggaggact acaccaactt    12960
tgtgagcgca ctgcggctaa tggtgactga dacaccgcaa agtgaggtgt accagtctgg    13020
gccagactat tttttccaga ccagtagaca aggcctgcag accgtaaacc tgagccaggc    13080
tttcaaaaac ttgcaggggc tgtgggggt gcgggctccc acaggcgacc gcgcgaccgt    13140
gtctagcttg ctgacgccca actcgcgcct gttgctgctg ctaatagcgc ccttcacgga    13200
cagtggcagc gtgtcccggg acacatacct aggtcacttg ctgacactgt accgcgaggc    13260
cataggtcag gcgcatgtgg acgagcatac tttccaggag attacaagtg tcagccgcgc    13320
gctggggcag gaggacacgg gcagcctgga ggcaaccta aactacctgc tgaccaaccg    13380
gcggcagaag atcccctcgt tgcacagttt aaacagcgag gaggagcgca ttttgcgcta    13440
cgtgcagcag agcgtgagcc ttaacctgat gcgcgacggg gtaacgccca gcgtggcgct    13500
ggacatgacc gcgcgcaaca tggaaccggg catgtatgcc tcaaaccggc cgtttatcaa    13560
ccgcctaatg gactacttgc atcgcgcggc cgccgtgaac cccgagtatt tcaccaatgc    13620
catcttgaac ccgcactggc taccgccccc tggtttctac accgggggat tcgaggtgcc    13680
cgagggtaac gatggattcc tctgggacga catagacgac agcgtgtttt ccccgcaacc    13740
gcagaccctg ctagagttgc aacagcgcga gcaggcagag gcggcgctgc gaaaggaaag    13800
cttccgcagg ccaagcagct tgtccgatct aggcgctgcg gccccgcggt cagatgctag    13860
tagcccattt ccaagcttga tagggtctct taccagcact cgcaccaccc gcccgcgcct    13920
gctgggcgag gaggagtacc taaacaactc gctgctgcag ccgcagcgcg aaaaaaacct    13980
gcctccggca tttcccaaca cgggataga gagcctagtg acaagatga gtagatggaa    14040 gacgtacgcg caggagcaca gggacgtgcc aggcccgcgc ccgcccaccc gtcgtcaaag    14100
gcacgaccgt cagcggggtc tggtgtggga ggacgatgac tcggcagacg acagcagcgt    14160
cctggatttg ggagggagtg gcaacccgtt tgcgcacctt cgccccaggc tggggagaat    14220
gttttaaaaa aaaaaagca tgatgcaaaa taaaaaactc accaaggcca tggcaccgag    14280
cgttggtttt cttgtattcc ccttagtatg cggcgcgcgg cgatgtatga ggaaggtcct    14340
cctccctcct acgagagtgt ggtgagcgcg gcgccagtgg cggcggcgct gggttctccc    14400
ttcgatgctc ccctggaccc gccgtttgtg cctccgcgt acctgcggcc taccgggggg    14460
agaaacagca tccgttactc tgagttggca cccctattcg acaccaccg tgtgtacctg    14520 gtggacaaca agtcaacgga tgtggcatcc ctgaactacc agaacgacca cagcaacttt    14580
ctgaccacgg tcattcaaaa caatgactac agcccggggg aggcaagcac acagaccatc    14640
aatcttgacg accggtcgca ctggggcggc gacctgaaaa ccatcctgca taccaacatg    14700
ccaaatgtga acgagttcat gtttaccaat aagtttaagg cgcgggtgat ggtgtcgcgc    14760
ttgcctacta aggacaatca ggtggagctg aaatacgagt gggtggagtt cacgctgccc    14820
gagggcaact actccgagac catgaccata gaccttatga acaacgcgat cgtggagcac    14880
tacttgaaag tgggcagaca gaacgggggt ctggaaagcg acatcggggt aaagtttgac    14940
acccgcaact tcagactggg gtttgacccc gtcactggtc ttgtcatgcc tgggggtatat    15000 acaaacgaag ccttccatcc agacatcatt ttgctgccag gatgcgggt ggacttcacc    15060 cacagccgcc tgagcaactt gttgggcatc cgcaagcggc aacccttcca ggagggcttt    15120
```

```
aggatcacct acgatgatct ggagggtggt aacattcccg cactgttgga tgtggacgcc    15180
taccaggcga gcttgaaaga tgacaccgaa cagggcgggg gtggcgcagg cggcagcaac    15240
agcagtggca gcggcgcgga agagaactcc aacgcggcag ccgcggcaat gcagccggtg    15300
gaggacatga acgatcatgc cattcgcggc gacacctttg ccacacgggc tgaggagaag    15360
cgcgctgagg ccgaagcagc ggccgaagct gccgcccccg ctgcgcaacc cgaggtcgag    15420
aagcctcaga gaaaccggt gatcaaaccc ctgacagagg acagcaagaa acgcagttac     15480
aacctaataa gcaatgacag caccttcacc cagtaccgca gctggtacct tgcatacaac    15540 tacgcgacc ctcagaccgg aatccgctca tggaccctgc tttgcactcc tgacgtaacc     15600
tgcggctcgg agcaggtcta ctggtcgttg ccagacatga tgcaagaccc cgtgaccttc    15660
cgctccacgc gccagatcag caactttccg gtggtgggcg ccgagctgtt gcccgtgcac    15720
tccaagagct tctacaacga ccaggccgtc tactcccaac tcatccgcca gtttacctct    15780
ctgacccacg tgttcaatcg ctttcccgag aaccagattt ggcgcgccc gccagccccc    15840 accatcacca ccgtcagtga aaacgttcct gctctcacag atcacgggac gctaccgctg    15900
cgcaacagca tcggaggagt ccagcgagtg accattactg acgccagacg ccgcacctgc    15960
ccctacgttt acaaggccct gggcatagtc tcgccgcgcg tcctatcgag ccgcactttt    16020
tgagcaagca tgtccatcct tatatcgccc agcaataaca caggctgggg cctgcgcttc    16080
ccaagcaaga tgtttggcgg ggccaagaag cgctccgacc aacacccagt gcgcgtgcgc    16140
gggcactacc gcgcgccctg gggcgcgcac aaacgcggcc gcactgggcg caccaccgtc    16200
gatgacgcca tcgacgcggt ggtggaggag gcgcgcaact acacgcccac gccgccacca    16260
gtgtccacag tggacgcggc cattcagacc gtggtgcgcg gagcccggcg ctatgctaaa    16320
atgaagagac ggcggaggcg cgtagcacgt cgccaccgcc gccgacccgg cactgccgcc    16380
caacgcgcgg cggcggccct gcttaaccgc gcacgtcgca ccggccgacg ggcggccatg    16440
cgggccgctc gaaggctggc cgcgggtatt gtcactgtgc ccccaggtc caggcgacga     16500 gcggccgccg cagcagccgc ggccattagt gctatgactc agggtcgcag ggcaacgtg     16560 tattgggtgc gcgactcggt tagcggcctg cgcgtgcccg tgcgcacccg ccccccgcgc    16620
aactagattg caagaaaaaa ctacttagac tcgtactgtt gtatgtatcc agcggcggcg    16680
gcgcgcaacg aagctatgtc caagcgcaaa atcaaagaag atgctcca ggtcatcgcg      16740 ccggagatct atggccccc gaagaaggaa gagcaggatt acaagcccg aaagctaaag      16800 cgggtcaaaa agaaaaagaa agatgatgat gatgaacttg acgacgaggt ggaactgctg    16860
cacgctaccg cgcccaggcg acgggtacag tggaaaggtc gacgcgtaaa acgtgttttg    16920
cgacccggca ccaccgtagt ctttacgccc ggtgagcgct ccaccccgcac ctacaagcgc   16980 gtgtatgatg aggtgtacgg cgacgaggac ctgcttgagc aggccaacga gcgcctcggg    17040
gagtttgcct acgaaagcg gcataaggac atgctggcgt tgccgctgga cgagggcaac    17100
ccaacaccta gcctaaagcc cgtaacactg cagcaggtgc tgcccgcgct tgcaccgtcc    17160
gaagaaaagc gcggcctaaa gcgcgagtct ggtgacttgg cacccaccgt gcagctgatg    17220
gtacccaagc ccagcgact ggaagatgtc ttggaaaaaa tgaccgtgga acctgggctg     17280
gagcccgagg tccgcgtgcg gccaatcaag caggtggcgc cgggactggg cgtgcagacc    17340
gtggacgttc agatacccac taccagtagc accagtattg ccaccgccac agagggcatg    17400
gagacacaaa cgtccccggt tgcctcagcg gtggcggatg ccgcggtgca ggcggtcgct    17460
```

```
gcggccgcgt ccaagacctc tacggaggtg caaacggacc cgtggatgtt tcgcgtttca  17520
gcccccggc gcccgcgcgg ttcgaggaag tacggcgccg ccagcgcgct actgcccgaa  17580
tatgccctac atccttccat tgcgcctacc cccggctatc gtggctacac ctaccgcccc  17640
agaagacgag caactacccg acgccgaacc accactggaa cccgccgccg ccgtcgccgt  17700
cgccagcccg tgctggcccc gatttccgtg cgcagggtgg ctcgcgaagg aggcaggacc  17760
ctggtgctgc aacagcgcg ctaccacccc agcatcgttt aaaagccggt ctttgtggtt  17820
cttgcagata tggccctcac ctgccgcctc cgtttcccgg tgccgggatt ccgaggaaga  17880
atgcaccgta ggaggggcat ggccggccac ggcctgacgg gcggcatgcg tcgtgcgcac  17940
caccggcggc ggcgcgcgtc gcaccgtcgc atgcgcggcg gtatcctgcc cctccttatt  18000
ccactgatcg ccgcggcgat tggcgccgtg cccggaattg catccgtggc cttgcaggcg  18060
cagagacact gattaaaaac aagttgcatg tggaaaaatc aaaataaaaa gtctggactc  18120
tcacgctcgc ttggtcctgt aactattttg tagaatggaa gacatcaact ttgcgtctct  18180
ggccccgcga cacggctcgc gcccgttcat gggaaactgg caagatatcg gcaccagcaa  18240
tatgagcggt ggcgccttca gctggggctc gctgtggagc ggcattaaaa atttcggttc  18300
caccgttaag aactatggca gcaaggcctg gaacagcagc acaggccaga tgctgaggga  18360
taagttgaaa gagcaaaatt tccaacaaaa ggtggtagat ggcctggcct ctggcattag  18420
cggggtggtg gacctggcca accaggcagt gcaaaataag attaacagta agcttgatcc  18480
ccgccctccc gtagaggagc ctccaccggc cgtggagaca gtgtctccag aggggcgtgg  18540
cgaaaagcgt ccgcgccccg cagggaaga aactctggtg acgcaaatag acgagcctcc  18600
ctcgtacgag gaggcactaa agcaaggcct gcccaccacc cgtcccatcg cgcccatggc  18660
taccggagtg ctgggccagc acacaccccgt aacgctggac ctgcctcccc ccgccgacac  18720
ccagcagaaa cctgtgctgc caggcccgac cgccgttgtt gtaacccgtc ctagccgcgc  18780
gtccctgcgc cgcgccgcca gcggtccgcg atcgttgcgg cccgtagcca gtggcaactg  18840
gcaaagcaca ctgaacagca tcgtgggtct gggggtgcaa tccctgaagc gccgacgatg  18900
cttctgaata gctaacgtgt cgtatgtgtg tcatgtatgc gtccatgtcg ccgccagagg  18960
agctgctgag ccgccgcgcg cccgctttcc aagatggcta ccccttcgat gatgccgcag  19020
tggtcttaca tgcacatctc gggccaggac gcctcggagt acctgagccc cgggctggtg  19080
cagtttgccc gcgccaccga gacgtacttc agcctgaata caagtttag aaaccccacg  19140
gtggcgccta cgcacgacgt gaccacagac cggtcccagc gtttgacgct gcggttcatc  19200
cctgtggacc gtgaggatac tgcgtactcg tacaaggcgc ggttcaccct agctgtgggt  19260
gataaccgtg tgctggacat ggcttccacg tactttgaca tccgcggcgt gctggacagg  19320
ggccctactt ttaagcccta ctctggcact gcctacaacg ccctggctcc caagggtgcc  19380
ccaaatcctt gcgaatggga tgaagctgct actgctcttg aaataaacct agaagaagag  19440
gacgatgaca acgaagacga agtagacgag caagctgagc agcaaaaaac tcacgtattt  19500
gggcaggcgc cttattctgg tataaatatt acaaaggagg gtattcaaat aggtgtcgaa  19560
ggtcaaacac ctaaatatgc cgataaaaca tttcaacctg aacctcaaat aggagaatct  19620
cagtggtacg aaactgaaat taatcatgca gctgggagag tccttaaaaa gactacccca  19680
atgaaaccat gttacggttc atatgcaaaa cccacaaatg aaaatggagg caaggcatt  19740
cttgtaaagc aacaaatgg aaagctagaa agtcaagtgg aaatgcaatt tttctcaact  19800
actgaggcga ccgcaggcaa tggtgataac ttgactccta agtggtatt gtacagtgaa  19860
```

```
gatgtagata tagaaacccc agacactcat atttcttaca tgcccactat taaggaaggt   19920
aactcacgag aactaatggg ccaacaatct atgcccaaca ggcctaatta cattgctttt   19980
agggacaatt ttattggtct aatgtattac aacagcacgg gtaatatggg tgttctggcg   20040
ggccaagcat cgcagttgaa tgctgttgta gatttgcaag acagaaacac agagctttca   20100
taccagcttt tgcttgattc cattggtgat agaaccaggt acttttctat gtggaatcag   20160
gctgttgaca gctatgatcc agatgttaga attattgaaa atcatggaac tgaagatgaa   20220
cttccaaatt actgctttcc actgggaggt gtgattaata cagagactct taccaaggta   20280
aaacctaaaa caggtcagga aaatggatgg gaaaaagatg ctacagaatt ttcagataaa   20340
aatgaaataa gagttggaaa taattttgcc atggaaatca atctaaatgc caacctgtgg   20400
agaaatttcc tgtactccaa catagcgctg tatttgcccg acaagctaaa gtacagtcct   20460
tccaacgtaa aaatttctga taacccaaac acctacgact acatgaacaa gcgagtggtg   20520
gctcccgggt tagtggactg ctacattaac cttggagcac gctggtccct tgactatatg   20580
gacaacgtca acccatttaa ccaccaccgc aatgctggcc tgcgctaccg ctcaatgttg   20640
ctgggcaatg gtcgctatgt gcccttccac atccaggtgc ctcagaagtt ctttgccatt   20700
aaaaacctcc ttctcctgcc gggctcatac acctacgagt ggaacttcag gaaggatgtt   20760
aacatggttc tgcagagctc cctaggaaat gacctaaggg ttgacggagc cagcattaag   20820
tttgatagca tttgccttta cgccaccttc ttccccatgg cccacaacac cgcctccacg   20880
cttgaggcca tgcttagaaa cgacaccaac gaccagtcct ttaacgacta tctctccgcc   20940
gccaacatgc tctaccctat acccgccaac gctaccaacg tgcccatatc catcccctcc   21000
cgcaactggg cggcttttcc cggctgggcc ttcacgcgcc ttaagactaa ggaaaccccca   21060 tcactgggct cgggctacga cccttattac acctactctg gctctatacc ctacctagat   21120
ggaacctttt acctcaacca caccttttaag aaggtggcca ttacctttga ctcttctgtc   21180
agctggcctg gcaatgaccg cctgcttacc cccaacgagt ttgaaattaa gcgctcagtt   21240
gacggggagg gttacaacgt tgcccagtgt aacatgacca aagactggtt cctggtacaa   21300
atgctagcta actacaacat tggctaccag ggcttctata tcccagagag ctacaaggac   21360
cgcatgtact ccttctttag aaacttccag cccatgagcc gtcaggtggt ggatgatact   21420
aaatacaagg actaccaaca ggtgggcatc ctacaccaac acaacaactc tggatttgtt   21480
ggctaccttg cccccaccat gcgcgaagga caggcctacc ctgctaactt cccctatccg   21540
cttataggca agaccgcagt tgacagcatt acccagaaaa agtttctttg cgatcgcacc   21600
ctttggcgca tcccattctc cagtaacttt atgtccatgg gcgcactcac agacctgggc   21660
caaaaccttc tctacgccaa ctccgcccac cgcgctagaca tgactttga ggtggatccc   21720 atggacgagc ccaccccttct ttatgttttg tttgaagtct ttgacgtggt ccgtgtgcac   21780
cggccgcacc gcgcgtcat cgaaaccgtg tacctgcgca cgcccttctc ggccggcaac   21840
gccacaacat aaagaagcaa gcaacatcaa caacagctgc cgccatgggc tccagtgagc   21900
aggaactgaa agccattgtc aaagatcttg gttgtgggcc atattttttg ggcacctatg   21960
acaagcgctt tccaggcttt gtttctccac acaagctcgc ctgcgccata gtcaatacgg   22020
ccggtcgcga gactgggggc gtacactgga tggcctttgc ctggaacccg cactcaaaaa   22080
catgctacct ctttgagccc tttggctttt ctgaccagcg actcaagcag gtttaccagt   22140
ttgagtacga gtcactcctg cgccgtagcg ccattgcttc ttccccgac cgctgtataa   22200
```

```
cgctggaaaa gtccacccaa agcgtacagg ggcccaactc ggccgcctgt ggactattct   22260
gctgcatgtt tctccacgcc tttgccaact ggccccaaac tcccatggat cacaacccca   22320
ccatgaacct tattaccggg gtacccaact ccatgctcaa cagtccccag gtacagccca   22380
ccctgcgtcg caaccaggaa cagctctaca gcttcctgga gcgccactcg ccctacttcc   22440
gcagccacag tgcgcagatt aggagcgcca cttcttttg tcacttgaaa aacatgtaaa   22500
aataatgtac tagagacact ttcaataaag gcaaatgctt ttatttgtac actctcgggt   22560
gattatttac ccccacccct gccgtctgcg ccgttttaaaa atcaaagggg ttctgccgcg   22620
catcgctatg cgccactggc agggacacgt tgcgatactg gtgtttagtg ctccacttaa   22680
actcaggcac aaccatccgc ggcagctcgg tgaagttttc actccacagg ctgcgcacca   22740
tcaccaacgc gtttagcagg tcgggcgccg atatcttgaa gtcgcagttg gggcctccgc   22800
cctgcgcgcg cgagttgcga tacacagggt tgcagcactg gaacactatc agcgccgggt   22860
ggtgcacgct ggccagcacg ctcttgtcgg agatcagatc cgcgtccagg tcctccgcgt   22920
tgctcagggc gaacggagtc aactttggta gctgccttcc caaaaagggc gcgtgcccag   22980
gctttgagtt gcactcgcac cgtagtggca tcaaaaggtg accgtgcccg gtctgggcgt   23040
taggatacag cgcctgcata aaagccttga tctgcttaaa agccacctga gcctttgcgc   23100
cttcagagaa gaacatgccc caagacttgc cggaaaactg attggccgga caggccgcgt   23160
cgtgcacgca gcaccttgcg tcggtgttgg agatctgcac cacatttcgg ccccaccggt   23220
tcttcacgat cttggccttg ctagactgct ccttcagcgc gcgctgcccg ttttcgctcg   23280
tcacatccat ttcaatcacg tgctccttat ttatcataat gcttccgtgt agacacttaa   23340
gctcgccttc gatctcagcg cagcggtgca gccacaacgc gcagcccgtg ggctcgtgat   23400
gcttgtaggt cacctctgca aacgactgca ggtacgcctg caggaatcgc cccatcatcg   23460
tcacaaaggt cttgttgctg gtgaaggtca gctgcaaccc gcggtgctcc tcgttcagcc   23520
aggtcttgca tacggccgcc agagcttcca cttggtcagg cagtagtttg aagttcgcct   23580
ttagatcgtt atccacgtgg tacttgtcca tcagcgcgcg cgcagcctcc atgcccttct   23640
cccacgcaga cacgatcggc acactcagcg ggttcatcac cgtaatttca ctttccgctt   23700
cgctgggctc ttcctcttcc tcttgcgtcc gcataccacg cgccactggg tcgtcttcat   23760
tcagccgccg cactgtgcgc ttacctcctt tgccatgctt gattagcacc ggtgggttgc   23820
tgaaacccac catttgtagc gccacatctt ctctttcttc ctcgctgtcc acgattacct   23880
ctggtgatgg cgggcgctcg ggcttgggag aagggcgctt cttttctc ttgggcgcaa   23940 tggccaaatc cgccgccgag gtcgatggcc gcgggctggg tgtgcgcggc accagcgcgt   24000
cttgtgatga gtcttcctcg tcctcggact cgatacgccg cctcatccgc ttttttgggg   24060
gcgcccgggg aggcggcggc gacggggacg gggacgacac gtcctccatg gttggggac   24120 gtcgcgccgc accgcgtccg cgctcggggg tggtttcgcg ctgctcctct tcccgactgg   24180
ccatttcctt ctcctataagg cagaaaaaga tcatggagtc agtcgagaag aaggacagcc   24240
taaccgcccc ctctgagttc gccaccaccg cctccaccga tgccgccaac gcgcctacca   24300
ccttccccgt cgaggcaccc ccgcttgagg aggaggaagt gattatcgag caggacccag   24360
gttttgtaag cgaagacgac gaggaccgct cagtaccaac agaggataaa aagcaagacc   24420
aggacaacgc agaggcaaac gaggaacaag tcgggcgggg ggacgaaagg catggcgact   24480
acctagatgt gggagacgac gtgctgttga agcatctgca gcgccagtgc gccattatct   24540
gcgacgcgtt gcaagagcgc agcgatgtgc ccctcgccat agcggatgtc agccttgcct   24600
```

```
acgaacgcca cctattctca ccgcgcgtac cccccaaacg ccaagaaaac ggcacatgcg   24660
agcccaaccc gcgcctcaac ttctaccccg tatttgccgt gccagaggtg cttgccacct   24720
atcacatctt tttccaaaac tgcaagatac ccctatcctg ccgtgccaac cgcagccgag   24780
cggacaagca gctggccttg cggcagggcg ctgtcatacc tgatatcgcc tcgctcaacg   24840
aagtgccaaa aatctttgag ggtcttggac gcgacgagaa gcgcgcggca aacgctctgc   24900
aacaggaaaa cagcgaaaat gaaagtcact ctggagtgtt ggtggaactc gagggtgaca   24960
acgcgcgcct agccgtacta aaacgcagca tcgaggtcac ccactttgcc tacccggcac   25020
ttaacctacc ccccaaggtc atgagcacag tcatgagtga gctgatcgtg cgccgtgcgc   25080
agcccctgga gagggatgca aatttgcaag aacaaacaga ggagggccta cccgcagttg   25140
gcgacgagca gctagcgcgc tggcttcaaa cgcgcgagcc tgccgacttg gaggagcgac   25200
gcaaactaat gatggccgca gtgctcgtta ccgtggagct tgagtgcatg cagcggttct   25260
ttgctgaccc ggagatgcag cgcaagctag aggaaacatt gcactacacc tttcgacagg   25320
gctacgtacg ccaggcctgc aagatctcca acgtggagct ctgcaacctg gtctcctacc   25380
ttggaatttt gcacgaaaac cgccttgggc aaaacgtgct tcattccacg ctcaagggcg   25440
aggcgcgccg cgactacgtc cgcgactgcg tttacttatt tctatgctac acctggcaga   25500
cggccatggg cgtttggcag cagtgcttgg aggagtgcaa cctcaaggag ctgcagaaac   25560
tgctaaagca aaacttgaag gacctatgga cggccttcaa cgagcgctcc gtggccgcgc   25620
acctggcgga catcattttc cccgaacgcc tgcttaaaac cctgcaacag ggtctgccag   25680
acttcaccag tcaaagcatg ttgcagaact ttaggaactt tatcctagag cgctcaggaa   25740
tcttgcccgc cacctgctgt gcacttccta gcgactttgt gcccattaag taccgcgaat   25800
gccctccgcc gctttgggc cactgctacc ttctgcagct agccaactac cttgcctacc   25860
actctgacat aatggaagac gtgagcggtg acggtctact ggagtgtcac tgtcgctgca   25920
acctatgcac cccgcaccgc tccctggttt gcaattcgca gctgcttaac gaaagtcaaa   25980
ttatcggtac ctttgagctg cagggtcccc cgcctgacga aaagtccgcg gctccggggt   26040
tgaaactcac tccggggctg tggacgtcgg cttaccttcg caaatttgta cctgaggact   26100
accacgccca cgagattagg ttctacgaag accaatcccg cccgccaaat gcggagctta   26160
ccgcctgcgt cattacccag ggccacattc ttggccaatt gcaagccatc aacaaagccc   26220
gccaagagtt tctgctacga aagggacggg gggtttactt ggaccccag tccggcgagg   26280 agctcaaccc aatccccccg ccgccgcagc cctatcagca gcagccgcgg gccctttgctt   26340 cccaggatgg caccaaaaa gaagctgcag ctgccgccgc cacccacgga cgaggaggaa   26400
tactgggaca gtcaggcaga ggaggttttg gacgaggagg aggaggacat gatggaagac   26460
tgggagagcc tagacgagga agcttccgag gtcgaagagg tgtcagacga aacaccgtca   26520
ccctcggtcg cattcccctc gccggcgccc cagaaatcgg caaccggttc cagcatggct   26580
acaacctccg ctcctcaggc gccgccggca ctgcccgttc gccgacccaa ccgtagatgg   26640
gacaccactg gaaccagggc cggtaagtcc aagcagccgc cgccgttagc ccaagagcaa   26700
caacagcgcc aaggctaccg ctcatggcgc gggcacaaga acgccatagt tgcttgcttg   26760
caagactgtg ggcaacat ctccttcgcc cgccgctttc ttctctacca tcacggcgtg   26820
gccttccccc gtaacatcct gcattactac cgtcatctct acagcccata ctgcaccggc   26880
ggcagcggca gcggcagcaa cagcagcggc cacacagaag caaaggcgac cggatagcaa   26940
```

```
gactctgaca aagcccaaga atccacagc ggcggcagca gcaggaggag gagcgctgcg    27000
tctggcgccc aacgaacccg tatcgacccg cgagcttaga aacaggattt ttcccactct    27060
gtatgctata tttcaacaga gcaggggcca agaacaagag ctgaaaataa aaaacaggtc    27120
tctgcgatcc ctcacccgca gctgcctgta tcacaaaagc gaagatcagc ttcggcgcac    27180
gctggaagac gcggaggctc tcttcagtaa atactgcgcg ctgactctta aggactagtt    27240
tcgcgccctt tctcaaattt aagcgcgaaa actacgtcat ctccagcggc cacacccggc    27300
gccagcacct gtcgtcagcg ccattatgag caaggaaatt cccacgccct acatgtggag    27360
ttaccagcca caaatgggac ttgcggctgg agctgcccaa gactactcaa cccgaataaa    27420
ctacatgagc gcgggacccc acatgatatc ccgggtcaac ggaatccgcg cccaccgaaa    27480
ccgaattctc ttggaacagg cggctattac caccacacct cgtaataacc ttaatccccg    27540
tagttggccc gctgccctgg tgtaccagga aagtcccgct cccaccactg tggtacttcc    27600
cagagacgcc caggccgaag ttcagatgac taactcaggg gcgcagcttg cgggcggctt    27660
tcgtcacagg gtgcggtcgc ccgggcaggg tataactcac ctgacaatca gagggcgagg    27720
tattcagctc aacgacgagt cggtgagctc ctcgcttggt ctccgtccgg acgggacatt    27780
tcagatcggc ggcgccggcc gtccttcatt cacgcctcgt caggcaatcc taactctgca    27840
gacctcgtcc tctgagccgc gctctggagg cattggaact ctgcaattta ttgaggagtt    27900
tgtgccatcg gtctacttta accccttctc gggacctccc ggccactatc cggatcaatt    27960
tattcctaac tttgacgcgg taaaggactc ggcggacggc tacgactgaa tgttaagtgg    28020
agaggcagag caactgcgcc tgaaacacct ggtccactgt cgccgccaca agtgctttgc    28080
ccgcgactcc ggtgagtttt gctactttga attgcccgag gatcatatcg agggcccggc    28140
gcacggcgtc cggcttaccg cccagggaga gcttgcccgt agcctgattc gggagtttac    28200
ccagcgcccc ctgctagttg agcgggacag gggaccctgt gttctcactg tgatttgcaa    28260
ctgtcctaac cttggattac atcaagatcc tctagttata actagagtac ccggggatct    28320
tattcccttt aactaataaa aaaaaataat aaagcatcac ttacttaaaa tcagttagca    28380
aatttctgtc cagtttattc agcagcacct ccttgccctc ctcccagctc tggtattgca    28440
gcttcctcct ggctgcaaac tttctccaca atctaaatgg aatgtcagtt tcctcctgtt    28500
cctgtccatc cgcacccact atcttcatgt tgttgcagat gaagcgcgca agaccgtctg    28560
aagataccct caaccccgtg tatccatatg acacggaaac cggtcctcca actgtgcctt    28620
ttcttactcc tcccttgta tcccccaatg ggtttcaaga gagtcccct ggggtactct    28680 ctttgcgcct atccgaacct ctagttacct ccaatggcat gcttgcgctc aaaatgggca    28740
acggcctctc tctggacgag gccggcaacc ttacctccca aaatgtaacc actgtgagcc    28800
cacctctcaa aaaaccaag tcaaacataa acctggaaat atctgcaccc ctcacagtta    28860
cctcagaagc cctaactgtg gctgccgccg cacctctaat ggtcgcgggc aacacactca    28920
ccatgcaatc acaggccccg ctaaccgtgc acgactccaa acttagcatt gccacccaag    28980
gacccctcac agtgtcagaa ggaaagctag ccctgcaaac atcaggcccc ctcaccacca    29040
ccgatagcag taccccttact atcactgcct cacccctct aactactgcc actggtagct    29100
tgggcattga cttgaaagag cccatttata cacaaaatgg aaaactagga ctaaagtacg    29160
gggctccttt gcatgtaaca gacgacctaa acactttgac cgtagcaact ggtccaggtg    29220
tgactattaa taatacttcc ttgcaaacta agttactgg agccttgggt tttgattcac    29280
aaggcaatat gcaacttaat gtagcaggag gactaaggat tgattctcaa aacagacgcc    29340
```

```
ttatacttga tgttagttat ccgtttgatg ctcaaaacca actaaatcta agactaggac   29400
agggccctct ttttataaac tcagcccaca acttggatat taactacaac aaaggccttt   29460
acttgtttac agcttcaaac aattccaaaa agcttgaggt taacctaagc actgccaagg   29520
ggttgatgtt tgacgctaca gccatagcca ttaatgcagg agatgggctt gaatttggtt   29580
cacctaatgc accaaacaca aatcccctca aaacaaaaat tggccatggc ctagaatttg   29640
attcaaacaa ggctatggtt cctaaactag gaactggcct tagttttgac agcacaggtg   29700
ccattacagt aggaaacaaa aataatgata agctaaccct atggacaggt ccaaaaccag   29760
aagccaactg cataattgaa tacgggaaac aaaacccaga tagcaaacta actttaatcc   29820
ttgtaaaaaa tggaggaatt gttaatggat atgtaacgct aatgggagcc tcagactacg   29880
ttaacaccct atttaaaaac aaaaatgtct ccattaatgt agaactatac tttgatgcca   29940
ctggtcatat attaccagac tcatcttctc ttaaaacaga tctagaacta aaatacaagc   30000
aaaccgctga cttagtgca agaggtttta tgccaagtac tacagcgtat ccatttgtcc    30060
ttcctaatgc gggaacacat aatgaaaatt atatttttgg tcaatgctac tacaaagcaa   30120
gcgatggtgc cctttttccg ttggaagtta ctgttatgct taataaacgc ctgccagata   30180
gtcgcacatc ctatgttatg acttttttat ggtccttgaa tgctggtcta gctccagaaa   30240
ctactcagga aaccctcata acctccccat ttacctttc ctatattaga gaagatgacg     30300
gtggaggcgg ttcaggcgga ggtggctctg gcggtggcgg atcctgtgac tgccgcggag   30360 actgttctg ctaataaact ctaaagaatc gtttgtgtta tgtttcaacg tgttatttt      30420 tcaattgcag aaaatttcaa gtcatttttc attcagtagt atagccccac caccacatag   30480
cttatacaga tcaccgtacc ttaatcaaac tcacagaacc ctagtattca acctgccacc   30540
tccctcccaa cacacagagt acacagtcct ttctccccgg ctggccttaa aaagcatcat   30600
atcatgggta acagacatat tcttaggtgt tatattccac acggtttcct gtcgagccaa   30660
acgctcatca gtgatattaa taaactcccc gggcagctca cttaagttca tgtcgctgtc   30720
cagctgctga gccacaggct gctgtccaac ttgcggttgc ttaacgggcg gcgaaggaga   30780
agtccacgcc tacatgggg tagagtcata atcgtgcatc aggataggc ggtggtgctg      30840 cagcagcgcg cgaataaact gctgccgccg ccgctccgtc ctgcaggaat acaacatggc   30900
agtggtctcc tcagcgatga ttcgcaccgc ccgcagcata aggcgccttg tcctccgggc   30960
acagcagcgc accctgatct cacttaaatc agcacagtaa ctgcagcaca gcaccacaat   31020
attgttcaaa atcccacagt gcaaggcgct gtatccaaag ctcatggcgg ggaccacaga   31080
acccacgtgg ccatcatacc acaagcgcag gtagattaag tggcgacccc tcataaacac   31140 gctgacata aacattacct cttttggcat gttgtaattc accacctccc ggtaccatat    31200
aaacctctga ttaaacatgg cgccatccac caccatccta aaccagctgg ccaaaacctg   31260
cccgccggct atacactgca gggaaccggg actggaacaa tgacagtgga gagcccagga   31320
ctcgtaacca tggatcatca tgctcgtcat gatatcaatg ttggcacaac acaggcacac   31380
gtgcatacac ttcctcagga ttacaagctc ctcccgcgtt agaaccatat cccagggaac   31440
aacccattcc tgaatcagcg taaatcccac actgcaggga agacctcgca cgtaactcac   31500
gttgtgcatt gtcaaagtgt tacattcggg cagcagcgga tgatcctcca gtatggtagc   31560
gcgggtttct gtctcaaaag gaggtagacg atccctactg tacggagtgc gccgagacaa   31620
ccgagatcgt gttggtcgta gtgtcatgcc aaatggaacg ccggacgtag tcatatttcc   31680
```

```
tgaagcaaaa ccaggtgcgg gcgtgacaaa cagatctgcg tctccggtct cgccgcttag   31740
atcgctctgt gtagtagttg tagtatatcc actctctcaa agcatccagg cgcccctgg    31800 cttcgggttc tatgtaaact ccttcatgcg ccgctgccct gataacatcc accaccgcag   31860
aataagccac acccagccaa cctacacatt cgttctgcga gtcacacacg ggaggagcgg   31920
gaagagctgg aagaaccatg tttttttttt tattccaaaa gattatccaa aacctcaaaa   31980
tgaagatcta ttaagtgaac gcgctcccct ccggtggcgt ggtcaaactc tacagccaaa   32040
gaacagataa tggcatttgt aagatgttgc acaatggctt ccaaaaggca acggccctc    32100 acgtccaagt ggacgtaaag gctaaaccct tcagggtgaa tctcctctat aaacattcca   32160
gcaccttcaa ccatgcccaa ataattctca tctcgccacc ttctcaatat atctctaagc   32220
aaatcccgaa tattaagtcc ggccattgta aaaatctgct ccagagcgcc ctccaccttc   32280
agcctcaagc agcgaatcat gattgcaaaa attcaggttc ctcacagacc tgtataagat   32340
tcaaaagcgg aacattaaca aaataccgc gatcccgtag gtcccttcgc agggccagct    32400
gaacataatc gtgcaggtct gcacggacca gcgcggccac ttccccgcca ggaaccttga   32460
caaaagaacc cacactgatt atgacacgca tactcggagc tatgctaacc agcgtagccc   32520
cgatgtaagc tttgttgcat gggcggcgat ataaaatgca aggtgctgct caaaaaatca   32580
ggcaaagcct cgcgcaaaaa agaaagcaca tcgtagtcat gctcatgcag ataaaggcag   32640
gtaagctccg gaaccaccac agaaaaagac accattttc tctcaaacat gtctgcgggt    32700
ttctgcataa acacaaaata aaataacaaa aaacattta acattagaa gcctgtctta     32760 caacaggaaa acaacccctt ataagcataa gacggactac ggccatgccg gcgtgaccgt   32820
aaaaaaactg gtcaccgtga ttaaaaagca ccaccgacag ctcctcggtc atgtccggag   32880
tcataatgta agactcggta acacatcag gttgattcat cggtcagtgc taaaagcga     32940 ccgaaatagc ccgggggaat acatacccgc aggcgtagag acaacattac agcccccata   33000
ggaggtataa caaattaat aggagagaaa acacataaa cacctgaaaa accctcctgc     33060
ctaggcaaaa tagcacccct ccgctccaga acaacataca gcgcttcaca gcggcagcct   33120
aacagtcagc cttaccagta aaaagaaaa cctattaaaa aaacaccact cgacacggca    33180
ccagctcaat cagtcacagt gtaaaaaagg gccaagtgca gagcgagtat atataggact   33240
aaaaaatgac gtaacggtta aagtccacaa aaaacaccca gaaaaccgca cgcgaaccta   33300
cgcccagaaa cgaaagccaa aaaacccaca acttcctcaa atcgtcactt ccgttttccc   33360
acgttacgta acttcccatt ttaagaaaac tacaattccc aacacataca agttactccg   33420
ccctaaaacc tacgtcaccc gccccgttcc cacgccccgc gccacgtcac aaactccacc   33480
ccctcattat catattggct tcaatccaaa ataaggtata ttattgatga tnnnnnttaa   33540
t                                                                  33541

<210> SEQ ID NO 5
<211> LENGTH: 37005
<212> TYPE: DNA
<213> ORGANISM: Artificial sequence
<220> FEATURE:
<223> OTHER INFORMATION: Recombnant adenovirus AdEz5/3-RGD IXRFP D24,
      n=A,C,G,T
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: misc_feature
<222> LOCATION: (36996)..(37000)
```

<223> OTHER INFORMATION: n is a, c, g, or t

<400> SEQUENCE: 5

```
aggatccnnn cggtgtgaaa taccgcacag atgcgtaagg agaaaatacc gcatcaggcg      60
ctcttccgct tcctcgctca ctgactcgct gcgctcggtc gttcggctgc ggcgagcggt     120
atcagctcac tcaaaggcgg taatacggtt atccacagaa tcaggggata acgcaggaaa     180
gaacatgtga gcaaaaggcc agcaaaaggc caggaaccgt aaaaaggccg cgttgctggc     240
gttttttccat aggctccgcc cccctgacga gcatcacaaa aatcgacgct caagtcagag     300
gtggcgaaac ccgacaggac tataaagata ccaggcgttt ccccctggaa gctccctcgt     360
gcgctctcct gttccgaccc tgccgcttac cggatacctg tccgcctttc tcccttcggg     420
aagcgtggcg ctttctcata gctcacgctg taggtatctc agttcggtgt aggtcgttcg     480
ctccaagctg ggctgtgtgc acgaaccccc cgttcagccc gaccgctgcg ccttatccgg     540
taactatcgt cttgagtcca acccggtaag acacgactta tcgccactgg cagcagccac     600
tggtaacagg attagcagag cgaggtatgt aggcggtgct acagagttct tgaagtggtg     660
gcctaactac ggctacacta aaggacagt atttggtatc tgcgctctgc tgaagccagt     720
taccttcgga aaaagagttg gtagctcttg atccggcaaa caaaccaccg ctggtagcgg     780
tggttttttt gtttgcaagc agcagattac gcgcagaaaa aaaggatctc aagaagatcc     840
tttgatcttt tctacggggt ctgacgctca gtggaacgaa aactcacgtt aagggatttt     900
ggtcatgaga ttatcaaaaa ggatcttcac ctagatcctt ttaaattaaa aatgaagttt     960
taaatcaatc taaagtatat atgagtaaac ttggtctgac agttaccaat gcttaatcag    1020
tgaggcacct atctcagcga tctgtctatt tcgttcatcc atagttgcct gactccccgt    1080
cgtgtagata actacgatac gggagggctt accatctggc cccagtgctg caatgatacc    1140
gcgagaccca cgctcaccgg ctccagattt atcagcaata aaccagccag ccggaagggc    1200
cgagcgcaga agtggtcctg caactttatc cgcctccatc cagtctatta attgttgccg    1260
ggaagctaga gtaagtagtt cgccagttaa tagtttgcgc aacgttgttg ccattgctgc    1320
agccatgaga ttatcaaaaa ggatcttcac ctagatcctt ttcacgtaga aagccagtcc    1380
gcagaaacgg tgctgacccc ggatgaatgt cagctactgg gctatctgga caagggaaaa    1440
cgcaagcgca aagagaaagc aggtagcttg cagtgggctt acatggcgat agctagactg    1500
ggcggtttta tggacagcaa gcgaaccgga attgccagct ggggcgccct ctggtaaggt    1560
tgggaagccc tgcaaagtaa actggatggc tttctcgccg ccaaggatct gatggcgcag    1620
gggatcaagc tctgatcaag agacaggatg aggatcgttt cgcatgattg aacaagatgg    1680
attgcacgca ggttctccgg ccgcttgggt ggagaggcta ttcggctatg actgggcaca    1740
acagacaatc ggctgctctg atgccgccgt gttccggctg tcagcgcagg ggcgcccggt    1800
tcttttttgtc aagaccgacc tgtccggtgc cctgaatgaa ctgcaagacg aggcagcgcg    1860
gctatcgtgg ctggccacga cgggcgttcc ttgcgcagct gtgctcgacg ttgtcactga    1920
agcgggaagg gactggctgc tattgggcga agtgccgggg caggatctcc tgtcatctca    1980
ccttgctcct gccgagaaag tatccatcat ggctgatgca atgcggcggc tgcatacgct    2040
tgatccggct acctgcccat tcgaccacca agcgaaacat cgcatcgagc gagcacgtac    2100
tcggatggaa gccggtcttg tcgatcagga tgatctggac gaagagcatc aggggctcgc    2160
gccagccgaa ctgttcgcca ggctcaaggc gagcatgccc gacggcgagg atctcgtcgt    2220
gacccatggc gatgcctgct tgccgaatat catggtggaa aatggccgct ttctggatt    2280
```

```
catcgactgt ggccggctgg gtgtggcgga ccgctatcag gacatagcgt tggctacccg    2340
tgatattgct gaagagcttg gcggcgaatg ggctgaccgc ttcctcgtgc tttacggtat    2400
cgccgctccc gattcgcagc gcatcgcctt ctatcgcctt cttgacgagt tcttctgaat    2460
tttgttaaaa tttttgttaa atcagctcat tttttaacca ataggccgaa atcggcaaca    2520
tcccttataa atcaaaagaa tagaccgcga tagggttgag tgttgttcca gtttggaaca    2580
agagtccact attaaagaac gtggactcca acgtcaaagg gcgaaaaacc gtctatcagg    2640
gcgatggccc actacgtgaa ccatcaccca aatcaagttt tttgcggtcg aggtgccgta    2700
aagctctaaa tcggaacccct aaagggagcc cccgatttag agcttgacgg ggaaagccgg    2760
cgaacgtggc gagaaaggaa gggaagaaag cgaaaggagc gggcgctagg gcgctggcaa    2820
gtgtagcggt cacgctgcgc gtaaccacca cacccgcgcg cttaatgcgc cgctacaggg    2880
cgcgtccatt cgccattcag gatcgaatta attcttaatt aacatcatca ataatatacc    2940
ttattttgga ttgaagccaa tatgataatg aggggtgga gtttgtgacg tggcgcgggg    3000
cgtgggaacg gggcgggtga cgtagtagtg tggcggaagt gtgatgttgc aagtgtggcg    3060
gaacacatgt aagcgacgga tgtggcaaaa gtgacgtttt tggtgtgcgc cggtgtacac    3120
aggaagtgac aattttcgcg cggttttagg cggatgttgt agtaaatttg ggcgtaaccg    3180
agtaagattt ggccattttc gcgggaaaac tgaataagag gaagtgaaat ctgaataatt    3240
ttgtgttact catagcgcgt aatatttgtc tagggccgcg gggactttga ccgtttacgt    3300
ggagactcgc ccaggtgttt ttctcaggtg ttttccgcgt tccgggtcaa agttggcgtt    3360
ttattattat agtcagctga cgtgtagtgt atttataccc ggtgagttcc tcaagaggcc    3420
actcttgagt gccagcgagt agagttttct cctccgagcc gctccgacac cgggactgaa    3480
aatgagacat attatctgcc acggaggtgt tattaccgaa gaaatggccg ccagtctttt    3540
ggaccagctg atcgaagagg tactggctga taatcttcca cctcctagcc attttgaacc    3600 acctacccctt cacgaactgt atgatttaga cgtgacggcc cccgaagatc ccaacgagga    3660
ggcggtttcg cagatttttc ccgactctgt aatgttggcg gtgcaggaag ggattgactt    3720
actcactttt ccgccggcgc ccggttctcc ggagccgcct cacctttccc ggcagcccga    3780
gcagccggag cagagagcct tgggtccggt ttctatgcca aaccttgtac cggaggtgat    3840
cgatccaccc agtgacgacg aggatgaaga gggtgaggag tttgtgttag attatgtgga    3900
gcaccccggg cacggttgca ggtcttgtca ttatcaccgg aggaatacgg gggacccaga    3960
tattatgtgt tcgctttgct atatgaggac ctgtggcatg tttgtctaca gtaagtgaaa    4020
attatgggca gtgggtgata gagtggtggg tttggtgtgg taatttttt tttaattttt    4080 acagttttgt ggtttaaaga attttgtatt gtgatttttt taaaaggtcc tgtgtctgaa    4140
cctgagcctg agcccgagcc agaaccggag cctgcaagac ctacccgccg tcctaaaatg    4200
gcgcctgcta tcctgagacg cccgacatca cctgtgtcta gagaatgcaa tagtagtacg    4260
gatagctgtg actccggtcc ttctaacaca cctcctgaga tacacccggt ggtcccgctg    4320
tgccccatta aaccagttgc cgtgagagtt ggtgggcgtc gccaggctgt ggaatgtatc    4380
gaggacttgc ttaacgagcc tggcaacct ttggacttga gctgtaaacg ccccaggcca    4440
taaggtgtaa acctgtgatt gcgtgtgtgg ttaacgcctt tgtttgctga atgagttgat    4500
gtaagtttaa taaagggtga gataatgttt aacttgcatg gcgtgttaaa tggggcgggg    4560
cttaaagggt atataatgcg ccgtgggcta atcttggtta catctgacct catggaggct    4620
```

-continued

```
tgggagtgtt tggaagattt ttctgctgtg cgtaacttgc tggaacagag ctctaacagt    4680
acctcttggt tttggaggtt tctgtggggc tcatcccagg caaagttagt ctgcagaatt    4740
aaggaggatt acaagtggga atttgaagag cttttgaaat cctgtggtga gctgtttgat    4800
tctttgaatc tgggtcacca ggcgcttttc aagagaagg tcatcaagac tttggatttt     4860
tccacaccgg ggcgcgctgc ggctgctgtt gcttttttga gttttataaa ggataaatgg    4920
agcgaagaaa cccatctgag cgggggggtac ctgctggatt ttctggccat gcatctgtgg   4980
agagcggttg tgagacacaa gaatcgcctg ctactgttgt cttccgtccg cccggcgata    5040
ataccgacgg aggagcagca gcagcagcag gaggaagcca ggcggcggcg gcaggagcag    5100
agcccatgga acccgagagc cggcctggac cctcgggaat gaatgttgta caggtggctg    5160
aactgtatcc agaactgaga cgcatttga caattacaga ggatgggcag gggctaaagg     5220
gggtaaagag ggagcggggg gcttgtgagg ctacagagga ggctaggaat ctagctttta    5280
gcttaatgac cagacaccgt cctgagtgta ttacttttca acagatcaag gataattgcg    5340
ctaatgagct tgatctgctg gcgcagaagt attcccatga gcagctgacc acttactggc    5400
tgcagccagg ggatgatttt gaggaggcta ttagggtata tgcaaaggtg gcacttaggc    5460
cagattgcaa gtacaagatc agcaaacttg taaatatcag gaattgttgc tacatttctg    5520
ggaacggggc cgaggtggag atagatacgg aggataggt ggcctttaga tgtagcatga     5580
taaatatgtg gccgggggtg cttggcatgg acggggtggt tattatgaat gtaaggttta    5640
ctggccccaa ttttagcggt acggttttcc tggccaatac caaccttatc ctacacggtg    5700
taagcttcta tgggttaac aatacctgtg tggaagcctg gaccgatgta agggttcggg     5760
gctgtgcctt ttactgctgc tggaaggggg tggtgtgtcg ccccaaaagc agggcttcaa    5820
ttaagaaatg cctctttgaa aggtgtacct tgggtatcct gtctgagggt aactccaggg    5880
tgcgccacaa tgtggcctcc gactgtggtt gcttcatgct agtgaaaagc gtggctgtga    5940
ttaagcataa catggtatgt ggcaactgcg aggacagggc ctctcagatg ctgacctgct    6000
cggacggcaa ctgtcacctg ctgaagacca ttcacgtagc cagccactct cgcaaggcct    6060
ggccagtgtt tgagcataac atactgaccc gctgttcctt gcatttgggt aacaggaggg    6120
gggtgttcct accttaccaa tgcaatttga gtcacactaa gatattgctt gagcccgaga    6180
gcatgtccaa ggtgaacctg aacgggtgt ttgacatgac catgaagatc tggaaggtgc     6240
tgaggtacga tgagacccgc accaggtgca gaccctgcga gtgtggcggt aaacatatta    6300
ggaaccagcc tgtgatgctg gatgtgaccg aggagctgag gcccgatcac ttggtgctgg    6360
cctgcacccg cgctgagttt ggctctagcg atgaagatac agattgaggt actgaaatgt    6420
gtgggcgtgg cttaagggtg ggaaagaata tataaggtgg gggtcttatg tagttttgta    6480
tctgttttgc agcagccgcc gccgccatga gcaccaactc gtttgatgga agcattgtga    6540
gctcatattt gacaacgcgc atgccccat gggccggggt gcgtcagaat gtgatgggct     6600
ccagcattga tggtcgcccc gtcctgcccg caaactctac taccttgacc tacgagaccg    6660
tgtctggaac gccgttggag actgcagcct ccgccgccgc ttcagccgct gcagccaccg    6720
cccgcgggat tgtgactgac tttgcttttcc tgagcccgct tgcaagcagt gcagcttccc    6780
gttcatccgc ccgcgatgac aagttgacgg ctctttttggc acaattggat tctttgaccc    6840
gggaacttaa tgtcgtttct cagcagctgt tggatctgcg ccagcaggtt tctgccctga    6900
aggcttcctc ccctcccaat gcggtttctg ccgattataa ggatgacgat gacaagctag    6960
ccatggcctc ctccgaggac gtcatcaagg agttcatgcg cttcaaggtg cgcatggagg    7020
```

```
gctccgtgaa cggccacgag ttcgagatcg agggcgaggg cgaggccgc ccctacgagg    7080 gcacccagac cgccaagctg aaggtgacca agggcggccc cctgcccttc gcctgggaca    7140
tcctgtcccc tcagttccag tacggctcca aggcctacgt gaagcacccc gccgacatcc    7200
ccgactactt gaagctgtcc ttccccgagg gcttcaagtg ggagcgcgtg atgaacttcg    7260
aggacggcgg cgtggtgacc gtgacccagg actcctccct gcaggacggc gagttcatct    7320
acaaggtgaa gctgcgcggc accaacttcc cctccgacgg ccccgtaatg cagaagaaga    7380
ccatgggctg ggaggcctcc accgagcgga tgtaccccga ggacggcgcc ctgaagggcg    7440
agatcaagat gaggctgaag ctgaaggacg gcggccacta cgacgccgag gtcaagacca    7500
cctacatggc caagaagccc gtgcagctgc ccggcgccta caagaccgac atcaagctgg    7560
acatcacctc ccacaacgag gactacacca tcgtggaaca gtacgagcgc gccgagggcc    7620
gccactccac cggcgcctaa cgtcgactag ccataaataa aaaaccagac tctgtttgga    7680
tttggatcaa gcaagtgtct tgctgtcttt atttagggt tttgcgcgcg cggtaggccc    7740
gggaccagcg gtctcggtcg ttgagggtcc tgtgtatttt ttccaggacg tggtaaaggt    7800
gactctggat gttcagatac atgggcataa gcccgtctct ggggtggagg tagcaccact    7860
gcagagcttc atgctgcggg gtggtgttgt agatgatcca gtcgtagcag gagcgctggg    7920
cgtggtgcct aaaatgtct ttcagtagca agctgattgc caggggcagg cccttggtgt    7980
aagtgtttac aaagcggtta agctgggatg ggtgcatacg tggggatatg agatgcatct    8040
tggactgtat ttttaggttg gctatgttcc cagccatatc cctccgggga ttcatgttgt    8100
gcagaaccac cagcacagtg tatccggtgc acttgggaaa tttgtcatgt agcttagaag    8160
gaaatgcgtg gaagaacttg gagacgcccct tgtgacctcc aagattttcc atgcattcgt    8220
ccataatgat ggcaatgggc ccacggggcgg cggcctgggc gaagatattt ctgggatcac    8280
taacgtcata gttgtgttcc aggatgagat cgtcataggc catttttaca aagcgcgggc    8340
ggagggtgcc agactgcggt ataatggttc catccggccc aggggcgtag ttaccctcac    8400
agatttgcat ttcccacgct ttgagttcag atgggggat catgtctacc tgcggggcga    8460
tgaagaaaac ggtttccggg gtaggggaga tcagctggga agaaagcagg ttcctgagca    8520
gctgcgactt accgcagccg gtgggcccgt aaatcacacc tattaccggg tgcaactggt    8580
agttaagaga gctgcagctg ccgtcatccc tgagcagggg ggccacttcg ttaagcatgt    8640
ccctgactcg catgttttcc ctgaccaaat ccgccagaag gcgctcgccg cccagcgata    8700
gcagttcttg caaggaagca aagtttttca acggtttgag accgtccgcc gtaggcatgc    8760
ttttgagcgt ttgaccaagc agttccaggc ggtcccacag ctcggtcacc tgctctacgg    8820
catctcgatc cagcatatct cctcgtttcg cgggttgggg cggctttcgc tgtacggcag    8880
tagtcggtgc tcgtccagac gggccagggt catgtctttc cacgggcgca gggtcctcgt    8940
cagcgtagtc tgggtcacgg tgaaggggtg cgctccgggc tgcgcgctgg ccagggtgcg    9000
cttgaggctg gtcctgctgg tgctgaagcg ctgccggtct tcgccctgcg cgtcggccag    9060
gtagcatttg accatggtgt catagtccag cccctccgcg gcgtggccct tggcgcgcag    9120
cttgcccttg gaggaggcgc cgcacagggg gcagtgcaga cttttgaggg cgtagagctt    9180
gggcgcgaga aataccgatt ccggggagta ggcatccgcg ccgcaggccc cgcagacggt    9240
ctcgcattcc acgagccagg tgagctctgg ccgttcgggg tcaaaaacca ggtttccccc    9300
atgctttttg atgcgtttct tacctctggt ttccatgagc cggtgtccac gctcggtgac    9360
```

```
gaaaaggctg tccgtgtccc cgtatacaga cttgagaggc ctgtcctcga gcggtgttcc    9420
gcggtcctcc tcgtatagaa actcggacca ctctgagaca aaggctcgcg tccaggccag    9480
cacgaaggag gctaagtggg aggggtagcg gtcgttgtcc actaggggggt ccactcgctc   9540
cagggtgtga agacacatgt cgccctcttc ggcatcaagg aaggtgattg gtttgtaggt    9600
gtaggccacg tgaccgggtg ttcctgaagg ggggctataa aaggggggtgg gggcgcgttc   9660
gtcctcactc tcttccgcat cgctgtctgc gagggccagc tgttgggggtg agtactccct  9720
ctgaaaagcg ggcatgactt ctgcgctaag attgtcagtt tccaaaaacg aggaggattt    9780
gatattcacc tggcccgcgg tgatgccttt gagggtggcc gcatccatct ggtcagaaaa    9840
gacaatcttt ttgttgtcaa gcttggtggc aaacgacccg tagagggcgt tggacagcaa    9900
cttggcgatg gagcgcaggg tttggttttt gtcgcgatcg gcgcgctcct tggccgcgat    9960
gtttagctgc acgtattcgc gcgcaacgca ccgccattcg ggaaagacgg tggtgcgctc   10020
gtcgggcacc aggtgcacgc gccaaccgcg gttgtgcagg gtgacaaggt caacgctggt   10080
ggctacctct ccgcgtaggc gctcgttggt ccagcagagg cggccgccct tgcgcgagca   10140
gaatggcggt aggggggtcta gctgcgtctc gtccgggggg tctgcgtcca cggtaaagac  10200
cccgggcagc aggcgcgcgt cgaagtagtc tatcttgcat ccttgcaagt ctagcgcctg   10260
ctgccatgcg cgggcggcaa gcgcgcgctc gtatggggttg agtgggggac cccatggcat  10320
ggggtgggtg agcgcggagg cgtacatgcc gcaaatgtcg taaacgtaga gggggctctct 10380
gagtattcca agatatgtag ggtagcatct tccaccgcgg atgctggcgc gcacgtaatc   10440
gtatagttcg tgcgagggag cgaggaggtc gggaccgagg ttgctacggg cgggctgctc   10500
tgctcggaag actatctgcc tgaagatggc atgtgagttg gatgatatgg ttggacgctg   10560
gaagacgttg aagctggcgt ctgtgagacc taccgcgtca cgcacgaagg aggcgtagga   10620
gtcgcgcagc ttgttgacca gctcggcggt gacctgcacg tctagggcgc agtagtccag   10680
ggttccttg atgatgtcat acttatcctg tccctttttt ttccacagct cgcggttgag    10740
gacaaactct tcgcggtctt tccagtactc ttggatcgga aacccgtcgg cctccgaacg   10800
gtaagagcct agcatgtaga actggttgac ggcctggtag gcgcagcatc ccttttctac   10860
gggtagcgcg tatgcctgcg cggccttccg gagcgaggtg tgggtgagcg caaaggtgtc   10920
cctgaccatg actttgaggt actggtattt gaagtcagtg tcgtcgcatc cgccctgctc   10980
ccagagcaaa aagtccgtgc gcttttgga acgcggattt ggcagggcga aggtgacatc    11040
gttgaagagt atctttcccg cgcgaggcat aaagttgcgt gtgatgcgga agggtcccgg   11100
cacctcggaa cggttgttaa ttacctgggc ggcgagcacg atctcgtcaa agccgttgat   11160
gttgtggccc acaatgtaaa gttccaagaa gcgcgggatg cccttgatgg aaggcaattt   11220
tttaagttcc tcgtaggtga gctcttcagg ggagctgagc ccgtgctctg aaagggccca   11280
gtctgcaaga tgaggggttgg aagcgacgaa tgagctccac aggtcacggg ccattagcat  11340
ttgcaggtgg tcgcgaaagg tcctaaactg gcgacctatg gccattttt ctggggtgat    11400
gcagtagaag gtaagcgggt cttgttccca gcggtcccat ccaaggttcg cggctaggtc   11460
tcgcgcggca gtcactagag gctcatctcc gccgaacttc atgaccagca tgaagggcac   11520
gagctgcttc ccaaaggccc ccatccaagt ataggtctct acatcgtagg tgacaaagag   11580
acgctcggtg cgaggatgcg agccgatcgg gaagaactgg atctcccgcc accaattgga   11640
ggagtggcta ttgatgtggt gaaagtagaa gtccctgcga cgggccgaac actcgtgctg   11700
gcttttgtaa aaacgtgcgc agtactggca gcggtgcacg ggctgtacat cctgcacgag   11760
```

```
gttgacctga cgaccgcgca caaggaagca gagtgggaat ttgagcccct cgcctggcgg    11820
gtttggctgg tggtcttcta cttcggctgc ttgtccttga ccgtctggct gctcgagggg    11880
agttacggtg gatcggacca ccacgccgcg cgagcccaaa gtccagatgt ccgcgcgcgg    11940
cggtcggagc ttgatgacaa catcgcgcag atgggagctg tccatggtct ggagctcccg    12000
cggcgtcagg tcaggcggga gctcctgcag gtttacctcg catagacggg tcagggcgcg    12060
ggctagatcc aggtgatacc taatttccag gggctggttg gtggcggcgt cgatggcttg    12120
caagaggccg catccccgcg gcgcgactac ggtaccgcgc ggcgggcggt gggccgcggg    12180
ggtgtccttg gatgatgcat ctaaaagcgg tgacgcgggc gagcccccgg aggtaggggg    12240
ggctccggac ccgccgggag aggggggcagg ggcacgtcgg cgccgcgcgc gggcaggagc   12300
tggtgctgcg cgcgtaggtt gctggcgaac gcgacgacgc ggcggttgat ctcctgaatc    12360
tggcgcctct gcgtgaagac gacgggcccg gtgagcttga gcctgaaaga gagttcgaca    12420
gaatcaattt cggtgtcgtt gacggcggcc tggcgcaaaa tctcctgcac gtctcctgag    12480
ttgtcttgat aggcgatctc ggccatgaac tgctcgatct cttcctcctg gagatctccg    12540
cgtccggctc gctccacggt ggcggcgagg tcgttggaaa tgcgggccat gagctgcgag    12600
aaggcgttga ggcctccctc gttccagacg cggctgtaga ccacgccccc ttcggcatcg    12660
cgggcgcgca tgaccacctg cgcgagattg agctccacgt gccgggcgaa gacggcgtag    12720
tttcgcaggc gctgaaagag gtagttgagg gtggtggcgg tgtgttctgc cacgaagaag    12780
tacataaccc agcgtcgcaa cgtggattcg ttgatatccc ccaaggcctc aaggcgctcc    12840
atggcctcgt agaagtccac ggcgaagttg aaaaactggg agttgcgcgc cgacacggtt    12900
aactcctcct ccagaagacg gatgagctcg gcgacagtgt cgcgcacctc gcgctcaaag    12960
gctacagggg cctcttcttc ttcttcaatc tcctcttcca taagggcctc cccttcttct    13020
tcttctggcg gcggtgggggg agggggggaca cggcggcgac gacggcgcac cgggaggcgg    13080
tcgacaaagc gctcgatcat ctccccgcgg cgacggcgca tggtctcggt gacggcgcgg    13140
ccgttctcgc gggggcgcag ttggaagacg ccgcccgtca tgtcccggtt atgggttggc    13200
ggggggctgc catgcggcag ggatacggcg ctaacgatgc atctcaacaa ttgttgtgta    13260
ggtactccgc cgccgaggga cctgagcgag tccgcatcga ccggatcgga aaacctctcg    13320
agaaaggcgt ctaaccagtc acagtcgcaa ggtaggctga gcaccgtggc gggcggcagc    13380
gggcggcggt cggggttgtt tctggcggag gtgctgctga tgatgtaatt aaagtaggcg    13440
gtcttgagac ggcggatggt cgacagaagc accatgtcct gggtccggc ctgctgaatg     13500 cgcaggcggt cggccatgcc ccaggcttcg ttttgacatc ggcgcaggtc tttgtagtag    13560
tcttgcatga gcctttctac cggcacttct tcttctcctt cctcttgtcc tgcatctctt    13620
gcatctatcg ctgcggcggc ggcggagttt ggccgtaggt ggcgccctct tcctcccatg    13680
cgtgtgaccc cgaagcccct catcggctga agcaggcta ggtcggcgac aacgcgctcg     13740
gctaatatgg cctgctgcac ctgcgtgagg gtagactgga agtcatccat gtccacaaag    13800
cggtggtatg cgcccgtgtt gatggtgtaa gtgcagttgg ccataacgga ccagttaacg    13860
gtctggtgac ccgcctgcga gagctcggtg tacctgagac gcgagtaagc cctcgagtca    13920
aatacgtagt cgttgcaagt ccgcaccagg tactggtatc ccaccaaaaa gtgcggcggc    13980
ggctggcggt agaggggcca gcgtagggtg gccggggctc cggggcgag atcttccaac     14040 ataaggcgat gatatccgta gatgtacctg gacatccagg tgatgccggc ggcggtggtg    14100
```

```
gaggcgcgcg gaaagtcgcg gacgcggttc cagatgttgc gcagcggcaa aaagtgctcc   14160
atggtcggga cgctctggcc ggtcaggcgc gcgcaatcgt tgacgctcta ccgtgcaaaa   14220
ggagagcctg taagcgggca ctcttccgtg gtctggtgga taaattcgca agggtatcat   14280
ggcggacgac cggggttcga gccccgtatc cggccgtccg ccgtgatcca tgcggttacc   14340
gcccgcgtgt cgaacccagg tgtgcgacgt cagacaacgg gggagtgctc cttttggctt   14400
ccttccaggc gcggcggctg ctgcgctagc ttttttggcc actggccgcg cgcagcgtaa   14460
gcggttaggc tggaaagcga aagcattaag tggctcgctc cctgtagccg gagggttatt   14520
ttccaagggt tgagtcgcgg gaccccggt tcgagtctcg gaccggccgg actgcggcga    14580
acgggggttt gcctccccgt catgcaagac cccgcttgca aattcctccg gaaacaggga   14640
cgagcccctt ttttgctttt cccagatgca tccggtgctg cggcagatgc gccccctcc    14700 tcagcagcgg caagagcaag agcagcggca gacatgcagg gcaccctccc ctcctcctac   14760
cgcgtcagga ggggcgacat ccgcggttga cgcggcagca gatggtgatt acgaaccccc   14820
gcggcgccgg gcccggcact acctggactt ggaggagggc gagggcctgg cgcggctagg   14880
agcgccctct cctgagcggt acccaagggt gcagctgaag cgtgatacgc gtgaggcgta   14940
cgtgccgcgc cagaacctgt ttcgcgaccg cgagggagag gagcccgagg agatgcggga   15000
tcgaaagttc cacgcagggc gcgagctgcg gcatggcctg aatcgcgagc ggttgctgcg   15060
cgaggaggac tttgagcccg acgcgcgaac cgggattagt cccgcgcgcg cacacgtggc   15120
ggccgccgac ctggtaaccg catacgagca gacggtgaac caggagatta actttcaaaa   15180
aagctttaac aaccacgtgc gtacgcttgt ggcgcgcgag gaggtggcta taggactgat   15240
gcatctgtgg gactttgtaa gcgcgctgga gcaaaaccca aatagcaagc cgctcatggc   15300
gcagctgttc cttatagtgc agcacagcag ggacaacgag gcattcaggg atgcgctgct   15360
aaacatagta gagcccgagg gccgctggct gctcgatttg ataaacatcc tgcagagcat   15420
agtggtgcag gagcgcagct tgagcctggc tgacaaggtg gccgccatca actattccat   15480
gcttagcctg ggcaagtttt acgcccgcaa gatataccat accccttacg ttcccataga   15540
caaggaggta aagatcgagg ggttctacat gcgcatggcg ctgaaggtgc ttaccttgag   15600
cgacgacctg ggcgtttatc gcaacgagcg catccacaag gccgtgagcg tgagccggcg   15660
gcgcgagctc agcgaccgcg agctgatgca cagcctgcaa agggccctgg ctggcacggg   15720
cagcggcgat agagaggccg agtcctactt tgacgcgggc gctgacctgc gctgggcccc   15780
aagccgacgc gccctggagg cagctgggc cggacctggg ctggcggtgg cacccgcgcg    15840
cgctggcaac gtcggcggcg tggaggaata tgacgaggac gatgagtacg agccagagga   15900
cggcgagtac taagcggtga tgtttctgat cagatgatgc aagacgcaac ggacccggcg   15960
gtgcgggcgg cgctgcagag ccagccgtcc ggccttaact ccacggacga ctggcgccag   16020
gtcatggacc gcatcatgtc gctgactgcg cgcaatcctg acgcgttccg gcagcagccg   16080
caggccaacc ggctctccgc aattctggaa gcggtggtcc cggcgcgcgc aaaccccacg   16140
cacgagaagg tgctggcgat cgtaaacgcg ctggccgaaa acagggccat ccggcccgac   16200
gaggccggcc tggtctacga cgcgctgctt cagcgcgtgg ctcgttacaa cagcggcaac   16260
gtgcagacca acctggaccg gctggtgggg gatgtgcgcg aggccgtggc gcagcgtgag   16320
cgcgcgcagc agcagggcaa cctgggctcc atggttgcac taaacgcctt cctgagtaca   16380 cagccccgcca acgtgccgcg gggacaggag gactacacca actttgtgag cgcactgcgg   16440
ctaatggtga ctgagacacc gcaaagtgag gtgtaccagt ctgggccaga ctatttttc    16500
```

```
cagaccagta gacaaggcct gcagaccgta aacctgagcc aggctttcaa aaacttgcag  16560
gggctgtggg gggtgcgggc tcccacaggc gaccgcgcga ccgtgtctag cttgctgacg  16620
cccaactcgc gcctgttgct gctgctaata gcgcccttca cggacagtgg cagcgtgtcc  16680
cgggacacat acctaggtca cttgctgaca ctgtaccgcg aggccatagg tcaggcgcat  16740
gtggacgagc atactttcca ggagattaca agtgtcagcc gcgcgctggg gcaggaggac  16800
acgggcagcc tggaggcaac cctaaactac ctgctgacca accggcggca gaagatcccc  16860
tcgttgcaca gtttaaacag cgaggaggag cgcattttgc gctacgtgca gcagagcgtg  16920
agccttaacc tgatgcgcga cggggtaacg cccagcgtgg cgctggacat gaccgcgcgc  16980
aacatggaac cgggcatgta tgcctcaaac cggccgttta tcaaccgcct aatggactac  17040
ttgcatcgcg cggccgccgt gaaccccgag tatttcacca atgccatctt gaacccgcac  17100
tggctaccgc ccctggtttt ctacaccggg ggattcgagg tgcccgaggg taacgatgga  17160
ttcctctggg acgacataga cgacagcgtg ttttccccgc aaccgcagac cctgctagag  17220
ttgcaacagc gcgagcaggc agaggcggcg ctgcgaaagg aaagcttccg caggccaagc  17280
agcttgtccg atctaggcgc tgcggccccg cggtcagatg ctagtagccc atttccaagc  17340
ttgatagggt ctcttaccag cactcgcacc acccgcccgc gcctgctggg cgaggaggag  17400
tacctaaaca actcgctgct gcagccgcag cgcgaaaaaa acctgcctcc ggcatttccc  17460
aacaacggga tagagagcct agtggacaag atgagtagat ggaagacgta cgcgcaggag  17520
cacagggacg tgccaggccc gcgcccgccc accgtcgtc aaaggcacga ccgtcagcgg  17580
ggtctggtgt gggaggacga tgactcggca gacgacagca gcgtcctgga tttgggaggg  17640
agtggcaacc cgtttgcgca ccttcgcccc aggctgggga gaatgttta aaaaaaaaaa  17700 agcatgatgc aaaataaaaa actcaccaag gccatggcac cgagcgttgg ttttcttgta  17760
ttccccttag tatgcggcgc gcggcgatgt atgaggaagg tcctcctccc tcctacgaga  17820
gtgtggtgag cgcggcgcca gtggcggcgg cgctgggttc tcccttcgat gctccctgg  17880 acccgccgtt tgtgcctccg cggtacctgc ggcctaccgg ggggagaaac agcatccgtt  17940
actctgagtt ggcaccccta ttcgacacca cccgtgtgta cctggtggac aacaagtcaa  18000
cggatgtggc atccctgaac taccagaacg accacagcaa ctttctgacc acggtcattc  18060
aaaacaatga ctacagcccg ggggaggcaa gcacacagac catcaatctt gacgaccggt  18120
cgcactgggg cggcgacctg aaaaccatcc tgcataccaa catgccaaat gtgaacgagt  18180
tcatgtttac caataagttt aaggcgcggg tgatggtgtc gcgcttgcct actaaggaca  18240
atcaggtgga gctgaaatac gagtgggtgg agttcacgct gcccgagggc aactactccg  18300
agaccatgac catagacctt atgaacaacg cgatcgtgga gcactacttg aaagtgggca  18360
gacagaacgg ggttctggaa agcgacatcg gggtaaagtt tgacacccgc aacttcagac  18420
tggggtttga ccccgtcact ggtcttgtca tgcctgggt atatacaaac gaagccttcc  18480
atccagacat cattttgctg ccaggatgcg gggtggactt cacccacagc cgcctgagca  18540
acttgttggg catccgcaag cggcaaccct tccaggaggg ctttaggatc acctacgatg  18600
atctggaggg tggtaacatt cccgcactgt tggatgtgga cgcctaccag gcgagcttga  18660
aagatgacac cgaacagggc gggggtggcg caggcggcag caacagcagt ggcagcggcg  18720
cggaagagaa ctccaacgcg gcagccgcgg caatgcagcc ggtggaggac atgaacgatc  18780
atgccattcg cggcgacacc tttgccacac gggctgagga gaagcgcgct gaggccgaag  18840
```

```
cagcggccga agctgccgcc cccgctgcgc aacccgaggt cgagaagcct cagaagaaac    18900
cggtgatcaa acccctgaca gaggacagca agaaacgcag ttacaaccta ataagcaatg    18960
acagcacctt cacccagtac cgcagctggt accttgcata caactacggc gaccctcaga    19020
ccggaatccg ctcatggacc ctgctttgca ctcctgacgt aacctgcggc tcggagcagg    19080
tctactggtc gttgccagac atgatgcaag accccgtgac cttccgctcc acgcgccaga    19140
tcagcaactt tccggtggtg ggcgccgagc tgttgcccgt gcactccaag agcttctaca    19200
acgaccaggc cgtctactcc caactcatcc gccagtttac ctctctgacc cacgtgttca    19260
atcgctttcc cgagaaccag attttggcgc gcccgccagc ccccaccatc accaccgtca    19320
gtgaaaacgt tcctgctctc acagatcacg ggacgctacc gctgcgcaac agcatcggag    19380
gagtccagcg agtgaccatt actgacgcca acgccgcac ctgcccctac gtttacaagg    19440
ccctgggcat agtctcgccg cgcgtcctat cgagccgcac ttttttgagca agcatgtcca    19500 tccttatatc gcccagcaat aacacaggct ggggcctgcg cttccaagc aagatgtttg    19560 gcggggccaa gaagcgctcc gaccaacacc cagtgcgcgt gcgcgggcac taccgcgcgc    19620
cctggggcgc gcacaaacgc ggccgcactg ggcgcaccac cgtcgatgac gccatcgacg    19680
cggtggtgga ggaggcgcgc aactacacgc ccacgccgcc accagtgtcc acagtggacg    19740
cggccattca gaccgtggtg gcggagccc ggcgctatgc taaaatgaag agacggcgga    19800
ggcgcgtagc acgtcgccac cgccgccgac ccggcactgc cgcccaacgc gcggcggcgg    19860
ccctgcttaa ccgcgcacgt cgcaccggcc gacgggcggc catgcgggcc gctcgaaggc    19920
tggccgcggg tattgtcact gtgccccccca ggtccaggcg acgagcggcc gccgcagcag    19980
ccgcggccat tagtgctatg actcagggtc gcaggggcaa cgtgtattgg gtgcgcgact    20040
cggttagcgg cctgcgcgtg cccgtgcgca cccgccccccc gcgcaactag attgcaagaa    20100
aaaactactt agactcgtac tgttgtatgt atccagcggc ggcggcgcgc aacgaagcta    20160
tgtccaagcg caaaatcaaa gaagagatgc tccaggtcat cgcgccggag atctatggcc    20220
ccccgaagaa ggaagagcag gattacaagc cccgaaagct aaagcgggtc aaaaagaaaa    20280
agaaagatga tgatgatgaa cttgacgacg aggtggaact gctgcacgct accgcgccca    20340
ggcgacgggt acagtggaaa ggtcgacgcg taaaacgtgt tttgcgaccc ggcaccaccg    20400
tagtctttac gcccggtgag cgctccaccc gcacctacaa gcgcgtgtat gatgaggtgt    20460
acggcgacga ggacctgctt gagcaggcca acgagcgcct cggggagttt gcctacggaa    20520
agcggcataa ggacatgctg gcgttgccgc tggacgaggg caacccaaca cctagcctaa    20580
agcccgtaac actgcagcag gtgctgcccg cgcttgcacc gtccgaagaa aagcgcggcc    20640
taaagcgcga gtctggtgac ttggcaccca ccgtgcagct gatggtaccc aagcgccagc    20700
gactggaaga tgtcttggaa aaaatgaccg tggaacctgg gctggagccc gaggtccgcg    20760
tgcggccaat caagcaggtg gcgccggac tgggcgtgca gaccgtggac gttcagatac    20820
ccactaccag tagcaccagt attgccaccg ccacagaggg catggagaca caaacgtccc    20880
cggttgcctc agcggtggcg gatgccgcgg tgcaggcggt cgctgcggcc gcgtccaaga    20940
cctctacgga ggtgcaaacg gacccgtgga tgtttcgcgt ttcagccccc ggcgcccgc    21000 gcggttcgag gaagtacggc gccgccagcg cgctactgcc cgaatatgcc ctacatcctt    21060
ccattgcgcc tacccccggc tatcgtggct acacctaccg ccccagaaga cgagcaacta    21120
cccgacgcca aaccaccact ggaacccgcc gccgccgtcg ccgtcgccag ccgtgctgg    21180 ccccgatttc cgtgcgcagg gtggctcgcg aaggaggcag gaccctggtg ctgccaacag    21240
```

```
cgcgctacca ccccagcatc gtttaaaagc cggtctttgt ggttcttgca gatatggccc   21300
tcacctgccg cctccgtttc ccggtgccgg gattccgagg aagaatgcac cgtaggaggg   21360
gcatggccgg ccacgccctg acgggcggca tgcgtcgtgc gcaccaccgg cggcggcgcg   21420
cgtcgcaccg tcgcatgcgc ggcggtatcc tgcccctcct tattccactg atcgccgcgg   21480
cgattggcgc cgtgcccgga attgcatccg tggccttgca ggcgcagaga cactgattaa   21540
aaacaagttg catgtggaaa aatcaaaata aaaagtctgg actctcacgc tcgcttggtc   21600
ctgtaactat tttgtagaat ggaagacatc aactttgcgt ctctggcccc gcgacacggc   21660
tcgcgcccgt tcatgggaaa ctggcaagat atcggcacca gcaatatgag cggtggcgcc   21720
ttcagctggg gctcgctgtg gagcggcatt aaaaatttcg gttccaccgt taagaactat   21780
ggcagcaagg cctggaacag cagcacaggc cagatgctga gggataagtt gaagagcaa   21840 aatttccaac aaaaggtggt agatggcctg gcctctggca ttagcggggt ggtggacctg   21900
gccaaccagc cagtgcaaaa taagattaac agtaagcttg atccccgccc tcccgtagag   21960
gagcctccac cggccgtgga gacagtgtct ccagaggggc gtggcgaaaa gcgtccgcgc   22020
cccgacaggg aagaaactct ggtgacgcaa atagacgagc ctccctcgta cgaggaggca   22080
ctaaagcaag gcctgcccac cacccgtccc atcgcgccca tggctaccgg agtgctgggc   22140
cagcacacac ccgtaacgct ggacctgcct ccccccgccg acacccagca gaaacctgtg   22200
ctgccaggcc cgaccgccgt tgttgtaacc cgtcctagcc gcgcgtccct gcgccgcgcc   22260
gccagcggtc cgcgatcgtt gcggcccgta gccagtggca actggcaaag cacactgaac   22320
agcatcgtgg gtctgggggt gcaatccctg aagcgccgac gatgcttctg aatagctaac   22380
gtgtcgtatg tgtgtcatgt atgcgtccat gtcgccgcca gaggagctgc tgagccgccg   22440
cgcgcccgct ttccaagatg gctacccctt cgatgatgcc gcagtggtct acatgcaca   22500 tctcgggcca ggacgcctcg gagtacctga gccccgggct ggtgcagttt gcccgcgcca   22560
ccgagacgta cttcagcctg aataacaagt ttagaaaccc cacggtggcg cctacgcacg   22620
acgtgaccac agaccggtcc cagcgtttga cgctgcggtt catccctgtg accgtgagg   22680 atactgcgta ctcgtacaag gcgcggttca ccctagctgt gggtgataac cgtgtgctgg   22740
acatggcttc cacgtacttt gacatccgcg gcgtgctgga caggggccct acttttaagc   22800
cctactctgg cactgcctac aacgccctgg ctcccaaggg tgcccaaat ccttgcgaat   22860 gggatgaagc tgctactgct cttgaaataa acctagaaga agaggacgat gacaacgaag   22920
acgaagtaga cgagcaagct gagcagcaaa aaactcacgt atttgggcag gcgccttatt   22980
ctggtataaa tattacaaag gagggtattc aaataggtgt cgaaggtcaa acacctaaat   23040
atgccgataa aacatttcaa cctgaacctc aaataggaga atctcagtgg tacgaaactg   23100
aaattaatca tgcagctggg agagtcctta aaaagactac cccaatgaaa ccatgttacg   23160
gttcatatgc aaaacccaca aatgaaaatg gagggcaagg cattcttgta aagcaacaaa   23220
atggaaagct agaaagtcaa gtggaaatgc aattttctc aactactgag gcgaccgcag   23280
gcaatggtga taacttgact cctaaagtgg tattgtacag tgaagatgta gatatagaaa   23340
ccccagacac tcatatttct tacatgccca ctattaagga aggtaactca cgagaactaa   23400
tgggccaaca atctatgccc aacaggccta attacattgc ttttagggac aattttattg   23460
gtctaatgta ttcaacagc acgggtaata tgggtgttct ggcggccaa gcatcgcagt   23520 tgaatgctgt tgtagatttg caagacagaa acacagagct ttcataccag cttttgcttg   23580
```

```
attccattgg tgatagaacc aggtactttt ctatgtggaa tcaggctgtt gacagctatg    23640
atccagatgt tagaattatt gaaaatcatg gaactgaaga tgaacttcca aattactgct    23700
ttccactggg aggtgtgatt aatacagaga ctcttaccaa ggtaaaacct aaaacaggtc    23760
aggaaaatgg atgggaaaaa gatgctacag aattttcaga taaaaatgaa ataagagttg    23820
gaaataattt tgccatggaa atcaatctaa atgccaacct gtggagaaat ttcctgtact    23880
ccaacatagc gctgtatttg cccgacaagc taaagtacag tccttccaac gtaaaaattt    23940
ctgataaccc aaacacctac gactacatga acaagcgagt ggtggctccc gggttagtgg    24000
actgctacat taaccttgga gcacgctggt cccttgacta tatggacaac gtcaacccat    24060
ttaaccacca ccgcaatgct ggcctgcgct accgctcaat gttgctgggc aatggtcgct    24120
atgtgccctt ccacatccag gtgcctcaga agttctttgc cattaaaaac ctccttctcc    24180
tgccgggctc atacacctac gagtggaact tcaggaagga tgttaacatg gttctgcaga    24240
gctccctagg aaatgaccta agggttgacg gagccagcat taagtttgat agcatttgcc    24300
tttacgccac cttcttcccc atggcccaca acaccgcctc cacgcttgag gccatgctta    24360
gaaacgacac caacgaccag tcctttaacg actatctctc cgccgccaac atgctctacc    24420
ctatacccgc caacgctacc aacgtgccca tatccatccc ctcccgcaac tgggcggctt    24480
tccgcggctg ggccttcacg cgccttaaga ctaaggaaac cccatcactg ggctcgggct    24540
acgacccttc ttacacctac tctggctcta taccctacct agatggaacc ttttacctca    24600
accacacctt taagaaggtg gccattacct ttgactcttc tgtcagctgg cctggcaatg    24660
accgcctgct tacccccaac gagtttgaaa ttaagcgctc agttgacggg gagggttaca    24720
acgttgccca gtgtaacatg accaaagact ggttcctggt acaaatgcta gctaactaca    24780
acattggcta ccagggcttc tatatcccag agagctacaa ggaccgcatg tactccttct    24840
ttagaaactt ccagcccatg agccgtcagg tggtggatga tactaaatac aaggactacc    24900
aacaggtggg catcctacac caacacaaca actctggatt tgttggctac cttgccccca    24960
ccatgcgcga aggacaggcc taccctgcta acttccccta tccgcttata ggcaagaccg    25020
cagttgacag cattacccag aaaaagtttt tttgcgatcg caccctttgg cgcatccctt    25080
tctccagtaa ctttatgtcc atgggcgcac tcacagacct gggccaaaac cttctctacg    25140
ccaactccgc ccacgcgcta gacatgactt tgaggtggga tcccatggac gagcccaccc    25200
ttctttatgt tttgtttgaa gtctttgacg tggtccgtgt gcaccggccg caccgcggcg    25260
tcatcgaaac cgtgtacctg cgcacgccct tctcggccgg caacgccaca acataaagaa    25320
gcaagcaaca tcaacaacag ctgccgccat gggctccagt gagcaggaac tgaaagccat    25380
tgtcaaagat cttggttgtg gccatatttt tttgggcacc tatgacaagc gctttccagg    25440 cttttgtttct ccacacaagc tcgcctgcgc catagtcaat acggccggtc gcgagactgg    25500
gggcgtacac tggatggcct ttgcctggaa cccgcactca aaaacatgct acctctttga    25560 gcccttggc ttttctgacc agcgactcaa gcaggtttac cagtttgagt acgagtcact    25620
cctgcgccgt agcgccattg cttcttcccc cgaccgctgt ataacgctgg aaaagtccac    25680
ccaaagcgta caggggccca actcggccgc ctgtggacta ttctgctgca tgtttctcca    25740
cgcctttgcc aactggcccc aaactcccat ggatcacaac cccaccatga accttattac    25800
cggggtaccc aactccatgc tcaacagtcc ccaggtacag cccaccctgc gtcgcaacca    25860
ggaacagctc tacagcttcc tggagcgcca ctcgccctac ttccgcagcc acagtgcgca    25920
gattaggagc gccacttctt tttgtcactt gaaaaacatg taaaaataat gtactagaga    25980
```

```
cactttcaat aaaggcaaat gcttttattt gtacactctc gggtgattat ttaccccac    26040
ccttgccgtc tgcgccgttt aaaaatcaaa ggggttctgc cgcgcatcgc tatgcgccac    26100
tggcagggac acgttgcgat actggtgttt agtgctccac ttaaactcag cacaaccat    26160
ccgcggcagc tcggtgaagt tttcactcca caggctgcgc accatcacca acgcgtttag    26220
caggtcgggc gccgatatct tgaagtcgca gttggggcct ccgccctgcg cgcgcgagtt    26280
gcgatacaca gggttgcagc actggaacac tatcagcgcc gggtggtgca cgctggccag    26340
cacgctcttg tcggagatca gatccgcgtc caggtcctcc gcgttgctca gggcgaacgg    26400
agtcaacttt ggtagctgcc ttcccaaaaa gggcgcgtgc ccaggctttg agttgcactc    26460
gcaccgtagt ggcatcaaaa ggtgaccgtg cccggtctgg gcgttaggat acagcgcctg    26520
cataaaagcc ttgatctgct taaaagccac ctgagccttt gcgccttcag agaagaacat    26580
gccgcaagac ttgccggaaa actgattggc cggacaggcc gcgtcgtgca cgcagcacct    26640
tgcgtcggtg ttggagatct gcaccacatt tcggccccac cggttcttca cgatcttggc    26700
cttgctagac tgctccttca gcgcgcgctg cccgttttcg ctcgtcacat ccatttcaat    26760
cacgtgctcc ttatttatca taatgcttcc gtgtagacac ttaagctcgc cttcgatctc    26820
agcgcagcgg tgcagccaca acgcgcagcc cgtgggctcg tgatgcttgt aggtcacctc    26880
tgcaaacgac tgcaggtacg cctgcaggaa tcgccccatc atcgtcacaa aggtcttgtt    26940
gctggtgaag gtcagctgca acccgcggtg ctcctcgttc agccaggtct tgcatacggc    27000
cgccagagct tccacttggt caggcagtag tttgaagttc gcctttagat cgttatccac    27060
gtggtacttg tccatcagcg cgcgcgcagc ctccatgccc ttctcccacg cagacacgat    27120
cggcacactc agcgggttca tcaccgtaat ttcactttcc gcttcgctgg gctcttcctc    27180
ttcctcttgc gtccgcatac cacgcgccac tgggtcgtct tcattcagcc gccgcactgt    27240
gcgcttacct cctttgccat gcttgattag caccggtggg ttgctgaaac ccaccatttg    27300
tagcgccaca tcttctcttt cttcctcgct gtccacgatt acctctggtg atggcgggcg    27360
ctcgggcttg ggagaagggc gcttcttttt cttcttgggc gcaatggcca aatccgccgc    27420
cgaggtcgat ggccgcgggc tgggtgtgcg cggcaccagc gcgtcttgtg atgagtcttc    27480
ctcgtcctcg gactcgatac gccgcctcat ccgcttttttt gggggcgccc ggggaggcgg    27540
cggcgacggg gacggggacg acacgtcctc catggttggg ggacgtcgcg ccgcaccgcg    27600
tccgcgctcg ggggtggttt cgcgctgctc ctcttcccga ctggccattt ccttctccta    27660
taggcagaaa aagatcatgg agtcagtcga gaagaaggac agcctaaccg cccccctctga    27720
gttcgccacc accgcctcca ccgatgccgc caacgcgcct accaccttcc ccgtcgaggc    27780
accccccgctt gaggaggagg aagtgattat cgagcaggac ccaggttttg taagcgaaga    27840
cgacgaggac cgctcagtac caacagagga taaaaagcaa gaccaggaca acgcagaggc    27900
aaacgaggaa caagtcgggc gggggacga aaggcatggc gactacctag atgtgggaga    27960
cgacgtgctg ttgaagcatc tgcagcgcca gtgcgccatt atctgcgacg cgttgcaaga    28020
gcgcagcgat gtgcccctcg ccatagcgga tgtcagcctt gcctacgaac gccacctatt    28080
ctcaccgcgc gtaccccca aacgccaaga aaacggcaca tgcgagccca cccgcgcct    28140
caacttctac cccgtatttg ccgtgccaga ggtgcttgcc acctatcaca tcttttttcca    28200
aaactgcaag ataccctat cctgccgtgc caaccgcagc cgagcggaca agcagctggc    28260
cttgcggcag ggcgctgtca tacctgatat cgcctcgctc aacgaagtgc caaaaatctt    28320
```

-continued

```
tgagggtctt ggacgcgacg agaagcgcgc ggcaaacgct ctgcaacagg aaacagcga    28380 aaatgaaagt cactctggag tgttggtgga actcgaggt gacaacgcgc gcctagccgt    28440
actaaaacgc agcatcgagg tcacccactt tgcctacccg gcacttaacc tacccccaa    28500 ggtcatgagc acagtcatga gtgagctgat cgtgcgccgt gcgcagcccc tggagaggga    28560
tgcaaatttg caagaacaaa cagaggaggg cctacccgca gttggcgacg agcagctagc    28620
gcgctggctt caaacgcgcg agcctgccga cttggaggag cgacgcaaac taatgatggc    28680
cgcagtgctc gttaccgtgg agcttgagtg catgcagcgg ttctttgctg acccggagat    28740
gcagcgcaag ctagaggaaa cattgcacta cacctttcga cagggctacg tacgccaggc    28800
ctgcaagatc tccaacgtgg agctctgcaa cctggtctcc taccttggaa ttttgcacga    28860
aaaccgcctt gggcaaaacg tgcttcattc cacgctcaag ggcgaggcgc gccgcgacta    28920
cgtccgcgac tgcgtttact tatttctatg ctacacctgg cagacggcca tgggcgtttg    28980
gcagcagtgc ttggaggagt gcaacctcaa ggagctgcag aaactgctaa agcaaaactt    29040
gaaggaccta tggacggcct tcaacgagcg ctccgtggcc gcgcacctgg cggacatcat    29100
tttccccgaa cgcctgctta aaaccctgca acagggtctg ccagacttca ccagtcaaag    29160
catgttgcag aactttagga actttatcct agagcgctca ggaatcttgc ccgccacctg    29220
ctgtgcactt cctagcgact ttgtgcccat taagtaccgc gaatgccctc gccgctttg    29280 gggccactgc taccttctgc agctagccaa ctaccttgcc taccactctg acataatgga    29340
agacgtgagc ggtgacggtc tactggagtg tcactgtcgc tgcaacctat gcaccccgca    29400
ccgctccctg gtttgcaatt cgcagctgct taacgaaagt caaattatcg gtacctttga    29460
gctgcagggt ccctcgcctg acgaaaagtc cgcggctccg gggttgaaac tcactccggg    29520
gctgtggacg tcggcttacc ttcgcaaatt tgtacctgag gactaccacg cccacgagat    29580
taggttctac gaagaccaat cccgcccgcc aaatgcggag cttaccgcct gcgtcattac    29640
ccagggccac attcttggcc aattgcaagc catcaacaaa gcccgccaag agtttctgct    29700
acgaaaggga cgggggggttt acttggaccc ccagtccggc gaggagctca acccaatccc    29760
cccgccgccg cagccctatc agcagcagcc gcgggcccctt gcttcccagg atggcaccca    29820
aaaagaagct gcagctgccg ccgccaccca cggacgagga ggaatactgg gacagtcagg    29880
cagaggaggt tttggacgag gaggaggagg acatgatgga agactgggag agcctagacg    29940
aggaagcttc cgaggtcgaa gaggtgtcag acgaaacacc gtcaccctcg gtcgcattcc    30000
cctcgccggc gccccagaaa tcggcaaccg gttccagcat ggctacaacc tccgctcctc    30060
aggcgccgcc ggcactgccc gttcgccgac ccaaccgtag atgggacacc actggaacca    30120 gggcggtaa gtccaagcag ccgccgccgt tagcccaaga gcaacaacag cgccaaggct    30180
accgctcatg gcgcgggcac aagaacgcca tagttgcttg cttgcaagac tgtggggca    30240 acatctcctt cgcccgccgc tttcttctct accatcacgg cgtggccttc ccccgtaaca    30300
tcctgcatta ctaccgtcat ctctacagcc atactgcac cggcggcagc ggcagcggca    30360
gcaacagcag cggccacaca gaagcaaagg cgaccggata gcaagactct gacaaagccc    30420
aagaaatcca cagcggcggc agcagcagga ggaggagcgc tgcgtctggc gcccaacgaa    30480
cccgtatcga cccgcgagct tagaaacagg atttttccca ctctgtatgc tatatttcaa    30540
cagagcaggg gccaagaaca agagctgaaa ataaaaaaca ggtctctgcg atccctcacc    30600
cgcagctgcc tgtatcacaa aagcgaagat cagcttcggc gcacgctgga agacgcggag    30660
gctctcttca gtaaatactg cgcgctgact cttaaggact agtttcgcgc cctttctcaa    30720
```

```
atttaagcgc gaaaactacg tcatctccag cggccacacc cggcgccagc acctgtcgtc    30780
agcgccatta tgagcaagga aattcccacg ccctacatgt ggagttacca gccacaaatg    30840
ggacttgcgg ctggagctgc ccaagactac tcaacccgaa taaactacat gagcgcggga    30900
ccccacatga tatcccgggt caacggaatc cgcgcccacc gaaaccgaat tctcttggaa    30960
caggcggcta ttaccaccac acctcgtaat aaccttaatc cccgtagttg gcccgctgcc    31020
ctggtgtacc aggaaagtcc cgctcccacc actgtggtac ttcccagaga cgcccaggcc    31080
gaagttcaga tgactaactc aggggcgcag cttgcgggcg gctttcgtca cagggtgcgg    31140
tcgcccgggc agggtataac tcacctgaca atcagagggc gaggtattca gctcaacgac    31200
gagtcggtga gctcctcgct tggtctccgt ccggacggga catttcagat cggcggcgcc    31260
ggccgtcctt cattcacgcc tcgtcaggca atcctaactc tgcagacctc gtcctctgag    31320
ccgcgctctg gaggcattgg aactctgcaa tttattgagg agtttgtgcc atcggtctac    31380
tttaacccct tctcgggacc tcccggccac tatccggatc aatttattcc taactttgac    31440
gcggtaaagg actcggcgga cggctacgac tgaatgttaa gtggagaggc agagcaactg    31500
cgcctgaaac acctggtcca ctgtcgccgc acaagtgct  ttgcccgcga ctccggtgag    31560
ttttgctact ttgaattgcc cgaggatcat atcgagggcc cggcgcacgg cgtccggctt    31620
accgcccagg gagagcttgc ccgtagcctg attcggagt  ttacccagcg cccctgcta    31680 gttgagcggg acagggacc  ctgtgttctc actgtgattt gcaactgtcc taaccttgga    31740
ttacatcaag atcctctagt tataactaga gtacccgggg atcttattcc ctttaactaa    31800
taaaaaaaaa taataaagca tcacttactt aaaatcagtt agcaaatttc tgtccagttt    31860
attcagcagc acctccttgc cctcctccca gctctggtat tgcagcttcc tcctggctgc    31920
aaactttctc cacaatctaa atggaatgtc agtttcctcc tgttcctgtc catccgcacc    31980
cactatcttc atgttgttgc agatgaagcg cgcaagaccg tctgaagata ccttcaaccc    32040
cgtgtatcca tatgacacgg aaaccggtcc tccaactgtg cctttcttta ctcctcccctt   32100 tgtatccccc aatgggtttc aagagagtcc ccctggggta ctctctttgc gcctatccga    32160
acctctagtt acctccaatg gcatgcttgc gctcaaaatg ggcaacggcc tctctctgga    32220
cgaggccggc aaccttacct cccaaaatgt aaccactgtg agcccactc  tcaaaaaaac    32280 caagtcaaac ataaacctgg aaatatctgc accctcaca  gttacctcag aagccctaac    32340
tgtggctgcc gccgcacctc taatggtcgc gggcaacaca ctcaccatgc aatcacaggc    32400
cccgctaacc gtgcacgact ccaaacttag cattgccacc caaggacccc tcacagtgtc    32460
agaaggaaag ctagccctgc aaacatcagg cccctcacc accaccgata gcagtaccct    32520
tactatcact gcctcacccc ctctaactac tgccactggt agcttgggca ttgacttgaa    32580
agagcccatt tatacacaaa atggaaaact aggactaaag tacggggctc ctttgcatgt    32640
aacagacgac ctaaacactt tgaccgtagc aactggtcca ggtgtgacta ttaataatac    32700
ttccttgcaa actaaagtta ctggagcctt gggttttgat tcacaaggca atatgcaact    32760
taatgtagca ggaggactaa ggattgattc tcaaaacaga cgccttatac ttgatgttag    32820
ttatccgttt gatgctcaaa accaactaaa tctaagacta ggacagggcc ctcttttat    32880 aaactcagcc cacaacttgg atattaacta caacaaaggc ctttacttgt ttacagcttc    32940
aaacaattcc aaaagcttg aggttaacct aagcactgcc aaggggttga tgtttgacgc    33000
tacagccata gccattaatg caggagatgg gcttgaattt ggttcaccta atgcaccaaa    33060
```

-continued

| | |
|---|---|
| cacaaatccc ctcaaaacaa aaattggcca tggcctagaa tttgattcaa acaaggctat | 33120 |
| ggttcctaaa ctaggaactg gccttagttt tgacagcaca ggtgccatta cagtaggaaa | 33180 |
| caaaaataat gataagctaa ccctatggac aggtccaaaa ccagaagcca actgcataat | 33240 |
| tgaatacggg aaacaaaacc cagatagcaa actaacttta atccttgtaa aaaatggagg | 33300 |
| aattgttaat ggatatgtaa cgctaatggg agcctcagac tacgttaaca ccttatttaa | 33360 |
| aaacaaaaat gtctccatta atgtagaact atactttgat gccactggtc atatattacc | 33420 |
| agactcatct tctcttaaaa cagatctaga actaaaatac aagcaaaccg ctgactttag | 33480 |
| tgcaagaggt tttatgccaa gtactacagc gtatccattt gtccttccta atgcgggaac | 33540 |
| acataatgaa aattatattt ttggtcaatg ctactacaaa gcaagcgatg gtgcccttt | 33600 |
| tccgttggaa gttactgtta tgcttaataa acgcctgcca gatagtcgca catcctatgt | 33660 |
| tatgactttt ttatggtcct tgaatgctgg tctagctcca gaaactactc aggcaaccct | 33720 |
| cataacctcc ccatttacct tttcctatat tagagaagat gacggtggag gcggttcagg | 33780 |
| cggaggtggc tctggcggtg gcggatcctg tgactgccgc ggagactgtt tctgctaata | 33840 |
| aactctaaag aatcgtttgt gttatgtttc aacgtgttta tttttcaatt gcagaaaatt | 33900 |
| tcaagtcatt tttcattcag tagtatagcc ccaccaccac atagcttata cagatcaccg | 33960 |
| taccttaatc aaactcacag aaccctagta ttcaacctgc cacctccctc ccaacacaca | 34020 |
| gagtacacag tcctttctcc ccggctggcc ttaaaaagca tcatatcatg ggtaacagac | 34080 |
| atattcttag gtgttatatt ccacacggtt tcctgtcgag ccaaacgctc atcagtgata | 34140 |
| ttaataaact ccccgggcag ctcacttaag ttcatgtcgc tgtccagctg ctgagccaca | 34200 |
| ggctgctgtc caacttgcgg ttgcttaacg ggcggcgaag gagaagtcca cgcctacatg | 34260 |
| ggggtagagt cataatcgtg catcaggata gggcggtggt gctgcagcag cgcgcgaata | 34320 |
| aactgctgcc gccgccgctc cgtcctgcag gaatacaaca tggcagtggt ctcctcagcg | 34380 |
| atgattcgca ccgcccgcag cataaggcgc cttgtcctcc gggcacagca gcgcaccctg | 34440 |
| atctcactta aatcagcaca gtaactgcag cacagcacca caatattgtt caaaatccca | 34500 |
| cagtgcaagg cgctgtatcc aaagctcatg gcggggacca cagaacccac gtggccatca | 34560 |
| taccacaagc gcaggtagat taagtggcga cccctcataa acacgctgga cataaacatt | 34620 |
| acctcttttg gcatgttgta attcaccacc tcccggtacc atataaacct ctgattaaac | 34680 |
| atggcgccat ccaccaccat cctaaaccag ctggccaaaa cctgcccgcc ggctatacac | 34740 |
| tgcagggaac cggactgga acaatgacag tggagagccc aggactcgta accatggatc | 34800 |
| atcatgctcg tcatgatatc aatgttggca caacacaggc acacgtgcat acacttcctc | 34860 |
| aggattacaa gctcctcccg cgttagaacc atatcccagg gaacaaccca ttcctgaatc | 34920 |
| agcgtaaatc ccacactgca gggaagacct cgcacgtaac tcacgttgtg cattgtcaaa | 34980 |
| gtgttacatt cgggcagcag cggatgatcc tccagtatgg tagcgcgggt ttctgtctca | 35040 |
| aaaggaggta gacgatccct actgtacgga gtgcgccgag acaaccgaga tcgtgttggt | 35100 |
| cgtagtgtca tgccaaatgg aacgccggac gtagtcatat ttcctgaagc aaaaccaggt | 35160 |
| gcgggcgtga caaacagatc tgcgtctccg gtctcgccgc ttagatcgct ctgtgtagta | 35220 |
| gttgtagtat atccactctc tcaaagcatc caggcgcccc ctggcttcgg gttctatgta | 35280 |
| aactccttca tgcgccgctg ccctgataac atccaccacc gcagaataag ccacacccag | 35340 |
| ccaacctaca cattcgttct gcgagtcaca cacgggagga gcgggaagag ctggaagaac | 35400 |
| catgtttttt tttttattcc aaaagattat ccaaaacctc aaaatgaaga tctattaagt | 35460 |

```
gaacgcgctc ccctccggtg gcgtggtcaa actctacagc caaagaacag ataatggcat    35520
ttgtaagatg ttgcacaatg gcttccaaaa ggcaaacggc cctcacgtcc aagtggacgt    35580
aaaggctaaa cccttcaggg tgaatctcct ctataaacat tccagcacct tcaaccatgc    35640
ccaaataatt ctcatctcgc caccttctca atatatctct aagcaaatcc cgaatattaa    35700
gtccggccat tgtaaaaatc tgctccagag cgccctccac cttcagcctc aagcagcgaa    35760
tcatgattgc aaaaattcag gttcctcaca gacctgtata agattcaaaa gcggaacatt    35820
aacaaaaata ccgcgatccc gtaggtccct tcgcagggcc agctgaacat aatcgtgcag    35880
gtctgcacgg accagcgcgg ccacttcccc gccaggaacc ttgacaaaag acccacact    35940
gattatgaca cgcatactcg gagctatgct aaccagcgta gccccgatgt aagctttgtt    36000
gcatgggcgg cgatataaaa tgcaaggtgc tgctcaaaaa atcaggcaaa gcctcgcgca    36060
aaaaagaaag cacatcgtag tcatgctcat gcagataaag gcaggtaagc tccggaacca    36120
ccacagaaaa agacaccatt tttctctcaa acatgtctgc gggtttctgc ataaacacaa    36180
aataaaataa caaaaaaaca tttaaacatt agaagcctgt cttacaacag gaaaaacaac    36240
ccttataagc ataagacgga ctacggccat gccggcgtga ccgtaaaaaa actggtcacc    36300
gtgattaaaa agcaccaccg acagctcctc ggtcatgtcc ggagtcataa tgtaagactc    36360
ggtaaacaca tcaggttgat tcatcggtca gtgctaaaaa gcgaccgaaa tagcccgggg    36420
gaatacatac ccgcaggcgt agagacaaca ttacagcccc cataggaggt ataacaaaat    36480
taataggaga gaaaaacaca taaacacctg aaaaaccctc ctgcctaggc aaaatagcac    36540
cctcccgctc cagaacaaca tacagcgctt cacagcggca gcctaacagt cagccttacc    36600
agtaaaaaag aaaacctatt aaaaaaacac cactcgacac ggcaccagct caatcagtca    36660
cagtgtaaaa aagggccaag tgcagagcga gtatatatag gactaaaaaa tgacgtaacg    36720
gttaaagtcc acaaaaaaca cccagaaaac cgcacgcgaa cctacgccca gaaacgaaag    36780
ccaaaaaacc cacaacttcc tcaaatcgtc acttccgttt tcccacgtta cgtaacttcc    36840
cattttaaga aaactacaat tcccaacaca tacaagttac tccgccctaa aacctacgtc    36900
acccgccccg ttcccacgcc ccgcgccacg tcacaaactc caccccctca ttatcatatt    36960
ggcttcaatc caaaataagg tatattattg atgatnnnnn ttaat                   37005
```

```
<210> SEQ ID NO 6
<211> LENGTH: 33541
<212> TYPE: DNA
<213> ORGANISM: Artificial sequence
<220> FEATURE:
<223> OTHER INFORMATION: Recombinant shuttle virus AdEz5/3-RGDsv 1stHR,
      n=A,C,G,T
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (3655)..(3657)
<223> OTHER INFORMATION: n is a, c, g, or t
<220> FEATURE:
<221> NAME/KEY: misc_feature
<222> LOCATION: (3684)..(3686)
<223> OTHER INFORMATION: n is a, c, g, or t
<220> FEATURE:
<221> NAME/KEY: misc_feature
<222> LOCATION: (33532)..(33536)
<223> OTHER INFORMATION: n is a, c, g, or t

<400> SEQUENCE: 6
```

```
taaggatccn nncctgtcct cgaccgatgc ccttgagagc cttcaaccca gtcagctcct    60
tccggtgggc gcggggcatg actatcgtcg ccgcacttat gactgtcttc tttatcatgc   120
aactcgtagg acaggtgccg gcagcgctct gggtcatttt cggcgaggac cgctttcgct   180
ggagcgcgac gatgatcggc ctgtcgcttg cggtattcgg aatcttgcac gccctcgctc   240
aagccttcgt cactggtccc gccaccaaac gtttcggcga aagcaggcc attatcgccg    300
gcatggcggc cgacgcgctg ggctacgtct tgctggcgtt cgcgacgcga ggctggatgg   360
ccttccccat tatgattctt ctcgcttccg gcggcatcgg gatgcccgcg ttgcaggcca   420
tgctgtccag gcaggtagat gacgaccatc agggacagct tcaaggatcg ctcgcggctc   480
ttaccagcct aacttcgatc actggaccgc tgatcgtcac ggcgatttat gccgcctcgg   540
cgagcacatg gaacgggttg gcatggattg taggcgccgc cctatacctt gtctgcctcc   600
ccgcgttgcg tcgcggtgca tggagccggg ccacctcgac ctgaatggaa gccggcggca   660
cctcgctaac ggattcacca ctccaagaat tggagccaat caattcttgc ggagaactgt   720
gaatgcgcaa accaacccct tggcagaaca tatccatcgcg tccgccatct ccagcagccg   780
cacgcggcgc atctcgggca gcgttgggtc ctggccacgg gtgcgcatga tcgtgctcct   840
gtcgttgagg acccggctag gctggcgggg ttgccttact ggttagcaga atgaatcacc   900
gatacgcgag cgaacgtgaa gcgactgctg ctgcaaaacg tctgcgacct gagcaacaac   960
atgaatggtc ttcggtttcc gtgtttcgta aagtctggaa acgcggaagt cagcgccctg  1020
caccattatg ttccggatct gcatcgcagg atgctgctgg ctaccctgtg aacacctac   1080
atctgtatta acgaagcgct ggcattgacc ctgagtgatt tttctctggt cccgccgcat  1140
ccataccgcc agttgtttac cctcacaacg ttccagtaac cgggcatgtt catcatcagt  1200
aacccgtatc gtgagcatcc tctctcgttt catcggtatc attaccccca tgaacagaaa  1260
ttccccctta cacggaggca tcaagtgacc aaacaggaaa aaaccgccct taacatggcc  1320
cgctttatca gaagccagac attaacgctt ctggagaaac tcaacgagct ggacgcggat  1380
gaacaggcag acatctgtga atcgcttcac gaccacgctg atgagcttta ccgcagctgc  1440
ctcgcgcgtt tcggtgatga cggtgaaaac ctctgacaca tgcagctccc ggagacggtc  1500
acagcttgtc tgtaagcgga tgccgggagc agacaagccc gtcagggcgc gtcagcgggt  1560
gttggcgggt gtcggggcgc agccatgacc cagtcacgta gcgatagcgg agtgtatact  1620
ggcttaacta tgcggcatca gagcagattg tactgagagt gcaccatatg cggtgtgaaa  1680
taccgcacag atgcgtaagg agaaaatacc gcatcaggcg ctcttccgct tcctcgctca  1740
ctgactcgct gcgctcggtc gttcggctgc ggcgagcggt atcagctcac tcaaaggcgg  1800
taatacggtt atccacagaa tcaggggata acgcaggaaa gaacatgtga gcaaaaggcc  1860
agcaaaaggc caggaaccgt aaaaaggccg cgttgctggc gtttttccat aggctccgcc  1920
cccctgacga gcatcacaaa aatcgacgct caagtcagag gtggcgaaac ccgacaggac  1980
tataaagata ccaggcgttt ccccctggaa gctccctcgt gcgctctcct gttccgaccc  2040
tgccgcttac cggatacctg tccgcctttc tcccttcggg aagcgtggcg ctttctcaat  2100
gctcacgctg taggtatctc agttcggtgt aggtcgttcg ctccaagctg ggctgtgtgc  2160
acgaaccccc cgttcagccc gaccgctgcg ccttatccgg taactatcgt cttgagtcca  2220
acccggtaag acacgactta tcgccactgg cagcagccac tggtaacagg attagcagag  2280
cgaggtatgt aggcggtgct acagagttct tgaagtggtg gcctaactac ggctacacta  2340
```

```
gaaggacagt atttggtatc tgcgctctgc tgaagccagt taccttcgga aaaagagttg    2400
gtagctcttg atccggcaaa caaaccaccg ctggtagcgg tggttttttt gtttgcaagc    2460
agcagattac gcgcagaaaa aaaggatctc aagaagatcc tttgatcttt tctacggggt    2520
ctgacgctca gtggaacgaa aactcacgtt aagggatttt ggtcatgaga ttatcaaaaa    2580
ggatcttcac ctagatcctt ttaaattaaa aatgaagttt taaatcaatc taaagtatat    2640
atgagtaaac ttggtctgac agttaccaat gcttaatcag tgaggcacct atctcagcga    2700
tctgtctatt tcgttcatcc atagttgcct gactccccgt cgtgtagata actacgatac    2760
gggagggctt accatctggc cccagtgctg caatgatacc gcgagaccca cgctcaccgg    2820
ctccagattt atcagcaata aaccagccag ccggaagggc cgagcgcaga agtggtcctg    2880
caactttatc cgcctccatc cagtctatta attgttgccg gaagctaga gtaagtagtt    2940 cgccagttaa tagtttgcgc aacgttgttg ccattgctgc aggcatcgtg gtgtcacgct    3000
cgtcgtttgg tatggcttca ttcagctccg gttcccaacg atcaaggcga gttacatgat    3060
cccccatgtt gtgcaaaaaa gcggttagct ccttcggtcc tccgatcgtt gtcagaagta    3120
agttggccgc agtgttatca ctcatggtta tggcagcact gcataattct cttactgtca    3180
tgccatccgt aagatgcttt tctgtgactg gtgagtactc aaccaagtca ttctgagaat    3240
agtgtatgcg gcgaccgagt tgctcttgcc cggcgtcaac acgggataat accgcgccac    3300
atagcagaac tttaaaagtg ctcatcattg gaaaacgttc ttcggggcga aaactctcaa    3360
ggatcttacc gctgttgaga tccagttcga tgtaacccac tcgtgcaccc aactgatctt    3420
cagcatcttt tactttcacc agcgtttctg ggtgagcaaa aacaggaagg caaaatgccg    3480
caaaaaaggg aataagggcg acacggaaat gttgaatact catactcttc ctttttcaat    3540
attattgaag catttatcag ggttattgtc tcatgagcgg atacatattt gaatgtattt    3600
agaaaaataa acaaataggg gttccgcgca catttccccg aaaagtgcca cctgnnngaa    3660
ttcgaatcta gtatcgattc gaannncta agggtgggaa agaatatata aggtgggggt    3720
cttatgtagt tttgtatctg ttttgcagca gccgccgccg ccatgagcac caactcgttt    3780
gatggaagca ttgtgagctc atatttgaca acgcgcatgc ccccatgggc cggggtgcgt    3840
cagaatgtga tgggctccag cattgatggt cgccccgtcc tgcccgcaaa ctctactacc    3900
ttgacctacg agaccgtgtc tggaacgccg ttggagactg cagcctccgc cgccgcttca    3960
gccgctgcag ccaccgcccg cgggattgtg actgactttg ctttcctgag cccgcttgca    4020
agcagtgcag cttcccgttc atccgcccgc gatgacaagt tgacggctct tttggcacaa    4080
ttggattctt tgacccggga acttaatgtc gtttctcagc agctgttgga tctgcgccag    4140
caggtttctg ccctgaaggc ttcctcccct cccaatgcgg tttaaaacat aaataaaaaa    4200
ccagactctg tttggatttg gatcaagcaa gtgtcttgct gtctttattt aggggttttg    4260
cgcgcgcggt aggcccggga ccagcggtct cggtcgttga gggtcctgtg tatttttcc    4320 aggacgtggt aaaggtgact ctggatgttc agatacatgg gcataagccc gtctctgggg    4380
tggaggtagc accactgcag agcttcatgc tgcggggtgg tgttgtagat gatccagtcg    4440
tagcaggagc gctgggcgtg gtgcctaaaa atgtctttca gtagcaagct gattgccagg    4500
ggcaggccct tggtgtaagt gtttacaaag cggttaagct gggatgggtg catacgtggg    4560
gatatgagat gcatcttgga ctgtattttt aggttggcta tgttcccagc catatccctc    4620
cggggattca tgttgtgcag aaccaccagc acagtgtatc cggtgcactt gggaaatttg    4680
tcatgtagct tagaaggaaa tgcgtggaag aacttggaga cgcccttgtg acctccaaga    4740
```

-continued

```
tttccatgc attcgtccat aatgatggca atgggcccac gggcggcggc ctgggcgaag    4800
atatttctgg gatcactaac gtcatagttg tgttccagga tgagatcgtc ataggccatt    4860
tttacaaagc gcgggcggag ggtgccagac tgcggtataa tggttccatc cggcccaggg    4920
gcgtagttac cctcacagat ttgcatttcc cacgctttga gttcagatgg ggggatcatg    4980
tctacctgcg gggcgatgaa gaaaacggtt ccggggtag gggagatcag ctgggaagaa     5040
agcaggttcc tgagcagctg cgacttaccg cagccgtgg gcccgtaaat cacacctatt     5100
accgggtgca actggtagtt aagagagctg cagctgccgt catccctgag caggggggcc    5160
acttcgttaa gcatgtccct gactcgcatg ttttccctga ccaaatccgc cagaaggcgc    5220
tcgccgccca gcgatagcag ttcttgcaag gaagcaaagt ttttcaacgg tttgagaccg    5280
tccgccgtag gcatgctttt gagcgtttga ccaagcagtt ccaggcggtc ccacagctcg    5340
gtcacctgct ctacggcatc tcgatccagc atatctcctc gtttcgcggg ttgggcggc    5400 tttcgctgta cggcagtagt cggtgctcgt ccagacgggc cagggtcatg tctttccacg    5460
ggcgcagggt cctcgtcagc gtagtctggg tcacggtgaa ggggtgcgct ccgggctgcg    5520
cgctggccag ggtgcgcttg aggctggtcc tgctggtgct gaagcgctgc cggtcttcgc    5580
cctgcgcgtc ggccaggtag catttgacca tggtgtcata gtccagcccc tccgcggcgt    5640
ggcccttggc gcgcagcttg cccttggagg aggcgccgca cgaggggcag tgcagacttt    5700
tgagggcgta gagcttgggc gcgagaaata ccgattccgg ggagtaggca tccgcgccgc    5760
aggccccgca gacggtctcg cattccacga gccaggtgag ctctggccgt tcggggtcaa    5820
aaaccaggtt tcccccatgc ttttttgatgc gtttcttacc tctggtttcc atgagccggt    5880
gtccacgctc ggtgacgaaa aggctgtccg tgtcccgta tacagacttg agaggcctgt    5940
cctcgagcgg tgttccgcgg tcctcctcgt atagaaactc ggaccactct gagacaaagg    6000
ctcgcgtcca ggccagcacg aaggaggcta agtgggaggg gtagcggtcg ttgtccacta    6060
gggggtccac tcgctccagg gtgtgaagac acatgtcgcc ctcttcggca tcaaggaagg    6120
tgattggttt gtaggtgtag gccacgtgac cgggtgttcc tgaagggggg ctataaaagg    6180 gggtggggc gcgttcgtcc tcactctctt ccgcatcgct gtctgcgagg gccagctgtt    6240
ggggtgagta ctccctctga aaagcgggca tgacttctgc gctaagattg tcagtttcca    6300
aaaacgagga ggatttgata ttcacctggc ccgcggtgat gcctttgagg gtggccgcat    6360
ccatctggtc agaaaagaca atctttttgt tgtcaagctt ggtggcaaac gacccgtaga    6420
gggcgttgga cagcaacttg gcgatggagc gcagggtttg gttttttgtcg cgatcggcgc    6480 gctccttggc cgcgatgttt agctgcacgt attcgcgcgc aacgcaccgc cattcgggaa    6540
agacggtggt gcgctcgtcg ggcaccaggt gcacgcgcca accgcggttg tgcagggtga    6600
caaggtcaac gctggtggct acctctccgc gtaggcgctc gttggtccag cagaggcggc    6660
cgcccttgcg cgagcagaat ggcggtaggg ggtctagctg cgtctcgtcc gggggtctg    6720 cgtccacggt aaagaccccg ggcagcaggc gcgcgtcgaa gtagtctatc ttgcatcctt    6780
gcaagtctag cgcctgctgc catgcgcggg cggcaagcgc gcgctcgtat gggttgagtg    6840
ggggacccca tggcatgggg tgggtgagcg cggaggcgta catgccgcaa atgtcgtaaa    6900
cgtagagggg ctctctgagt attccaagat atgtagggta gcatcttcca ccgcggatgc    6960
tggcgcgcac gtaatcgtat agttcgtgcg agggagcgag gaggtcggga ccgaggttgc    7020
tacgggcggg ctgctctgct cggaagacta tctgcctgaa gatggcatgt gagttggatg    7080
```

```
atatggttgg acgctggaag acgttgaagc tggcgtctgt gagacctacc gcgtcacgca   7140
cgaaggaggc gtaggagtcg cgcagcttgt tgaccagctc ggcggtgacc tgcacgtcta   7200
gggcgcagta gtccagggtt tccttgatga tgtcatactt atcctgtccc ttttttttcc   7260
acagctcgcg gttgaggaca aactcttcgc ggtctttcca gtactcttgg atcggaaacc   7320
cgtcggcctc cgaacggtaa gagcctagca tgtagaactg gttgacggcc tggtaggcgc   7380
agcatccctt ttctacgggt agcgcgtatg cctgcgcggc cttccggagc gaggtgtggg   7440
tgagcgcaaa ggtgtccctg accatgactt tgaggtactg gtatttgaag tcagtgtcgt   7500
cgcatccgcc ctgctcccag agcaaaaagt ccgtgcgctt tttggaacgc ggatttggca   7560
gggcgaaggt gacatcgttg aagagtatct ttcccgcgcg aggcataaag ttgcgtgtga   7620
tgcgaagggg tcccggcacc tcggaacggt tgttaattac ctgggcgcg agcacgatct    7680
cgtcaaagcc gttgatgttg tggcccacaa tgtaaagttc caagaagcgc gggatgccct   7740
tgatggaagg caattttta agttcctcgt aggtgagctc ttcaggggag ctgagcccgt     7800
gctctgaaag ggcccagtct gcaagatgag ggttggaagc gacgaatgag ctccacaggt   7860
cacgggccat tagcatttgc aggtggtcgc gaaaggtcct aaactggcga cctatggcca   7920
ttttttctgg ggtgatgcag tagaaggtaa gcgggtcttg ttcccagcgg tcccatccaa   7980
ggttcgcggc taggtctcgc gcggcagtca ctagaggctc atctccgccg aacttcatga   8040
ccagcatgaa gggcacgagc tgcttcccaa aggcccccat ccaagtatag gtctctacat   8100
cgtaggtgac aaagagacgc tcggtgcgag gatgcgagcc gatcgggaag aactggatct   8160
cccgccacca attggaggag tggctattga tgtggtgaaa gtagaagtcc ctgcgacggg   8220
ccgaacactc gtgctggctt ttgtaaaaac gtgcgcagta ctggcagcgg tgcacgggct   8280
gtacatcctg cacgaggttg acctgacgac cgcgcacaag gaagcagagt gggaatttga   8340
gccctcgcc tggcgggttt ggctggtggt cttctacttc ggctgcttgt ccttgaccgt    8400
ctggctgctc gaggggagtt acggtggatc ggaccaccac gccgcgcgag cccaaagtcc   8460
agatgtccgc gcgcggcggt cggagcttga tgacaacatc gcgcagatgg gagctgtcca   8520
tggtctggag ctcccgcggc gtcaggtcag gcgggagctc ctgcaggttt acctcgcata   8580
gacgggtcag ggcgcgggct agatccaggt gatacctaat ttccaggggc tggttggtgg   8640
cggcgtcgat ggcttgcaag aggccgcatc ccgcggcgc gactacggta ccgcgcggcg    8700
ggcggtgggc cgcggggggtg tccttggatg atgcatctaa aagcggtgac gcgggcgagc   8760
ccccggaggt aggggggggct ccggacccgc cgggagaggg ggcaggggca cgtcggcgcc   8820
gcgcgcgggc aggagctggt gctgcgcgcg taggttgctg gcgaacgcga cgacgcggcg   8880
gttgatctcc tgaatctggc gcctctgcgt gaagacgacg ggcccggtga gcttgagcct   8940
gaaagagagt tcgacagaat caatttcggt gtcgttgacg gcggcctggc gcaaaatctc   9000
ctgcacgtct cctgagttgt cttgataggc gatctcggcc atgaactgct cgatctcttc   9060
ctcctggaga tctccgcgtc cggctcgctc cacggtggcg gcgaggtcgt tggaaatgcg   9120
ggccatgagc tgcgagaagg cgttgaggcc tccctcgttc cagacgcggc tgtagaccac   9180
gccccttcg gcatcgcggg cgcgcatgac cacctgcgcg agattgagct ccacgtgccg    9240
ggcgaagacg gcgtagtttc gcaggcgctg aaagaggtag ttgagggtgg tggcggtgtg   9300
ttctgccacg aagaagtaca taacccagcg tcgcaacgtg gattcgttga tatccccaa    9360
ggcctcaagg cgctccatgg cctcgtagaa gtccacggcg aagttgaaaa actgggagtt   9420
gcgcgccgac acggttaact cctcctccag aagacggatg agctcggcga cagtgtcgcg   9480
```

```
cacctcgcgc tcaaaggcta caggggcctc ttcttcttct tcaatctcct cttccataag    9540
ggcctcccct tcttcttctt ctggcggcgg tgggggaggg gggacacggc ggcgacgacg    9600
gcgcaccggg aggcggtcga caaagcgctc gatcatctcc ccgcggcgac ggcgcatggt    9660
ctcggtgacg gcgcggccgt tctcgcgggg gcgcagttgg aagacgccgc ccgtcatgtc    9720
ccggttatgg gttggcgggg ggctgccatg cggcagggat acggcgctaa cgatgcatct    9780
caacaattgt tgtgtaggta ctccgccgcc gagggacctg agcgagtccg catcgaccgg    9840
atcggaaaac ctctcgagaa aggcgtctaa ccagtcacag tcgcaaggta ggctgagcac    9900
cgtggcgggc ggcagcgggc ggcggtcggg gttgtttctg gcggaggtgc tgctgatgat    9960
gtaattaaag taggcggtct tgagacggcg gatggtcgac agaagcacca tgtccttggg   10020
tccggcctgc tgaatgcgca ggcggtcggc catgccccag gcttcgtttt gacatcggcg   10080
caggtctttg tagtagtctt gcatgagcct ttctaccggc acttcttctt ctccttcctc   10140
ttgtcctgca tctcttgcat ctatcgctgc ggcggcggcg gagtttggcc gtaggtggcg   10200
ccctcttcct cccatgcgtg tgaccccgaa gcccctcatc ggctgaagca gggctaggtc   10260
ggcgacaacg cgctcggcta atatggcctg ctgcacctgc gtgagggtag actggaagtc   10320
atccatgtcc acaaagcggt ggtatgcgcc cgtgttgatg gtgtaagtgc agttggccat   10380
aacggaccag ttaacggtct ggtgacccgg ctgcgagagc tcggtgtacc tgagacgcga   10440
gtaagccctc gagtcaaata cgtagtcgtt gcaagtccgc accaggtact ggtatcccac   10500
caaaaagtgc ggcggcggct ggcggtagag gggccagcgt agggtggccg gggctccggg   10560
ggcgagatct tccaacataa ggcgatgata tccgtagatg tacctggaca tccaggtgat   10620
gccggcggcg gtggtggagg cgcgcggaaa gtcgcggacg cggttccaga tgttgcgcag   10680
cggcaaaaag tgctccatgg tcgggacgct ctggccggtc aggcgcgcgc aatcgttgac   10740
gctctaccgt gcaaaggag agcctgtaag cgggcactct tccgtggtct ggtggataaa   10800
ttcgcaaggg tatcatggcg gacgaccggg gttcgagccc cgtatccggc cgtccgccgt   10860
gatccatgcg gttaccgccc gcgtgtcgaa cccaggtgtg cgacgtcaga acggggga    10920
gtgctccttt tggcttcctt ccaggcgcgg cggctgctgc gctagctttt ttggccactg   10980
gccgcgcgca gcgtaagcgg ttaggctgga aagcgaaagc attaagtggc tcgctccctg   11040
tagccggagg gttattttcc aagggttgag tcgcgggacc cccggttcga gtctcggacc   11100
ggccggactg cggcgaacgg gggtttgcct ccccgtcatg caagaccccg cttgcaaatt   11160
cctccggaaa cagggacgag cccctttttt gcttttccca gatgcatccg gtgctgcggc   11220
agatgcgccc ccctcctcag cagcggcaag agcaagagca gcggcagaca tgcagggcac   11280
cctcccctcc tcctaccgcg tcaggagggg cgacatccgc ggttgacgcg gcagcagatg   11340
gtgattacga accccgcgg cgccgggccc ggcactacct ggacttggag gagggcgagg   11400
gcctggcgcg gctaggagcg ccctctcctg agccggtaccc aagggtgcag ctgaagcgtg   11460
atacgcgtga ggcgtacgtg ccgcggcaga acctgtttcg cgaccgcgag ggagaggagc   11520
ccgaggagat gcgggatcga aagttccacg cagggcgcga gctgcggcat ggcctgaatc   11580
gcgagcggtt gctgcgcgag gaggactttg agcccgacgc gcgaaccggg attagtcccg   11640
cgcgcgcaca cgtggcggcc gccgacctgg taaccgcata cgagcagacg gtgaaccagg   11700
agattaactt tcaaaaaagc tttaacaacc acgtgcgtac gcttgtggcg cgcgaggagg   11760
tggctatagg actgatgcat ctgtgggact ttgtaagcgc gctggagcaa aacccaaata   11820
```

```
gcaagccgct catggcgcag ctgttcctta tagtgcagca cagcagggac aacgaggcat   11880
tcagggatgc gctgctaaac atagtagagc ccgagggccg ctggctgctc gatttgataa   11940
acatcctgca gagcatagtg gtgcaggagc gcagcttgag cctggctgac aaggtggccg   12000
ccatcaacta ttccatgctt agcctgggca agttttacgc ccgcaagata taccataccc   12060
cttacgttcc catagacaag gaggtaaaga tcgaggggtt ctacatgcgc atggcgctga   12120
aggtgcttac cttgagcgac gacctgggcg tttatcgcaa cgagcgcatc cacaaggccg   12180
tgagcgtgag ccggcggcgc gagctcagcg accgcgagct gatgcacagc ctgcaaaggg   12240
ccctggctgg cacgggcagc ggcgatagag aggccgagtc ctactttgac gcgggcgctg   12300
acctgcgctg ggccccaagc cgacgcgccc tggaggcagc tggggccgga cctgggctgg   12360
cggtggcacc cgcgcgcgct ggcaacgtcg gcggcgtgga ggaatatgac gaggacgatg   12420
agtacgagcc agaggacggc gagtactaag cggtgatgtt tctgatcaga tgatgcaaga   12480
cgcaacggac ccggcggtgc gggcggcgct gcagagccag ccgtccggcc ttaactccac   12540
ggacgactgg cgccaggtca tggaccgcat catgtcgctg actgcgcgca atcctgacgc   12600
gttccggcag cagccgcagg ccaaccggct ctccgcaatt ctggaagcgg tggtcccggc   12660
gcgcgcaaac cccacgcacg agaaggtgct ggcgatcgta aacgcgctgg ccgaaaacag   12720
ggccatccgg cccgacgagg ccggcctggt ctacgacgcg ctgcttcagc gcgtggctcg   12780
ttacaacagc ggcaacgtgc agaccaacct ggaccggctg gtggggatg tgcgcgaggc   12840 cgtggcgcag cgtgagcgcg cgcagcagca gggcaacctg ggctccatgg ttgcactaaa   12900
cgccttcctg agtacacagc ccgccaacgt gccgcgggga caggaggact acaccaactt   12960
tgtgagcgca ctgcggctaa tggtgactga cacccgcaa agtgaggtgt accagtctgg   13020
gccagactat tttttccaga ccagtagaca aggcctgcag accgtaaacc tgagccaggc   13080
tttcaaaaac ttgcaggggc tgtggggggt gcgggctccc acaggcgacc gcgcgaccgt   13140
gtctagcttg ctgacgccca actcgcgcct gttgctgctg ctaatagcgc ccttcacgga   13200
cagtggcagc gtgtcccggg acacatacct aggtcacttg ctgacactgt accgcgaggc   13260
cataggtcag gcgcatgtgg acgagcatac tttccaggag attacaagtg tcagccgcgc   13320
gctggggcag gaggacacgg gcagcctgga ggcaacccta aactacctgc tgaccaaccg   13380
gcggcagaag atcccctcgt tgcacagttt aaacagcgag gaggagcgca ttttgcgcta   13440
cgtgcagcag agcgtgagcc ttaacctgat gcgcgacggg gtaacgccca gcgtggcgct   13500
ggacatgacc gcgcgcaaca tggaaccggg catgtatgcc tcaaaccggc cgtttatcaa   13560
ccgcctaatg gactacttgc atcgcgcggc cgccgtgaac cccgagtatt tcaccaatgc   13620
catcttgaac ccgcactggc taccgccccc tggtttctac accggggat tcgaggtgcc   13680 cgagggtaac gatggattcc tctgggacga catagacgac agcgtgtttt ccccgcaacc   13740
gcagaccctg ctagagttgc aacagcgcga caggcagag gcggcgctgc gaaaggaaag   13800
cttccgcagg ccaagcagct tgtccgatct aggcgctgcg gccccgcggt cagatgctag   13860
tagcccattt ccaagcttga tagggtctct taccagcact cgcaccaccc gcccgcgcct   13920
gctgggcgag gaggagtacc taaacaactc gctgctgcag ccgcagcgcg aaaaaaacct   13980
gcctccggca tttcccaaca cgggataga gagcctagtg acaagatga gtagatggaa   14040 gacgtacgcg caggagcaca gggacgtgcc aggcccgcgc ccgcccaccc gtcgtcaaag   14100
gcacgaccgt cagcggggtc tggtgtggga ggacgatgac tcggcagacg acagcagcgt   14160
cctggatttg ggagggagtg caacccgtt tgcgcacctt cgccccaggc tggggagaat   14220
```

```
gttttaaaaa aaaaaaagca tgatgcaaaa taaaaaactc accaaggcca tggcaccgag    14280
cgttggtttt cttgtattcc ccttagtatg cggcgcgcgg cgatgtatga ggaaggtcct    14340
cctccctcct acgagagtgt ggtgagcgcg gcgccagtgg cggcggcgct gggttctccc    14400
ttcgatgctc ccctggaccc gccgtttgtg cctccgcggt acctgcggcc taccgggggg    14460
agaaacagca tccgttactc tgagttggca cccctattcg acaccacccg tgtgtacctg    14520
gtggacaaca agtcaacgga tgtggcatcc ctgaactacc agaacgacca cagcaacttt    14580
ctgaccacgg tcattcaaaa caatgactac agcccggggg aggcaagcac acagaccatc    14640
aatcttgacg accggtcgca ctgggcggc gacctgaaaa ccatcctgca taccaacatg    14700
ccaaatgtga acgagttcat gtttaccaat aagtttaagg cgcgggtgat ggtgtcgcgc    14760
ttgcctacta aggacaatca ggtggagctg aaatacgagt gggtggagtt cacgctgccc    14820
gagggcaact actccgagac catgaccata gaccttatga caacgcgat cgtggagcac    14880 tacttgaaag tgggcagaca gaacgggggtt ctggaaagcg catcgggtt aaagtttgac    14940 acccgcaact tcagactggg gtttgacccc gtcactggtc ttgtcatgcc tggggtatat    15000
acaaacgaag ccttccatcc agacatcatt ttgctgccag gatgcggggt ggacttcacc    15060
cacagccgcc tgagcaactt gttgggcatc cgcaagcggc aacccttcca ggagggcttt    15120
aggatcacct acgatgatct ggaggtggt aacattcccg cactgttgga tgtggacgcc    15180
taccaggcga gcttgaaaga tgacaccgaa cagggcgggg gtggcgcagg cggcagcaac    15240
agcagtggca gcgcgcgga agagaactcc aacgcggcag ccgcggcaat gcagccggtg    15300
gaggacatga acgatcatgc cattcgcggc gacaccttg ccacacgggc tgaggagaag    15360
cgcgctgagg ccgaagcagc ggccgaagct gccgcccccg ctgcgcaacc cgaggtcgag    15420
aagcctcaga gaaaccggt gatcaaaccc ctgacagagg acagcaagaa acgcagttac    15480
aacctaataa gcaatgacag cacctcacc cagtaccgca gctggtacct tgcatacaac    15540
tacggcgacc ctcagaccgg aatccgctca tggaccctgc tttgcactcc tgacgtaacc    15600
tgcggctcgg agcaggtcta ctggtcgttg ccagacatga tgcaagaccc cgtgaccttc    15660
cgctccacgc gccagatcag caactttccg gtggtgggcg ccgagctgtt gccagtgcac    15720
tccaagagct tctacaacga ccaggccgtc tactcccaac tcatccgcca gtttacctct    15780
ctgacccacg tgttcaatcg ctttcccgag aaccagattt ggcgcgccc gccagccccc    15840 accatcacca ccgtcagtga aaacgttcct gctctcacag atcacgggac gctaccgctg    15900
cgcaacagca tcgaggagt ccagcgagtg accattactg acgccagacg ccgcacctgc    15960
ccctacgttt acaaggccct gggcatagtc tcgccgcgcg tcctatcgag ccgcactttt    16020
tgagcaagca tgtccatcct tatatcgccc agcaataaca caggctgggg cctgcgcttc    16080
ccaagcaaga tgtttggcgg ggccaagaag cgctccgacc aacacccagt gcgcgtgcgc    16140
gggcactacc gcgcgccctg gggcgcgcac aaacgcggcc gcactgggcg caccaccgtc    16200
gatgacgcca tcgacgcggt ggtggaggag gcgcgcaact acacgcccac gccgccacca    16260
gtgtccacag tggacgcggc cattcagacc gtggtgcgcg gagcccggcg ctatgctaaa    16320
atgaagagac ggcggaggcg cgtagcacgt cgccaccgcc gccacccggg cactgccgcc    16380
caacgcgcgg cggcgccct gcttaaccgc gcacgtcgca ccggccgacg ggcggccatg    16440
cgggccgctc gaaggctggc cgcgggtatt gtcactgtgc ccccaggtc caggcgacga    16500 gcggccgccg cagcagccgc ggccattagt gctatgactc agggtcgcag gggcaacgtg    16560
```

```
tattgggtgc gcgactcggt tagcggcctg cgcgtgcccg tgcgcacccg cccccgcgc    16620 aactagattg caagaaaaaa ctacttagac tcgtactgtt gtatgtatcc agcggcggcg    16680
gcgcgcaacg aagctatgtc caagcgcaaa atcaaagaag agatgctcca ggtcatcgcg    16740
ccggagatct atggcccccc gaagaaggaa gagcaggatt acaagcccg aaagctaaag     16800 cgggtcaaaa agaaaaagaa agatgatgat gatgaacttg acgacgaggt ggaactgctg    16860
cacgctaccg cgcccaggcg acgggtacag tggaaaggtc gacgcgtaaa acgtgttttg    16920
cgacccggca ccaccgtagt ctttacgccc ggtgagcgct ccacccgcac ctacaagcgc    16980
gtgtatgatg aggtgtacgg cgacgaggac ctgcttgagc aggccaacga gcgcctcggg    17040
gagtttgcct acggaaagcg gcataaggac atgctggcgt tgccgctgga cgagggcaac    17100
ccaacaccta gcctaaagcc cgtaacactg cagcaggtgc tgcccgcgct tgcaccgtcc    17160
gaagaaaagc gcggcctaaa gcgcgagtct ggtgacttgg cacccaccgt gcagctgatg    17220
gtacccaagc gccagcgact ggaagatgtc ttggaaaaaa tgaccgtgga acctgggctg    17280
gagcccgagg tccgcgtgcg gccaatcaag caggtggcgc cgggactggg cgtgcagacc    17340
gtggacgttc agatacccac taccagtagc accagtattg ccaccgccac agagggcatg    17400
gagacacaaa cgtccccggt tgcctcagcg gtggcggatg ccgcggtgca ggcggtcgct    17460
gcggccgcgt ccaagacctc tacggaggtg caaacggacc cgtggatgtt tcgcgtttca    17520
gccccccggc gcccgcgcgg ttcgaggaag tacgcgcccg ccagcgcgct actgcccgaa    17580
tatgccctac atccttccat tgcgcctacc cccggctatc gtggctacac ctaccgcccc    17640
agaagacgag caactacccg acgccgaacc accactggaa cccgccgccg ccgtcgccgt    17700
cgccagcccg tgctggcccc gatttccgtg cgcagggtgg ctcgcgaagg aggcaggacc    17760
ctggtgctgc caacagcgcg ctaccacccc agcatcgttt aaaagccggt ctttgtggtt    17820
cttgcagata tggccctcac ctgccgcctc cgtttcccgg tgccgggatt ccgaggaaga    17880
atgcaccgta ggaggggcat ggccggccac ggcctgacgg gcggcatgcg tcgtgcgcac    17940
caccggcggc ggcgcgcgtc gcaccgtcgc atgcgcggcg gtatcctgcc cctccttatt    18000
ccactgatcg ccgcggcgat tggcgccgtg cccggaattg catccgtggc cttgcaggcg    18060
cagagacact gattaaaaac aagttgcatg tggaaaaatc aaaataaaaa gtctggactc    18120
tcacgctcgc ttggtcctgt aactattttg tagaatggaa gacatcaact ttgcgtctct    18180
ggccccgcga cacggctcgc gcccgttcat gggaaactgg caagatatcg gcaccagcaa    18240
tatgagcggt ggcgccttca gctggggctc gctgtggagc ggcattaaaa atttcggttc    18300
caccgttaag aactatggca gcaaggcctg gaacagcagc acaggccaga tgctgaggga    18360
taagttgaaa gagcaaaatt tccaacaaaa ggtggtagat ggcctggcct ctggcattag    18420
cggggtggtg gacctggcca accaggcagt gcaaaataag attaacagta agcttgatcc    18480
ccgccctccc gtagaggagc ctccaccggc cgtggagaca gtgtctccag aggggcgtgg    18540
cgaaaagcgt ccgcgcccg acaggaagaa aactctggtg acgcaaatag acgagcctcc    18600
ctcgtacgag gaggcactaa agcaaggcct gcccaccacc cgtcccatcg cgcccatggc    18660
taccggagtc ctgggccagc acacaccgt aacgctggac ctgcctcccc ccgccgacac    18720
ccagcagaaa cctgtgctgc caggcccgac cgccgttgtt gtaaccccgtc ctagccgcgc    18780 gtccctgcgc cgcgccgcca gcggtccgcg atcgttgcgg cccgtagcca gtggcaactg    18840
gcaaagcaca ctgaacagca tcgtgggtct ggggggtgcaa tccctgaagc gccgacgatg    18900
cttctgaata gctaacgtgt cgtatgtgtg tcatgtatgc gtccatgtcg ccgccagagg    18960
```

```
agctgctgag ccgccgcgcg cccgctttcc aagatggcta ccccttcgat gatgccgcag    19020
tggtcttaca tgcacatctc gggccaggac gcctcggagt acctgagccc cgggctggtg    19080
cagtttgccc gcgccaccga gacgtacttc agcctgaata caagtttag aaaccccacg    19140 gtggcgccta cgcacgacgt gaccacagac cggtcccagc gtttgacgct gcggttcatc    19200
cctgtggacc gtgaggatac tgcgtactcg tacaaggcgc ggttcaccct agctgtgggt    19260
gataaccgtg tgctggacat ggcttccacg tactttgaca tccgcggcgt gctggacagg    19320
ggccctactt ttaagcccta ctctggcact gcctacaacg ccctggctcc aagggtgcc    19380 ccaaatcctt gcgaatggga tgaagctgct actgctcttg aaataaacct agaagaagag    19440
gacgatgaca acgaagacga agtagacgag caagctgagc agcaaaaaac tcacgtattt    19500
gggcaggcgc cttattctgg tataaatatt acaaaggagg gtattcaaat aggtgtcgaa    19560
ggtcaaacac ctaaatatgc cgataaaaca tttcaacctg aacctcaaat aggagaatct    19620
cagtggtacg aaactgaaat taatcatgca gctgggagag tccttaaaaa gactacccca    19680
atgaaaccat gttacggttc atatgcaaaa cccacaaatg aaaatggagg gcaaggcatt    19740
cttgtaaagc aacaaaatgg aaagctagaa agtcaagtgg aaatgcaatt tttctcaact    19800
actgaggcga ccgcaggcaa tggtgataac ttgactccta aagtggtatt gtacagtgaa    19860
gatgtagata tagaaacccc agacactcat atttcttaca tgcccactat taaggaaggt    19920
aactcacgag aactaatggg ccaacaatct atgcccaaca ggcctaatta cattgctttt    19980
agggacaatt ttattggtct aatgtattac aacagcacgg gtaatatggg tgttctggcg    20040
ggccaagcat cgcagttgaa tgctgttgta gatttgcaag acagaaacac agagctttca    20100
taccagcttt tgcttgattc cattggtgat agaaccaggt acttttctat gtggaatcag    20160
gctgttgaca gctatgatcc agatgttaga attattgaaa atcatggaac tgaagatgaa    20220
cttccaaatt actgctttcc actgggaggt gtgattaata cagagactct taccaaggta    20280
aaacctaaaa caggtcagga aaatggatgg gaaaaagatg ctacagaatt ttcagataaa    20340
aatgaaataa gagttggaaa taattttgcc atggaaatca atctaaatgc caacctgtgg    20400
agaaatttcc tgtactccaa catagcgctg tatttgcccg acaagctaaa gtacagtcct    20460
tccaacgtaa aaattctga taacccaaac acctacgact acatgaacaa gcgagtggtg    20520
gctcccgggt tagtggactg ctacattaac cttggagcac gctggtccct tgactatatg    20580
gacaacgtca acccatttaa ccaccaccgc aatgctggcc tgcgctaccg ctcaatgttg    20640
ctgggcaatg tcgctatgt gcccttccac atccaggtgc ctcagaagtt ctttgccatt    20700
aaaaacctcc ttctcctgcc gggctcatac acctacgagt ggaacttcag gaaggatgtt    20760
aacatggttc tgcagagctc cctaggaaat gacctaaggg ttgacggagc cagcattaag    20820
tttgatagca tttgccttta cgccaccttc ttccccatgg cccacaacac cgcctccacg    20880
cttgaggcca tgcttagaaa cgacaccaac gaccagtcct ttaacgacta tctctccgcc    20940
gccaacatgc tctaccctat acccgccaac gctaccaacg tgcccatatc catcccctcc    21000
cgcaactggg cggctttccg cggctgggcc ttcacgcgcc ttaagactaa ggaaacccca    21060
tcactgggct cgggctacga cccttattac acctactctg ctctataccc ctacctagat    21120
ggaacctttt acctcaacca cacctttaag aaggtggcca ttaccttga ctcttctgtc    21180 agctggcctg gcaatgaccg cctgcttacc cccaacgagt ttgaaattaa gcgctcagtt    21240
gacggggagg gttacaacgt tgcccagtgt aacatgacca aagactggtt cctggtacaa    21300
```

```
atgctagcta actacaacat tggctaccag ggcttctata tcccagagag ctacaaggac   21360
cgcatgtact ccttctttag aaacttccag cccatgagcc gtcaggtggt ggatgatact   21420
aaatacaagg actaccaaca ggtgggcatc ctacaccaac acaacaactc tggatttgtt   21480
ggctaccttg cccccaccat gcgcgaagga caggcctacc ctgctaactt cccctatccg   21540
cttataggca agaccgcagt tgacagcatt acccagaaaa agtttctttg cgatcgcacc   21600
ctttggcgca tcccattctc cagtaacttt atgtccatgg gcgcactcac agacctgggc   21660
caaaaccttc tctacgccaa ctccgcccac gcgctagaca tgacttttga ggtggatccc   21720
atggacgagc ccaccttct ttatgttttg tttgaagtct tgacgtggt ccgtgtgcac    21780
cggccgcacc gcggcgtcat cgaaaccgtg tacctgcgca cgcccttctc ggccggcaac   21840
gccacaacat aaagaagcaa gcaacatcaa caacagctgc cgccatgggc tccagtgagc   21900
aggaactgaa agccattgtc aaagatcttg gttgtgggcc atattttttg ggcacctatg   21960
acaagcgctt tccaggcttt gtttctccac acaagctcgc ctgcgccata gtcaatacgg   22020
ccggtcgcga gactgggggc gtacactgga tggcctttgc ctggaacccg cactcaaaaa   22080
catgctacct cttgagccc tttggctttt ctgaccagcg actcaagcag gtttaccagt    22140
ttgagtacga gtcactcctg cgccgtagcg ccattgcttc ttcccccgac cgctgtataa   22200
cgctggaaaa gtccacccaa agcgtacagg gcccaactc ggccgcctgt ggactattct    22260
gctgcatgtt tctccacgcc tttgccaact ggccccaaac tcccatggat cacaaccccca  22320
ccatgaacct tattaccggg gtacccaact ccatgctcaa cagtccccag gtacagccca   22380
ccctgcgtcg caaccaggaa cagctctaca gcttcctgga gcgccactcg ccctacttcc   22440
gcagccacag tgcgcagatt aggagcgcca cttcttttg tcacttgaaa aacatgtaaa    22500
aataatgtac tagagacact ttcaataaag gcaaatgctt ttatttgtac actctcgggt   22560
gattatttac ccccacccct tgccgtctgcg ccgtttaaaa atcaaagggg ttctgccgcg   22620
catcgctatg cgccactggc agggacacgt tgcgatactg tgtttagtg ctccacttaa    22680
actcaggcac aaccatccgc ggcagctcgg tgaagttttc actccacagg ctgcgcacca   22740
tcaccaacgc gtttagcagg tcgggcgccg atatcttgaa gtcgcagttg gggcctccgc   22800
cctgcgcgcg cgagttgcga tacacagggt tgcagcactg gaacactatc agcgccgggt   22860
ggtgcacgct ggccagcacg ctcttgtcgg agatcagatc cgcgtccagg tcctccgcgt   22920
tgctcagggc gaacggagtc aactttggta gctgccttcc caaaagggc gcgtgcccag    22980
gctttgagtt gcactcgcac cgtagtggca tcaaaggtg accgtgcccg gtctgggcgt    23040
taggatacag cgcctgcata aaagccttga tctgcttaaa agccacctga gcctttgcgc   23100
cttcagagaa gaacatgccg caagacttgc cggaaaactg attggccgga caggccgcgt   23160
cgtgcacgca gcaccttgcg tcggtgttgg agatctgcac cacatttcgg ccccaccggt   23220
tcttcacgat cttggccttg ctagactgct ccttcagcgc gcgctgcccg ttttcgctcg   23280
tcacatccat ttcaatcacg tgctccttat ttatcataat gcttccgtgt agacacttaa   23340
gctcgccttc gatctcagcg cagcggtgca gccacaacgc gcagcccgtg ggctcgtgat   23400
gcttgtaggt cacctctgca aacgactgca ggtacgcctg caggaatcgc ccatcatcg    23460
tcacaaaggt cttgttgctg gtgaaggtca gctgcaaccc gcggtgctcc tcgttcagcc   23520
aggtcttgca tacggccgcc agagcttcca cttggtcagg cagtagtttg aagttcgcct   23580
ttagatcgtt atccacgtgg tacttgtcca tcagcgcgcg cgcagcctcc atgcccttct   23640
cccacgcaga cacgatcggc acactcagcg ggttcatcac cgtaatttca ctttccgctt   23700
```

```
cgctgggctc ttcctcttcc tcttgcgtcc gcataccacg cgccactggg tcgtcttcat   23760
tcagccgccg cactgtgcgc ttacctcctt tgccatgctt gattagcacc ggtgggttgc   23820
tgaaacccac catttgtagc gccacatctt ctctttcttc ctcgctgtcc acgattacct   23880
ctggtgatgg cgggcgctcg ggcttgggag aagggcgctt cttttcttc ttgggcgcaa    23940 tggccaaatc cgccgccgag gtcgatggcc gcgggctggg tgtgcgcggc accagcgcgt   24000
cttgtgatga gtcttcctcg tcctcggact cgatacgccg cctcatccgc tttttgggg    24060 gcgcccgggg aggcggcggc gacggggacg gggacgacac gtcctccatg gttggggac    24120 gtcgcgccgc accgcgtccg cgctcggggg tggtttcgcg ctgctcctct tcccgactgg   24180
ccatttcctt ctcctatagg cagaaaaaga tcatggagtc agtcgagaag aaggacagcc   24240
taaccgcccc ctctgagttc gccaccaccg cctccaccga tgccgccaac gcgcctacca   24300
ccttccccgt cgaggcaccc ccgcttgagg aggaggaagt gattatcgag caggacccag   24360
gttttgtaag cgaagacgac gaggaccgct cagtaccaac agaggataaa aagcaagacc   24420
aggacaacgc agaggcaaac gaggaacaag tcgggcgggg ggacgaaagg catggcgact   24480
acctagatgt gggagacgac gtgctgttga agcatctgca gcgccagtgc gccattatct   24540
gcgacgcgtt gcaagagcgc agcgatgtgc ccctcgccat agcggatgtc agccttgcct   24600
acgaacgcca cctattctca ccgcgcgtac ccccaaaacg ccaagaaaac ggcacatgcg   24660
agcccaaccc gcgcctcaac ttctaccccg tatttgccgt gccagaggtg cttgccacct   24720
atcacatctt tttccaaaac tgcaagatac ccctatcctg ccgtgccaac cgcagccgag   24780
cggacaagca gctggccttg cggcagggcg ctgtcatacc tgatatcgcc tcgctcaacg   24840
aagtgccaaa aatctttgag ggtcttggac gcgacgagaa gcgcgcggca aacgctctgc   24900
aacaggaaaa cagcgaaaat gaaagtcact ctggagtgtt ggtggaactc gagggtgaca   24960
acgcgcgcct agccgtacta aaacgcagca tcgaggtcac ccactttgcc tacccggcac   25020
ttaacctacc ccccaaggtc atgagcacag tcatgagtga gctgatcgtg cgccgtgcgc   25080 agccctgga gagggatgca aatttgcaag aacaaacaga ggagggccta cccgcagttg   25140
gcgacgagca gctagcgcgc tggcttcaaa cgcgcgagcc tgccgacttg gaggagcgac   25200
gcaaactaat gatggccgca gtgctcgtta ccgtggagct tgagtgcatg cagcggttct   25260
ttgctgaccc ggagatgcag cgcaagctag aggaaacatt gcactacacc tttcgacagg   25320
gctacgtacg ccaggcctgc aagatctcca acgtggagct ctgcaacctg gtctcctacc   25380
ttggaatttt gcacgaaaac cgccttgggc aaaacgtgct tcattccacg ctcaagggcg   25440
aggcgcgccg cgactacgtc cgcgactgcg tttacttatt tctatgctac acctggcaga   25500
cggccatggg cgtttggcag cagtgcttgg aggagtgcaa cctcaaggag ctgcagaaac   25560
tgctaaagca aacttgaag gacctatgga cggccttcaa cgagcgctcc gtggccgcgc    25620
acctggcgga catcattttc cccgaacgcc tgcttaaaac cctgcaacag gtctgccag    25680 acttcaccag tcaaagcatg ttgcagaact ttaggaactt tatcctagag cgctcaggaa   25740 tcttgccccgc cacctgctgt gcacttccta gcgactttgt gcccattaag taccgcgaat   25800
gccctccgcc gctttgggc cactgctacc ttctgcagct agccaactac cttgcctacc    25860
actctgacat aatggaagac gtgagcggtg acggtctact ggagtgtcac tgtcgctgca   25920
acctatgcac cccgcaccgc tccctggttt gcaattcgca gctgcttaac gaaagtcaaa   25980
ttatcggtac ctttgagctg caggtccctc gcctgacga aagtccgcg gctccggggt     26040
```

```
tgaaactcac tccggggctg tggacgtcgg cttaccttcg caaatttgta cctgaggact    26100
accacgccca cgagattagg ttctacgaag accaatcccg cccgccaaat gcggagctta    26160
ccgcctgcgt cattacccag ggccacattc ttggccaatt gcaagccatc aacaaagccc    26220
gccaagagtt tctgctacga aagggacggg gggtttactt ggaccccccag tccggcgagg   26280 agctcaaccc aatccccccg ccgccgcagc cctatcagca gcagccgcgg gcccttgctt    26340
cccaggatgg cacccaaaaa gaagctgcag ctgccgccgc cacccacgga cgaggaggaa    26400
tactgggaca gtcaggcaga ggaggttttg gacgaggagg aggaggacat gatggaagac    26460
tgggagagcc tagacgagga agcttccgag gtcgaagagg tgtcagacga aacaccgtca    26520
ccctcggtcg cattcccctc gccggcgccc cagaaatcgg caaccggttc cagcatggct    26580
acaacctccg ctcctcaggc gccgccggca ctgcccgttc gccgacccaa ccgtagatgg    26640
gacaccactg gaaccagggc cggtaagtcc aagcagccgc cgccgttagc ccaagagcaa    26700
caacagcgcc aaggctaccg ctcatggcgc gggcacaaga cgccatagt tgcttgcttg     26760 caagactgtg ggggcaacat ctccttcgcc cgccgctttc ttctctacca tcacggcgtg    26820
gccttccccc gtaacatcct gcattactac cgtcatctct acagcccata ctgcaccggc    26880
ggcagcggca gcgcagcaa cagcagcggc cacacagaag caaaggcgac cggatagcaa    26940
gactctgaca aagcccaaga aatccacagc ggcggcagca gcaggaggag gagcgctgcg    27000
tctggcgccc aacgaacccg tatcgacccg cgagcttaga aacaggatt ttcccactct    27060 gtatgctata tttcaacaga gcaggggcca agaacaagag ctgaaaataa aaaacaggtc    27120
tctgcgatcc ctcacccgca gctgcctgta tcacaaaagc gaagatcagc ttcggcgcac   27180
gctggaagac gcggaggctc tcttcagtaa atactgcgcg ctgactctta aggactagtt    27240
tcgcgccctt tctcaaattt aagcgcgaaa actacgtcat ctccagcggc cacacccggc    27300
gccagcacct gtcgtcagcg ccattatgag caaggaaatt cccacgccct acatgtggag    27360
ttaccagcca caaatgggac ttgcggctgg agctgcccaa gactactcaa cccgaataaa    27420
ctacatgagc gcgggacccc acatgatatc ccgggtcaac ggaatccgcg cccaccgaaa    27480
ccgaattctc ttggaacagg cggctattac caccacacct cgtaataacc ttaatccccg    27540
tagttggccc gctgccctgg tgtaccagga aagtcccgct cccaccactg tggtacttcc    27600
cagagacgcc caggccgaag ttcagatgac taactcaggg gcgcagcttg cgggcggctt    27660
tcgtcacagg gtgcggtcgc ccgggcaggg tataactcac ctgacaatca gagggcgagg    27720
tattcagctc aacgacgagt cggtgagctc ctcgcttggt ctccgtccgg acgggacatt    27780
tcagatcggc ggcgccggcc gtccttcatt cacgcctcgt caggcaatcc taactctgca    27840
gacctcgtcc tctgagccgc gctctggagg cattggaact ctgcaatta ttgaggagtt     27900 tgtgccatcg gtctacttta accccttctc gggacctccc ggccactatc cggatcaatt    27960
tattcctaac tttgacgcgg taaaggactc ggcggacggc tacgactgaa tgttaagtgg    28020
agaggcagag caactgcgcc tgaaacacct ggtccactgt cgccgccaca agtgctttgc    28080
ccgcgactcc ggtgagtttt gctactttga attgcccgag gatcatatcg agggcccggc    28140
gcacggcgtc cggcttaccg cccagggaga gcttgcccgt agcctgattc gggagtttac    28200
ccagcgcccc ctgctagttg agcgggacag gggaccctgt gttctcactg tgatttgcaa    28260
ctgtcctaac cttggattac atcaagatcc tctagttata actagagtac ccggggatct    28320
tattcccttt aactaataaa aaaaataat aaagcatcac ttacttaaaa tcagttagca    28380
aatttctgtc cagtttattc agcagcacct ccttgccctc ctcccagctc tggtattgca    28440
```

```
gcttcctcct ggctgcaaac tttctccaca atctaaatgg aatgtcagtt tcctcctgtt   28500
cctgtccatc cgcacccact atcttcatgt tgttgcagat gaagcgcgca agaccgtctg   28560
aagataccct caaccccgtg tatccatatg acacggaaac cggtcctcca actgtgcctt   28620
ttcttactcc tcctttgta tcccccaatg ggtttcaaga gagtccccct ggggtactct   28680
ctttgcgcct atccgaacct ctagttacct ccaatggcat gcttgcgctc aaaatgggca   28740
acggcctctc tctggacgag gccggcaacc ttacctccca aaatgtaacc actgtgagcc   28800
cacctctcaa aaaaccaag tcaaacataa acctggaaat atctgcaccc ctcacagtta   28860
cctcagaagc cctaactgtg gctgccgccg cacctctaat ggtcgcgggc aacacactca   28920
ccatgcaatc acaggccccg ctaaccgtgc acgactccaa acttagcatt gccacccaag   28980
gacccctcac agtgtcagaa ggaaagctag ccctgcaaac atcaggcccc ctcaccacca   29040
ccgatagcag tacccttact atcactgcct caccccctct aactactgcc actggtagct   29100
tgggcattga cttgaaagag cccatttata cacaaaatgg aaaactagga ctaaagtacg   29160
gggctccttt gcatgtaaca gacgacctaa acactttgac cgtagcaact ggtccaggtg   29220
tgactattaa taatacttcc ttgcaaacta agttactgg agccttgggt tttgattcac   29280
aaggcaatat gcaacttaat gtagcaggag gactaaggat tgattctcaa aacagacgcc   29340
ttatacttga tgttagttat ccgtttgatg ctcaaaacca actaaatcta agactaggac   29400
agggccctct ttttataaac tcagcccaca acttggatat taactacaac aaaggccttt   29460
acttgtttac agcttcaaac aattccaaaa agcttgaggt taacctaagc actgccaagg   29520
ggttgatgtt tgacgctaca gccatagcca ttaatgcagg agatgggctt gaatttggtt   29580
cacctaatgc accaaacaca aatcccctca aaacaaaaat tggccatggc ctagaatttg   29640
attcaaacaa ggctatggtt cctaaactag gaactggcct tagttttgac agcacaggtg   29700
ccattacagt aggaaacaaa ataatgata agctaaccct atggacaggt ccaaaaccag   29760
aagccaactg cataattgaa tacgggaaac aaaacccaga tagcaaacta actttaatcc   29820
ttgtaaaaaa tggaggaatt gttaatggat atgtaacgct aatgggagcc tcagactacg   29880
ttaacaccct atttaaaaac aaaaatgtct ccattaatgt agaactatac tttgatgcca   29940
ctggtcatat attaccagac tcatcttctc ttaaaacaga tctagaacta aaatacaagc   30000
aaaccgctga ctttagtgca agaggtttta tgccaagtac tacagcgtat ccatttgtcc   30060
ttcctaatgc gggaacacat aatgaaaatt atatttttgg tcaatgctac tacaaagcaa   30120
gcgatggtgc ccttttccg ttggaagtta ctgttatgct aataaacgc ctgccagata   30180 gtcgcacatc ctatgttatg acttttttat ggtccttgaa tgctggtcta gctccagaaa   30240
ctactcaggc aaccctcata acctcccat ttaccttttc ctatattaga gaagatgacg   30300
gtggaggcgg ttcaggcgga ggtggctctg gcggtggcgg atcctgtgac tgccgcggag   30360 actgttctg ctaataaact ctaaagaatc gtttgtgtta tgtttcaacg tgtttatttt   30420
tcaattgcag aaaatttcaa gtcattttc attcagtagt atagccccac caccacatag   30480
cttatacaga tcaccgtacc ttaatcaaac tcacagaacc ctagtattca acctgccacc   30540
tccctcccaa cacacagagt acacagtcct ttctccccgg ctggccttaa aaagcatcat   30600
atcatgggta acagacatat tcttaggtgt tatattccac acggtttcct gtcgagccaa   30660
acgctcatca gtgatattaa taaactcccc gggcagctca cttaagttca tgtcgctgtc   30720
cagctgctga gccacaggct gctgtccaac ttgcggttgc ttaacgggcg gcgaaggaga   30780
```

```
agtccacgcc tacatggggg tagagtcata atcgtgcatc aggataqggc ggtggtgctg   30840 cagcagcgcg cgaataaact gctgccgccg ccgctccgtc ctgcaggaat acaacatggc   30900
agtggtctcc tcagcgatga ttcgcaccgc ccgcagcata aggcgccttg tcctccgggc   30960
acagcagcgc accctgatct cacttaaatc agcacagtaa ctgcagcaca gcaccacaat   31020
attgttcaaa atcccacagt gcaaggcgct gtatccaaag ctcatggcgg ggaccacaga   31080
acccacgtgg ccatcatacc acaagcgcag gtagattaag tggcgacccc tcataaacac   31140
gctggacata acattacct cttttggcat gttgtaattc accacctccc ggtaccatat    31200
aaacctctga ttaaacatgg cgccatccac caccatccta aaccagctgg ccaaaacctg   31260
cccgccggct atacactgca gggaaccggg actggaacaa tgacagtgga gagcccagga   31320
ctcgtaacca tggatcatca tgctcgtcat gatatcaatg ttggcacaac acaggcacac   31380
gtgcatacac ttcctcagga ttacaagctc ctcccgcgtt agaaccatat cccagggaac   31440 aaccattcc tgaatcagcg taaatcccac actgcaggga agacctcgca cgtaactcac    31500
gttgtgcatt gtcaaagtgt tacattcggg cagcagcgga tgatcctcca gtatggtagc   31560
gcgggtttct gtctcaaaag gaggtagacg atccctactg tacggagtgc gccgagacaa   31620
ccgagatcgt gttggtcgta gtgtcatgcc aaatggaacg ccggacgtag tcatatttcc   31680
tgaagcaaaa ccaggtgcgg gcgtgacaaa cagatctgcg tctccggtct cgccgcttag   31740
atcgctctgt gtagtagttg tagtatatcc actctctcaa agcatccagg cgccccctgg   31800
cttcgggttc tatgtaaact ccttcatgcg ccgctgccct gataacatcc accaccgcag   31860
aataagccac acccagccaa cctacacatt cgttctgcga gtcacacacg ggaggagcgg   31920
gaagagctgg aagaaccatg tttttttttt tattccaaaa gattatccaa aacctcaaaa   31980
tgaagatcta ttaagtgaac gcgctcccct ccggtgbcgt ggtcaaactc tacagccaaa   32040
gaacagataa tggcatttgt aagatgttgc acaatggctt ccaaaaggca aacggccctc   32100
acgtccaagt ggacgtaaag gctaaaccct tcagggtgaa tctcctctat aaacattcca   32160
gcaccttcaa ccatgcccaa ataattctca tctcgccacc ttctcaatat atctctaagc   32220
aaatcccgaa tattaagtcc ggccattgta aaaatctgct ccagagcgcc ctccaccttc   32280
agcctcaagc agcgaatcat gattgcaaaa attcaggttc ctcacagacc tgtataagat   32340
tcaaaagcgg aacattaaca aaaataccgc gatcccgtag gtcccttcgc agggccagct   32400
gaacataatc gtgcaggtct gcacggacca gcgcggccac ttccccgcca ggaaccttga   32460
caaaagaacc cacactgatt atgacacgca tactcggagc tatgctaacc agcgtagccc   32520
cgatgtaagc tttgttgcat gggcggcgat ataaaatgca aggtgctgct caaaaaatca   32580
ggcaaagcct cgcgcaaaaa agaaagcaca tcgtagtcat gctcatgcag ataaaggcag   32640
gtaagctccg gaaccaccac agaaaaagac accattttc tctcaaacat gtctgcgggt    32700
ttctgcataa acacaaaata aataacaaa aaacattta acattagaa gcctgtctta      32760 caacaggaaa acaacccctt ataagcataa gacggactac ggccatgccg gcgtgaccgt   32820
aaaaaaactg gtcaccgtga ttaaaaagca ccaccgacag ctcctcggtc atgtccggag   32880
tcataatgta agactcggta aacacatcag gttgattcat cggtcagtgc taaaaagcga   32940
ccgaaatagc ccgggggaat acatacccgc aggcgtagag acaacattac agcccccata   33000
ggaggtataa caaaattaat aggagagaaa aacacataaa cacctgaaaa accctcctgc   33060
ctaggcaaaa tagcaccctc ccgctccaga acaaatataca gcgcttcaca gcggcagcct   33120
aacagtcagc cttaccagta aaaagaaaa cctattaaaa aaacaccact cgacacggca   33180
```

```
ccagctcaat cagtcacagt gtaaaaaagg gccaagtgca gagcgagtat atataggact   33240
aaaaaatgac gtaacggtta aagtccacaa aaaacaccca gaaaaccgca cgcgaaccta   33300
cgcccagaaa cgaaagccaa aaacccaca acttcctcaa atcgtcactt ccgttttccc    33360
acgttacgta acttcccatt ttaagaaaac tacaattccc aacacataca agttactccg   33420
ccctaaaacc tacgtcaccc gccccgttcc cacgccccgc gccacgtcac aaactccacc   33480
ccctcattat catattggct tcaatccaaa ataaggtata ttattgatga tnnnnnttaa   33540
t                                                                   33541

<210> SEQ ID NO 7
<211> LENGTH: 34026
<212> TYPE: DNA
<213> ORGANISM: Artificial sequence
<220> FEATURE:
<223> OTHER INFORMATION: Recombinant adenovirus AdEzE3 53rgd 1stHR,
      n=A,C,G,T
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (3655)..(3657)
<223> OTHER INFORMATION: n is a, c, g, or t
<220> FEATURE:
<221> NAME/KEY: misc_feature
<222> LOCATION: (3684)..(3686)
<223> OTHER INFORMATION: n is a, c, g, or t
<220> FEATURE:
<221> NAME/KEY: misc_feature
<222> LOCATION: (34017)..(34021)
<223> OTHER INFORMATION: n is a, c, g, or t

<400> SEQUENCE: 7
taaggatccn nncctgtcct cgaccgatgc ccttgagagc cttcaaccca gtcagctcct    60
tccggtgggc gcggggcatg actatcgtcg ccgcacttat gactgtcttc tttatcatgc   120
aactcgtagg acaggtgccg gcagcgctct gggtcatttt cggcgaggac cgctttcgct   180
ggagcgcgac gatgatcggc ctgtcgcttg cggtattcgg aatcttgcac gccctcgctc   240
aagccttcgt cactggtccc gccaccaaac gtttcggcga aagcaggcc attatcgccg    300 gcatggcggc cgacgcgctg ggctacgtct tgctggcgtt cgcgacgcga ggctggatgg   360
ccttccccat tatgattctt ctcgcttccg gcggcatcgg gatgcccgcg ttgcaggcca   420
tgctgtccag gcaggtagat gacgaccatc agggacagct tcaaggatcg ctcgcggctc   480
ttaccagcct aacttcgatc actggaccgc tgatcgtcac ggcgatttat gccgcctcgg   540
cgagcacatg gaacgggttg gcatggattg taggcgccgc cctatacctt gtctgcctcc   600
ccgcgttgcg tcgcggtgca tggagccggg ccacctcgac ctgaatggaa gccggcggca   660
cctcgctaac ggattcacca ctccaagaat tggagccaat caattcttgc ggagaactgt   720
gaatgcgcaa accaacccct tgcagaacat atccatcgcg tccgccatct ccagcagccg   780
cacgcggcgc atctcgggca gcgttgggtc ctggccacgg gtgcgcatga tcgtgctcct   840
gtcgttgagg acccggctag gctggcgggg ttgccttact ggttagcaga atgaatcacc   900
gatacgcgag cgaacgtgaa gcgactgctg ctgcaaaacg tctgcgacct gagcaacaac   960
atgaatggtc ttcggtttcc gtgtttcgta aagtctggaa acgcggaagt cagcgccctg  1020
caccattatg ttccggatct gcatcgcagg atgctgctgg ctaccctgtg gaacacctac  1080
atctgtatta acgaagcgct ggcattgacc ctgagtgatt tttctctggt cccgccgcat  1140
```

```
ccataccgcc agttgtttac cctcacaacg ttccagtaac cgggcatgtt catcatcagt    1200
aacccgtatc gtgagcatcc tctctcgttt catcggtatc attacccca tgaacagaaa     1260 ttccccctta cacggaggca tcaagtgacc aaacaggaaa aaaccgccct taacatggcc    1320
cgctttatca gaagccagac attaacgctt ctggagaaac tcaacgagct ggacgcggat    1380
gaacaggcag acatctgtga atcgcttcac gaccacgctg atgagcttta ccgcagctgc    1440
ctcgcgcgtt tcggtgatga cggtgaaaac ctctgacaca tgcagctccc ggagacggtc    1500
acagcttgtc tgtaagcgga tgccgggagc agacaagccc gtcagggcgc gtcagcgggt    1560
gttggcgggt gtcggggcgc agccatgacc cagtcacgta gcgatagcgg agtgtatact    1620
ggcttaacta tgcggcatca gagcagattg tactgagagt gcaccatatg cggtgtgaaa    1680
taccgcacag atgcgtaagg agaaaatacc gcatcaggcg ctcttccgct tcctcgctca    1740
ctgactcgct gcgctcggtc gttcggctgc ggcgagcggt atcagctcac tcaaaggcgg    1800
taatacggtt atccacagaa tcaggggata acgcaggaaa gaacatgtga gcaaaaggcc    1860
agcaaaaggc caggaaccgt aaaaaggccg cgttgctggc gtttttccat aggctccgcc    1920
cccctgacga gcatcacaaa aatcgacgct caagtcagag gtggcgaaac ccgacaggac    1980
tataaagata ccaggcgttt ccccctggaa gctccctcgt gcgctctcct gttccgaccc    2040
tgccgcttac cggatacctg tccgcctttc tcccttcggg aagcgtggcg ctttctcaat    2100
gctcacgctg taggtatctc agttcggtgt aggtcgttcg ctccaagctg ggctgtgtgc    2160
acgaaccccc cgttcagccc gaccgctgcg ccttatccgg taactatcgt cttgagtcca    2220
acccggtaag acacgactta tcgccactgg cagcagccac tggtaacagg attagcagag    2280
cgaggtatgt aggcggtgct acagagttct tgaagtggtg gcctaactac ggctacacta    2340
gaaggacagt atttggtatc tgcgctctgc tgaagccagt taccttcgga aaaagagttg    2400
gtagctcttg atccggcaaa caaaccaccg ctggtagcgg tggtttttt gtttgcaagc     2460 agcagattac gcgcagaaaa aaaggatctc aagaagatcc tttgatcttt tctacggggt    2520
ctgacgctca gtggaacgaa aactcacgtt aagggatttt ggtcatgaga ttatcaaaaa    2580
ggatcttcac ctagatcctt ttaaattaaa aatgaagttt taaatcaatc taagtatat     2640 atgagtaaac ttggtctgac agttaccaat gcttaatcag tgaggcacct atctcagcga    2700
tctgtctatt tcgttcatcc atagttgcct gactccccgt cgtgtagata actacgatac    2760
gggagggctt accatctggc cccagtgctg caatgatacc gcgagaccca cgctcaccgg    2820
ctccagattt atcagcaata aaccagccag ccggaagggc cgagcgcaga agtggtcctg    2880
caactttatc cgcctccatc cagtctatta attgttgccg ggaagctaga gtaagtagtt    2940
cgccagttaa tagtttgcgc aacgttgttg ccattgctgc aggcatcgtg gtgtcacgct    3000
cgtcgtttgg tatggcttca ttcagctccg gttcccaacg atcaaggcga gttacatgat    3060
cccccatgtt gtgcaaaaaa gcggttagct ccttcggtcc tccgatcgtt gtcagaagta    3120
agttggccgc agtgttatca ctcatggtta tggcagcact gcataattct cttactgtca    3180
tgccatccgt aagatgcttt tctgtgactg gtgagtactc aaccaagtca ttctgagaat    3240
agtgtatgcg gcgaccgagt tgctcttgcc cggcgtcaac acgggataat accgcgccac    3300
atagcagaac tttaaaagtg ctcatcattg gaaaacgttc ttcggggcga aaactctcaa    3360
ggatcttacc gctgttgaga tccagttcga tgtaacccac tcgtgcaccc aactgatctt    3420
cagcatcttt tactttcacc agcgtttctg ggtgagcaaa aacaggaagg caaaatgccg    3480
```

-continued

```
caaaaaaggg aataagggcg acacggaaat gttgaatact catactcttc cttttttcaat    3540 attattgaag catttatcag ggttattgtc tcatgagcgg atacatattt gaatgtattt    3600
agaaaaataa acaaataggg gttccgcgca catttccccg aaaagtgcca cctgnnngaa    3660
ttcgaatcta gtatcgattc gaannnctta agggtgggaa agaatatata aggtgggggt    3720
cttatgtagt tttgtatctg ttttgcagca gccgccgccg ccatgagcac caactcgttt    3780
gatggaagca ttgtgagctc atatttgaca acgcgcatgc ccccatgggc cggggtgcgt    3840
cagaatgtga tgggctccag cattgatggt cgccccgtcc tgcccgcaaa ctctactacc    3900
ttgacctacg agaccgtgtc tggaacgccg ttggagactg cagcctccgc cgccgcttca    3960
gccgctgcag ccaccgcccg cgggattgtg actgactttg cttcctgag cccgcttgca    4020 agcagtgcag cttcccgttc atccgcccgc gatgacaagt tgacggctct tttggcacaa    4080
ttggattctt tgacccggga acttaatgtc gtttctcagc agctgttgga tctgcgccag    4140
caggtttctg ccctgaaggc ttcctcccct cccaatgcgg tttaaaacat aaataaaaaa    4200
ccagactctg tttggatttg gatcaagcaa gtgtcttgct gtctttattt aggggttttg    4260
cgcgcgcggt aggcccggga ccagcggtct cggtcgttga gggtcctgtg tattttttcc    4320
aggacgtggt aaaggtgact ctggatgttc agatacatgg gcataagccc gtctctgggg    4380
tggaggtagc accactgcag agcttcatgc tgcggggtgg tgttgtagat gatccagtcg    4440
tagcaggagc gctgggcgtg gtgcctaaaa atgtctttca gtagcaagct gattgccagg    4500
ggcaggccct tggtgtaagt gtttacaaag cggttaagct gggatgggtg catacgtggg    4560
gatatgagat gcatcttgga ctgtatttt aggttggcta tgttcccagc catatccctc    4620
cggggattca tgttgtgcag aaccaccagc acagtgtatc cggtgcactt gggaaatttg    4680
tcatgtagct tagaaggaaa tgcgtggaag aacttggaga cgcccttgtg acctccaaga    4740 tttttccatgc attcgtccat aatgatggca atgggcccac gggcggcggc ctgggcgaag    4800
atatttctgg gatcactaac gtcatagttg tgttccagga tgagatcgtc ataggccatt    4860
tttacaaagc gcgggcggag ggtgccagac tgcggtataa tggttccatc cggcccaggg    4920
gcgtagttac cctcacagat ttgcatttcc cacgctttga gttcagatgg ggggatcatg    4980
tctacctgcg gggcgatgaa gaaaacggtt ccgggggtag gggagatcag ctgggaagaa    5040
agcaggttcc tgagcagctg cgacttaccg cagccgtggg gcccgtaaat cacacctatt    5100
accgggtgca actggtagtt aagagagctg cagctgccgt catccctgag cagggggggcc    5160 acttcgttaa gcatgtccct gactcgcatg ttttccctga ccaaatccgc cagaaggcgc    5220
tcgccgccca gcgatagcag tcttgcaag gaagcaaagt ttttcaacgg tttgagaccg    5280
tccgccgtag gcatgctttt gagcgtttga ccaagcagtt ccaggcggtc ccacagctcg    5340
gtcacctgct ctacggcatc tcgatccagc atatctcctc gtttcgcggg ttggggcggc    5400
tttcgctgta cggcagtagt cggtgctcgt ccagacgggc cagggtcatg tctttccacg    5460
ggcgcagggt cctcgtcagc gtagtctggg tcacggtgaa ggggtgcgct ccgggctgcg    5520
cgctggccag ggtgcgcttg aggctggtcc tgctggtgct gaagcgctgc cggtcttcgc    5580
cctgcgcgtc ggccaggtag catttgacca tggtgtcata gtccagcccc tccgcggcgt    5640
ggcccttggc gcgcagcttg cccttggagg aggcgccgca cgaggggcag tgcagacttt    5700
tgagggcgta gagcttgggc gcgagaaata ccgattccgg ggagtaggca tccgcgccgc    5760
aggccccgca gacggtctcg cattccacga gccaggtgag ctctgccgt tcggggtcaa    5820 aaaccaggtt tcccccatgc ttttttgatgc gtttcttacc tctggtttcc atgagccggt    5880
```

```
gtccacgctc ggtgacgaaa aggctgtccg tgtccccgta tacagacttg agaggcctgt    5940
cctcgagcgg tgttccgcgg tcctcctcgt atagaaactc ggaccactct gagacaaagg    6000
ctcgcgtcca ggccagcacg aaggaggcta agtgggaggg gtagcggtcg ttgtccacta    6060
gggggtccac tcgctccagg gtgtgaagac acatgtcgcc ctcttcggca tcaaggaagg    6120
tgattggttt gtaggtgtag gccacgtgac cgggtgttcc tgaagggggg ctataaaagg    6180
gggtgggggc gcgttcgtcc tcactctctt ccgcatcgct gtctgcgagg ccagctgtt     6240 ggggtgagta ctccctctga aaagcgggca tgacttctgc gctaagattg tcagtttcca    6300
aaaacgagga ggatttgata ttcacctggc ccgcggtgat gcctttgagg gtggccgcat    6360
ccatctggtc agaaaagaca atcttttttgt tgtcaagctt ggtggcaaac gacccgtaga   6420
gggcgttgga cagcaacttg gcgatggagc cagggtttg gttttttgtcg cgatcggcgc    6480 gctccttggc cgcgatgttt agctgcacgt attcgcgcgc aacgcaccgc cattcgggaa    6540
agacggtggt gcgctcgtcg ggcaccaggt gcacgcgcca accgcggttg tgcagggtga    6600
caaggtcaac gctggtggct acctctccgc gtaggcgctc gttggtccag cagaggcggc    6660
cgcccttgcg cgagcagaat ggcggtaggg ggtctagctg cgtctcgtcc gggggggtctg   6720 cgtccacggt aaagaccccg ggcagcaggc gcgcgtcgaa gtagtctatc ttgcatcctt    6780
gcaagtctag cgcctgctgc catgcgcggg cggcaagcgc gcgctcgtat gggttgagtg    6840 gggggaccccca tggcatgggg tgggtgagcg cggaggcgta catgccgcaa atgtcgtaaa   6900
cgtagagggg ctctctgagt attccaagat atgtagggta gcatcttcca ccgcggatgc    6960
tggcgcgcac gtaatcgtat agttcgtgcg agggagcgag gaggtcggga ccgaggttgc    7020
tacgggcggg ctgctctgct cggaagacta tctgcctgaa gatggcatgt gagttggatg    7080
atatggttgg acgctggaag acgttgaagc tggcgtctgt gagacctacc gcgtcacgca    7140
cgaaggaggc gtaggagtcg cgcagcttgt tgaccagctc ggcggtgacc tgcacgtcta    7200
gggcgcagta gtccagggtt tccttgatga tgtcatactt atcctgtccc tttttttttcc   7260 acagctcgcg gttgaggaca aactcttcgc ggtctttcca gtactcttgg atcggaaacc    7320
cgtcggcctc cgaacggtaa gagcctagca tgtagaactg gttgacggcc tggtaggcgc    7380
agcatccctt ttctacgggt agcgcgtatg cctgcgcggc cttccggagc gaggtgtggg    7440
tgagcgcaaa ggtgtccctg accatgactt tgaggtactg gtatttgaag tcagtgtcgt    7500
cgcatccgcc ctgctcccag agcaaaaagt ccgtgcgctt tttggaacgc ggatttggca    7560
gggcgaaggt gacatcgttg aagagtatct ttcccgcgcg aggcataaag ttgcgtgtga    7620
tgcggaaggg tcccggcacc tcggaacggt tgttaattac ctgggcggcg agcacgatct    7680
cgtcaaagcc gttgatgttg tgcccacaa tgtaaagttc caagaagcgc gggatgccct    7740
tgatggaagg caattttttta agttcctcgt aggtgagctc ttcagggag ctgagcccgt     7800 gctctgaaag ggcccagtct gcaagatgag ggttggaagc gacgaatgag ctccacaggt    7860
cacgggccat tagcatttgc aggtggtcgc gaaaggtcct aaactggcga cctatggcca    7920
ttttttctgg ggtgatgcag tagaaggtaa gcgggtcttg ttcccagcgg tcccatccaa    7980
ggttcgcggc taggtctcgc gcggcagtca ctagaggctc atctccgccg aacttcatga    8040
ccagcatgaa gggcacgagc tgcttcccaa aggcccccat ccaagtatag gtctctacat    8100
cgtaggtgac aaagagacgc tcggtgcgag gatgcgagcc gatcgggaag aactggatct    8160
cccgccacca attggaggag tggctattga tgtggtgaaa gtagaagtcc ctgcgacggg    8220
```

```
ccgaacactc gtgctggctt ttgtaaaaac gtgcgcagta ctggcagcgg tgcacgggct    8280
gtacatcctg cacgaggttg acctgacgac cgcgcacaag gaagcagagt gggaatttga    8340
gccctcgcc tggcgggttt ggctggtggt cttctacttc ggctgcttgt ccttgaccgt     8400
ctggctgctc gaggggagtt acggtggatc ggaccaccac gccgcgcgag cccaaagtcc    8460
agatgtccgc gcgcggcggt cggagcttga tgacaacatc gcgcagatgg agctgtcca    8520
tggtctggag ctcccgcggc gtcaggtcag gcgggagctc ctgcaggttt acctcgcata    8580
gacgggtcag ggcgcgggct agatccaggt gatacctaat ttccaggggc tggttggtgg    8640
cggcgtcgat ggcttgcaag aggccgcatc ccgcggcgc gactacggta ccgcgcggcg     8700
ggcggtgggc cgcgggggtg tccttggatg atgcatctaa aagcggtgac gcgggcgagc    8760
ccccggaggt agggggggct ccggacccgc cgggagaggg ggcaggggca cgtcggcgcc    8820
gcgcgcgggc aggagctggt gctgcgcgcg taggttgctg gcgaacgcga cgacgcggcg    8880
gttgatctcc tgaatctggc gcctctgcgt gaagacgacg ggcccggtga gcttgagcct    8940
gaaagagagt tcgacagaat caatttcggt gtcgttgacg gcggcctggc gcaaaatctc    9000
ctgcacgtct cctgagttgt cttgataggc gatctcggcc atgaactgct cgatctcttc    9060
ctcctggaga tctccgcgtc cggctcgctc acggtggcg gcgaggtcgt tggaaatgcg     9120
ggccatgagc tgcgagaagg cgttgaggcc tccctcgttc cagacgcggc tgtagaccac    9180
gccccttcg gcatcgcggg gcgcatgac cacctgcgcg agattgagct ccacgtgccg      9240
ggcgaagacg gcgtagtttc gcaggcgctg aaagaggtag ttgagggtgg tggcggtgtg    9300
ttctgccacg aagaagtaca taacccagcg tcgaacgtg gattcgttga tatcccccaa     9360
ggcctcaagg cgctccatgg cctcgtagaa gtccacggcg aagttgaaaa actgggagtt    9420
gcgcgccgac acggttaact cctcctccag aagacggatg agctcggcga cagtgtcgcg    9480
cacctcgcgc tcaaaggcta caggggcctc ttcttcttct tcaatctcct cttccataag    9540
ggcctccct tcttcttctt ctggcggcgg tgggggaggg gggacacggc ggcgacgacg     9600
gcgcaccggg aggcggtcga caaagcgctc gatcatctcc ccgcggcgac ggcgcatggt    9660
ctcggtgacg gcgcggccgt tctcgcgggg gcgcagttgg aagacgccgc ccgtcatgtc    9720
ccggttatgg gttggcgggg ggctgccatg cggcagggat acggcgctaa cgatgcatct    9780
caacaattgt tgtgtaggta ctccgccgcc gagggacctg agcgagtccg catcgaccgg    9840
atcggaaaac ctctcgagaa aggcgtctaa ccagtcacag tcgcaaggta ggctgagcac    9900
cgtggcgggc ggcagcgggc ggcggtcggg gttgtttctg gcggaggtgc tgctgatgat    9960
gtaattaaag taggcggtct tgagacggcg gatggtcgac agaagcacca tgtccttggg   10020
tccggcctgc tgaatgcgca ggcggtcggc catgccccag gcttcgtttt gacatcggcg   10080
caggtctttg tagtagtctt gcatgagcct ttctaccggc acttcttctt ctccttcctc   10140
ttgtcctgca tctcttgcat ctatcgctgc ggcggcggcg gagtttggcc gtaggtggcg   10200
ccctcttcct cccatgcgtg tgaccccgaa gcccctcatc ggctgaagca gggctaggtc   10260
ggcgacaacg cgctcggcta atatggcctg ctgcacctgc gtgagggtag actggaagtc   10320
atccatgtcc acaaagcggt ggtatgcgcc cgtgttgatg gtgtaagtgc agttggccat   10380
aacggaccag ttaacggtct ggtgacccgg ctgcgagagc tcggtgtacc tgagacgcga   10440
gtaagccctc gagtcaaata cgtagtcgtt gcaagtccgc accaggtact ggtatcccac   10500
caaaagtgc ggcggcggct ggcggtagag gggccagcgt agggtggccg gggctccggg    10560
ggcgagatct tccaacataa ggcgatgata tccgtagatg tacctggaca tccaggtgat   10620
```

-continued

```
gccggcggcg gtggtggagg cgcgcggaaa gtcgcggacg cggttccaga tgttgcgcag    10680
cggcaaaaag tgctccatgg tcgggacgct ctggccggtc aggcgcgcgc aatcgttgac    10740
gctctaccgt gcaaaaggag agcctgtaag cgggcactct tccgtggtct ggtggataaa    10800
ttcgcaaggg tatcatggcg gacgaccggg gttcgagccc cgtatccggc cgtccgccgt    10860
gatccatgcg gttaccgccc gcgtgtcgaa cccaggtgtg cgacgtcaga aacggggga    10920 gtgctccttt tggcttcctt ccaggcgcgg cggctgctgc gctagctttt ttggccactg    10980
gccgcgcgca gcgtaagcgg ttaggctgga aagcgaaagc attaagtggc tcgctccctg    11040
tagccggagg gttatttccc aagggttgag tcgcgggacc cccggttcga gtctcggacc    11100
ggccggactg cggcgaacgg gggtttgcct ccccgtcatg caagaccccg cttgcaaatt    11160
cctccggaaa cagggacgag ccccttttt gcttttccca gatgcatccg gtgctgcggc    11220
agatgcgccc ccctcctcag cagcggcaag agcaagagca gcggcagaca tgcagggcac    11280
cctcccctcc tcctaccgcg tcaggagggg cgacatccgc ggttgacgcg gcagcagatg    11340
gtgattacga accccgcgg cgccgggccc ggcactacct ggacttggag gagggcgagg    11400
gcctggcgcg gctaggagcg ccctctcctg agcggtaccc aagggtgcag ctgaagcgtg    11460
atacgcgtga ggcgtacgtg ccgcggcaga acctgtttcg cgaccgcgag ggagaggagc    11520
ccgaggagat gcgggatcga aagttccacg cagggcgcga gctgcggcat ggcctgaatc    11580
gcgagcggtt gctgcgcgag gaggactttg agcccgacgc gcgaaccggg attagtcccg    11640
cgcgcgcaca cgtggcggcc gccgacctgg taaccgcata cgagcagacg gtgaaccagg    11700
agattaactt tcaaaaaagc tttaacaacc acgtgcgtac gcttgtggcg cgcgaggagg    11760
tggctatagg actgatgcat ctgtgggact ttgtaagcgc gctggagcaa aacccaaata    11820
gcaagccgct catggcgcag ctgttcctta tagtgcagca cagcagggac aacgaggcat    11880
tcagggatgc gctgctaaac atagtagagc ccgagggccg ctggctgctc gatttgataa    11940
acatcctgca gagcatagtg gtgcaggagc gcagcttgag cctggctgac aaggtggccg    12000
ccatcaacta ttccatgctt agcctgggca agtttttacgc ccgcaagata taccatacccc    12060 cttacgttcc catagacaag gaggtaaaga tcgaggggtt ctacatgcgc atggcgctga    12120
aggtgcttac cttgagcgac gacctgggcg tttatcgcaa cgagcgcatc cacaaggccg    12180
tgagcgtgag ccggcggcgc gagctcagcg accgcgagct gatgcacagc ctgcaaaggg    12240
ccctggctgg cacgggcagc ggcgatagag aggccgagtc ctactttgac gcgggcgctg    12300
acctgcgctg ggccccaagc cgacgcgccc tggaggcagc tggggccgga cctgggctgg    12360
cggtggcacc cgcgcgcgct ggcaacgtcg gcggcgtgga ggaatatgac gaggacgatg    12420
agtacgagcc agaggacggc gagtactaag cggtgatgtt tctgatcaga tgatgcaaga    12480
cgcaacggac ccggcggtgc gggcggcgct gcagagccag ccgtccggcc ttaactccac    12540
ggacgactgg cgccaggtca tggaccgcat catgtcgctg actgcgcgca atcctgacgc    12600
gttccggcag cagccgcagg ccaaccggct ctccgcaatt ctggaagcgg tggtcccggc    12660
gcgcgcaaac cccacgcacg agaaggtgct ggcgatcgta aacgcgctgg ccgaaaacag    12720
ggccatccgg cccgacgagg ccggcctggt ctacgacgcg ctgcttcagc gcgtggctcg    12780
ttacaacagc ggcaacgtgc agaccaacct ggaccggctg gtggggatg tgcgcgaggc    12840 cgtggcgcag cgtgagcgcg cgcagcagca gggcaacctg ggctccatgg ttgcactaaa    12900
cgccttcctg agtacacagc ccgccaacgt gccgcgggga caggaggact acaccaactt    12960
```

```
tgtgagcgca ctgcggctaa tggtgactga gacaccgcaa agtgaggtgt accagtctgg    13020
gccagactat ttttccaga ccagtagaca aggcctgcag accgtaaacc tgagccaggc    13080
tttcaaaaac ttgcaggggc tgtgggggt gcgggctccc acaggcgacc gcgcgaccgt    13140
gtctagcttg ctgacgccca actcgcgcct gttgctgctg ctaatagcgc ccttcacgga    13200
cagtggcagc gtgtcccggg acacatacct aggtcacttg ctgacactgt accgcgaggc    13260
cataggtcag gcgcatgtgg acgagcatac tttccaggag attacaagtg tcagccgcgc    13320
gctggggcag gaggacacgg gcagcctgga ggcaaccta aactacctgc tgaccaaccg    13380
gcggcagaag atcccctcgt tgcacagttt aaacagcgag gaggagcgca ttttgcgcta    13440
cgtgcagcag agcgtgagcc ttaacctgat gcgcgacggg gtaacgccca gcgtggcgct    13500
ggacatgacc gcgcgcaaca tggaaccggg catgtatgcc tcaaaccggc cgtttatcaa    13560
ccgcctaatg gactacttgc atcgcgcggc cgccgtgaac cccgagtatt tcaccaatgc    13620
catcttgaac ccgcactggc taccgccccc tggtttctac accgggggat tcgaggtgcc    13680
cgagggtaac gatggattcc tctgggacga catagacgca agcgtgtttt ccccgcaacc    13740
gcagaccctg ctagagttgc aacagcgcga gcaggcagag gcggcgctgc gaaaggaaag    13800
cttccgcagg ccaagcagct tgtccgatct aggcgctgcg gccccgcggt cagatgctag    13860
tagcccattt ccaagcttga tagggtctct taccagcact cgcaccaccc gcccgcgcct    13920
gctgggcgag gaggagtacc taaacaactc gctgctgcag ccgcagcgcg aaaaaaacct    13980
gcctccggca tttcccaaca cgggataga gagcctagtg acaagatga gtagatggaa    14040 gacgtacgcg caggagcaca gggacgtgcc aggcccgcgc ccgcccaccc gtcgtcaaag    14100
gcacgaccgt cagcggggtc tggtgtggga ggacgatgac tcggcagacg acagcagcgt    14160
cctggatttg ggagggagtg gcaacccgtt tgcgcacctt cgcccaggc tggggagaat    14220 gttttaaaaa aaaaaaagca tgatgcaaaa taaaaactc accaaggcca tggcaccgag    14280
cgttggtttt cttgtattcc ccttagtatg cggcgcgcgg cgatgtatga ggaaggtcct    14340
cctccctcct acgagagtgt ggtgagcgcg gcgccagtgg cggcggcgct gggttctccc    14400
ttcgatgctc ccctggaccc gccgtttgtg cctccgcggt acctgcggcc taccgggggg    14460
agaaacagca tccgttactc tgagttggca cccctattcg acaccacccg tgtgtacctg    14520
gtggacaaca agtcaacgga tgtggcatcc ctgaactacc agaacgacca cagcaacttt    14580
ctgaccacgg tcattcaaaa caatgactac agcccggggg aggcaagcac acagaccatc    14640
aatcttgacg accggtcgca ctggggcggc gacctgaaaa ccatcctgca taccaacatg    14700
ccaaatgtga acgagttcat gtttaccaat aagtttaagg cgcgggtgat ggtgtcgcgc    14760
ttgcctacta aggacaatca ggtggagctg aaatacgagt gggtggagtt cacgctgccc    14820
gagggcaact actccgagac catgaccata gaccttatga caacgcgat cgtggagcac    14880 tacttgaaag tgggcagaca gaacgggtt ctggaaagcg acatcgggt aaagtttgac    14940 acccgcaact tcagactggg gtttgacccc gtcactggtc ttgtcatgcc tggggtatat    15000
acaaacgaag ccttccatcc agacatcatt ttgctgccag gatgcggggt ggacttcacc    15060
cacagccgcc tgagcaactt gttgggcatc cgcaagcggc aacccttcca ggagggcttt    15120
aggatcacct acgatgatct ggagggtggt aacattcccg cactgttgga tgtggacgcc    15180
taccaggcga gcttgaaaga tgacaccgaa cagggcgggg gtggcgcagg cggcagcaac    15240
agcagtggca gcgcgcgcga agagaactcc aacgcggcag ccgcggcaat gcagccggtg    15300
gaggacatga acgatcatgc cattcgcggc gacacctttg ccacacgggc tgaggagaag    15360
```

```
cgcgctgagg ccgaagcagc ggccgaagct gccgccccg ctgcgcaacc cgaggtcgag    15420
aagcctcaga agaaaccggt gatcaaaccc ctgacagagg acagcaagaa acgcagttac    15480
aacctaataa gcaatgacag caccttcacc cagtaccgca gctggtacct tgcatacaac    15540 tacgcgacc ctcagaccgg aatccgctca tggaccctgc tttgcactcc tgacgtaacc    15600
tgcggctcgg agcaggtcta ctggtcgttg ccagacatga tgcaagaccc cgtgaccttc    15660
cgctccacgc gccagatcag caactttccg gtggtgggcg ccgagctgtt gcccgtgcac    15720
tccaagagct tctacaacga ccaggccgtc tactcccaac tcatccgcca gtttacctct    15780
ctgacccacg tgttcaatcg ctttcccgag aaccagattt ggcgcgccc gccagccccc    15840 accatcacca ccgtcagtga aaacgttcct gctctcacag atcacgggac gctaccgctg    15900
cgcaacagca tcggaggagt ccagcgagtg accattactg acgccagacg ccgcacctgc    15960
ccctacgttt acaaggccct gggcatagtc tcgccgcgcg tcctatcgag ccgcactttt    16020
tgagcaagca tgtccatcct tatatcgccc agcaataaca caggctgggg cctgcgcttc    16080
ccaagcaaga tgtttggcgg ggccaagaag cgctccgacc aacacccagt gcgcgtgcgc    16140
gggcactacc gcgcgccctg gggcgcgcac aaacgcggcc gcactgggcg caccaccgtc    16200
gatgacgcca tcgacgcggt ggtggaggag gcgcgcaact acacgcccac gccgccacca    16260
gtgtccacag tggacgcggc cattcagacc gtggtgcgcg gagcccggcg ctatgctaaa    16320
atgaagagac ggcggaggcg cgtagcacgt cgccaccgcc gccgacccgg cactgccgcc    16380
caacgcgcgg cggcggccct gcttaaccgc gcacgtcgca ccggccgacg ggcggccatg    16440
cgggccgctc gaaggctggc cgcgggtatt gtcactgtgc cccccaggtc caggcgacga    16500
gcggccgccg cagcagccgc ggccattagt gctatgactc agggtcgcag gggcaacgtg    16560
tattgggtgc gcgactcggt tagcggcctg cgcgtgcccg tgcgcacccg ccccccgcgc    16620
aactagattg caagaaaaaa ctacttagac tcgtactgtt gtatgtatcc agcggcggcg    16680
gcgcgcaacg aagctatgtc caagcgcaaa atcaaagaag gatgctcca ggtcatcgcg    16740 ccggagatct atggcccccc gaagaaggaa gagcaggatt acaagcccg aaagctaaag    16800 cgggtcaaaa agaaaagaa agatgatgat gatgaacttg acgacgaggt ggaactgctg    16860
cacgctaccg cgcccaggcg acgggtacag tggaaaggtc gacgcgtaaa acgtgttttg    16920 cgaccccggca ccaccgtagt ctttacgccc ggtgagcgct ccaccgcac ctacaagcgc    16980 gtgtatgatg aggtgtacgg cgacgaggac ctgcttgagc aggccaacga gcgcctcggg    17040
gagtttgcct acgaaagcg gcataaggac atgctggcgt tgccgctgga cgagggcaac    17100
ccaacaccta gcctaaagcc cgtaacactg cagcaggtgc tgcccgcgct tgcaccgtcc    17160
gaagaaaagc gcggcctaaa gcgcgagtct ggtgacttgg cacccaccgt gcagctgatg    17220
gtacccaagc gccagcgact ggaagatgtc ttggaaaaaa tgaccgtgga acctgggctg    17280
gagcccgagg tccgcgtgcg gccaatcaag caggtggcgc cggactgggg cgtgcagacc    17340
gtggacgttc agatacccac taccagtagc accagtattg ccaccgccac agagggcatg    17400
gagacacaaa cgtccccggt tgcctcagcg gtggcggatg ccgcggtgca ggcggtcgct    17460
gcggccgcgt ccaagacctc tacggagtg caaacggacc cgtggatgtt tcgcgtttca    17520
gccccccggc gcccgcgcgg ttcgaggaag tacggcgccg ccagcgcgct actgcccgaa    17580
tatgccctac atccttccat tgcgcctacc cccggctatc gtggctacac ctaccgcccc    17640
agaagacgag caactacccg acgccgaacc accactggaa cccgccgccg ccgtcgccgt    17700
```

```
cgccagcccg tgctggcccc gatttccgtg cgcagggtgg ctcgcgaagg aggcaggacc   17760
ctggtgctgc caacagcgcg ctaccacccc agcatcgttt aaaagccggt ctttgtggtt   17820
cttgcagata tggccctcac ctgccgcctc cgtttcccgg tgccgggatt ccgaggaaga   17880
atgcaccgta ggaggggcat ggccggccac ggcctgacgg gcggcatgcg tcgtgcgcac   17940
caccggcggc ggcgcgcgtc gcaccgtcgc atgcgcggcg gtatcctgcc cctccttatt   18000
ccactgatcg ccgcggcgat tggcgccgtg cccggaattg catccgtggc cttgcaggcg   18060
cagagacact gattaaaaac aagttgcatg tggaaaaatc aaaataaaaa gtctggactc   18120
tcacgctcgc ttggtcctgt aactattttg tagaatggaa gacatcaact ttgcgtctct   18180
ggccccgcga cacggctcgc gcccgttcat gggaaactgg caagatatcg gcaccagcaa   18240
tatgagcggt ggcgccttca gctgggggctc gctgtggagc ggcattaaaa atttcggttc   18300
caccgttaag aactatggca gcaaggcctg gaacagcagc acaggccaga tgctgaggga   18360
taagttgaaa gagcaaaatt tccaacaaaa ggtggtagat ggcctggcct ctggcattag   18420
cggggtggtg gacctggcca accaggcagt gcaaaataag attaacagta agcttgatcc   18480
ccgccctccc gtagaggagc ctccaccggc cgtggagaca gtgtctccag aggggcgtgg   18540
cgaaaagcgt ccgcgcccccg acagggaaga aactctggtg acgcaaatag acgagcctcc   18600
ctcgtacgag gaggcactaa agcaaggcct gcccaccacc cgtcccatcg cgcccatggc   18660
taccggagtg ctgggccagc acacaccccgt aacgctggac ctgcctcccc ccgccgacac   18720
ccagcagaaa cctgtgctgc caggcccgac cgccgttgtt gtaacccgtc ctagccgcgc   18780
gtccctgcgc cgcgccgcca gcggtccgcg atcgttgcgg cccgtagcca gtggcaactg   18840
gcaaagcaca ctgaacagca tcgtgggtct ggggggtgcaa tccctgaagc gccgacgatg   18900
cttctgaata gctaacgtgt cgtatgtgtg tcatgtatgc gtccatgtcg ccgccagagg   18960
agctgctgag ccgccgcgcg cccgcttttcc aagatggcta ccccttcgat gatgccgcag   19020
tggtcttaca tgcacatctc gggccaggac gcctcggagt acctgagccc cgggctggtg   19080
cagtttgccc gcgccaccga gacgtacttc agcctgaata acaagtttag aaaccccacg   19140
gtggcgccta cgcacgacgt gaccacagac cggtcccagc gttgacgct gcggttcatc    19200 cctgtggacc gtgaggatac tgcgtactcg tacaaggcgc ggttcaccct agctgtgggt   19260
gataaccgtg tgctggacat ggcttccacg tactttgaca tccgcggcgt gctggacagg   19320
ggccctactt ttaagcccta ctctggcact gcctacaacg ccctggctcc caagggtgcc   19380
ccaaatcctt gcgaatggga tgaagctgct actgctcttg aaataaacct agaagaagag   19440
gacgatgaca acgaagacga agtagacgag caagctgagc agcaaaaaac tcacgtattt   19500
gggcaggcgc cttattctgg tataaatatt acaaaggagg gtattcaaat aggtgtcgaa   19560
ggtcaaacac ctaaatatgc cgataaaaca tttcaacctg aacctcaaat aggagaatct   19620
cagtggtacg aaactgaaat taatcatgca gctgggagag tccttaaaaa gactacccca   19680
atgaaaccat gttacggttc atatgcaaaa cccacaaatg aaaatggagg caaggcatt    19740 cttgtaaagc aacaaatgg aaagctagaa agtcaagtgg aaatgcaatt tttctcaact   19800
actgaggcga ccgcaggcaa tggtgataac ttgactccta agtggtatt gtacagtgaa   19860 gatgtagata tagaaacccc agacactcat atttcttaca tgcccactat taaggaaggt   19920
aactcacgag aactaatggg ccaacaatct atgcccaaca ggcctaatta cattgctttt   19980
agggacaatt ttattggtct aatgtattac aacagcacgg gtaatatggg tgttctggcg   20040
ggccaagcat cgcagttgaa tgctgttgta gatttgcaag acagaaacac agagctttca   20100
```

```
taccagctttt tgcttgattc cattggtgat agaaccaggt acttttctat gtggaatcag  20160
gctgttgaca gctatgatcc agatgttaga attattgaaa atcatggaac tgaagatgaa  20220
cttccaaatt actgctttcc actgggaggt gtgattaata cagagactct taccaaggta  20280
aaacctaaaa caggtcagga aaatggatgg gaaaaagatg ctacagaatt ttcagataaa  20340
aatgaaataa gagttggaaa taattttgcc atggaaatca atctaaatgc caacctgtgg  20400
agaaatttcc tgtactccaa catagcgctg tatttgcccg acaagctaaa gtacagtcct  20460
tccaacgtaa aaatttctga taacccaaac acctacgact acatgaacaa gcgagtggtg  20520
gctcccgggt tagtggactg ctacattaac cttggagcac gctggtccct tgactatatg  20580
gacaacgtca acccatttaa ccaccaccgc aatgctggcc tgcgctaccg ctcaatgttg  20640
ctgggcaatg gtcgctatgt gcccttccac atccaggtgc ctcagaagtt ctttgccatt  20700
aaaaacctcc ttctcctgcc gggctcatac acctacgagt ggaacttcag gaaggatgtt  20760
aacatggttc tgcagagctc cctaggaaat gacctaaggg ttgacggagc cagcattaag  20820
tttgatagca tttgccttta cgccaccttc ttccccatgg cccacaacac cgcctccacg  20880
cttgaggcca tgcttagaaa cgacaccaac gaccagtcct ttaacgacta tctctccgcc  20940
gccaacatgc tctaccctat acccgccaac gctaccaacg tgcccatatc catcccctcc  21000
cgcaactggg cggctttccg cggctgggcc ttcacgcgcc ttaagactaa ggaaaccccca  21060
tcactgggct cgggctacga cccttattac acctactctg gctctatacc ctacctagat  21120
ggaaccttt acctcaacca cacctttaag aaggtggcca ttacctttga ctcttctgtc  21180
agctggcctg gcaatgaccg cctgcttacc cccaacgagt ttgaaattaa gcgctcagtt  21240
gacggggagg gttacaacgt tgcccagtgt aacatgacca aagactggtt cctggtacaa  21300
atgctagcta actacaacat tggctaccag ggcttctata tcccagagag ctacaaggac  21360
cgcatgtact ccttctttag aaacttccag cccatgagcc gtcaggtggt ggatgatact  21420
aaatacaagg actaccaaca ggtgggcatc ctacaccaac acaacaactc tggatttgtt  21480
ggctaccttg cccccaccat gcgcgaagga caggcctacc ctgctaactt ccccctatccg  21540
cttataggca agaccgcagt tgacagcatt acccagaaaa agtttctttg cgatcgcacc  21600
ctttggcgca tcccattctc cagtaacttt atgtccatgg gcgcactcac agacctgggc  21660
caaaaccttc tctacgccaa ctccgcccac gcgctagaca tgactttga ggtggatccc  21720
atggacgagc ccaccctttct ttatgttttg tttgaagtct ttgacgtggt ccgtgtgcac  21780
cggccgcacc gcggcgtcat cgaaaccgtg tacctgcgca cgcccttctc ggccggcaac  21840
gccacaacat aaagaagcaa gcaacatcaa caacagctgc cgccatgggc tccagtgagc  21900
aggaactgaa agccattgtc aaagatcttg ttgtgtgggc atatttttg ggcacctatg  21960
acaagcgctt tccaggcttt gtttctccac acaagctcgc ctgcgccata gtcaatacgg  22020
ccggtcgcga gactggggc gtacactgga tggcctttgc ctggaacccg cactcaaaaa  22080
catgctacct ctttgagccc tttggctttt ctgaccagcg actcaagcag gtttaccagt  22140
ttgagtacga gtcactcctg cgccgtagcg ccattgcttc ttccccgac cgctgtataa  22200
cgctggaaaa gtcacccaa agcgtacagg ggcccaactc ggccgcctgt ggactattct  22260
gctgcatgtt tctccacgcc tttgccaact ggccccaaac tcccatggat cacaaccca  22320
ccatgaacct tattaccggg gtacccaact ccatgctcaa cagtccccag gtacagccca  22380
ccctgcgtcg caaccaggaa cagctctaca gcttcctgga gcgccactcg ccctacttcc  22440
```

```
gcagccacag tgcgcagatt aggagcgcca cttcttttg tcacttgaaa aacatgtaaa    22500
aataatgtac tagagacact ttcaataaag gcaaatgctt ttatttgtac actctcgggt    22560
gattatttac ccccacccct tgccgtctgcg ccgtttaaaa atcaaagggg ttctgccgcg    22620
catcgctatg cgccactggc agggacacgt tgcgatactg gtgtttagtg ctccacttaa    22680
actcaggcac aaccatccgc ggcagctcgg tgaagttttc actccacagg ctgcgcacca    22740
tcaccaacgc gtttagcagg tcgggcgccg atatcttgaa gtcgcagttg gggcctccgc    22800
cctgcgcgcg cgagttgcga tacacagggt tgcagcactg gaacactatc agcgccgggt    22860
ggtgcacgct ggccagcacg ctcttgtcgg agatcagatc cgcgtccagg tcctccgcgt    22920
tgctcagggc gaacggagtc aactttggta gctgccttcc caaaagggc gcgtgcccag    22980 gctttgagtt gcactcgcac cgtagtggca tcaaaaggtg accgtgcccg gtctgggcgt    23040
taggatacag cgcctgcata aaagccttga tctgcttaaa agccacctga gcctttgcgc    23100
cttcagagaa gaacatgccg caagacttgc cggaaaactg attggccgga caggccgcgt    23160
cgtgcacgca gcaccttgcg tcggtgttgg agatctgcac cacatttcgg ccccaccggt    23220
tcttcacgat cttggccttg ctagactgct ccttcagcgc gcgctgcccg ttttcgctcg    23280
tcacatccat ttcaatcacg tgctcctatt ttatcataat gcttccgtgt agacacttaa    23340
gctcgccttc gatctcagcg cagcggtgca gccacaacgc gcagcccgtg ggctcgtgat    23400
gcttgtaggt cacctctgca aacgactgca ggtacgcctg caggaatcgc ccatcatcg    23460 tcacaaaggt cttgttgctg gtgaaggtca gctgcaaccc gcggtgctcc tcgttcagcc    23520
aggtcttgca tacggccgcc agagcttcca cttggtcagg cagtagttg aagttcgcct    23580 ttagatcgtt atccacgtgg tacttgtcca tcagcgcgcg cgcagcctcc atgcccttct    23640
cccacgcaga cacgatcggc acactcagcg ggttcatcac cgtaatttca ctttccgctt    23700
cgctgggctc ttcctcttcc tcttgcgtcc gcataccacg cgccactggg tcgtcttcat    23760
tcagccgccg cactgtgcgc ttacctcctt tgccatgctt gattagcacc ggtgggttgc    23820
tgaaacccac catttgtagc gccacatctt ctctttcttc ctcgctgtcc acgattacct    23880
ctggtgatgg cgggcgctcg ggcttgggag aagggcgctt ctttttcttc ttgggcgcaa    23940
tggccaaatc cgccgccgag gtcgatggcc gcgggctggg tgtgcgcggc accagcgcgt    24000
cttgtgatga gtcttcctcg tcctcggact cgatacgccg cctcatccgc ttttttgggg    24060
gcgcccgggg aggcggcggc gacggggacg gggacgacac gtcctccatg gttggggac    24120 gtcgcgccgc accgcgtccg cgctcggggg tggtttcgcg ctgctcctct tcccgactgg    24180
ccatttcctt ctcctatagg cagaaaaaga tcatggagtc agtcgagaag aaggacagcc    24240
taaccgcccc ctctgagttc gccaccaccg cctccaccga tgccgccaac gcgcctacca    24300 ccttcccgt cgaggcaccc ccgcttgagg aggaggaagt gattatcgag caggacccag    24360
gttttgtaag cgaagacgac gaggaccgct cagtaccaac agaggataaa aagcaagacc    24420
aggacaacgc agaggcaaac gaggaacaag tcgggcgggg ggacgaaagg catggcgact    24480
acctagatgt gggagacgac gtgctgttga agcatctgca gcgccagtgc gccattatct    24540
gcgacgcgtt gcaagagcgc agcgatgtgc ccctcgccat agcggatgtc agccttgcct    24600
acgaacgcca cctattctca ccgcgcgtac cccccaaacg ccaagaaaac ggcacatgcg    24660
agcccaaccc gcgcctcaac ttctaccccg tatttgccgt gccagaggtg cttgccacct    24720
atcacatctt tttccaaaac tgcaagatac ccctatcctg ccgtgccaac cgcagccgag    24780
cggacaagca gctggccttg cggcagggcg ctgtcatacc tgatatcgcc tcgctcaacg    24840
```

```
aagtgccaaa aatctttgag ggtcttggac gcgacgagaa gcgcgcggca aacgctctgc   24900
aacaggaaaa cagcgaaaat gaaagtcact ctggagtgtt ggtggaactc gagggtgaca   24960
acgcgcgcct agccgtacta aaacgcagca tcgaggtcac ccactttgcc tacccggcac   25020
ttaacctacc cccaaggtc atgagcacag tcatgagtga gctgatcgtg cgccgtcgc    25080 agcccctgga gagggatgca aatttgcaag aacaaacaga ggagggccta cccgcagttg   25140
gcgacgagca gctagcgcgc tggcttcaaa cgcgcgagcc tgccgacttg gaggagcgac   25200
gcaaactaat gatggccgca gtgctcgtta ccgtggagct tgagtgcatg cagcggttct   25260
ttgctgaccc ggagatgcag cgcaagctag aggaaacatt gcactacacc tttcgacagg   25320
gctacgtacg ccaggcctgc aagatctcca acgtggagct ctgcaacctg gtctcctacc   25380
ttggaatttt gcacgaaaac cgccttgggc aaaacgtgct tcattccacg ctcaagggcg   25440
aggcgcgccg cgactacgtc cgcgactgcg tttacttatt tctatgctac acctggcaga   25500
cggccatggg cgtttggcag cagtgcttgg aggagtgcaa cctcaaggag ctgcagaaac   25560
tgctaaagca aaacttgaag gacctatgga cggccttcaa cgagcgctcc gtggccgcgc   25620
acctggcgga catcattttc cccgaacgcc tgcttaaaac cctgcaacag gtctgccag    25680 acttcaccag tcaaagcatg ttgcagaact ttaggaactt tatcctagag cgctcaggaa   25740
tcttgcccgc cacctgctgt gcacttccta gcgactttgt gcccattaag taccgcgaat   25800
gccctccgcc gctttggggc cactgctacc ttctgcagct agccaactac cttgcctacc   25860
actctgacat aatggaagac gtgagcggtg acggtctact ggagtgtcac tgtcgctgca   25920
acctatgcac cccgcaccgc tccctggttt gcaattcgca gctgcttaac gaaagtcaaa   25980
ttatcggtac ctttgagctg cagggtccct cgcctgacga aaagtccgcg gctccggggt   26040
tgaaactcac tccggggctg tggacgtcgg cttaccttcg caaatttgta cctgaggact   26100
accacgccca cgagattagg ttctacgaag accaatcccg cccgccaaat gcggagctta   26160
ccgcctgcgt cattacccag ggccacattc ttggccaatt gcaagccatc aacaaagccc   26220
gccaagagtt tctgctacga aagggacggg gggtttactt ggaccccag tccggcgagg   26280 agctcaaccc aatccccccg ccgccgcagc cctatcagca gcagccgcgg gcccttgctt   26340
cccaggatgg cacccaaaaa gaagctgcag ctgccgccgc cacccacgga cgaggaggaa   26400
tactgggaca gtcaggcaga ggaggttttg gacgaggagg aggaggacat gatgaagac    26460 tgggagagcc tagacgagga agcttccgag gtcgaagagg tgtcagacga acaccgtca    26520 ccctcggtcg cattccctc gccggcgccc cagaaatcgg caaccggttc cagcatggct    26580
acaacctccg ctcctcaggc gccgccggca ctgcccgttc gccgacccaa ccgtagatgg   26640
gacaccactg gaaccagggc cggtaagtcc aagcagccgc cgccgttagc ccaagagcaa   26700
caacagcgcc aaggctaccg ctcatggcgc gggcacaaga acgccatagt tgcttgcttg   26760
caagactgtg ggggcaacat ctccttcgcc cgccgctttc ttctctacca tcacggcgtg   26820
gccttccccc gtaacatcct gcattactac cgtcatctct acagcccata ctgcaccggc   26880
ggcagcggca gcggcagcaa cagcagcggc cacacagaag caaaggcgac cggatagcaa   26940
gactctgaca aagcccaaga atccacagc ggcggcagca gcaggaggag gagcgctgcg    27000
tctggcgccc aacgaacccg tatcgacccg cgagcttaga acaggatttt ttcccactct   27060
gtatgctata tttcaacaga gcaggggcca agaacaagag ctgaaaataa aaacaggtc    27120 tctgcgatcc ctcacccgca gctgcctgta tcacaaaagc gaagatcagc ttcggcgcac   27180
```

```
gctggaagac gcggaggctc tcttcagtaa atactgcgcg ctgactctta aggactagtt  27240
tcgcgccctt tctcaaattt aagcgcgaaa actacgtcat ctccagcggc cacacccggc  27300
gccagcacct gtcgtcagcg ccattatgag caaggaaatt cccacgccct acatgtggag  27360
ttaccagcca caaatgggac ttgcggctgg agctgcccaa gactactcaa cccgaataaa  27420
ctacatgagc gcgggacccc acatgatatc ccgggtcaac ggaatccgcg cccaccgaaa  27480
ccgaattctc ttggaacagg cggctattac caccacacct cgtaataacc ttaatccccg  27540
tagttggccc gctgccctgg tgtaccagga aagtcccgct cccaccactg tggtacttcc  27600
cagagacgcc caggccgaag ttcagatgac taactcaggg gcgcagcttg cgggcggctt  27660
tcgtcacagg gtgcggtcgc ccgggcaggg tataactcac ctgacaatca gagggcgagg  27720
tattcagctc aacgacgagt cggtgagctc ctcgcttggt ctccgtccgg acgggacatt  27780
tcagatcggc ggcgccggcc gtccttcatt cacgcctcgt caggcaatcc taactctgca  27840
gacctcgtcc tctgagccgc gctctggagg cattggaact ctgcaattta ttgaggagtt  27900
tgtgccatcg gtctacttta accccttctc gggacctccc ggccactatc cggatcaatt  27960
tattcctaac tttgacgcgg taaaggactc ggcggacggc tacgactgat tattaagtgg  28020
agaggcagag caactgcgcc tgaaacacct ggtccactgt cgccgccaca agtgctttgc  28080
ccgcgactcc ggtgagtttt gctactttga attgcccgag gatcatatcg aggatctttg  28140
ttgccatctc tgtgctgagt ataataaata cagaaattaa aatatactgg ggctcctatc  28200
gccatcctgt aaacgccacc gtcttcaccc gcccaagcaa accaaggcga accttacctg  28260
gtacttttaa catctctccc tctgtgattt acaacagttt caacccagac ggagtgagtc  28320
tacgagagaa cctctccgag ctcagctact ccatcagaaa aaacaccacc ctccttacct  28380
gccgggaacg tacccttata taaaagtcag gcttcctgga tgtcagcatc tgactttggc  28440
cagcacctgt cccgcggatt tgttccagtc caactacagc gacccaccct aacagagatg  28500
accaacacaa ccaacgcggc cgccgctacc ggacttacat ctaccacaaa tacaccccaa  28560
gtttctgcct ttgtcaataa ctgggataac ttgggcatgt ggtggttctc catagcgctt  28620
atgtttgtat gccttattat tatgtggctc atctgctgcc taaagcgcaa acgcgcccga  28680
ccacccatct atagtcccat cattgtgcta caccaaaaca atgatggaat ccatagattg  28740
gacggactga aacacatgtt cttttctctt acagtatgat taaatgagaa ttttaattcg  28800
aatttaaatg aattcgagct cggtacccgg ggatcctcta gagtcgacct gcaggaaatg  28860
gaatttctgt ccagtttatt cagcagcacc tccttgccct cctcccagct ctggtattgc  28920
agcttcctcc tggctgcaaa ctttctccac aatctaaatg gaatgtcagt ttcctcctgt  28980
tcctgtccat ccgcacccac tatcttcatg ttgttgcaga tgaagcgcgc aagaccgtct  29040
gaagatacct tcaaccccgt gtatccatat gacacggaaa ccggtcctcc aactgtgcct  29100
tttcttactc ctcccttgt atccccaat gggtttcaag agagtccccc tggggtactc  29160
tctttgcgcc tatccgaacc tctagttacc tccaatggca tgcttgcgct caaaatgggc  29220
aacggcctct ctctggacga ggccggcaac cttacctccc aaaatgtaac cactgtgagc  29280
ccacctctca aaaaaccaa gtcaaacata aacctggaaa tatctgcacc cctcacagtt  29340
acctcagaag ccctaactgt ggctgccgcc gcacctctaa tggtcgcggg caacacactc  29400
accatgcaat cacaggcccc gctaaccgtg cacgactcca aacttagcat tgccaccca  29460
ggaccctca cagtgtcaga aggaaagcta gccctgcaaa catcaggccc cctcaccacc  29520
accgatagca gtaccttac tatcactgcc tcacccctc taactactgc cactggtagc  29580
```

```
ttgggcattg acttgaaaga gcccatttat acacaaaatg gaaaactagg actaaagtac    29640
ggggctcctt tgcatgtaac agacgaccta aacactttga ccgtagcaac tggtccaggt    29700
gtgactatta ataatacttc cttgcaaact aaagttactg gagccttggg ttttgattca    29760
caaggcaata tgcaacttaa tgtagcagga ggactaagga ttgattctca aaacagacgc    29820
cttatacttg atgttagtta tccgtttgat gctcaaaacc aactaaatct aagactagga    29880
cagggccctc tttttataaa ctcagcccac aacttggata ttaactacaa caaaggcctt    29940
tacttgttta cagcttcaaa caattccaaa aagcttgagg ttaacctaag cactgccaag    30000
gggttgatgt ttgacgctac agccatagcc attaatgcag gagatgggct tgaatttggt    30060
tcacctaatg caccaaacac aaatcccctc aaaacaaaaa ttggccatgg cctagaattt    30120
gattcaaaca aggctatggt tcctaaacta ggaactggcc ttagttttga cagcacaggt    30180
gccattacag taggaaacaa aaataatgat aagctaaccc tatggacagg tccaaaacca    30240
gaagccaact gcataattga atacgggaaa gaaaacccag atagcaaact aactttaatc    30300
cttgtaaaaa atggaggaat tgttaatgga tatgtaacgc taatgggagc ctcagactat    30360
gttaacacct tatttaaaaa caaaaatgtc tccattaatg tagaattata ctttgatgcc    30420
actggtcata tattaccaga cttatcttct cttaaaacag atctagaact aaaatacaag    30480
caaaccactc actttagtgc aagaggtttt atgccaagta ctacagcgta tccatttgtc    30540
cttcctaatg cgggaacaga taatgaaaat tatattttg gtcaatgcta ctacaaagca    30600
agcgatggcg ccctttttcc gttggaagtt actgttacgc ttaataaacg cctgccagat    30660
agtcgcacat cctatgttat gactttttta tggtccttga atgctggtct agctccagaa    30720
actactcagg caaccctcat aacctcccca tttaccttt cctatattag agaagatgac    30780
tgacggtgga ggcggttcag gcggaggtgg ctctggcggt ggcggatcct gtgactgccg    30840
cggagactgt ttctgctaat aaactctaaa gaatcgtttg tgttatgttt caacgtgttt    30900 attttcaat tgcagaaaat ttcaagtcat ttttcattca gtagtatagc cccaccacca    30960
catagcttat acagatcacc gtaccttaat caaactcaca gaaccctagt attcaacctg    31020
ccacctccct cccaacacac agagtacaca gtcctttctc cccggctggc cttaaaaagc    31080
atcatatcat gggtaacaga catattctta ggtgttatat tccacacggt ttcctgtcga    31140
gccaaacgct catcagtgat attaataaac tccccgggca gctcacttaa gttcatgtcg    31200
ctgtccagct gctgagccac aggctgctgt ccaacttgcg gttgcttaac gggcggcgaa    31260
ggagaagtcc acgcctacat gggggtagag tcataatcgt gcatcaggat agggcggtgg    31320
tgctgcagca gcgcgcgaat aaactgctgc cgccgccgct ccgtcctgca ggaatacaac    31380
atggcagtgt ctcctcagc gatgattcgc accgccgca gcataaggcg ccttgtcctc    31440
cgggcacagc agcgcaccct gatctcactt aaatcagcac agtaactgca gcacagcacc    31500
acaatattgt tcaaaatccc acagtgcaag gcgctgtatc caaagctcat ggcgggacc    31560 acagaaccca cgtggccatc ataccacaag cgcaggtaga ttaagtggcg acccctcata    31620
aacacgctgg acataaacat tacctctttt ggcatgttgt aattcaccac ctcccggtac    31680
catataaacc tctgattaaa catggcgcca tccaccacca tcctaaacca gctggccaaa    31740
acctgcccgc cggctataca ctgcagggaa ccgggactgg aacaatgaca gtggagagcc    31800
caggactcgt aaccatggat catcatgctc gtcatgatat caatgttggc acaacacagg    31860
cacacgtgca tacacttcct caggattaca agctcctccc gcgttagaac catatcccag    31920
```

```
ggaacaaccc attcctgaat cagcgtaaat cccacactgc agggaagacc tcgcacgtaa    31980
ctcacgttgt gcattgtcaa agtgttacat tcgggcagca gcggatgatc ctccagtatg    32040
gtagcgcggg tttctgtctc aaaaggaggt agacgatccc tactgtacgg agtgcgccga    32100
gacaaccgag atcgtgttgg tcgtagtgtc atgccaaatg aacgccgga cgtagtcata    32160
tttcctgaag caaaccagg tgcgggcgtg acaaacagat ctgcgtctcc ggtctcgccg    32220
cttagatcgc tctgtgtagt agttgtagta tatccactct ctcaaagcat ccaggcgccc    32280
cctggcttcg ggttctatgt aaactccttc atgcgccgct gccctgataa catccaccac    32340
cgcagaataa gccacaccca gccaacctac acattcgttc tgcgagtcac acacgggagg    32400
agcgggaaga gctggaagaa ccatgttttt tttttttattc caaaagatta tccaaaacct    32460
caaaatgaag atctattaag tgaacgcgct ccctccggt ggcgtggtca aactctacag    32520
ccaaagaaca gataatggca tttgtaagat gttgcacaat ggcttccaaa aggcaaacgg    32580
ccctcacgtc caagtggacg taaaggctaa accttcagg gtgaatctcc tctataaaca    32640
ttccagcacc ttcaaccatg cccaaataat tctcatctcg ccaccttctc aatatatctc    32700
taagcaaatc ccgaatatta agtccggcca ttgtaaaaat ctgctccaga gcgccctcca    32760
ccttcagcct caagcagcga atcatgattg caaaaattca ggttcctcac agacctgtat    32820
aagattcaaa agcggaacat taacaaaaat accgcgatcc cgtaggtccc ttcgcagggc    32880
cagctgaaca taatcgtgca ggtctgcacg gaccagcgcg gccacttccc cgccaggaac    32940
catgacaaaa gaacccacac tgattatgac acgcatactc ggagctatgc taaccagcgt    33000
agccccgatg taagctttgt tgcatgggcg gcgatataaa atgcaaggtg ctgctcaaaa    33060
aatcaggcaa agcctcgcgc aaaaaagaaa gcacatcgta gtcatgctca tgcagataaa    33120
ggcaggtaag ctccggaacc accacagaaa aagacaccat ttttctctca acatgtctg    33180
cggggtttctg cataaacaca aaataaaata acaaaaaaac atttaaacat tagaagcctg    33240
tcttacaaca ggaaaaacaa cccttataag cataagacgg actacggcca tgccggcgtg    33300
accgtaaaaa aactggtcac cgtgattaaa aagcaccacc gacagctcct cggtcatgtc    33360
cggagtcata atgtaagact cggtaaacac atcaggttga ttcatcggtc agtgctaaaa    33420
agcgaccgaa atagcccggg ggaatacata cccgcaggcg tagagacaac attacagccc    33480
ccataggagg tataacaaaa ttaataggag agaaaaacac ataaacacct gaaaaaccct    33540
cctgcctagg caaaatagca ccctcccgct ccagaacaac atacagcgct tcacagcggc    33600
agcctaacag tcagccttac cagtaaaaaa gaaaacctat taaaaaaaca ccactcgaca    33660
cggcaccagc tcaatcagtc acagtgtaaa aaagggccaa gtgcagagcg agtatatata    33720
ggactaaaaa atgacgtaac ggttaaagtc cacaaaaaac acccagaaaa ccgcacgcga    33780
acctacgccc agaaacgaaa gccaaaaaac ccacaacttc ctcaaatcgt cacttccgtt    33840
ttcccacgtt acgtaacttc ccattttaag aaaactacaa ttcccaacac atacaagtta    33900
ctccgcccta aaacctacgt caccccgcccc gttccacgc cccgcgccac gtcacaaact    33960
ccacccctc attatcatat tggcttcaat ccaaaataag gtatattatt gatgatnnnn    34020
nttaat                                                              34026
```

<210> SEQ ID NO 8
<211> LENGTH: 31756
<212> TYPE: DNA
<213> ORGANISM: Artificial sequence
<220> FEATURE:
<223> OTHER INFORMATION: Recombinant adenovirus AdEz swa1

<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (3655)..(3657)
<223> OTHER INFORMATION: n is a, c, g, or t
<220> FEATURE:
<221> NAME/KEY: misc_feature
<222> LOCATION: (3684)..(3686)
<223> OTHER INFORMATION: n is a, c, g, or t
<220> FEATURE:
<221> NAME/KEY: misc_feature
<222> LOCATION: (31747)..(31751)
<223> OTHER INFORMATION: n is a, c, g, or t

<400> SEQUENCE: 8

| | | | | | |
|---|---|---|---|---|---|
| taaggatccn | nncctgtcct | cgaccgatgc | ccttgagagc | cttcaaccca | gtcagctcct | 60 |
| tccggtgggc | gcggggcatg | actatcgtcg | ccgcacttat | gactgtcttc | tttatcatgc | 120 |
| aactcgtagg | acaggtgccg | gcagcgctct | gggtcatttt | cggcgaggac | cgctttcgct | 180 |
| ggagcgcgac | gatgatcggc | ctgtcgcttg | cggtattcgg | aatcttgcac | gccctcgctc | 240 |
| aagccttcgt | cactggtccc | gccaccaaac | gtttcggcga | gaagcaggcc | attatcgccg | 300 |
| gcatggcggc | cgacgcgctg | ggctacgtct | tgctggcgtt | cgcgacgcga | ggctggatgg | 360 |
| ccttccccat | tatgattctt | ctcgcttccg | gcggcatcgg | gatgcccgcg | ttgcaggcca | 420 |
| tgctgtccag | gcaggtagat | gacgaccatc | agggacagct | tcaaggatcg | ctcgcggctc | 480 |
| ttaccagcct | aacttcgatc | actgaccgc | tgatcgtcac | ggcgatttat | gccgcctcgg | 540 |
| cgagcacatg | gaacgggttg | gcatggattg | taggcgccgc | cctatacctt | gtctgcctcc | 600 |
| ccgcgttgcg | tcgcggtgca | tggagccggg | ccacctcgac | ctgaatggaa | gccggcggca | 660 |
| cctcgctaac | ggattcacca | ctccaagaat | tggagccaat | caattcttgc | ggagaactgt | 720 |
| gaatgcgcaa | accaacccctt | ggcagaacat | atccatcgcg | tccgccatct | ccagcagccg | 780 |
| cacgcggcgc | atctcgggca | gcgttgggtc | ctggccacgg | gtgcgcatga | tcgtgctcct | 840 |
| gtcgttgagg | acccggctag | gctggcgggg | ttgccttact | ggttagcaga | atgaatcacc | 900 |
| gatacgcgag | cgaacgtgaa | gcgactgctg | ctgcaaaacg | tctgcgacct | gagcaacaac | 960 |
| atgaatggtc | ttcggtttcc | gtgtttcgta | aagtctggaa | acgcggaagt | cagcgccctg | 1020 |
| caccattatg | ttccggatct | gcatcgcagg | atgctgctgg | ctaccctgtg | gaacacctac | 1080 |
| atctgtatta | acgaagcgct | ggcattgacc | ctgagtgatt | tttctctggt | cccgccgcat | 1140 |
| ccataccgcc | agttgtttac | cctcacaacg | ttccagtaac | cgggcatgtt | catcatcagt | 1200 |
| aacccgtatc | gtgagcatcc | tctctcgttt | catcggtatc | attaccccca | tgaacagaaa | 1260 |
| ttcccccctta | cacggaggca | tcaagtgacc | aaacaggaaa | aaaccgccct | taacatggcc | 1320 |
| cgctttatca | gaagccagac | attaacgctt | ctggagaaac | tcaacgagct | ggacgcggat | 1380 |
| gaacaggcag | acatctgtga | atcgcttcac | gaccacgctg | atgagcttta | ccgcagctgc | 1440 |
| ctcgcgcgtt | tcggtgatga | cggtgaaaac | ctctgacaca | tgcagctccc | ggagacggtc | 1500 |
| acagcttgtc | tgtaagcgga | tgccgggagc | agacaagccc | gtcagggcgc | gtcagcgggt | 1560 |
| gttggcgggt | gtcggggcgc | agccatgacc | cagtcacgta | gcgatagcgg | agtgtatact | 1620 |
| ggcttaacta | tgcggcatca | gagcagattg | tactgagagt | gcaccatatg | cggtgtgaaa | 1680 |
| taccgcacag | atgcgtaagg | agaaaatacc | gcatcaggcg | ctcttccgct | tcctcgctca | 1740 |
| ctgactcgct | gcgctcggtc | gttcggctgc | ggcgagcggt | atcagctcac | tcaaaggcgg | 1800 |

-continued

```
taatacggtt atccacagaa tcagggata  acgcaggaaa gaacatgtga gcaaaaggcc    1860
agcaaaaggc caggaaccgt aaaaaggccg cgttgctggc gttttccat  aggctccgcc    1920 ccctgacga  gcatcacaaa atcgacgct  caagtcagag gtggcgaaac ccgacaggac    1980
tataaagata ccaggcgttt ccccctggaa gctccctcgt gcgctctcct gttccgaccc    2040
tgccgcttac cggatacctg tccgccttc  tcccttcggg aagcgtggcg ctttctcaat    2100
gctcacgctg taggtatctc agttcggtgt aggtcgttcg ctccaagctg gctgtgtgc    2160 acgaaccccc cgttcagccc gaccgctgcg ccttatccgg taactatcgt cttgagtcca    2220
acccggtaag acacgactta tcgccactgg cagcagccac tggtaacagg attagcagag    2280
cgaggtatgt aggcggtgct acagagttct tgaagtggtg gcctaactac ggctacacta    2340
gaaggacagt atttggtatc tgcgctctgc tgaagccagt taccttcgga aaaagagttg    2400
gtagctcttg atccggcaaa caaaccaccg ctggtagcgg tggtttttt  gtttgcaagc    2460 agcagattac gcgcagaaaa aaggatctc  aagaagatcc tttgatcttt tctacggggt    2520
ctgacgctca gtggaacgaa aactcacgtt aagggatttt ggtcatgaga ttatcaaaaa    2580
ggatcttcac ctagatcctt ttaaattaaa aatgaagttt taaatcaatc taaagtatat    2640
atgagtaaac ttggtctgac agttaccaat gcttaatcag tgaggcacct atctcagcga    2700
tctgtctatt tcgttcatcc atagttgcct gactccccgt cgtgtagata actacgatac    2760
gggagggctt accatctggc cccagtgctg caatgatacc gcgagaccca cgctcaccgg    2820
ctccagattt atcagcaata aaccagccag ccggaagggc cgagcgcaga agtggtcctg    2880
caactttatc cgcctccatc cagtctatta attgttgccg ggaagctaga gtaagtagtt    2940
cgccagttaa tagtttgcgc aacgttgttg ccattgctgc aggcatcgtg gtgtcacgct    3000
cgtcgtttgg tatggcttca ttcagctccg gttcccaacg atcaaggcga gttacatgat    3060
cccccatgtt gtgcaaaaaa gcggttagct ccttcggtcc tccgatcgtt gtcagaagta    3120
agttggccgc agtgttatca ctcatggtta tggcagcact gcataattct cttactgtca    3180
tgccatccgt aagatgcttt tctgtgactg gtgagtactc aaccaagtca ttctgagaat    3240
agtgtatgcg gcgaccgagt tgctcttgcc cggcgtcaac acgggataat accgcgccac    3300
atagcagaac tttaaaagtg ctcatcattg gaaaacgttc ttcggggcga aaactctcaa    3360
ggatcttacc gctgttgaga tccagttcga tgtaacccac tcgtgcaccc aactgatctt    3420
cagcatcttt tactttcacc agcgtttctg ggtgagcaaa aacaggaagg caaaatgccg    3480
caaaaaaggg aataagggcg acacggaaat gttgaatact catactcttc cttttttcaat    3540 attattgaag catttatcag ggttattgtc tcatgagcgg atacatattt gaatgtattt    3600
agaaaaataa acaaataggg gttccgcgca catttcccg  aaaagtgcca cctgnnngaa    3660
ttcgaatcta gtatcgattc gaannncta  agggtgggaa agaatatata aggtgggggt    3720
cttatgtagt tttgtatctg ttttgcagca gccgccgccg ccatgagcac caactcgttt    3780
gatggaagca ttgtgagctc atatttgaca acgcgcatgc ccccatgggc cggggtgcgt    3840
cagaatgtga tgggctccag cattgatggt cgccccgtcc tgcccgcaaa ctctactacc    3900
ttgacctacg agaccgtgtc tggaacgccg ttggagactg cagcctccgc cgccgcttca    3960
gccgctgcag ccaccgcccg cgggattgtg actgactttg ctttcctgag cccgcttgca    4020
agcagtgcag cttcccgttc atccgcccgc gatgacaagt tgacggctct tttggcacaa    4080
ttggattctt tgacccggga acttaatgtc gtttctcagc agctgttgga tctgcgccag    4140
caggtttctg ccctgaaggc ttcctcccct cccaatgcgg tttaaaacat aaataaaaaa    4200
```

```
ccagactctg tttggatttg gatcaagcaa gtgtcttgct gtctttattt aggggttttg   4260
cgcgcgcggt aggcccggga ccagcggtct cggtcgttga gggtcctgtg tattttttcc   4320
aggacgtggt aaaggtgact ctggatgttc agatacatgg gcataagccc gtctctgggg   4380
tggaggtagc accactgcag agcttcatgc tgcggggtgg tgttgtagat gatccagtcg   4440
tagcaggagc gctgggcgtg gtgcctaaaa atgtctttca gtagcaagct gattgccagg   4500
ggcaggccct tggtgtaagt gtttacaaag cggttaagct gggatgggtg catacgtggg   4560
gatatgagat gcatcttgga ctgtattttt aggttggcta tgttcccagc catatccctc   4620
cggggattca tgttgtgcag aaccaccagc acagtgtatc cggtgcactt gggaaatttg   4680
tcatgtagct tagaaggaaa tgcgtggaag aacttggaga cgcccttgtg acctccaaga   4740
ttttccatgc attcgtccat aatgatggca atgggcccac gggcggcggc ctgggcgaag   4800
atatttctgg gatcactaac gtcatagttg tgttccagga tgagatcgtc ataggccatt   4860
tttacaaagc gcgggcggag ggtgccgagac tgccgtataa tggttccatc cggcccaggg   4920
gcgtagttac cctcacagat ttgcatttcc cacgctttga gttcagatgg ggggatcatg   4980
tctacctgcg gggcgatgaa gaaaacggtt tccggggtag gggagatcag ctgggaagaa   5040
agcaggttcc tgagcagctg cgacttaccg cagccggtgg gcccgtaaat cacacctatt   5100
accgggtgca actggtagtt aagagagctg cagctgccgt catccctgag caggggggcc   5160
acttcgttaa gcatgtccct gactcgcatg ttttccctga ccaaatccgc cagaaggcgc   5220
tcgccgccca gcgatagcag ttcttgcaag gaagcaaagt ttttcaacgg tttgagaccg   5280
tccgccgtag gcatgctttt gagcgtttga ccaagcagtt ccaggcggtc ccacagctcg   5340
gtcacctgct ctacggcatc tcgatccagc atatctcctc gtttcgcggg ttggggcggc   5400
tttcgctgta cggcagtagt cggtgctcgt ccagacgggc cagggtcatg tctttccacg   5460
ggcgcagggt cctcgtcagc gtagtctggg tcacggtgaa ggggtgcgct ccgggctgcg   5520
cgctggccag ggtgcgcttg aggctggtcc tgctggtgct gaagcgctgc cggtcttcgc   5580
cctgcgcgtc ggccaggtag catttgacca tggtgtcata gtccagcccc tccgcggcgt   5640
ggcccttggc gcgcagcttg cccttggagg aggcgccgca cgaggggcag tgcagacttt   5700
tgagggcgta gagcttgggc gcgagaaata ccgattccgg ggagtaggca tccgcgccgc   5760
aggccccgca gacggtctcg cattccacga gccaggtgag ctctggccgt tcggggtcaa   5820
aaaccaggtt tccccccatgc tttttgatgc gtttcttacc tctggttttcc atgagccggt   5880
gtccacgctc ggtgacgaaa aggctgtccg tgtcccgta tacagacttg agaggcctgt   5940
cctcgagcgg tgttccgcgg tcctcctcgt atagaaactc ggaccactct gagacaaagg   6000
ctcgcgtcca ggccagcacg aaggaggcta agtgggaggg gtagcggtcg ttgtccacta   6060
gggggtccac tcgctccagg gtgtgaagac acatgtcgcc ctcttcggca tcaaggaagg   6120
tgattggttt gtaggtgtag gccacgtgac cgggtgttcc tgaaggggggg ctataaaagg   6180
gggtgggggc gcgttcgtcc tcactctctt ccgcatcgct gtctgcgagg ccagctgtt   6240
ggggtgagta ctccctctga aaagcgggca tgacttctgc gctaagattg tcagtttcca   6300
aaaacgagga ggatttgata ttcacctggc ccgcggtgat gcctttgagg gtggccgcat   6360
ccatctggtc agaaaagaca atcttttttgt tgtcaagctt ggtggcaaac gacccgtaga   6420
gggcgttgga cagcaacttg gcgatggagc gcagggtttg gtttttgtcg cgatcggcgc   6480
gctccttggc cgcgatgttt agctgcacgt attcgcgcgc aacgcaccgc cattcgggaa   6540
```

```
agacggtggt gcgctcgtcg ggcaccaggt gcacgcgcca accgcggttg tgcagggtga    6600
caaggtcaac gctggtggct acctctccgc gtaggcgctc gttggtccag cagaggcggc    6660
cgcccttgcg cgagcagaat ggcggtaggg ggtctagctg cgtctcgtcc gggggggtctg   6720
cgtccacggt aaagaccccg ggcagcaggc gcgcgtcgaa gtagtctatc ttgcatcctt    6780
gcaagtctag cgcctgctgc catgcgcggg cggcaagcgc gcgctcgtat gggttgagtg    6840
ggggaccccca tggcatgggg tgggtgagcg cggaggcgta catgccgcaa atgtcgtaaa   6900
cgtagagggg ctctctgagt attccaagat atgtagggta gcatcttcca ccgcggatgc    6960
tggcgcgcac gtaatcgtat agttcgtgcg agggagcgag gaggtcggga ccgaggttgc    7020
tacgggcggg ctgctctgct cggaagacta tctgcctgaa gatggcatgt gagttggatg    7080
atatggttgg acgctggaag acgttgaagc tggcgtctgt gagacctacc gcgtcacgca    7140
cgaaggaggc gtaggagtcg cgcagcttgt tgaccagctc ggcggtgacc tgcacgtcta    7200
gggcgcagta gtccagggtt tccttgatga tgtcatactt atcctgtccc ttttttttcc    7260
acagctcgcg gttgaggaca aactcttcgc ggtctttcca gtactcttgg atcggaaacc    7320
cgtcggcctc cgaacggtaa gagcctagca tgtagaactg gttgacggcc tggtaggcgc    7380
agcatcccctt ttctacgggt agcgcgtatg cctgcgcggc cttccggagc gaggtgtggg   7440
tgagcgcaaa ggtgtccctg accatgactt tgaggtactg gtatttgaag tcagtgtcgt    7500
cgcatccgcc ctgctcccag agcaaaaagt ccgtgcgctt tttggaacgc ggatttggca    7560
gggcgaaggt gacatcgttg aagagtatct ttcccgcgcg aggcataaag ttgcgtgtga    7620
tgcggaaggg tcccggcacc tcggaacggt tgttaattac ctgggcggcg agcacgatct    7680
cgtcaaagcc gttgatgttg tggcccacaa tgtaaagttc caagaagcgc gggatgccct    7740
tgatggaagg caatttttta agttcctcgt aggtgagctc ttcaggggag ctgagcccgt    7800
gctctgaaag ggcccagtct gcaagatgag ggttggaagc gacgaatgag ctccacaggt    7860
cacgggccat tagcatttgc aggtggtcgc gaaaggtcct aaactggcga cctatggcca    7920
ttttttctgg ggtgatgcag tagaaggtaa gcgggtcttg ttcccagcgg tcccatccaa    7980
ggttcgcggc taggtctcgc gcggcagtca ctagaggctc atctccgccg aacttcatga    8040
ccagcatgaa gggcacgagc tgcttcccaa aggcccccat ccaagtatag gtctctacat    8100
cgtaggtgac aaagagacgc tcggtgcgag gatgcgagcc gatcgggaag aactggatct    8160
cccgccacca attggaggag tggctattga tgtggtgaaa gtagaagtcc ctgcgacggg    8220
ccgaacactc gtgctggctt ttgtaaaaac gtgcgcagta ctggcagcgg tgcacgggct    8280
gtacatcctg cacgaggttg acctgacgac cgcgcacaag gaagcagagt gggaatttga    8340
gccctcgcc tggcgggttt ggctggtggt cttctacttc ggctgcttgt ccttgaccgt    8400
ctggctgctc gagggggagtt acggtggatc ggaccaccac gccgcgcgag cccaaagtcc    8460
agatgtccgc gcgcggcggt cggagcttga tgacaacatc gcgcagatgg gagctgtcca    8520
tggtctggag ctcccgcggc gtcaggtcag gcgggagctc ctgcaggttt acctcgcata    8580
gacgggtcag ggcgcgggct agatccaggt gataccaat ttccaggggc tggttggtgg     8640
cggcgtcgat ggcttgcaag aggccgcatc ccgcgcgcgc gactacggta ccgcgcggcg    8700
ggcggtgggc gcgggggtg tccttggatg atgcatctaa aagcggtgac gcgggcgagc    8760
ccccggaggt aggggggggct ccggacccgc cgggagaggg ggcaggggca cgtcggcgcc    8820
gcgcgcgggc aggagctggt gctgcgcgcg taggttgctg gcgaacgcga cgacgcggcg    8880
gttgatctcc tgaatctggc gcctctgcgt gaagacgacg ggcccggtga gcttgagcct    8940
```

-continued

```
gaaagagagt tcgacagaat caatttcggt gtcgttgacg gcggcctggc gcaaaatctc    9000
ctgcacgtct cctgagttgt cttgataggc gatctcggcc atgaactgct cgatctcttc    9060
ctcctggaga tctccgcgtc cggctcgctc cacggtggcg gcgaggtcgt tggaaatgcg    9120
ggccatgagc tgcgagaagg cgttgaggcc tccctcgttc cagacgcggc tgtagaccac    9180
gcccccttcg gcatcgcggg cgcgcatgac cacctgcgcg agattgagct ccacgtgccg    9240
ggcgaagacg gcgtagtttc gcaggcgctg aaagaggtag ttgagggtgg tggcggtgtg    9300
ttctgccacg aagaagtaca taacccagcg tcgcaacgtg gattcgttga tatcccccaa    9360
ggcctcaagg cgctccatgg cctcgtagaa gtccacggcg aagttgaaaa actgggagtt    9420
gcgcgccgac acggttaact cctcctccag aagacggatg agctcggcga cagtgtcgcg    9480
cacctcgcgc tcaaaggcta cagggggcctc ttcttcttct tcaatctcct cttccataag    9540
ggcctcccct tcttcttctt ctggcggcgg tggggagggg gggacacggc ggcgacgacg    9600
gcgcaccgga aggcggtcga caaagcgctc gatcatctcc ccgcggcgac ggcgcatggt    9660
ctcggtgacg gcgcggccgt tctcgcgggg gcgcagttgg aagacgccgc ccgtcatgtc    9720
ccggttatgg gttggcgggg ggctgccatg cggcagggat acggcgctaa cgatgcatct    9780
caacaattgt tgtgtaggta ctccgccgcc gagggacctg agcgagtccg catcgaccgg    9840
atcggaaaac ctctcgagaa aggcgtctaa ccagtcacag tcgcaaggta ggctgagcac    9900
cgtggcgggc ggcagcgggc ggcggtcggg gttgtttctg gcggaggtgc tgctgatgat    9960
gtaattaaag taggcggtct tgagacggcg gatggtcgac agaagcacca tgtccttggg   10020
tccggcctgc tgaatgcgca ggcggtcggc catgccccag gcttcgtttt gacatcggcg   10080
caggtctttg tagtagtctt gcatgagcct ttctaccggc acttcttctt ctccttcctc   10140
ttgtcctgca tctcttgcat ctatcgctgc ggcggcggcg gagtttggcc gtaggtggcg   10200
ccctcttcct cccatgcgtg tgaccccgaa gccctcatc ggctgaagca gggctaggtc   10260
ggcgacaacg cgctcggcta atatggcctg ctgcacctgc gtgagggtag actggaagtc   10320
atccatgtcc acaaagcggt ggtatgcgcc cgtgttgatg gtgtaagtgc agttggccat   10380
aacggaccag ttaacggtct ggtgacccgg ctgcgagagc tcggtgtacc tgagacgcga   10440
gtaagccctc gagtcaaata cgtagtcgtt gcaagtccgc accaggtact ggtatcccac   10500 caaaagtgc ggcggcggct ggcggtagag gggccagcgt agggtggccg gggctccggg    10560
ggcgagatct tccaacataa ggcgatgata tccgtagatg tacctggaca tccaggtgat   10620
gccggcggcg gtggtggagg cgcgcggaaa gtcgcggacg cggttccaga tgttgcgcag   10680
cggcaaaaag tgctccatgg tcgggacgct ctggccggtc aggcgcgcgc aatcgttgac   10740
gctctaccgt gcaaaggag agcctgtaag cgggcactct tccgtggtct ggtggataaa   10800
ttcgcaaggg tatcatggcg gacgaccggg gttcgagccc cgtatccggc cgtccgccgt   10860
gatccatgcg gttaccgccc gcgtgtcgaa cccaggtgtg cgacgtcaga aacggggga   10920 gtgctccttt tggcttcctt ccaggcgcgg cggctgctgc gctagctttt ttggccactg   10980
gccgcgcgca gcgtaagcgg ttaggctgga aagcgaaagc attaagtggc tcgctccctg   11040
tagccggagg gttattttcc aagggttgag tcgcgggacc cccggttcga gtctcggacc   11100
ggccggactg cggcgaacgg gggtttgcct ccccgtcatg caagacccccg cttgcaaatt   11160 cctccggaaa cagggacgag cccctttttt gcttttccca gatgcatccg gtgctgcggc   11220
agatgcgccc ccctcctcag cagcggcaag agcaagagca gcggcagaca tgcagggcac   11280
```

```
cctcccctcc tcctaccgcg tcaggagggg cgacatccgc ggttgacgcg gcagcagatg    11340
gtgattacga accccccgcgg cgccgggccc ggcactacct ggacttggag gagggcgagg    11400
gcctggcgcg gctaggagcg ccctctcctg agcggtaccc aagggtgcag ctgaagcgtg    11460
atacgcgtga ggcgtacgtg ccgcggcaga acctgtttcg cgaccgcgag ggagaggagc    11520
ccgaggagat gcgggatcga aagttccacg cagggcgcga gctgcggcat ggcctgaatc    11580
gcgagcggtt gctgcgcgag gaggactttg agcccgacgc gcgaaccggg attagtcccg    11640
cgcgcgcaca cgtggcggcc gccgacctgg taaccgcata cgagcagacg gtgaaccagg    11700
agattaactt tcaaaaaagc tttaacaacc acgtgcgtac gcttgtgcg cgcgaggagg    11760 tggctatagg actgatgcat ctgtgggact ttgtaagcgc gctggagcaa aacccaaata    11820
gcaagccgct catggcgcag ctgttcctta tagtgcagca cagcagggac aacgaggcat    11880
tcagggatgc gctgctaaac atagtagagc ccgagggccg ctggctgctc gatttgataa    11940
acatcctgca gagcatagtg gtgcaggagc gcagcttgag cctggctgac aaggtggccg    12000
ccatcaacta ttccatgctt agcctgggca agttttacgc ccgcaagata taccataccc    12060
cttacgttcc catagacaag gaggtaaaga tcgaggggtt ctacatgcgc atggcgctga    12120
aggtgcttac cttgagcgac gacctgggcg tttatcgcaa cgagcgcatc cacaaggccg    12180
tgagcgtgag ccggcggcgc gagctcagcg accgcgagct gatgcacagc ctgcaaaggg    12240
ccctggctgg cacgggcagc ggcgatagag aggccgagtc ctactttgac gcgggcgctg    12300
acctgcgctg ggccccaagc cgacgcgccc tggaggcagc tggggccgga cctgggctgg    12360
cggtggcacc cgcgcgcgct ggcaacgtcg cggcgtgga ggaatatgac gaggacgatg    12420
agtacgagcc agaggacggc gagtactaag cggtgatgtt tctgatcaga tgatgcaaga    12480
cgcaacggac ccggcggtgc gggcggcgct gcagagccag ccgtccggcc ttaactccac    12540
ggacgactgg cgccaggtca tggaccgcat catgtcgctg actgcgcgca atcctgacgc    12600
gttccggcag cagccgcagg ccaaccggct ctccgcaatt ctggaagcgg tggtcccggc    12660
gcgcgcaaac cccacgcacg agaaggtgct ggcgatcgta aacgcgctgg ccgaaaacag    12720
ggccatccgg cccgacgagg ccggcctggt ctacgacgcg ctgcttcagc gcgtggctcg    12780
ttacaacagc ggcaacgtgc agaccaacct ggaccggctg gtgggggatg tgcgcgaggc    12840
cgtggcgcag cgtgagcgcg cgcagcagca gggcaacctg ggctccatgg ttgcactaaa    12900
cgccttcctg agtacacagc ccgccaacgt gccgcgggga caggaggact acaccaactt    12960
tgtgagcgca ctgcggctaa tggtgactga gacaccgcaa agtgaggtgt accagtctgg    13020
gccagactat tttttccaga ccagtagaca aggcctgcag accgtaaacc tgagccaggc    13080
tttcaaaaac ttgcagggc tgtgggggt gcgggctccc acaggcgacc gcgcgaccgt    13140
gtctagcttg ctgacgccca actcgcgcct gttgctgctg ctaatagcgc ccttcacgga    13200
cagtggcagc gtgtcccggg acacataccet aggtcacttg ctgacactgt accgcgaggc    13260
cataggtcag gcgcatgtgg acgagcatac tttccaggag attacaagtg tcagccgcgc    13320
gctggggcag gaggacacgg gcagcctgga ggcaacccta aactacctgc tgaccaaccg    13380
gcggcagaag atcccctcgt tgcacagttt aaacagcgag gaggagcgca ttttgcgcta    13440
cgtgcagcag agcgtgagcc ttaacctgat gcgcgacggg gtaacgccca gcgtggcgct    13500
ggacatgacc gcgcgcaaca tggaaccggg catgtatgcc tcaaaccggc cgtttatcaa    13560
ccgcctaatg gactacttgc atcgcgcggc cgccgtgaac cccgagtatt tcaccaatgc    13620
catcttgaac ccgcactggc taccgcccc tggtttctac accgggggat cgaggtgcc    13680
```

-continued

| | |
|---|---|
| cgagggtaac gatggattcc tctgggacga catagacgac agcgtgtttt ccccgcaacc | 13740 |
| gcagaccctg ctagagttgc aacagcgcga gcaggcagag gcggcgctgc gaaaggaaag | 13800 |
| cttccgcagg ccaagcagct tgtccgatct aggcgctgcg gccccgcggt cagatgctag | 13860 |
| tagcccattt ccaagcttga tagggtctct taccagcact cgcaccaccc gcccgcgcct | 13920 |
| gctgggcgag gaggagtacc taaacaactc gctgctgcag ccgcagcgcg aaaaaaacct | 13980 |
| gcctccggca tttcccaaca acgggataga gagcctagtg gacaagatga gtagatggaa | 14040 |
| gacgtacgcg caggagcaca gggacgtgcc aggcccgcgc ccgcccaccc gtcgtcaaag | 14100 |
| gcacgaccgt cagcggggtc tggtgtggga ggacgatgac tcggcagacg acagcagcgt | 14160 |
| cctggatttg ggagggagtg gcaacccgtt tgcgcacctt cgccccaggc tggggagaat | 14220 |
| gttttaaaaa aaaaaaagca tgatgcaaaa taaaaaactc accaaggcca tggcaccgag | 14280 |
| cgttggtttt cttgtattcc ccttagtatg cggcgcgcgg cgatgtatga ggaaggtcct | 14340 |
| cctccctcct acgagagtgt ggtgagcgcg gcgccagtgg cggcggcgct gggttctccc | 14400 |
| ttcgatgctc ccctggaccc gccgtttgtg cctccgcggt acctgcggcc taccgggggg | 14460 |
| agaaacagca tccgttactc tgagttggca cccctattcg acaccacccg tgtgtacctg | 14520 |
| gtggacaaca agtcaacgga tgtggcatcc ctgaactacc agaacgacca cagcaacttt | 14580 |
| ctgaccacgg tcattcaaaa caatgactac agcccggggg aggcaagcac acagaccatc | 14640 |
| aatcttgacg accggtcgca ctgggcggc gacctgaaaa ccatcctgca taccaacatg | 14700 |
| ccaaatgtga acgagttcat gtttaccaat aagtttaagg cgcgggtgat ggtgtcgcgc | 14760 |
| ttgcctacta aggacaatca ggtggagctg aaatacgagt gggtggagtt cacgctgccc | 14820 |
| gagggcaact actccgagac catgaccata gaccttatga caacgcgat cgtggagcac | 14880 |
| tacttgaaag tgggcagaca gaacgggtt ctggaaagcg acatcggggt aaagtttgac | 14940 |
| acccgcaact tcagactggg gtttgacccc gtcactggtc ttgtcatgcc tggggtatat | 15000 |
| acaaacgaag ccttccatcc agacatcatt ttgctgccag gatgcggggt ggacttcacc | 15060 |
| cacagccgcc tgagcaactt gttgggcatc cgcaagcggc aacccttcca ggagggcttt | 15120 |
| aggatcacct acgatgatct ggagggtggt aacattcccg cactgttgga tgtggacgcc | 15180 |
| taccaggcga gcttgaaaga tgacaccgaa cagggcgggg gtggcgcagg cggcagcaac | 15240 |
| agcagtggca gcgcgcgga agagaactcc aacgcggcag ccgcggcaat gcagccggtg | 15300 |
| gaggacatga acgatcatgc cattcgcggc gacacctttg ccacacgggc tgaggagaag | 15360 |
| cgcgctgagg ccgaagcagc ggccgaagct gccgcccccg ctgcgcaacc cgaggtcgag | 15420 |
| aagcctcaga agaaaccggt gatcaaaccc ctgacagagg acagcaagaa acgcagttac | 15480 |
| aacctaataa gcaatgacag caccttcacc cagtaccgca gctggtacct tgcatacaac | 15540 |
| tacggcgacc ctcagaccgg aatccgctca tggaccctgc tttgcactcc tgacgtaacc | 15600 |
| tgcggctcgg agcaggtcta ctggtcgttg ccagacatga tgcaagaccc cgtgaccttc | 15660 |
| cgctccacgc gccagatcag caacttccgg gtggtgggcg ccgagctgtt gcccgtgcac | 15720 |
| tccaagagct tctacaacga ccaggccgtc tactcccaac tcatccgcca gtttacctct | 15780 |
| ctgacccacg tgttcaatcg ctttcccgag aaccagattt ggcgcgccc gccagccccc | 15840 |
| accatcacca ccgtcagtga aaacgttcct gctctcacag atcacgggac gctaccgctg | 15900 |
| cgcaacagca tcgaggagt ccagcgagtg accattactg acgccagacg ccgcacctgc | 15960 |
| ccctacgttt acaaggccct gggcatagtc tcgccgcgcg tcctatcgag ccgcactttt | 16020 |

```
tgagcaagca tgtccatcct tatatcgccc agcaataaca caggctgggg cctgcgcttc   16080
ccaagcaaga tgtttggcgg ggccaagaag cgctccgacc aacacccagt gcgcgtgcgc   16140
gggcactacc gcgcgccctg gggcgcgcac aaacgcggcc gcactgggcg caccaccgtc   16200
gatgacgcca tcgacgcggt ggtggaggag gcgcgcaact acacgcccac gccgccacca   16260
gtgtccacag tggacgcggc cattcagacc gtggtgcgcg gagcccggcg ctatgctaaa   16320
atgaagagac ggcggaggcg cgtagcacgt cgccaccgcc gccgacccgg cactgccgcc   16380
caacgcgcgg cggcggccct gcttaaccgc gcacgtcgca ccggccgacg ggcggccatg   16440
cgggccgctc gaaggctggc cgcgggtatt gtcactgtgc ccccaggtc caggcgacga    16500 gcggccgccg cagcagccgc ggccattagt gctatgactc agggtcgcag gggcaacgtg   16560
tattgggtgc gcgactcggt tagcggcctg cgcgtgcccg tgcgcacccg cccccgcgc    16620 aactagattg caagaaaaaa ctacttagac tcgtactgtt gtatgtatcc agcggcggcg   16680
gcgcgcaacg aagctatgtc caagcgcaaa atcaaagaag atgctcca ggtcatcgcg     16740 ccggagatct atggcccccc gaagaaggaa gagcaggatt acaagcccg aaagctaaag    16800 cgggtcaaaa agaaaaagaa agatgatgat gatgaacttg acgacgaggt ggaactgctg   16860
cacgctaccg cgcccaggcg acgggtacag tggaaaggtc gacgcgtaaa acgtgttttg   16920
cgacccggca ccaccgtagt ctttacgccc ggtgagcgct ccaccccgcac ctacaagcgc  16980 gtgtatgatg aggtgtacgg cgacgaggac ctgcttgagc aggccaacga gcgcctcggg   17040
gagtttgcct acggaaagcg gcataaggac atgctggcgt tgccgctgga cgagggcaac   17100
ccaacaccta gcctaaagcc cgtaacactg cagcaggtgc tgcccgcgct tgcaccgtcc   17160
gaagaaaagc gcggcctaaa gcgcgagtct ggtgacttgg cacccaccgt gcagctgatg   17220
gtacccaagc gccagcgact ggaagatgtc ttggaaaaaa tgaccgtgga acctgggctg   17280
gagcccgagg tccgcgtgcg gccaatcaag caggtggcgc cgggactggg cgtgcagacc   17340
gtggacgttc agatacccac taccagtagc accagtattg ccaccgccac agagggcatg   17400
gagacacaaa cgtccccggt tgcctcagcg gtggcggatg ccgcggtgca ggcggtcgct   17460
gcggccgcgt ccaagacctc tacggaggtg caaacggacc cgtggatgtt tcgcgtttca   17520
gccccccggc gcccgcgcgg ttcgaggaag tacgcgcccg ccagcgcgct actgcccgaa   17580
tatgccctac atccttccat gcgcctaccc cccggctatc gtggctacac ctaccgcccc   17640
agaagacgag caactacccg acgccgaacc accactggaa cccgccgccg ccgtcgccgt   17700
cgccagcccg tgctggcccc gatttccgtg cgcagggtgg ctcgcgaagg aggcaggacc   17760
ctggtgctgc aacagcgcg ctaccacccc agcatcgttt aaaagccggt ctttgtggtt    17820
cttgcagata tggccctcac ctgccgcctc cgtttcccgg tgccgggatt ccgaggaaga   17880
atgcaccgta ggaggggcat ggccggccac ggcctgacgg gcggcatgcg tcgtgcgcac   17940
caccggcggc ggcgcgcgtc gcaccgtcgc atgcgcggcg gtatcctgcc cctccttatt   18000
ccactgatcg ccgcggcgat tggcgccgtg cccggaattg catccgtggc cttgcaggcg   18060
cagagacact gattaaaaac aagttgcatg tggaaaaatc aaaataaaaa gtctggactc   18120
tcacgctcgc ttggtcctgt aactattttg tagaatggaa gacatcaact ttgcgtctct   18180
ggccccgcga cacggctcgc gcccgttcat gggaaactgg caagatatcg gcaccagcaa   18240
tatgagcggt ggcgccttca gctgggctc gctgtggagc ggcattaaaa atttcggttc    18300
caccgttaag aactatggca gcaaggcctg gaacagcagc acaggccaga tgctgaggga   18360
taagttgaaa gagcaaaatt tccaacaaaa ggtggtagat ggcctggcct ctggcattag   18420
```

```
cggggtggtg gacctggcca accaggcagt gcaaaataag attaacagta agcttgatcc   18480
ccgccctccc gtagaggagc ctccaccggc cgtggagaca gtgtctccag aggggcgtgg   18540
cgaaaagcgt ccgcgccccg acagggaaga aactctggtg acgcaaatag acgagcctcc   18600
ctcgtacgag gaggcactaa agcaaggcct gcccaccacc cgtcccatcg cgcccatggc   18660
taccggagtg ctgggccagc acacaccgt aacgctggac ctgcctcccc ccgccgacac   18720
ccagcagaaa cctgtgctgc caggcccgac cgccgttgtt gtaacccgtc ctagccgcgc   18780
gtccctgcgc cgcgccgcca gcggtccgcg atcgttgcgg cccgtagcca gtggcaactg   18840
gcaaagcaca ctgaacagca tcgtgggtct ggggtgcaa tccctgaagc gccgacgatg   18900
cttctgaata gctaacgtgt cgtatgtgtg tcatgtatgc gtccatgtcg ccgccagagg   18960
agctgctgag ccgccgcgcg cccgcttttc aagatggcta ccccttcgat gatgccgcag   19020
tggtcttaca tgcacatctc gggccaggac gcctcggagt acctgagccc cgggctggtg   19080
cagtttgccc gcgccaccga gacgtacttc agcctgaata caagtttag aaaccccacg   19140 gtggcgccta cgcacgacgt gaccacagac cggtcccagc gtttgacgct gcggttcatc   19200
cctgtggacc gtgaggatac tgcgtactcg tacaaggcgc ggttcacccct agctgtgggt   19260 gataaccgtg tgctggacat ggcttccacg tactttgaca tccgcggcgt gctggacagg   19320
ggccctactt ttaagcccta ctctggcact gcctacaacg ccctggctcc caagggtgcc   19380
ccaaatcctt gcgaatggga tgaagctgct actgctcttg aaataaacct agaagaagag   19440
gacgatgaca acgaagacga agtagacgag caagctgagc agcaaaaaac tcacgtattt   19500
gggcaggcgc cttattctgg tataaatatt acaaaggagg gtattcaaat aggtgtcgaa   19560
ggtcaaacac ctaaatatgc cgataaaaca tttcaacctg aacctcaaat aggagaatct   19620
cagtggtacg aaactgaaat taatcatgca gctgggagag tccttaaaaa gactacccca   19680
atgaaaccat gttacggttc atatgcaaaa cccacaaatg aaaatggagg gcaaggcatt   19740
cttgtaaagc aacaaaatgg aaagctagaa agtcaagtgg aaatgcaatt tttctcaact   19800
actgaggcga ccgcaggcaa tggtgataac ttgactccta agtggtatt gtacagtgaa   19860 gatgtagata tagaaacccc agacactcat atttcttaca tgcccactat taaggaaggt   19920
aactcacgag aactaatggg ccaacaatct atgcccaaca ggcctaatta cattgctttt   19980
agggacaatt ttattggtct aatgtattac aacagcacgg taatatggg tgttctggcg   20040 ggccaagcat cgcagttgaa tgctgttgta gatttgcaag acagaaacac agagcttcca   20100
taccagcttt tgcttgattc cattggtgat agaaccaggt acttttctat gtggaatcag   20160
gctgttgaca gctatgatcc agatgttaga attattgaaa atcatggaac tgaagatgaa   20220
cttccaaatt actgctttcc actgggaggt gtgattaata cagagactct taccaaggta   20280
aaacctaaaa caggtcagga aaatggatgg gaaaaagatg ctacagaatt ttcagataaa   20340
aatgaaataa gagttggaaa taattttgcc atggaaatca atctaaatgc caacctgtgg   20400
agaaatttcc tgtactccaa catagcgctg tatttgcccg acaagctaaa gtacagtcct   20460
tccaacgtaa aaatttctga taacccaaac acctacgact acatgaacaa gcgagtggtg   20520
gctcccgggt tagtggactg ctacattaac cttggagcac gctggtccct tgactatatg   20580
gacaacgtca acccatttaa ccaccaccgc aatgctggcc tgcgctaccg ctcaatgttg   20640
ctgggcaatg tcgctatgt gcccttccac atccaggtgc ctcagaagtt ctttgccatt   20700
aaaaacctcc ttctcctgcc gggctcatac acctacgagt ggaacttcag gaaggatgtt   20760
```

```
aacatggttc tgcagagctc cctaggaaat gacctaaggg ttgacggagc cagcattaag    20820
tttgatagca tttgccttta cgccaccttc ttccccatgg cccacaacac cgcctccacg    20880
cttgaggcca tgcttagaaa cgacaccaac gaccagtcct ttaacgacta tctctccgcc    20940
gccaacatgc tctaccctat acccgccaac gctaccaacg tgcccatatc catcccctcc    21000
cgcaactggg cggctttccg cggctgggcc ttcacgcgcc ttaagactaa ggaaacccca    21060
tcactgggct cgggctacga cccttattac acctactctg gctctatacc ctacctagat    21120
ggaaccttt  acctcaacca caccttaag aaggtggcca ttacctttga ctcttctgtc    21180
agctggcctg gcaatgaccg cctgcttacc cccaacgagt ttgaaattaa gcgctcagtt    21240
gacgggagg gttacaacgt tgcccagtgt aacatgacca aagactggtt cctggtacaa    21300
atgctagcta actacaacat ggctaccag ggcttctata tcccagagag ctacaaggac    21360
cgcatgtact ccttctttag aaacttccag cccatgagcc gtcaggtggt ggatgatact    21420
aaatacaagg actaccaaca ggtgggcatc ctacaccaac acaacaactc tggatttgtt    21480
ggctaccttg cccccaccat gcgcgaagga caggcctacc ctgctaactt cccctatccg    21540
cttataggca agaccgcagt tgacagcatt acccagaaaa agtttctttg cgatcgcacc    21600
cttttggcgca tcccattctc cagtaacttt atgtccatgg gcgcactcac agacctgggc    21660
caaaaccttc tctacgccaa ctccgcccac gcgctagaca tgacttttga ggtggatccc    21720
atggacgagc ccaccctttct ttatgttttg tttgaagtct ttgacgtggt ccgtgtgcac    21780
cggccgcacc gcggcgtcat cgaaaccgtg tacctgcgca cgcccttctc ggccggcaac    21840
gccacaacat aaagaagcaa gcaacatcaa caacagctgc cgccatgggc tccagtgagc    21900
aggaactgaa agccattgtc aaagatcttg gttgtgggcc atattttttg ggcacctatg    21960
acaagcgctt tccaggcttt gtttctccac acaagctcgc ctgcgccata gtcaatacgg    22020
ccggtcgcga gactggggggc gtacactgga tggcctttgc ctggaacccg cactcaaaaa    22080
catgctacct ctttgagccc tttggctttt ctgaccagcg actcaagcag gtttaccagt    22140
ttgagtacga gtcactcctg cgccgtagcg ccattgcttc ttcccccgac cgctgtataa    22200
cgctggaaaa gtccacccaa agcgtacagg ggcccaactc ggccgcctgt ggactattct    22260
gctgcatgtt tctccacgcc tttgccaact ggccccaaac tcccatggat cacaacccca    22320
ccatgaacct tattaccggg gtacccaact ccatgctcaa cagtccccag gtacagccca    22380
ccctgcgtcg caaccaggaa cagctctaca gcttcctgga gcgccactcg ccctacttcc    22440
gcagccacag tgcgcagatt aggagcgcca cttcttttg tcacttgaaa acatgtaaa    22500
aataatgtac tagagacact ttcaataaag gcaaatgctt ttatttgtac actctcgggt    22560
gattatttac ccccaccctt gccgtctgcg ccgtttaaaa atcaaagggg ttctgccgcg    22620
catcgctatg cgccactggc agggacacgt tgcgatactg gtgtttagtg ctccacttaa    22680
actcaggcac aaccatccgc ggcagctcgg tgaagttttc actccacagg ctgcgcacca    22740
tcaccaacgc gtttagcagg tcgggcgccg atatcttgaa gtcgcagttg gggcctccgc    22800
cctgcgcgcg cgagttgcga tacacagggt tgcagcactg gaacactatc agcgccgggt    22860
ggtgcacgct ggccagcacg ctcttgtcgg agatcagatc cgcgtccagg tcctccgcgt    22920
tgctcagggc gaacggagtc aactttggta gctgccttcc caaaagggc gcgtgcccag    22980
gctttgagtt gcactcgcac cgtagtggca tcaaaggtg accgtgcccg gtctgggcgt    23040
taggatacag cgcctgcata aaagccttga tctgcttaaa agccacctga gcctttgcgc    23100
cttcagagaa gaacatgccg caagacttgc cggaaaactg attggccgga caggccgcgt    23160
```

```
cgtgcacgca gcaccttgcg tcggtgttgg agatctgcac cacatttcgg ccccaccggt   23220
tcttcacgat cttggccttg ctagactgct ccttcagcgc gcgctgcccg ttttcgctcg   23280
tcacatccat ttcaatcacg tgctccttat ttatcataat gcttccgtgt agacacttaa   23340
gctcgccttc gatctcagcg cagcggtgca gccacaacgc gcagcccgtg ggctcgtgat   23400
gcttgtaggt cacctctgca aacgactgca ggtacgcctg caggaatcgc cccatcatcg   23460
tcacaaaggt cttgttgctg gtgaaggtca gctgcaaccc gcggtgctcc tcgttcagcc   23520
aggtcttgca tacggccgcc agagcttcca cttggtcagg cagtagtttg aagttcgcct   23580
ttagatcgtt atccacgtgg tacttgtcca tcagcgcgcg cgcagcctcc atgcccttct   23640
cccacgcaga cacgatcggc acactcagcg ggttcatcac cgtaatttca ctttccgctt   23700
cgctgggctc ttcctcttcc tcttgcgtcc gcataccacg cgccactggg tcgtcttcat   23760
tcagccgccg cactgtgcgc ttacctcctt tgccatgctt gattagcacc ggtgggttgc   23820
tgaaacccac catttgtagc gccacatctt ctctttcttc ctcgctgtcc acgattacct   23880
ctggtgatgg cgggcgctcg ggcttgggag aagggcgctt cttttcttc ttgggcgcaa   23940 tggccaaatc cgccgccgag gtcgatggcc gcgggctggg tgtgcgcggc accagcgcgt   24000
cttgtgatga gtcttcctcg tcctcggact cgatacgccg cctcatccgc ttttttgggg   24060
gcgcccgggg aggcggcggc gacggggacg gggacgacac gtcctccatg gttggggac    24120 gtcgcgccgc accgcgtccg cgctcggggg tggtttcgcg ctgctcctct tcccgactgg   24180
ccatttcctt ctcctataggg cagaaaaaga tcatggagtc agtcgagaag aaggacagcc   24240
taaccgcccc ctctgagttc gccaccaccg cctccaccga tgccgccaac gcgcctacca   24300
ccttccccgt cgaggcaccc ccgcttgagg aggaggaagt gattatcgag caggacccag   24360
gttttgtaag cgaagacgac gaggaccgct cagtaccaac agaggataaa aagcaagacc   24420
aggacaacgc agaggcaaac gaggaacaag tcgggcgggg ggacgaaagg catggcgact   24480
acctagatgt gggagacgac gtgctgttga agcatctgca gcgccagtgc gccattatct   24540
gcgacgcgtt gcaagagcgc agcgatgtgc ccctcgccat agcggatgtc agccttgcct   24600
acgaacgcca cctattctca ccgcgcgtac ccccaaacg ccaagaaaac ggcacatgcg   24660
agcccaaccc gcgcctcaac ttctaccccg tatttgccgt gccagaggtg cttgccacct   24720
atcacatctt tttccaaaac tgcaagatac ccctatcctg ccgtgccaac cgcagccgag   24780
cggacaagca gctggccttg cggcagggcg ctgtcatacc tgatatcgcc tcgctcaacg   24840
aagtgccaaa aatctttgag ggtcttggac gcgacgagaa gcgcgcggca aacgctctgc   24900
aacaggaaaa cagcgaaaat gaaagtcact ctggagtgtt ggtggaactc gagggtgaca   24960
acgcgcgcct agccgtacta aaacgcagca tcgaggtcac ccactttgcc tacccggcac   25020
ttaacctacc ccccaaggtc atgagcacag tcatgagtga gctgatcgtg cgccgtgcgc   25080
agccctggga gagggatgca aatttgcaag aacaaacaga ggagggccta cccgcagttg   25140
gcgacgagca gctagcgcgc tggcttcaaa cgcgcgagcc tgccgacttg gaggagcgac   25200
gcaaactaat gatggccgca gtgctcgtta ccgtggagct tgagtgcatg cagcggttct   25260
ttgctgaccc ggagatgcag cgcaagctag aggaaacatt gcactacacc tttcgacagg   25320
gctacgtacg ccaggcctgc aagatctcca acgtggagct ctgcaacctg gtctcctacc   25380
ttggaatttt gcacgaaaac cgccttgggc aaaacgtgct tcattccacg ctcaagggcg   25440
aggcgcgccg cgactacgtc cgcgactgcg tttacttatt tctatgctac acctggcaga   25500
```

```
cggccatggg cgtttggcag cagtgcttgg aggagtgcaa cctcaaggag ctgcagaaac   25560
tgctaaagca aaacttgaag gacctatgga cggccttcaa cgagcgctcc gtggccgcgc   25620
acctggcgga catcattttc cccgaacgcc tgcttaaaac cctgcaacag ggtctgccag   25680
acttcaccag tcaaagcatg ttgcagaact ttaggaactt tatcctagag cgctcaggaa   25740
tcttgcccgc cacctgctgt gcacttccta gcgactttgt gcccattaag taccgcgaat   25800
gccctccgcc gctttgggc cactgctacc ttctgcagct agccaactac cttgcctacc     25860
actctgacat aatggaagac gtgagcggtg acggtctact ggagtgtcac tgtcgctgca   25920
acctatgcac cccgcaccgc tccctggttt gcaattcgca gctgcttaac gaaagtcaaa   25980
ttatcggtac ctttgagctg cagggtccct cgcctgacga aaagtccgcg gctccggggt   26040
tgaaactcac tccggggctg tggacgtcgg cttaccttcg caaatttgta cctgaggact   26100
accacgccca cgagattagg ttctacgaag accaatcccg cccgccaaat gcggagctta   26160
ccgcctgcgt cattacccag ggccacattc ttggccaatt gcaagccatc aacaaagccc   26220
gccaagagtt tctgctacga aagggacggg gggtttactt ggaccccag tccggcgagg      26280
agctcaaccc aatcccccg ccgccgcagc cctatcagca gcagccgcgg gcccttgctt      26340
cccaggatgg cacccaaaaa gaagctgcag ctgccgccgc cacccacgga cgaggaggaa   26400
tactgggaca gtcaggcaga ggaggttttg gacgaggagg aggaggacat gatggaagac   26460
tgggagagcc tagacgagga agcttccgag gtcgaagagg tgtcagacga acaccgtca      26520
ccctcggtcg cattcccctc gccggcgccc cagaaatcgg caaccggttc cagcatggct   26580
acaacctccg ctcctcaggc gccgccgca ctgcccgttc gccgacccaa ccgtagatgg       26640
gacaccactg gaaccagggc cggtaagtcc aagcagccgc cgccgttagc ccaagagcaa   26700
caacagcgca aaggctaccg ctcatggcgc gggcacaaga acgccatagt tgcttgcttg   26760
caagactgtg ggggcaacat ctccttcgcc cgccgctttc ttctctacca tcacggcgtg   26820
gccttccccc gtaacatcct gcattactac cgtcatctct acagcccata ctgcaccggc   26880
ggcagcggca gcggcagcaa cagcagcggc cacacagaag caaaggcgac cggatagcaa   26940
gactctgaca aagcccaaga aatccacagc ggcggcagca gcaggaggag gagcgctgcg   27000
tctggcgccc aacgaacccg tatcgacccg cgagcttaga aacaggattt ttcccactct   27060
gtatgctata tttcaacaga gcaggggcca agaacaagag ctgaaaataa aaacaggtc       27120
tctgcgatcc ctcacccgca gctgcctgta tcacaaaagc gaagatcagc ttcggcgcac   27180
gctggaagac gcggaggctc tcttcagtaa atactgcgcg ctgactctta aggactagtt   27240
tcgcgccctt tctcaaattt aagcgcgaaa actacgtcat ctccagcggc cacacccggc   27300
gccagcacct gtcgtcagcg ccattatgag caaggaaatt cccacgccct acatgtggag   27360
ttaccagcca caaatgggac ttgcggctgg agctgcccaa gactactcaa cccgaataaa   27420
ctacatgagc gcgggacccc acatgatatc ccgggtcaac ggaatccgcg cccaccgaaa   27480
ccgaattctc ttggaacagg cggctattac caccacacct cgtaataacc ttaatccccg   27540
tagttggccc gctgccctgg tgtaccagga aagtcccgct cccaccactg tggtacttcc   27600
cagagacgcc caggccgaag ttcagatgac taactcaggg gcgcagcttg cgggcggctt   27660
tcgtcacagg gtgcggtcgc ccgggcaggg tataactcac ctgacaatca gagggcgagg   27720
tattcagctc aacgacgagt cggtgagctc ctcgcttggt ctccgtccgg acgggacatt   27780
tcagatcggc ggcgccggcc gtccttcatt cacgcctcgt caggcaatcc taactctgca   27840
gacctcgtcc tctgagccgc gctctggagg cattggaact ctgcaattta ttgaggagtt   27900
```

```
tgtgccatcg gtctacttta acccttctc gggacctccc ggccactatc cggatcaatt   27960
tattcctaac tttgacgcgg taaaggactc ggcggacggc tacgactgaa tgttaagtgg   28020
agaggcagag caactgcgcc tgaaacacct ggtccactgt cgccgccaca agtgctttgc   28080
ccgcgactcc ggtgagtttt gctactttga attgcccgag gatcatatcg agggcccggc   28140
gcacggcgtc cggcttaccg cccagggaga gcttgcccgt agcctgattc gggagtttac   28200
ccagcgcccc ctgctagttg agcgggacag gggaccctgt gttctcactg tgatttgcaa   28260
ctgtcctaac cttggattac atcaagatcc tctagttata actagagtac ccggggatct   28320
tattcccttt aactaataaa aaaaataat aaagcatcac ttacttaaaa tcagttagca   28380
aatttctgtc cagtttattc agcagcacct ccttgccctc ctcccagctc tggtattgca   28440
gcttcctcct ggctgcaaac tttctccaca atctaaatgg aatgtcagtt tcctcctgtt   28500
cctgtccatc cgcacccact atcttcatgt tgttgcagat gaagcgcgca agaccgtctg   28560
aagatacctt caaccccgtg tatccatagg gatttaaata gaatcgtttg tgttatgttt   28620
caacgtgttt attttcaat tgcagaaaat ttcaagtcat ttttcattca gtagtatagc   28680
cccaccacca catagcttat acagatcacc gtaccttaat caaactcaca gaaccctagt   28740
attcaacctg ccacctccct cccaacacac agagtacaca gtcctttctc cccggctggc   28800
cttaaaaagc atcatatcat gggtaacaga catattctta ggtgttatat tccacacggt   28860
ttcctgtcga gccaaacgct catcagtgat attaataaac tccccgggca gctcacttaa   28920
gttcatgtcg ctgtccagct gctgagccac aggctgctgt ccaacttgcg gttgcttaac   28980
gggcggcgaa ggagaagtcc acgcctacat gggggtagag tcataatcgt gcatcaggat   29040
agggcggtgg tgctgcagca gcgcgcgaat aaactgctgc cgccgccgct ccgtcctgca   29100
ggaatacaac atggcagtgg tctcctcagc gatgattcgc accgcccgca gcataaggcg   29160
ccttgtcctc cgggcacagc agcgcaccct gatctcactt aaatcagcac agtaactgca   29220
gcacagcacc acaatattgt tcaaaatccc acagtgcaag gcgctgtatc caaagctcat   29280
ggcggggacc acagaaccca cgtggccatc ataccacaag cgcaggtaga ttaagtggcg   29340
acccctcata aacacgctgg acataaacat tacctctttt ggcatgttgt aattcaccac   29400
ctcccggtac catataaacc tctgattaaa catggcgcca tccaccacca tcctaaacca   29460
gctggccaaa acctgcccgc cggctataca ctgcagggaa ccgggactgg aacaatgaca   29520
gtggagagcc caggactcgt aaccatggat catcatgctc gtcatgatat caatgttggc   29580
acaacacagg cacacgtgca tacacttcct caggattaca agctcctccc gcgttagaac   29640
catatcccag ggaacaaccc attcctgaat cagcgtaaat cccacactgc agggaagacc   29700
tcgcacgtaa ctcacgttgt gcattgtcaa agtgttacat tcgggcagca gcggatgatc   29760
ctccagtatg gtagcgcggg tttctgtctc aaaaggaggt agacgatccc tactgtacgg   29820
agtgcgccga gacaaccgag atcgtgttgg tcgtagtgtc atgccaaatg aacgccgga   29880 cgtagtcata tttcctgaag caaaaccagg tgcgggcgtg acaaacagat ctgcgtctcc   29940
ggtctcgccg cttagatcgc tctgtgtagt agttgtagta tatccactct ctcaaagcat   30000
ccaggcgccc cctggcttcg ggttctatgt aaactccttc atgcgccgct gccctgataa   30060
catccaccac cgcagaataa gccacaccca gccaacctac acattcgttc tgcgagtcac   30120
acacgggagg agcgggaaga gctggaagaa ccatgttttt ttttttattc caaagatta   30180 tccaaaacct caaaatgaag atctattaag tgaacgcgct cccctccggt ggcgtggtca   30240
```

```
aactctacag ccaaagaaca gataatggca tttgtaagat gttgcacaat ggcttccaaa    30300
aggcaaacgg ccctcacgtc caagtggacg taaaggctaa acccttcagg gtgaatctcc    30360
tctataaaca ttccagcacc ttcaaccatg cccaaataat tctcatctcg ccaccttctc    30420
aatatatctc taagcaaatc ccgaatatta agtccggcca ttgtaaaaat ctgctccaga    30480
gcgcccctcca ccttcagcct caagcagcga atcatgattg caaaaattca ggttcctcac   30540
agacctgtat aagattcaaa agcggaacat taacaaaaat accgcgatcc cgtaggtccc    30600
ttcgcagggc cagctgaaca taatcgtgca ggtctgcacg gaccagcgcg gccacttccc    30660
cgccaggaac cttgacaaaa gaacccacac tgattatgac acgcatactc ggagctatgc    30720
taaccagcgt agccccgatg taagctttgt tgcatgggcg gcgatataaa atgcaaggtg    30780
ctgctcaaaa aatcaggcaa agcctcgcgc aaaaagaaa gcatcgta gtcatgctca       30840
tgcagataaa ggcaggtaag ctccggaacc accacagaaa aagacaccat tttctctca    30900
aacatgtctg cgggtttctg cataaacaca aaataaaata acaaaaaaac atttaaacat    30960
tagaagcctg tcttacaaca ggaaaaacaa cccttataag cataagacgg actacggcca    31020
tgccggcgtg accgtaaaaa aactggtcac cgtgattaaa aagcaccacc gacagctcct    31080
cggtcatgtc cggagtcata atgtaagact cggtaaacac atcaggttga ttcatcggtc    31140
agtgctaaaa agcgaccgaa atagcccggg ggaatacata cccgcaggcg tagagacaac    31200
attacagccc ccataggagg tataacaaaa ttaataggag agaaaaacac ataaacacct    31260
gaaaaaccct cctgcctagg caaaatagca ccctcccgct ccagaacaac atacagcgct    31320
tcacagcggc agcctaacag tcagccttac cagtaaaaaa gaaaacctat taaaaaaaca    31380
ccactcgaca cggcaccagc tcaatcagtc acagtgtaaa aagggccaa gtgcagagcg     31440
agtatatata ggactaaaaa atgacgtaac ggttaaagtc cacaaaaaac acccagaaaa    31500
ccgcacgcga acctacgccc agaaacgaaa gccaaaaaac ccacaacttc ctcaaatcgt    31560
cacttccgtt ttcccacgtt acgtaacttc ccattttaag aaaactacaa ttcccaacac    31620
atacaagtta ctccgcccta aaacctacgt cacccgcccc gttcccacgc cccgcgccac    31680
gtcacaaact ccaccccctc attatcatat tggcttcaat ccaaaataag gtatattatt    31740
gatgatnnnn nttaat                                                    31756
```

<210> SEQ ID NO 9
<211> LENGTH: 9725
<212> TYPE: DNA
<213> ORGANISM: Artificial sequence
<220> FEATURE:
<223> OTHER INFORMATION: Recombinant shuttle virus D24 pIX frame nhe sal
      sv, n=A,C,G,T
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (991)..(993)
<223> OTHER INFORMATION: n is a, c, g, or t
<220> FEATURE:
<221> NAME/KEY: misc_feature
<222> LOCATION: (1008)..(1010)
<223> OTHER INFORMATION: n is a, c, g, or t
<220> FEATURE:
<221> NAME/KEY: misc_feature
<222> LOCATION: (9714)..(9716)
<223> OTHER INFORMATION: n is a, c, g, or t

<400> SEQUENCE: 9

```
aattcnnnta taaaatgcaa ggtgctgctc aaaaaatcag gcaaagcctc gcgcaaaaaa         60
gaaagcacat cgtagtcatg ctcatgcaga taaaggcagg taagctccgg aaccaccaca        120
gaaaaagaca ccattttct ctcaaacatg tctgcgggtt tctgcataaa cacaaaataa         180
aataacaaaa aaacatttaa acattagaag cctgtcttac aacaggaaaa acaacccta         240
taagcataag acggactacg gccatgccgg cgtgaccgta aaaaaactgg tcaccgtgat        300
taaaaagcac caccgacagc tcctcggtca tgtccggagt cataatgtaa gactcggtaa       360
acacatcagg ttgattcatc ggtcagtgct aaaaagcgac cgaaatagcc cgggggaata       420
catacccgca ggcgtagaga caacattaca gcccccatag gaggtataac aaaattaata      480
ggagagaaaa acacataaac acctgaaaaa ccctcctgcc taggcaaaat agcaccctcc       540
cgctccagaa caacatacag cgcttcacag cggcagccta acagtcagcc ttaccagtaa       600
aaagaaaac ctattaaaaa aacaccactc gacacggcac cagctcaatc agtcacagtg       660
taaaaaggg ccaagtgcag agcgagtata tataggacta aaaaatgacg taacggttaa       720
agtccacaaa aaacacccag aaaaccgcac gcgaacctac gcccagaaac gaaagccaaa      780
aaacccacaa cttcctcaaa tcgtcacttc cgttttccca cgttacgtaa cttcccattt       840
taagaaaact acaattccca acacatacaa gttactccgc cctaaaacct acgtcacccg       900
ccccgttccc acgccccgcg ccacgtcaca aactccaccc cctcattatc atattggctt       960
caatccaaaa taaggtatat tattgatgat nnnttaatta aggatccnnn cggtgtgaaa      1020
taccgcacag atgcgtaagg agaaaatacc gcatcaggcg ctcttccgct tcctcgctca      1080
ctgactcgct gcgctcggtc gttcggctgc ggcgagcggt atcagctcac tcaaaggcgg      1140
taatacggtt atccacagaa tcaggggata acgcaggaaa gaacatgtga gcaaaaggcc      1200
agcaaaaggc caggaaccgt aaaaaggccg cgttgctggc gttttccat aggctccgcc      1260
cccctgacga gcatcacaaa aatcgacgct caagtcagag gtggcgaaac ccgacaggac      1320
tataaagata ccaggcgttt ccccctggaa gctccctcgt gcgctctcct gttccgaccc      1380
tgccgcttac cggatacctg tccgccttc tcccttcggg aagcgtggcg ctttctcata      1440
gctcacgctg taggtatctc agttcggtgt aggtcgttcg ctccaagctg ggctgtgtgc      1500
acgaaccccc cgttcagccc gaccgctgcg ccttatccgg taactatcgt cttgagtcca      1560
acccggtaag acacgactta tcgccactgg cagcagccac tggtaacagg attagcagag      1620
cgaggtatgt aggcggtgct acagagttct tgaagtggtg gcctaactac ggctacacta      1680
gaaggacagt atttggtatc tgcgctctgc tgaagccagt taccttcgga aaaagagttg      1740
gtagctcttg atccggcaaa caaaccaccg ctggtagcgg tggttttttt gtttgcaagc      1800
agcagattac gcgcagaaaa aaaggatctc aagaagatcc tttgatcttt tctacggggt      1860
ctgacgctca gtggaacgaa aactcacgtt aagggatttt ggtcatgaga ttatcaaaaa      1920
ggatcttcac ctagatcctt ttaaattaaa aatgaagttt taaatcaatc taagtatat       1980
atgagtaaac ttggtctgac agttaccaat gcttaatcag tgaggcacct atctcagcga      2040
tctgtctatt tcgttcatcc atagttgcct gactccccgt cgtgtagata actacgatac      2100
gggagggctt accatctggc cccagtgctg caatgatacc gcgagaccca cgctcaccgg      2160
ctccagattt atcagcaata accagccag ccggaagggc cgagcgcaga agtggtcctg      2220
caactttatc cgcctccatc cagtctatta attgttgccg ggaagctaga gtaagtagtt      2280
cgccagttaa tagtttgcgc aacgttgttg ccattgctgc agccatgaga ttatcaaaaa      2340
ggatcttcac ctagatcctt ttcacgtaga aagccagtcc gcagaaacgg tgctgacccc      2400
```

```
ggatgaatgt cagctactgg gctatctgga caagggaaaa cgcaagcgca aagagaaagc    2460
aggtagcttg cagtgggctt acatggcgat agctagactg gcggttttta tggacagcaa    2520
gcgaaccgga attgccagct ggggcgccct ctggtaaggt tgggaagccc tgcaaagtaa    2580 actgatggc tttctcgccg ccaaggatct gatggcgcag gggatcaagc tctgatcaag    2640
agacaggatg aggatcgttt cgcatgattg aacaagatgg attgcacgca ggttctccgg    2700
ccgcttgggt ggagaggcta ttcggctatg actgggcaca acagacaatc ggctgctctg    2760
atgccgccgt gttccggctg tcagcgcagg ggcgcccggt tctttttgtc aagaccgacc    2820
tgtccggtgc cctgaatgaa ctgcaagacg aggcagcgcg gctatcgtgg ctggccacga    2880
cgggcgttcc ttgcgcagct gtgctcgacg ttgtcactga agcgggaagg gactggctgc    2940
tattgggcga agtgccgggg caggatctcc tgtcatctca ccttgctcct gccgagaaag    3000
tatccatcat ggctgatgca atgcggcggc tgcatacgct tgatccggct acctgcccat    3060
tcgaccacca agcgaaacat cgcatcgagc gagcacgtac tcggatggaa gccggtcttg    3120
tcgatcagga tgatctggac gaagagcatc aggggctcgc gccagccgaa ctgttcgcca    3180
ggctcaaggc gagcatgccc gacggcgagg atctcgtcgt gacccatggc gatgcctgct    3240
tgccgaatat catggtggaa aatggccgct tttctggatt catcgactgt ggccggctgg    3300
gtgtggcgga ccgctatcag gacatagcgt tggctacccg tgatattgct gaagagcttg    3360
gcggcgaatg ggctgaccgc ttcctcgtgc tttacggtat cgccgctccc gattcgcagc    3420
gcatcgcctt ctatcgcctt cttgacgagt tcttctgaat tttgttaaaa tttttgttaa    3480
atcagctcat ttttaacca ataggccgaa atcggcaaca tcccttataa atcaaaagaa    3540
tagaccgcga tagggttgag tgttgttcca gtttggaaca agagtccact attaaagaac    3600
gtggactcca acgtcaaagg gcgaaaaacc gtctatcagg gcgatggccc actacgtgaa    3660
ccatcaccca aatcaagttt tttgcggtcg aggtgccgta aagctctaaa tcggaaccct    3720
aaagggagcc cccgatttag agcttgacgg ggaaagccgg cgaacgtggc gagaaaggaa    3780
gggaagaaag cgaaaggagc gggcgctagg gcgctggcaa gtgtagcggt cacgctgcgc    3840
gtaaccacca caccgcgcg cttaatgcgc cgctacaggg cgcgtccatt cgccattcag    3900
gatcgaatta attcttaatt aacatcatca ataatatacc ttattttgga ttgaagccaa    3960
tatgataatg aggggggtgga gtttgtgacg tggcgcgggg cgtgggaacg gggcgggtga    4020
cgtagtagtg tggcggaagt gtgatgttgc aagtgtggcg gaacacatgt aagcgacgga    4080
tgtggcaaaa gtgacgtttt tggtgtgcgc cggtgtacac aggaagtgac aattttcgcg    4140
cggttttagg cggatgttgt agtaaatttg ggcgtaaccg agtaagattt ggccattttc    4200
gcgggaaaac tgaataagag gaagtgaaat ctgaataatt ttgtgttact catagcgcgt    4260
aatatttgtc tagggccgcg gggactttga ccgtttacgt ggagactcgc ccaggtgttt    4320
ttctcaggtg ttttccgcgt tccgggtcaa agttggcgtt ttattattat agtcagctga    4380
cgtgtagtgt atttataccc ggtgagttcc tcaagaggcc actcttgagt gccagcgagt    4440
agagttttct cctccgagcc gctccgacac cgggactgaa aatgagacat attatctgcc    4500
acggaggtgt tattaccgaa gaaatggccg ccagtctttt ggaccagctg atcgaagagg    4560
tactggctga taatcttcca cctcctagcc attttgaacc acctacccct cacgaactgt    4620
atgatttaga cgtgacggcc cccgaagatc ccaacgagga ggcggtttcg cagatttttc    4680
ccgactctgt aatgttggcg gtgcaggaag ggattgactt actcactttt ccgccggcgc    4740
```

```
ccggttctcc ggagccgcct cacctttccc ggcagcccga gcagccggag cagagagcct    4800
tgggtccggt ttctatgcca aaccttgtac cggaggtgat cgatccaccc agtgacgacg    4860
aggatgaaga gggtgaggag tttgtgttag attatgtgga gcaccccggg cacggttgca    4920
ggtcttgtca ttatcaccgg aggaatacgg gggacccaga tattatgtgt tcgcttttgct    4980 atatgaggac ctgtggcatg tttgtctaca gtaagtgaaa attatgggca gtgggtgata    5040
gagtggtggg tttggtgtgg taattttttt tttaattttt acagttttgt ggtttaaaga    5100
attttgtatt gtgattttt taaaaggtcc tgtgtctgaa cctgagcctg agcccgagcc    5160
agaaccggag cctgcaagac ctacccgccg tcctaaaatg gcgcctgcta tcctgagacg    5220
cccgacatca cctgtgtcta gagaatgcaa tagtagtacg gatagctgtg actccggtcc    5280
ttctaacaca cctcctgaga tacacccggt ggtcccgctg tgccccatta aaccagttgc    5340
cgtgagagtt ggtgggcgtc gccaggctgt ggaatgtatc gaggacttgc ttaacgagcc    5400
tgggcaacct ttggacttga gctgtaaacg ccccaggcca aaggtgtaa acctgtgatt    5460 gcgtgtgtgg ttaacgcctt tgtttgctga atgagttgat gtaagtttaa taaagggtga    5520
gataatgttt aacttgcatg gcgtgttaaa tggggcgggg cttaaagggt atataatgcg    5580
ccgtgggcta atcttggtta catctgacct catggaggct tgggagtgtt tggaagattt    5640
ttctgctgtg cgtaacttgc tggaacagag ctctaacagt acctcttggt tttggaggtt    5700
tctgtggggc tcatcccagg caaagttagt ctgcagaatt aaggaggatt acaagtggga    5760
atttgaagag cttttgaaat cctgtggtga gctgtttgat tctttgaatc tgggtcacca    5820
ggcgcttttc caagagaagg tcatcaagac tttggatttt tccacaccgg ggcgcgctgc    5880
ggctgctgtt gcttttttga gttttataaa ggataaatgg agcgaagaaa cccatctgag    5940
cggggggtac ctgctggatt ttctggccat gcatctgtgg agagcggttg tgagacacaa    6000
gaatcgcctg ctactgttgt cttccgtccg cccggcgata ataccgacgg aggagcagca    6060
gcagcagcag gaggaagcca ggcggcggcg gcaggagcag agcccatgga acccgagagc    6120
cggcctggac cctcgggaat gaatgttgta caggtggctg aactgtatcc agaactgaga    6180
cgcattttga caattacaga ggatgggcag gggctaaagg gggtaaagag ggagcggggg    6240
gcttgtgagg ctacagagga ggctaggaat ctagctttta gcttaatgac cagacaccgt    6300
cctgagtgta ttacttttca acagatcaag gataattgcg ctaatgagct tgatctgctg    6360
gcgcagaagt attccataga gcagctgacc acttactggc tgcagccagg ggatgatttt    6420
gaggaggcta ttagggtata tgcaaaggtg gcacttaggc cagattgcaa gtacaagatc    6480
agcaaacttg taaatatcag gaattgttgc tacatttctg ggaacggggc cgaggtggag    6540
atagatacgg aggataggt ggcctttaga tgtagcatga taaatatgtg gccggggtg    6600 cttggcatgg acggggtggt tattatgaat gtaaggttta ctggccccaa ttttagcggt    6660
acggttttcc tggccaatac caaccttatc ctacacggtg taagcttcta tgggtttaac    6720
aatacctgtg tggaagcctg gaccgatgta agggttcggg gctgtgcctt ttactgctgc    6780 tggaagggg tggtgtgtcg ccccaaaagc agggcttcaa ttaagaaatg cctctttgaa    6840
aggtgtacct tgggtatcct gtctgagggt aactccaggg tgcgcacaa tgtggcctcc    6900 gactgtggtt gcttcatgct agtgaaaagc gtggctgtga ttaagcataa catggtatgt    6960
ggcaactgcg aggacagggc ctctcagatg ctgacctgct cggacggcaa ctgtcacctg    7020
ctgaagacca ttcacgtagc cagccactct cgcaaggcct ggccagtgtt tgagcataac    7080
atactgaccc gctgttcctt gcatttgggt aacaggaggg gggtgttcct accttaccaa    7140
```

```
tgcaatttga gtcacactaa gatattgctt gagcccgaga gcatgtccaa ggtgaacctg    7200 aacgggtgt ttgacatgac catgaagatc tggaaggtgc tgaggtacga tgagacccgc    7260
accaggtgca gaccctgcga gtgtggcggt aaacatatta ggaaccagcc tgtgatgctg    7320
gatgtgaccg aggagctgag gcccgatcac ttggtgctgg cctgcacccg cgctgagttt    7380
ggctctagcg atgaagatac agattgaggt actgaaatgt gtgggcgtgg cttaagggtg    7440
ggaaagaata tataaggtgg gggtcttatg tagttttgta tctgttttgc agcagccgcc    7500
gccgccatga gcaccaactc gtttgatgga agcattgtga gctcatattt gacaacgcgc    7560
atgcccccat gggccggggt gcgtcagaat gtgatgggct ccagcattga tggtcgcccc    7620
gtcctgcccg caaactctac taccttgacc tacgagaccg tgtctggaac gccgttggag    7680
actgcagcct ccgccgccgc ttcagccgct gcagccaccg cccgcgggat gtgactgac    7740 tttgctttcc tgagcccgct tgcaagcagt gcagcttccc gttcatccgc ccgcgatgac    7800
aagttgacgg ctcttttggc acaattggat tctttgaccc gggaacttaa tgtcgtttct    7860
cagcagctgt tggatctgcg ccagcaggtt tctgccctga aggcttcctc ccctcccaat    7920
gcggtttctg ccgattataa ggatgacgat gacaagctag ccgtcgacta gccataaata    7980
aaaaaccaga ctctgtttgg atttggatca agcaagtgtc ttgctgtctt tatttagggg    8040
ttttgcgcgc gcggtaggcc cgggaccagc ggtctcggtc gttgagggtc ctgtgtattt    8100
tttccaggac gtggtaaagg tgactctgga tgttcagata catgggcata agcccgtctc    8160 tgggggtggag gtagcaccac tgcagagctt catgctgcgg ggtggtgttg tagatgatcc    8220
agtcgtagca ggagcgctgg gcgtggtgcc taaaaatgtc tttcagtagc aagctgattg    8280
ccaggggcag gcccttggtg taagtgttta caaagcggtt aagctgggat gggtgcatac    8340
gtggggatat gagatgcatc ttggactgta tttttaggtt ggctatgttc ccagccatat    8400
ccctccgggg attcatgttg tgcagaacca ccagcacagt gtatccggtg cacttgggaa    8460
atttgtcatg tagcttagaa ggaaatgcgt ggaagaactt ggagacgccc ttgtgacctc    8520
caagattttc catgcattcg tccataatga tggcaatggg cccacgggcg gcggcctggg    8580
cgaagatatt tctgggatca ctaacgtcat agttgtgttc caggatgaga tcgtcatagg    8640
ccatttttac aaagcgcggg cggagggtgc cagactgcgg tataatggtt ccatccggcc    8700
caggggcgta gttaccctca cagatttgca tttcccacgc tttgagttca gatggggga    8760 tcatgtctac ctgcggggcg atgaagaaaa cggtttccgg ggtaggggag atcagctggg    8820
aagaaagcag gttcctgagc agctgcgact taccgcagcc ggtgggcccg taaatcacac    8880
ctattaccgg gtgcaactgg tagttaagag agctgcagct gccgtcatcc ctgagcaggg    8940
gggccacttc gttaagcatg tccctgactc gcatgttttc cctgaccaaa tccgccagaa    9000
ggcgctcgcc gcccagcgat agcagttctt gcaaggaagc aaagttttc aacggtttga    9060 gaccgtccgc cgtaggcatg cttttgagcg tttgaccaag cagttccagg cggtcccaca    9120
gctcggtcac ctgctctacg gcatctcgat ccagcatatc tcctcgtttc gcgggttggg    9180 gcggcttttcg ctgtacggca gtagtcggtg ctcgtccaga cgggccaggg tcatgtctttt   9240 ccacgggcgc agggtcctcg tcagcgtagt ctgggtcacg tgaagggtt gcgctccggg    9300 ctgcgcgctg gccagggtgc gcttgaggct ggtcctgctg gtgctgaagc gctgccggtc    9360
ttcgccctgc gcgtcggcca ggtagcattt gaccatggtg tcatagtcca gcccctccgc    9420
ggcgtggccc ttggcgcgca gcttgccctt ggaggaggcg ccgcacgagg ggcagtgcag    9480
```

```
accttttgagg gcgtagagct tgggcgcgag aaataccgat tccggggagt aggcatccgc    9540
gccgcaggcc ccgcagacgg tctcgcattc cacgagccag gtgagctctg gccgttcggg    9600
gtcaaaaacc aggtttcccc catgcttttt gatgcgtttc ttacctctgg tttccatgag    9660
ccggtgtcca cgctcggtga cgaaaaggct gtccgtgtcc ccgtatacag actnnngttt    9720
aaacg                                                                9725

<210> SEQ ID NO 10
<211> LENGTH: 10404
<212> TYPE: DNA
<213> ORGANISM: Artificial sequence
<220> FEATURE:
<223> OTHER INFORMATION: Recombinant shuttle sequence D24 pIX RFP frame
      sv, n=A,C,G,T
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (991)..(993)
<223> OTHER INFORMATION: n is a, c, g, or t
<220> FEATURE:
<221> NAME/KEY: misc_feature
<222> LOCATION: (1008)..(1010)
<223> OTHER INFORMATION: n is a, c, g, or t
<220> FEATURE:
<221> NAME/KEY: misc_feature
<222> LOCATION: (10393)..(10395)
<223> OTHER INFORMATION: n is a, c, g, or t

<400> SEQUENCE: 10
aattcnnnta taaaatgcaa ggtgctgctc aaaaaatcag gcaaagcctc gcgcaaaaaa      60
gaaagcacat cgtagtcatg ctcatgcaga taaaggcagg taagctccgg aaccaccaca     120
gaaaaagaca ccatttttct ctcaaacatg tctgcgggtt tctgcataaa cacaaaataa     180
aataacaaaa aaacatttaa acattagaag cctgtcttac aacaggaaaa acaacccttg     240
taagcataag acggactacg gccatgccgg cgtgaccgta aaaaaactgg tcaccgtgat     300 taaaagcac caccgacagc tcctcggtca tgtccggagt cataatgtaa gactcggtaa     360
acacatcagg ttgattcatc ggtcagtgct aaaaagcgac cgaaatagcc cggggggaata    420 cataccgca ggcgtagaga caacattaca gccccatag gaggtataac aaaattaata     480
ggagagaaaa acacataaac acctgaaaaa ccctcctgcc taggcaaaat agcaccctcc     540
cgctccagaa caacatacag cgcttcacag cggcagccta acagtcagcc ttaccagtaa     600
aaaagaaaac ctattaaaaa aacaccactc gacacggcac cagctcaatc agtcacagtg     660
taaaaaaggg ccaagtgcag agcgagtata tataggacta aaaaatgacg taacggttaa     720
agtccacaaa aaacacccag aaaaccgcac gcgaacctac gccagaaac gaaagccaaa     780 aaacccacaa cttcctcaaa tcgtcacttc cgttttccca cgttacgtaa cttcccattt     840
taagaaaact acaattccca acacataca gttactccgc cctaaaacct acgtcacccg     900
ccccgttccc acgcccgcg ccacgtcaca aactccaccc cctcattatc atattggctt     960
caatccaaaa taaggtatat tattgatgat nnnttaatta aggatccnnn cggtgtgaaa    1020
taccgcacag atgcgtaagg agaaaatacc gcatcaggcg ctcttccgct tcctcgctca    1080
ctgactcgct gcgctcggtc gttcggctgc ggcgagcggt atcagctcac tcaaaggcgg    1140
taatacggtt atccacagaa tcaggggata acgcaggaaa gaacatgtga gcaaaaggcc    1200
agcaaaaggc caggaaccgt aaaaaggccg cgttgctggc gtttttccat aggctccgcc    1260
```

```
cccctgacga gcatcacaaa aatcgacgct caagtcagag gtggcgaaac ccgacaggac     1320
tataaagata ccaggcgttt cccctggaa gctccctcgt gcgctctcct gttccgaccc      1380
tgccgcttac cggatacctg tccgcctttc tcccttcggg aagcgtggcg ctttctcata     1440
gctcacgctg taggtatctc agttcggtgt aggtcgttcg ctccaagctg gctgtgtgc     1500 acgaaccccc cgttcagccc gaccgctgcg ccttatccgg taactatcgt cttgagtcca     1560
acccggtaag acacgactta tcgccactgg cagcagccac tggtaacagg attagcagag     1620
cgaggtatgt aggcggtgct acagagttct tgaagtggtg gcctaactac ggctacacta     1680
gaaggacagt atttggtatc tgcgctctgc tgaagccagt taccttcgga aaaagagttg     1740
gtagctcttg atccggcaaa caaaccaccg ctggtagcgg tggtttttt gtttgcaagc      1800 agcagattac gcgcagaaaa aaggatctc aagaagatcc tttgatcttt tctacggggt      1860
ctgacgctca gtggaacgaa aactcacgtt aagggatttt ggtcatgaga ttatcaaaaa     1920
ggatcttcac ctagatcctt ttaaattaaa aatgaagttt taaatcaatc taaagtatat     1980
atgagtaaac ttggtctgac agttaccaat gcttaatcag tgaggcacct atctcagcga     2040
tctgtctatt tcgttcatcc atagttgcct gactccccgt cgtgtagata actacgatac     2100
gggagggctt accatctggc cccagtgctg caatgatacc gcgagaccca cgctcaccgg     2160
ctccagattt atcagcaata aaccagccag ccggaagggc cgagcgcaga agtggtcctg     2220
caactttatc cgcctccatc cagtctatta attgttgccg ggaagctaga gtaagtagtt     2280
cgccagttaa tagtttgcgc aacgttgttg ccattgctgc agccatgaga ttatcaaaaa     2340
ggatcttcac ctagatcctt ttcacgtaga aagccagtcc gcagaaacgg tgctgacccc     2400
ggatgaatgt cagctactgg gctatctgga caagggaaaa cgcaagcgca agagaaagc      2460 aggtagcttg cagtgggctt acatggcgat agctagactg gcggttttta tggacagcaa     2520
gcgaaccgga attgccagct ggggcgccct ctggtaaggt tgggaagccc tgcaaagtaa     2580 actgatggc tttctcgccg ccaaggatct gatggcgcag gggatcaagc tctgatcaag      2640
agacaggatg aggatcgttt cgcatgattg aacaagatgg attgcacgca ggttctccgg     2700
ccgcttgggt ggagaggcta ttcggctatg actgggcaca acagacaatc ggctgctctg     2760
atgccgccgt gttccggctg tcagcgcagg ggcgcccggt tcttttttgtc aagaccgacc     2820 tgtccggtgc cctgaatgaa ctgcaagacg aggcagcgcg gctatcgtgg ctggccacga    2880
cgggcgttcc ttgcgcagct gtgctcgacg ttgtcactga agcgggaagg gactggctgc    2940
tattgggcga agtgccgggg caggatctcc tgtcatctca ccttgctcct gccgagaaag    3000
tatccatcat ggctgatgca atgcggcggc tgcatacgct tgatccggct acctgcccat    3060
tcgaccacca agcgaaacat cgcatcgagc gagcacgtac tcggatggaa gccggtcttg    3120
tcgatcagga tgatctggac gaagagcatc agggctcgc gccagccgaa ctgttcgcca     3180
ggctcaaggc gagcatgccc gacggcgagg atctcgtcgt gacccatggc gatgcctgct    3240
tgccgaatat catggtggaa aatggccgct tttctggatt catcgactgt ggccggctgg    3300
gtgtggcgga ccgctatcag gacatagcgt tggctacccg tgatattgct gaagagcttg    3360
gcggcgaatg ggctgaccgc ttcctcgtgc tttacggtat cgccgctccc gattcgcagc    3420
gcatcgcctt ctatcgcctt cttgacgagt tcttctgaat tttgttaaaa tttttgttaa    3480
atcagctcat ttttttaacca ataggccgaa atcggcaaca tcccttataa atcaaaagaa    3540
tagaccgcga taggggttgag tgttgttcca gtttggaaca agagtccact attaaagaac    3600
gtggactcca acgtcaaagg gcgaaaaacc gtctatcagg gcgatggccc actacgtgaa    3660
```

```
ccatcaccca aatcaagttt tttgcggtcg aggtgccgta aagctctaaa tcggaaccct    3720
aaagggagcc cccgatttag agcttgacgg ggaaagccgg cgaacgtggc gagaaaggaa    3780
gggaagaaag cgaaaggagc gggcgctagg gcgctggcaa gtgtagcggt cacgctgcgc    3840
gtaaccacca caccccgcgcg cttaatgcgc cgctacaggg cgcgtccatt cgccattcag    3900
gatcgaatta attcttaatt aacatcatca ataatatacc ttattttgga ttgaagccaa    3960
tatgataatg aggggtgga gtttgtgacg tggcgcgggg cgtgggaacg gggcgggtga    4020
cgtagtagtg tggcggaagt gtgatgttgc aagtgtggcg gaacacatgt aagcgacgga    4080
tgtggcaaaa gtgacgtttt tggtgtgcgc cggtgtacac aggaagtgac aattttcgcg    4140
cggttttagg cggatgttgt agtaaatttg ggcgtaaccg agtaagattt ggccattttc    4200
gcggaaaaac tgaataagag gaagtgaaat ctgaataatt ttgtgttact catagcgcgt    4260
aatatttgtc tagggccgcg gggactttga ccgtttacgt ggagactcgc ccaggtgttt    4320
ttctcaggtg ttttccgcgt tccgggtcaa agttggcgtt ttattattat agtcagctga    4380
cgtgtagtgt atttataccc ggtgagttcc tcaagaggcc actcttgagt gccagcgagt    4440
agagttttct cctccgagcc gctccgacac cgggactgaa aatgagacat attatctgcc    4500
acggaggtgt tattaccgaa gaaatggccg ccagtctttt ggaccagctg atcgaagagg    4560
tactggctga taatcttcca cctcctagcc attttgaacc acctacccctt cacgaactgt    4620
atgatttaga cgtgacggcc cccgaagatc ccaacgagga ggcggtttcg cagattttc    4680
ccgactctgt aatgttggcg gtgcaggaag ggattgactt actcactttt ccgccggcgc    4740
ccggttctcc ggagccgcct caccttttccc ggcagcccga gcagccggag cagagagcct    4800
tgggtccggt ttctatgcca aaccttgtac cggaggtgat cgatccaccc agtgacgacg    4860
aggatgaaga gggtgaggag tttgtgttag attatgtgga gcaccccggg cacggttgca    4920
ggtcttgtca ttatcaccgg aggaatacgg gggacccaga tattatgtgt tcgctttgct    4980
atatgaggac ctgtggcatg tttgtctaca gtaagtgaaa attatgggca gtgggtgata    5040
gagtggtggg tttggtgtgg taattttttt tttaatttt acagttttgt ggtttaaaga    5100
attttgtatt gtgatttttt taaaaggtcc tgtgtctgaa cctgagcctg agcccgagcc    5160
agaaccggag cctgcaagac ctacccgccg tcctaaaatg gcgcctgcta tcctgagacg    5220
cccgacatca cctgtgtcta gagaatgcaa tagtagtacg gatagctgtg actccggtcc    5280
ttctaacaca cctcctgaga tacacccggt ggtcccgctg tgccccatta aaccagttgc    5340
cgtgagagtt ggtgggcgtc gccaggctgt ggaatgtatc gaggacttgc ttaacgagcc    5400
tgggcaacct ttggacttga gctgtaaacg ccccaggcca taaggtgtaa acctgtgatt    5460
gcgtgtgtgg ttaacgcctt tgtttgctga atgagttgat gtaagtttaa taagggtga    5520
gataatgttt aacttgcatg gcgtgttaaa tggggcgggg cttaaagggt atataatgcg    5580
ccgtgggcta atcttggtta catctgacct catggaggct tgggagtgtt tggaagattt    5640
ttctgctgtg cgtaacttgc tggaacagag ctctaacagt acctcttggt tttggaggtt    5700
tctgtggggc tcatcccagg caaagttagt ctgcagaatt aaggaggatt acaagtggga    5760
atttgaagag ctttgtaaat cctgtggtga gctgtttgat tctttgaatc tgggtcacca    5820
ggcgcttttc caagagaagg tcatcaagac tttggatttt tccacaccgg ggcgcgctgc    5880
ggctgctgtt gcttttttga gttttataaa ggataaatgg agcgaagaaa cccatctgag    5940
cgggggggtac ctgctggatt ttctggccat gcatctgtgg agagcggttg tgagacacaa    6000
```

```
gaatcgcctg ctactgttgt cttccgtccg cccggcgata ataccgacgg aggagcagca    6060
gcagcagcag gaggaagcca ggcggcggcg gcaggagcag agcccatgga acccgagagc    6120
cggcctggac cctcgggaat gaatgttgta caggtggctg aactgtatcc agaactgaga    6180
cgcattttga caattacaga ggatgggcag gggctaaagg gggtaaagag ggagcggggg    6240
gcttgtgagg ctacagagga ggctaggaat ctagctttta gcttaatgac cagacaccgt    6300
cctgagtgta ttacttttca acagatcaag gataattgcg ctaatgagct tgatctgctg    6360
gcgcagaagt attccataga gcagctgacc acttactggc tgcagccagg ggatgatttt    6420
gaggaggcta ttagggtata tgcaaaggtg gcacttaggc cagattgcaa gtacaagatc    6480
agcaaacttg taaatatcag gaattgttgc tacatttctg ggaacggggc cgaggtggag    6540
atagatacgg aggatagggt ggcctttaga tgtagcatga taaatatgtg gccggggtg     6600
cttggcatgg acgggtggt tattatgaat gtaaggttta ctggccccaa ttttagcggt    6660
acggttttcc tggccaatac caaccttatc ctacacggtg taagcttcta tgggtttaac    6720
aatacctgtg tggaagcctg gaccgatgta agggttcggg gctgtgcctt ttactgctgc    6780
tggaaggggg tggtgtgtcg ccccaaaagc agggcttcaa ttaagaaatg cctctttgaa    6840
aggtgtacct tgggtatcct gtctgagggt aactccaggg tgcgccacaa tgtggcctcc    6900
gactgtggtt gcttcatgct agtgaaaagc gtggctgtga ttaagcataa catggtatgt    6960
ggcaactgcg aggacagggc ctctcagatg ctgacctgct cggacggcaa ctgtcacctg    7020
ctgaagacca ttcacgtagc cagccactct cgcaaggcct ggccagtgtt tgagcataac    7080
atactgaccc gctgttcctt gcatttgggt aacaggaggg gggtgttcct accttaccaa    7140
tgcaatttga gtcacactaa gatattgctt gagcccgaga gcatgtccaa ggtgaacctg    7200
aacggggtgt ttgacatgac catgaagatc tggaaggtgc tgaggtacga tgagacccgc    7260
accaggtgca gaccctgcga gtgtggcggt aaacatatta ggaaccagcc tgtgatgctg    7320
gatgtgaccg aggagctgag gcccgatcac ttggtgctgg cctgcacccg cgctgagttt    7380
ggctctagcg atgaagatac agattgaggt actgaaatgt gtgggcgtgg cttaagggtg    7440
ggaaagaata tataaggtgg gggtcttatg tagttttgta tctgttttgc agcagccgcc    7500
gccgccatga gcaccaactc gtttgatgga agcattgtga gctcatattt gacaacgcgc    7560
atgcccccat gggccgggt gcgtcagaat gtgatgggct ccagcattga tggtcgcccc    7620
gtcctgcccg caaactctac taccttgacc tacgagaccg tgtctggaac gccgttggag    7680
actgcagcct ccgccgccgc ttcagccgct gcagccaccg cccgcgggat tgtgactgac    7740
tttgctttcc tgagcccgct tgcaagcagt gcagcttccc gttcatccgc ccgcgatgac    7800
aagttgacgg ctcttttggc acaattggat tctttgaccc gggaacttaa tgtcgtttct    7860
cagcagctgt tggatctgcg ccagcaggtt tctgccctga aggcttcctc ccctcccaat    7920
gcggtttctg ccgattataa ggatgacgat gacaagctag ccatggcctc ctccgaggac    7980
gtcatcaagg agttcatgcg cttcaaggtg cgcatggagg gctccgtgaa cggccacgag    8040
ttcgagatcg agggcgaggg cgagggccgc ccctacgagg gcacccagac cgccaagctg    8100
aaggtgacca agggcggccc cctgcccttc gcctgggaca cctgtcccc tcagttccag    8160
tacggctcca aggcctacgt gaagcacccc gccgacatcc ccgactactt gaagctgtcc    8220
ttccccgagg gcttcaagtg ggagcgcgtg atgaacttcg aggacggcgg cgtggtgacc    8280
gtgacccagg actcctccct gcaggacggc gagttcatct acaaggtgaa gctgcgcggc    8340
accaacttcc cctccgacgg ccccgtaatg cagaagaaga ccatgggctg ggaggcctcc    8400
```

```
accgagcgga tgtaccccga ggacggcgcc ctgaagggcg agatcaagat gaggctgaag   8460
ctgaaggacg gcggccacta cgacgccgag gtcaagacca cctacatggc caagaagccc   8520
gtgcagctgc ccggcgccta caagaccgac atcaagctgg acatcacctc ccacaacgag   8580
gactacacca tcgtggaaca gtacgagcgc gccgagggcc gccactccac cggcgcctaa   8640
cgtcgactag ccataaataa aaaaccagac tctgtttgga tttggatcaa gcaagtgtct   8700
tgctgtcttt atttaggggt tttgcgcgcg cggtaggccc gggaccagcg gtctcggtcg   8760
ttgagggtcc tgtgtatttt tccaggacg tggtaaaggt gactctggat gttcagatac   8820
atgggcataa gcccgtctct ggggtggagg tagcaccact gcagagcttc atgctgcggg   8880
gtggtgttgt agatgatcca gtcgtagcag gagcgctggg cgtggtgcct aaaaatgtct   8940
ttcagtagca agctgattgc caggggcagg cccttggtgt aagtgtttac aaagcggtta   9000
agctgggatg ggtgcatacg tggggatatg agatgcatct tggactgtat ttttaggttg   9060
gctatgttcc cagccatatc cctccgggga ttcatgttgt gcagaaccac cagcacagtg   9120
tatccggtgc acttgggaaa tttgtcatgt agcttagaag gaaatgcgtg gaagaacttg   9180
gagacgccct tgtgacctcc aagattttcc atgcattcgt ccataatgat ggcaatgggc   9240
ccacgggcgg cggcctgggc gaagatattt ctgggatcac taacgtcata gttgtgttcc   9300
aggatgagat cgtcataggc catttttaca aagcgcgggc ggagggtgcc agactgcggt   9360
ataatggttc catccggccc aggggcgtag ttaccctcac agatttgcat ttcccacgct   9420
ttgagttcag atgggggat catgtctacc tgcgggcga tgaagaaaac ggtttccggg   9480
gtaggggaga tcagctggga agaaagcagg ttcctgagca gctgcgactt accgcagccg   9540
gtgggcccgt aaatcacacc tattaccggg tgcaactggt agttaagaga gctgcagctg   9600
ccgtcatccc tgagcagggg ggccacttcg ttaagcatgt ccctgactcg catgttttcc   9660
ctgaccaaat ccgccagaag gcgctcgccg cccagcgata gcagttcttg caaggaagca   9720
aagttttca cggtttgag accgtccgcc gtaggcatgc ttttgagcgt ttgaccaagc   9780
agttccaggc ggtcccacag ctcggtcacc tgctctacgg catctcgatc cagcatatct   9840
cctcgtttcg cggggttgggg cggctttcgc tgtacgcgca tagtcggtgc tcgtccagac   9900
gggccagggt catgtctttc cacgggcgca gggtcctcgt cagcgtagtc tgggtcacgg   9960
tgaaggggtg cgctccggcc tgcgcgctgg ccagggtgcg cttgaggctg gtcctgctgg  10020
tgctgaagcg ctgccggtct tcgccctgcg cgtcggccag gtagcatttg accatggtgt  10080
catagtccag cccctccgcg gcgtggccct tggcgcgcag cttgcccttg gaggaggcgc  10140
cgcacgaggg gcagtgcaga cttttgaggg cgtagagctt gggcgcgaga aataccgatt  10200
ccggggagta ggcatccgcg ccgcaggccc cgcagacggt ctcgcattcc acgagccagg  10260
tgagctctgg ccgttcgggg tcaaaaacca ggtttccccc atgcttttg atgcgtttct  10320
tacctctggt ttccatgagc cggtgtccac gctcggtgac gaaaaggctg tccgtgtccc  10380
cgtatacaga ctnnngttta aacg                                         10404
```

<210> SEQ ID NO 11
<211> LENGTH: 9684
<212> TYPE: DNA
<213> ORGANISM: Artificial sequence
<220> FEATURE:
<223> OTHER INFORMATION: Recombinat shuttle virus D24 pIX stop sv,
      n=A,C,G,T
<220> FEATURE:
<221> NAME/KEY: misc_feature

```
<222> LOCATION: (6)..(8)
<223> OTHER INFORMATION: n is a, c, g, or t
<220> FEATURE:
<221> NAME/KEY: misc_feature
<222> LOCATION: (991)..(993)
<223> OTHER INFORMATION: n is a, c, g, or t
<220> FEATURE:
<221> NAME/KEY: misc_feature
<222> LOCATION: (1008)..(1010)
<223> OTHER INFORMATION: n is a, c, g, or t
<220> FEATURE:
<221> NAME/KEY: misc_feature
<222> LOCATION: (9673)..(9675)
<223> OTHER INFORMATION: n is a, c, g, or t

<400> SEQUENCE: 11
aattcnnnta taaaatgcaa ggtgctgctc aaaaaatcag gcaaagcctc gcgcaaaaaa      60
gaaagcacat cgtagtcatg ctcatgcaga taaaggcagg taagctccgg aaccaccaca     120
gaaaaagaca ccattttcct ctcaaacatg tctgcgggtt tctgcataaa cacaaaataa     180
aataacaaaa aaacatttaa acattagaag cctgtcttac aacaggaaaa acaacccctta    240
taagcataag acggactacg gccatgccgg cgtgaccgta aaaaaactgg tcaccgtgat     300
taaaaagcac caccgacagc tcctcggtca tgtccggagt cataatgtaa gactcggtaa     360
acacatcagg ttgattcatc ggtcagtgct aaaaagcgac cgaaatagcc cggggaata     420
catacccgca ggcgtagaga caacattaca gcccccatag gaggtataac aaaattaata     480
ggagagaaaa acacataaac acctgaaaaa ccctcctgcc taggcaaaat agcaccctcc     540
cgctccagaa caacatacag cgcttcacag cggcagccta acagtcagcc ttaccagtaa     600
aaagaaaaac ctattaaaaa aacaccactc gacacggcac cagctcaatc agtcacagtg     660
taaaaaaggg ccaagtgcag agcgagtata tataggacta aaaaatgacg taacggttaa     720
agtccacaaa aaacacccag aaaaccgcac gcgaacctac gcccagaaac gaaagccaaa     780
aaacccacaa cttcctcaaa tcgtcacttc cgttttccca cgttacgtaa cttcccattt     840
taagaaaact acaattccca acacatacaa gttactccgc cctaaaacct acgtcacccg     900
ccccgttccc acgccccgcg ccacgtcaca aactccaccc cctcattatc atattggctt     960
caatccaaaa taaggtatat tattgatgat nnnttaatta aggatccnnn cggtgtgaaa    1020
taccgcacag atgcgtaagg agaaaatacc gcatcaggcg ctcttccgct tcctcgctca    1080
ctgactcgct gcgctcggtc gttcggctgc ggcgagcggt atcagctcac tcaaaggcgg    1140
taatacggtt atccacagaa tcaggggata cgcaggaaa gaacatgtga gcaaaaggcc     1200
agcaaaaggc caggaaccgt aaaaaggccg cgttgctggc gttttccat aggctccgcc     1260
cccctgacga gcatcacaaa aatcgacgct caagtcagag gtggcgaaac ccgacaggac    1320
tataaagata ccaggcgttt ccccctggaa gctccctcgt gcgctctcct gttccgaccc    1380
tgccgcttac cggatacctg tccgccttc tcccttcggg aagcgtggcg ctttctcata    1440
gctcacgctg taggtatctc agttcggtgt aggtcgttcg ctccaagctg ggctgtgtgc    1500
acgaaccccc cgttcagccc gaccgctgcg ccttatccgg taactatcgt cttgagtcca    1560
acccggtaag acacgactta tcgccactgg cagcagccac tggtaacagg attagcagag    1620
cgaggtatgt aggcggtgct acagagttct tgaagtggtg cctaactac ggctacacta     1680
gaaggacagt atttggtatc tgcgctctgc tgaagccagt taccttcgga aaaagagttg    1740
gtagctcttg atccggcaaa caaaccaccg ctggtagcgg tggttttttt gtttgcaagc    1800
agcagattac gcgcagaaaa aaaggatctc aagaagatcc tttgatcttt tctacgggt    1860
```

```
ctgacgctca gtggaacgaa aactcacgtt aagggatttt ggtcatgaga ttatcaaaaa    1920
ggatcttcac ctagatcctt ttaaattaaa aatgaagttt taaatcaatc taaagtatat    1980
atgagtaaac ttggtctgac agttaccaat gcttaatcag tgaggcacct atctcagcga    2040
tctgtctatt tcgttcatcc atagttgcct gactcccgt cgtgtagata actacgatac     2100
gggagggctt accatctggc cccagtgctg caatgatacc gcgagaccca cgctcaccgg    2160
ctccagattt atcagcaata aaccagccag ccggaagggc cgagcgcaga agtggtcctg    2220
caactttatc cgcctccatc cagtctatta attgttgccg ggaagctaga gtaagtagtt    2280
cgccagttaa tagtttgcgc aacgttgttg ccattgctgc agccatgaga ttatcaaaaa    2340
ggatcttcac ctagatcctt ttcacgtaga aagccagtcc gcagaaacgg tgctgacccc    2400
ggatgaatgt cagctactgg gctatctgga caagggaaaa cgcaagcgca agagaaaagc    2460
aggtagcttg cagtgggctt acatggcgat agctagactg ggcggtttta tggacagcaa    2520
gcgaaccgga attgccagct ggggcgccct ctggtaaggt tgggaagccc tgcaaagtaa    2580
actgatggc tttctcgccg ccaaggatct gatggcgcag gggatcaagc tctgatcaag     2640
agacaggatg aggatcgttt cgcatgattg aacaagatgg attgcacgca ggttctccgg    2700
ccgcttgggt ggagaggcta tcggctatg actgggcaca acagacaatc ggctgctctg     2760
atgccgccgt gttccggctg tcagcgcagg ggcgcccggt tctttttgtc aagaccgacc    2820
tgtccggtgc cctgaatgaa ctgcaagacg aggcagcgcg gctatcgtgg ctggccacga    2880
cgggcgttcc ttgcgcagct gtgctcgacg ttgtcactga agcgggaagg gactggctgc    2940
tattgggcga agtgccgggg caggatctcc tgtcatctca ccttgctcct gccgagaaag    3000
tatccatcat ggctgatgca atgcggcggc tgcatacgct tgatccggct acctgcccat    3060
tcgaccacca agcgaaacat cgcatcgagc gagcacgtac tcggatggaa gccggtcttg    3120
tcgatcagga tgatctggac gaagagcatc aggggctcgc gccagccgaa ctgttcgcca    3180
ggctcaaggc gagcatgccc gacggcgagg atctcgtcgt gacccatggc gatgcctgct    3240
tgccgaatat catggtggaa aatggccgct tttctggatt catcgactgt ggccggctgg    3300
gtgtggcgga ccgctatcag gacatagcgt tggctacccg tgatattgct gaagagcttg    3360
gcggcgaatg ggctgaccgc ttcctcgtgc tttacggtat cgccgctccc gattcgcagc    3420
gcatcgcctt ctatcgcctt cttgacgagt tcttctgaat tttgttaaaa ttttttgttaa   3480
atcagctcat ttttttaacca ataggccgaa atcggcaaca tcccttataa atcaaaagaa   3540
tagaccgcga tagggttgag tgttgttcca gtttggaaca agagtccact attaaagaac    3600
gtggactcca acgtcaaagg gcgaaaaacc gtctatcagg gcgatggccc actacgtgaa    3660
ccatcaccca atcaagtttt ttgcggtcg aggtgccgta aagctctaaa tcggaaccct     3720
aaagggagcc cccgatttag agcttgacgg ggaaagccgg cgaacgtggc gagaaaggaa    3780
gggaagaaag cgaaaggagc gggcgctagg gcgctggcaa gtgtagcggt cacgctgcgc    3840
gtaaccacca caccccgcgcg cttaatgcgc cgctacaggg cgcgtccatt cgccattcag   3900
gatcgaatta attcttaatt aacatcatca ataatatacc ttattttgga ttgaagccaa    3960
tatgataatg aggggtgga gtttgtgacg tggcgcgggg cgtgggaacg gggcgggtga     4020
cgtagtagtg tggcggaagt gtgatgttgc aagtgtggcg gaacacatgt aagcgacgga    4080
tgtggcaaaa gtgacgtttt tggtgtgcgc cggtgtacac aggaagtgac aattttcgcg    4140
cggttttagg cggatgttgt agtaaatttg ggcgtaaccg agtaagattt ggccattttc    4200
gcgggaaaac tgaataagag gaagtgaaat ctgaataatt ttgtgttact catagcgcgt    4260
```

```
aatatttgtc tagggccgcg gggactttga ccgtttacgt ggagactcgc ccaggtgttt    4320
ttctcaggtg ttttccgcgt tccgggtcaa agttggcgtt ttattattat agtcagctga    4380
cgtgtagtgt atttataccc ggtgagttcc tcaagaggcc actcttgagt gccagcgagt    4440
agagttttct cctccgagcc gctccgacac cgggactgaa aatgagacat attatctgcc    4500
acggaggtgt tattaccgaa gaaatggccg ccagtctttt ggaccagctg atcgaagagg    4560
tactggctga taatcttcca cctcctagcc attttgaacc acctacccett cacgaactgt    4620
atgatttaga cgtgacggcc cccgaagatc ccaacgagga ggcggtttcg cagattttc    4680
ccgactctgt aatgttggcg gtgcaggaag ggattgactt actcacttt ccgccggcgc    4740
ccggttctcc ggagccgcct cacctttccc ggcagcccga gcagccggag cagagagcct    4800
tgggtccggt ttctatgcca aaccttgtac cggaggtgat cgatccaccc agtgacgacg    4860
aggatgaaga gggtgaggag tttgtgttag attatgtgga gcaccccggg cacggttgca    4920
ggtcttgtca ttatcaccgg aggaatacgg gggacccaga tattatgtgt tcgctttgct    4980
atatgaggac ctgtggcatg tttgtctaca gtaagtgaaa attatgggca gtgggtgata    5040
gagtggtggg tttggtgtgg taatttttt tttaatttt acagttttgt ggtttaaaga    5100
attttgtatt gtgattttt taaaaggtcc tgtgtctgaa cctgagcctg agcccgagcc    5160
agaaccggag cctgcaagac ctacccgccg tcctaaaatg gcgcctgcta tcctgagacg    5220
cccgacatca cctgtgtcta gagaatgcaa tagtagtacg gatagctgtg actccggtcc    5280
ttctaacaca cctcctgaga tacacccggt ggtcccgctg tgccccatta aaccagttgc    5340
cgtgagagtt ggtgggcgtc gccaggctgt ggaatgtatc gaggacttgc ttaacgagcc    5400
tgggcaacct ttggacttga gctgtaaacg ccccaggcca aaggtgtaa acctgtgatt    5460
gcgtgtgtgg ttaacgcctt tgtttgctga atgagttgat gtaagtttaa taagggtga    5520
gataatgttt aacttgcatg gcgtgttaaa tggggcgggg cttaaagggt atataatgcg    5580
ccgtgggcta atcttggtta catctgacct catggaggct tgggagtgtt tggaagattt    5640
ttctgctgtg cgtaacttgc tggaacagag ctctaacagt acctcttggt tttggaggtt    5700
tctgtggggc tcatcccagg caaagttagt ctgcagaatt aaggaggatt acaagtggga    5760
atttgaagag cttttgaaat cctgtggtga gctgtttgat tctttgaatc tgggtcacca    5820
ggcgcttttc caagagaagg tcatcaagac tttggatttt tccacaccgg ggcgcgctgc    5880
ggctgctgtt gcttttttga gttttataaa ggataaatgg agcgaagaaa cccatctgag    5940
cggggggtac ctgctggatt ttctggccat gcatctgtgg agagcggttg tgagacacaa    6000
gaatcgcctg ctactgttgt cttccgtccg cccggcgata ataccgacgg aggagcagca    6060
gcagcagcag gaggaagcca ggcggcggcg gcaggagcag agcccatgga acccgagagc    6120
cggcctggac cctcgggaat gaatgttgta caggtggctg aactgtatcc agaactgaga    6180
cgcattttga caattacaga ggatgggcag gggctaaagg gggtaaagag ggagcggggg    6240
gcttgtgagg ctacagagga ggctaggaat ctagctttta gcttaatgac cagacaccgt    6300
cctgagtgta ttacttttca acagatcaag gataattgcg ctaatgagct tgatctgctg    6360
gcgcagaagt attccataga gcagctgacc acttactggc tgcagccagg ggatgatttt    6420
gaggaggcta ttagggtata tgcaaaggtg gcacttaggc cagattgcaa gtacaagatc    6480
agcaaacttg taaatatcag gaattgttgc tacatttctg ggaacggggc cgaggtggag    6540
atagatacgg aggatagggt ggcctttaga tgtagcatga taaatatgtg gccgggggtg    6600
```

```
cttggcatgg acggggtggt tattatgaat gtaaggttta ctggccccaa ttttagcggt    6660
acggttttcc tggccaatac caaccttatc ctacacggtg taagcttcta tgggtttaac    6720
aatacctgtg tggaagcctg gaccgatgta agggttcggg gctgtgcctt ttactgctgc    6780 tggaagggg tggtgtgtcg ccccaaaagc agggcttcaa ttaagaaatg cctctttgaa     6840
aggtgtacct tgggtatcct gtctgagggt aactccaggg tgcgccacaa tgtggcctcc    6900
gactgtggtt gcttcatgct agtgaaaagc gtggctgtga ttaagcataa catggtatgt    6960
ggcaactgcg aggacagggc ctctcagatg ctgacctgct cggacggcaa ctgtcacctg    7020
ctgaagacca ttcacgtagc cagccactct cgcaaggcct ggccagtgtt tgagcataac    7080
atactgaccc gctgttcctt gcatttgggt aacaggaggg gggtgttcct accttaccaa    7140
tgcaatttga gtcacactaa gatattgctt gagcccgaga gcatgtccaa ggtgaacctg    7200 aacgggtgt ttgacatgac catgaagatc tggaaggtgc tgaggtacga tgagacccgc     7260
accaggtgca gaccctgcga gtgtggcggt aaacatatta ggaaccagcc tgtgatgctg    7320
gatgtgaccg aggagctgag gcccgatcac ttggtgctgg cctgcacccg cgctgagttt    7380
ggctctagcg atgaagatac agattgaggt actgaaatgt gtgggcgtgg cttaagggtg    7440
ggaaagaata tataaggtgg gggtcttatg tagttttgta tctgttttgc agcagccgcc    7500
gccgccatga gcaccaactc gtttgatgga agcattgtga gctcatattt gacaacgcgc    7560
atgcccccat gggccgggt gcgtcagaat gtgatgggct ccagcattga tggtcgcccc     7620
gtcctgcccg caaactctac taccttgacc tacgagaccg tgtctggaac gccgttggag    7680
actgcagcct ccgccgccgc ttcagccgct gcagccaccg cccgcgggat tgtgactgac    7740 tttgcttttcc tgagcccgct tgcaagcagt gcagcttccc gttcatccgc ccgcgatgac    7800
aagttgacgg ctcttttggc acaattggat tctttgaccc gggaacttaa tgtcgtttct    7860
cagcagctgt tggatctgcg ccagcaggtt tctgccctga aggcttcctc ccctcccaat    7920
gcggtttaaa acataaataa aaaaccagac tctgtttgga tttggatcaa gcaagtgtct    7980
tgctgtcttt atttaggggt tttgcgcgcg cggtaggccc gggaccagcg gtctcggtcg    8040
ttgagggtcc tgtgtatttt ttccaggacg tggtaaaggt gactctggat gttcagatac    8100
atgggcataa gcccgtctct ggggtggagg tagcaccact gcagagcttc atgctgcggg    8160
gtggtgttgt agatgatcca gtcgtagcag gagcgctggg cgtggtgcct aaaaatgtct    8220
ttcagtagca agctgattgc caggggcagg cccttggtgt aagtgtttac aaagcggtta    8280
agctgggatg ggtgcatacg tgggatatg agatgcatct tggactgtat ttttaggttg    8340
gctatgttcc cagccatatc cctccgggga ttcatgttgt gcagaaccac cagcacagtg    8400
tatccggtgc acttgggaaa tttgtcatgt agcttagaag gaaatgcgtg gaagaacttg    8460
gagacgccct tgtgacctcc aagatttcc atgcattcgt ccataatgat ggcaatgggc     8520
ccacgggcgg cggcctgggc gaagatattt ctgggatcac taacgtcata gttgtgttcc    8580
aggatgagat cgtcataggc catttttaca aagcgcgggc ggagggtgcc agactgcggt    8640
ataatggttc catccggccc aggggcgtag ttaccctcac agatttgcat ttcccacgct    8700
ttgagttcag atggggggat catgtctacc tgcgggggcga tgaagaaaac ggtttccggg    8760
gtaggggaga tcagctggga agaaagcagg ttcctgagca gctgcgactt accgcagccg    8820 gtgggccgt aaatcacacc tattaccggg tgcaactggt agttaagaga gctgcagctg     8880
ccgtcatccc tgagcagggg ggccacttcg ttaagcatgt ccctgactcg catgttttcc    8940
ctgaccaaat ccgccagaag gcgctcgccg cccagcgata gcagttcttg caaggaagca    9000
```

```
aagtttttca acggtttgag accgtccgcc gtaggcatgc ttttgagcgt ttgaccaagc    9060
agttccaggc ggtcccacag ctcggtcacc tgctctacgg catctcgatc cagcatatct    9120
cctcgtttcg cggggttgggg cggctttcgc tgtacggcag tagtcggtgc tcgtccagac    9180
gggccagggt catgtctttc cacgggcgca gggtcctcgt cagcgtagtc tgggtcacgg    9240
tgaaggggtg cgctccgggc tgcgcgctgg ccagggtgcg cttgaggctg gtcctgctgg    9300
tgctgaagcg ctgccggtct tcgccctgcg cgtcggccag gtagcatttg accatggtgt    9360
catagtccag cccctccgcg gcgtggccct tggcgcgcag cttgcccttg gaggaggcgc    9420
cgcacgaggg gcagtgcaga cttttgaggg cgtagagctt gggcgcgaga aataccgatt    9480
ccggggagta ggcatccgcg ccgcaggccc cgcagacggt ctcgcattcc acgagccagg    9540
tgagctctgg ccgttcgggg tcaaaaacca ggtttccccc atgcttttg atgcgtttct    9600 tacctctggt ttccatgagc cggtgtccac gctcggtgac gaaaaggctg tccgtgtccc    9660
cgtatacaga ctnnngttta aacg                                           9684

<210> SEQ ID NO 12
<211> LENGTH: 9879
<212> TYPE: DNA
<213> ORGANISM: Artificial sequence
<220> FEATURE:
<223> OTHER INFORMATION: Recombinant shuttle virus E3 53rgd bst sal sv,
      n=A,C,G,T
<220> FEATURE:
<221> NAME/KEY: misc_feature
<222> LOCATION: (9199)..(9199)
<223> OTHER INFORMATION: n is a, c, g, or t

<400> SEQUENCE: 12
tcggcttacc ttcgcaaatt tgtacctgag gactaccacg cccacgagat taggttctac      60
gaagaccaat cccgcccgcc aaatgcggag cttaccgcct gcgtcattac ccagggccac     120
attcttggcc aattgcaagc catcaacaaa gcccgcaag agtttctgct acgaaaggga     180 cgggggggttt acttggaccc ccagtccggc gaggagctca acccaatccc ccgccgccg     240 cagccctatc agcagcagcc gcgggcccctt gcttcccagg atggcaccca aaagaagct     300 gcagctgccg ccgccacccca cggacgagga ggaatactgg gacagtcagg cagaggaggt     360
tttggacgag gaggaggagg acatgatgga agactgggag agcctagacg aggaagcttc     420
cgaggtcgaa gaggtgtcag acgaaacacc gtcaccctcg gtcgcattcc cctcgccggc     480
gccccagaaa tcggcaaccg gttccagcat ggctacaacc tccgctcctc aggcgccgcc     540
ggcactgccc gttcgccgac ccaaccgtag atgggacacc actggaacca gggccggtaa     600
gtccaagcag ccgccgccgt tagcccaaga gcaacaacag cgccaaggct accgctcatg     660
gcgcgggcac aagaacgcca tagttgcttg cttgcaagac tgtgggggca acatctcctt     720
cgcccgccgc tttcttctct accatcacgg cgtggccttc cccgtaaca tcctgcatta     780 ctaccgtcat ctctacagcc catactgcac cggcggcagc ggcagcggca gcaacagcag     840
cggccacaca gaagcaaagg cgaccggata gcaagactct gacaaagccc aagaaatcca     900
cagcggcggc agcagcagga ggaggagcgc tgcgtctggc gcccaacgaa cccgtatcga     960
cccgcgagct tagaaacagg attttttccca ctctgtatgc tatatttcaa cagagcaggg    1020
gccaagaaca agagctgaaa ataaaaaaca ggtctctgcg atccctcacc cgcagctgcc    1080
tgtatcacaa aagcgaagat cagcttcggc gcacgctgga agacgcggag gctctcttca    1140
gtaaatactg cgcgctgact cttaaggact agtttcgcgc cctttctcaa atttaagcgc    1200
```

```
gaaaactacg tcatctccag cggccacacc cggcgccagc acctgtcgtc agcgccatta    1260
tgagcaagga aattcccacg ccctacatgt ggagttacca gccacaaatg ggacttgcgg    1320
ctggagctgc ccaagactac tcaacccgaa taaactacat gagcgcggga ccccacatga    1380
tatcccgggt caacggaatc cgcgccaccg aaaccgaatc tctcttggaa caggcggcta    1440
ttaccaccac acctcgtaat aaccttaatc cccgtagttg gcccgctgcc ctggtgtacc    1500
aggaaagtcc cgctcccacc actgtggtac ttcccagaga cgcccaggcc gaagttcaga    1560
tgactaactc aggggcgcag cttgcgggcg ctttcgtca cagggtgcgg tcgcccgggc    1620
agggtataac tcacctgaca atcagagggc gaggtattca gctcaacgac gagtcggtga    1680
gctcctcgct tggtctccgt ccggacggga catttcagat cggcggcgcc ggccgtcctt    1740
cattcacgcc tcgtcaggca atcctaactc tgcagacctc gtcctctgag ccgcgctctg    1800
gaggcattgg aactctgcaa tttattgagg agtttgtgcc atcggtctac tttaaccct     1860 tctcgggacc tcccgccac tatccggatc aatttattcc taactttgac gcggtaaagg     1920
actcggcgga cggctacgac tgattattaa gtggagaggc agagcaactg cgcctgaaac    1980
acctggtcca ctgtcgccgc cacaagtgct ttgcccgcga ctccggtgag ttttgctact    2040
ttgaattgcc cgaggatcat atcgaggatc tttgttgcca tctctgtgct gagtataata    2100
aatacagaaa ttaaaatata ctggggctcc tatcgccatc ctgtaaacgc caccgtcttc    2160
acccgcccaa gcaaaccaag gcgaaccta cctggtactt ttaacatctc tccctctgtg     2220
atttacaaca gtttcaaccc agacggagtg agtctacgag agaacctctc cgagctcagc    2280
tactccatca gaaaaaacac caccctcctt acctgccggg aacgtaccct tatataaaag    2340
tcaggcttcc tggatgtcag catctgactt tggccagcac ctgtcccgcg gatttgttcc    2400
agtccaacta cagcgaccca ccctaacaga gatgaccaac acaaccaacg cggccgccgc    2460
taccggactt acatctacca caaatacacc ccaagtttct gcctttgtca ataactggga    2520
taacttgggc atgtggtggt tctccatagc gcttatgttt gtatgcctta ttattatgtg    2580
gctcatctgc tgcctaaagc gcaaacgcgc ccgaccaccc atctatagtc ccatcattgt    2640
gctacaccca acaatgatg gaatccatag attggacgga ctgaaacaca tgttctttc     2700 tcttacagta tgattaaatg agaattttaa ttcgaattta aatgaattcg agctcggtac    2760
ccggggatcc tctagagtcg acctgcagga atggaatttt ctgtccagtt tattcagcag    2820
cacctccttg ccctcctccc agctctggta ttgcagcttc ctcctggctg caaactttct    2880
ccacaatcta aatggaatgt cagtttcctc ctgttcctgt ccatccgcac ccactatctt    2940
catgttgttg cagatgaagc gcgcaagacc gtctgaagat accttcaacc ccgtgtatcc    3000
atatgacacg gaaaccggtc ctccaactgt gccttttctt actcctccct ttgtatcccc    3060
caatgggttt caagagagtc cccctggggt actctctttg cgcctatccg aacctctagt    3120
tacctccaat ggcatgcttg cgctcaaaat gggcaacggc ctctctctgg acgaggccgg    3180
caaccttacc tcccaaaatg taaccactgt gagcccacct ctcaaaaaaa ccaagtcaaa    3240
cataaacctg gaaatatctg caccccctcac agttacctca gaagcccctaa ctgtggctgc   3300 cgccgcacct ctaatggtcg cgggcaacac actcaccatg caatcacagg ccccgctaac    3360
cgtgcacgac tccaaactta gcattgccac ccaaggaccc ctcacagtgt cagaaggaaa    3420
gctagccctg caaacatcag gcccctcac caccaccgat agcagtaccc ttactatcac     3480
tgcctcaccc cctctaacta ctgccactgg tagcttgggc attgacttga aagagcccat    3540
```

```
ttatacacaa aatggaaaac taggactaaa gtacggggct cctttgcatg taacagacga    3600
cctaaacact ttgaccgtag caactggtcc aggtgtgact attaataata cttccttgca    3660
aactaaagtt actggagcct tgggttttga ttcacaaggc aatatgcaac ttaatgtagc    3720
aggaggacta aggattgatt ctcaaaacag acgccttata cttgatgtta gttatccgtt    3780
tgatgctcaa aaccaactaa atctaagact aggacagggc cctctttta taaactcagc     3840 ccacaacttg gatattaact acaacaaagg cctttacttg tttacagctt caaacaattc    3900
caaaaagctt gaggttaacc taagcactgc caaggggttg atgtttgacg ctacagccat    3960
agccattaat gcaggagatg ggcttgaatt tggttcacct aatgcaccaa acacaaatcc    4020
cctcaaaaca aaaattggcc atggcctaga atttgattca acaaggcta tggttcctaa     4080 actaggaact ggccttagtt ttgacagcac aggtgccatt acagtaggaa acaaaaataa    4140
tgataagcta accctatgga caggtccaaa accagaagcc aactgcataa ttgaatacgg    4200
gaaagaaaac ccagatagca aactaacttt aatccttgta aaaaatggag gaattgttaa    4260
tggatatgta acgctaatgg gagcctcaga ctatgttaac accttattta aaacaaaaa     4320 tgtctccatt aatgtagaat tatactttga tgccactggt catatattac cagacttatc    4380
ttctcttaaa acagatctag aactaaaata caagcaaacc actcacttta gtgcaagagg    4440
ttttatgcca agtactacag cgtatccatt tgtccttcct aatgcgggaa cagataatga    4500
aaattatatt tttggtcaat gctactacaa agcaagcgat ggcgcccttt ttccgttgga    4560
agttactgtt acgcttaata acgcctgcc agatagtcgc acatcctatg ttatgacttt      4620
tttatggtcc ttgaatgctg gtctagctcc agaaactact caggcaaccc tcataacctc    4680
cccatttacc ttttcctata ttagagaaga tgactgacgg tggaggcggt tcaggcggag    4740
gtggctctgg cggtggcgga tcctgtgact gccgcggaga ctgtttctgc taataaactc    4800
taaagaatcg tttgtgttat gtttcaacgt gtttattttt caattgcaga aaatttcaag    4860 tcattttca ttcagtagta tagccccacc accacatagc ttatacagat caccgtacct     4920
taatcaaact cacagaaccc tagtattcaa cctgccacct ccctcccaac acacagagta    4980
cacagtcctt tctccccggc tggccttaaa aagcatcata tcatgggtaa cagacatatt    5040
cttaggtgtt atattccaca cggtttcctg tcgagccaaa cgctcatcag tgatattaat    5100
aaactccccg ggcagctcac ttaagttcat gtcgctgtcc agctgctgag ccacaggctg    5160
ctgtccaact tgcggttgct taacgggcgg cgaaggagaa gtccacgcct acatgggggt    5220
agagtcataa tcgtgcatca ggatagggcg gtggtgctgc agcagcgcgc gaataaactg    5280
ctgccgccgc cgctccgtcc tgcaggaata caacatggca gtggtctcct cagcgatgat    5340
tcgcaccgcc cgcagcataa ggcgccttgt cctccgggca cagcagcgca ccctgatctc    5400
acttaaatca gcacagtaac tgcagcacag caccacaata ttgttcaaaa tcccacagtg    5460
caaggcgctg tatccaaagc tcatggcggg gaccacagaa cccacgtggc catcatacca    5520
caagcgcagg tagattaagt ggcgacccct cataaacacg ctggacataa acattacctc    5580
ttttggcatg ttgtaattca ccacctcccg gtaccatata aacctctgat taaacatggc    5640
gccatccacc accatcctaa accagctggc caaaacctgc ccgccggcta tacactgcag    5700
ggaaccggga ctggaacaat gacagtggag agcccaggac tcgtaaccat ggatcatcat    5760
gctcgtcatg atatcaatgt tggcacaaca caggcacacg tgcatacact tcctcaggat    5820
tacaagctcc tcccgcgtta gaaccatatc ccagggaaca acccattcct gaatcagcgt    5880
aaatcccaca ctgcagggaa gacctcgcac gtaactcacg ttgtgcattg tcaaagtgtt    5940
```

-continued

```
acattcgggc agcagcggat gatcctccag tatggtagcg cgggtttctg tctcaaaagg      6000
aggtagacga tccctactgt acggagtgcg ccgagacaac cgagatcgtg ttggtcgtag      6060
tgtcatgcca aatggaacgc cggacgtagt catatttcct gaagcaaaac caggtgcggg      6120
cgtgacaaac agatctgcgt ctccggtctc gccgcttaga tcgctctgtg tagtagttgt      6180
agtatatcca ctctctcaaa gcatccaggc gcccctggc ttcgggttct atgtaaactc       6240
cttcatgcgc cgctgccctg ataacatcca ccaccgcaga ataagccaca cccagccaac      6300
ctacacattc gttctgcgag tcacacacgg gaggagcggg aagagctgga agaaccatgt      6360
tttttttttt attccaaaag attatccaaa acctcaaaat gaagatctat taagtgaacg      6420
cgctcccctc cggtggcgtg gtcaaactct acagccaaag aacagataat ggcatttgta      6480
agatgttgca caatggcttc caaaaggcaa acggccctca cgtccaagtg gacgtaaagg      6540 ctaaacccttt cagggtgaat ctcctctata acattccag caccttcaac catgcccaaa      6600
taattctcat ctcgccacct tctcaatata tctctaagca aatcccgaat attaagtccg      6660
gccattgtaa aaatctgctc cagagcgccc tccaccttca gcctcaagca gcgaatcatg      6720
attgcaaaaa ttcaggttcc tcacagacct gtataagatt caaaagcgga acattaacaa      6780
aaataccgcg atcccgtagg tcccttcgca gggccagctg aacataatcg tgcaggtctg      6840
cacggaccag cgcggccact tccccgccag gaaccatgac aaaagaaccc acactgatta      6900
tgacacgcat actcggagct atgctaacca gcgtagcccc gatgtaagct tgttgcatgg      6960
gcggcgatat aaaatgcaag gtgctgctca aaaaatcagg caaagcctcg cgcaaaaaag      7020
aaagcacatc gtagtcatgc tcatgcagat aaaggcaggt aagctccgga accaccacag      7080
aaaaagacac cattttctc tcaaacatgt ctgcgggttt ctgcataaac acaaaataaa       7140
ataacaaaaa aacatttaaa cattagaagc ctgtcttaca acaggaaaaa caacccttat      7200
aagcataaga cggactacgg ccatgccggc gtgaccgtaa aaaaactggt caccgtgatt      7260
aaaaagcacc accgacagct cctcggtcat gtccggagtc ataatgtaag actcggtaaa      7320
cacatcaggt tgattcacat cggtcagtgc taaaaagcga ccgaaatagc ccggggggaat     7380 acatacccgc aggcgtagag acaacattac agccccata ggaggtataa caaaattaat      7440
aggagagaaa aacacataaa cacctgaaaa accctcctgc ctaggcaaaa tagcaccctc      7500
ccgctccaga acaacataca gcgcttccac agcggcagcc ataacagtca gccttaccag      7560 taaaaagaa aacctattaa aaaaacacca ctcgacacgg caccagctca atcagtcaca      7620
gtgtaaaaaa gggccaagtg cagagcgagt atatatagga ctaaaaaatg acgtaacggt      7680
taaagtccac aaaaaacacc cagaaaaccg cacgcgaacc tacgcccaga acgaaagcc      7740 aaaaaaccca caacttcctc aaatcgtcac ttccgttttc ccacgttacg tcacttccca      7800
ttttaagaaa actacaattc ccaacacata caagttactc cgccctaaaa cctacgtcac      7860 ccgcccccgtt cccacgcccc gcgccacgtc acaaactcca cccctcatt atcatattgg      7920 cttcaatcca aaataaggta tattattgat gatgttaatt aagaattcgg atctgcgacg      7980
cgaggctgga tggccttccc cattatgatt cttctcgctt ccggcggcat cgggatgccc      8040
gcgttgcagg ccatgctgtc caggcaggta gatgacgacc atcagggaca gcttcacggc      8100
cagcaaaagg ccaggaaccg taaaaaggcc gcgttgctgg cgttttcca taggctccgc      8160 cccccctgacg agcatcacaa aaatcgacgc tcaagtcaga ggtggcgaaa cccgacagga      8220
ctataaagat accaggcgtt tccccctgga agctccctcg tgcgctctcc tgttccgacc      8280
```

```
ctgccgctta ccggatacct gtccgccttt ctcccttcgg gaagcgtggc gctttctcaa      8340
tgctcacgct gtaggtatct cagttcggtg taggtcgttc gctccaagct gggctgtgtg      8400
cacgaacccc ccgttcagcc cgaccgctgc gccttatccg gtaactatcg tcttgagtcc      8460
aacccggtaa gacacgactt atcgccactg gcagcagcca ctggtaacag gattagcaga      8520
gcgaggtatg taggcggtgc tacagagttc ttgaagtggt ggcctaacta cggctacact      8580
agaaggacag tatttggtat ctgcgctctg ctgaagccag ttaccttcgg aaaaagagtt      8640
ggtagctctt gatccggcaa acaaaccacc gctggtagcg tggtttttt tgtttgcaag      8700
cagcagatta cgcgcagaaa aaaggatct caagaagatc ctttgatctt ttctacgggg       8760
tctgacgctc agtggaacga aaactcacgt taagggattt tggtcatgag attatcaaaa      8820
aggatcttca cctagatcct tttaaatcaa tctaaagtat atatgagtaa acttggtctg      8880
acagttacca atgcttaatc agtgaggcac ctatctcagc gatctgtcta tttcgttcat      8940
ccatagttgc ctgactcccc gtcgtgtaga taactacgat acgggagggc ttaccatctg      9000
gccccagtgc tgcaatgata ccgcgagacc cacgctcacc ggctccagat ttatcagcaa      9060
taaaccagcc agccggaagg gccgagcgca gaagtggtcc tgcaacttta tccgcctcca      9120
tccagtctat taattgttgc cgggaagcta gagtaagtag ttcgccagtt aatagtttgc      9180
gcaacgttgt tgccattgnt gcaggcatcg tggtgtcacg ctcgtcgttt ggtatggctt      9240
cattcagctc cggttcccaa cgatcaaggc gagttacatg atccccatg ttgtgcaaaa       9300
aagcggttag ctccttcggt cctccgatcg ttgtcagaag taagttggcc gcagtgttat      9360
cactcatggt tatggcagca ctgcataatt ctcttactgt catgccatcc gtaagatgct      9420
tttctgtgac tggtgagtac tcaaccaagt cattctgaga atagtgtatg cggcgaccga      9480
gttgctcttg cccggcgtca cacgggata ataccgcgcc acatagcaga actttaaaag       9540
tgctcatcat tggaaaacgt tcttcgggc gaaaactctc aaggatctta ccgctgttga       9600
gatccagttc gatgtaaccc actcgtgcac ccaactgatc ttcagcatct tttactttca      9660
ccagcgtttc tgggtgagca aaaacaggaa ggcaaaatgc cgcaaaaaag ggaataaggg      9720
cgacacggaa atgttgaata ctcatactct ccttttttca atattattga agcatttatc      9780
agggttattg tctcatgagc ggatacatat ttgaatgtat ttagaaaaat aaacaaatag      9840
gggttccgcg cacatttccc cgaaaagtgc cacctgacg                             9879
```

<210> SEQ ID NO 13
<211> LENGTH: 10281
<212> TYPE: DNA
<213> ORGANISM: Artificial sequence
<220> FEATURE:
<223> OTHER INFORMATION: Recombinant shuttle virus E3 gmcsf 53rgd sv,
     n=A,C,G,T
<220> FEATURE:
<221> NAME/KEY: misc_feature
<222> LOCATION: (9601)..(9601)
<223> OTHER INFORMATION: n is a, c, g, or t

<400> SEQUENCE: 13

```
tcggcttacc ttcgcaaatt tgtacctgag gactaccacg cccacgagat taggttctac        60
gaagaccaat cccgcccgcc aaatgcggag cttaccgcct cgtcattac ccagggccac        120
attcttggcc aattgcaagc catcaacaaa gcccgccaag agtttctgct acgaaaggga      180
cggggggttt acttggaccc ccagtccggc gaggagctca acccaatccc ccgccgccg       240
cagccctatc agcagcagcc gcgggccctt gcttcccagg atggcaccca aaaagaagct      300
```

-continued

| | |
|---|---|
| gcagctgccg ccgccaccca cggacgagga ggaatactgg gacagtcagg cagaggaggt | 360 |
| tttggacgag gaggaggagg acatgatgga agactgggag agcctagacg aggaagcttc | 420 |
| cgaggtcgaa gaggtgtcag acgaaacacc gtcaccctcg gtcgcattcc cctcgccggc | 480 |
| gccccagaaa tcggcaaccg gttccagcat ggctacaacc tccgctcctc aggcgccgcc | 540 |
| ggcactgccc gttcgccgac ccaaccgtag atgggacacc actggaacca gggccggtaa | 600 |
| gtccaagcag ccgccgccgt tagcccaaga gcaacaacag cgccaaggct accgctcatg | 660 |
| gcgcgggcac aagaacgcca tagttgcttg cttgcaagac tgtggggca acatctcctt | 720 |
| cgcccgccgc tttcttctct accatcacgg cgtggcctc ccccgtaaca tcctgcatta | 780 |
| ctaccgtcat ctctacagcc catactgcac cggcggcagc ggcagcggca gcaacagcag | 840 |
| cggccacaca gaagcaaagg cgaccggata gcaagactct gacaaagccc aagaaatcca | 900 |
| cagcggcggc agcagcagga ggaggagcgc tgcgtctggc gcccaacgaa cccgtatcga | 960 |
| cccgcgagct tagaaacagg attttttccca ctctgtatgc tatatttcaa cagagcaggg | 1020 |
| gccaagaaca agagctgaaa ataaaaaaca ggtctctgcg atccctcacc cgcagctgcc | 1080 |
| tgtatcacaa aagcgaagat cagcttcggc gcacgctgga agacgcgag gctctcttca | 1140 |
| gtaaatactg cgcgctgact cttaaggact agtttcgcgc cctttctcaa atttaagcgc | 1200 |
| gaaaactacg tcatctccag cggccacacc cggcgccagc acctgtcgtc agcgccatta | 1260 |
| tgagcaagga aattcccacg ccctacatgt ggagttacca gccacaaatg ggacttgcgg | 1320 |
| ctggagctgc ccaagactac tcaacccgaa taaactacat gagcgcggga ccccacatga | 1380 |
| tatcccgggt caacggaatc cgcgcccacc gaaaccgaat tctcttggaa caggcggcta | 1440 |
| ttaccaccac acctcgtaat aaccttaatc cccgtagttg gcccgctgcc ctggtgtacc | 1500 |
| aggaaagtcc cgctcccacc actgtggtac ttcccagaga cgcccaggcc gaagttcaga | 1560 |
| tgactaactc aggggcgcag cttgcgggcg gctttcgtca cagggtgcgg tcgcccgggc | 1620 |
| agggtataac tcacctgaca atcagagggc gaggtattca gctcaacgac gagtcggtga | 1680 |
| gctcctcgct tggtctccgt ccggacggga catttcagat cggcggcgcc ggccgtcctt | 1740 |
| cattcacgcc tcgtcaggca atcctaactc tgcagacctc gtcctctgag ccgcgctctg | 1800 |
| gaggcattgg aactctgcaa tttattgagg agtttgtgcc atcggtctac tttaacccct | 1860 |
| tctcgggacc tccccggccac tatccggatc aatttattcc taactttgac gcggtaaagg | 1920 |
| actcggcgga cggctacgac tgattattaa gtggagaggc agagcaactg cgcctgaaac | 1980 |
| acctggtcca ctgtcgccgc cacaagtgct ttgcccgcga ctccggtgag ttttgctact | 2040 |
| ttgaattgcc cgaggatcat atcgaggatc tttgttgcca tctctgtgct gagtataata | 2100 |
| aatacagaaa ttaaaatata ctggggctcc tatcgccatc ctgtaaacgc caccgtcttc | 2160 |
| acccgcccaa gcaaaccaag gcgaaccta cctggtactt ttaacatctc tccctctgtg | 2220 |
| atttacaaca gtttcaaccc agacggagtg agtctacgag agaacctctc cgagctcagc | 2280 |
| tactccatca gaaaaaacac caccctcctt acctgccggg aacgtaccct tatataaaag | 2340 |
| tcaggcttcc tggatgtcag catctgactt tggccagcac ctgtcccgcg gatttgttcc | 2400 |
| agtccaacta cagcgaccca ccctaacaga gatgaccaac acaaccaacg cggccgccgc | 2460 |
| taccggactt acatctacca caaatacacc ccaagtttct gcctttgtca ataactggga | 2520 |
| taacttgggc atgtggtggt tctccatagc gcttatgttt gtatgcctta ttattatgtg | 2580 |
| gctcatctgc tgcctaaagc gcaaacgcgc ccgaccaccc atctatagtc ccatcattgt | 2640 |
| gctacaccca aacaatgatg gaatccatag attggacgga ctgaaacaca tgttctttc | 2700 |

```
tcttacagta tgattaaatg agaattttaa ttcgaatacc atgtggctgc agagcctgct    2760
gctcttgggc actgtggcct gcagcatctc tgcacccgcc cgctcgccca gccccagcac    2820
gcagccctgg gagcatgtga atgccatcca ggaggcccgg cgtctcctga acctgagtag    2880
agacactgct gctgagatga atgaaacagt agaagtcatc tcagaaatgt ttgacctcca    2940
ggagccgacc tgcctacaga cccgcctgga gctgtacaag cagggcctgc ggggcagcct    3000
caccaagctc aagggcccct tgaccatgat ggccagccac tacaagcagc actgccctcc    3060
aaccccggaa acttcctgtg caacccagac tatcaccttt gaaagtttca agagaacct    3120 gaaggacttt ctgcttgtca tcccctttga ctgctgggag ccagtccagg agtgaattgt    3180
cgacctgcag gaaatggaat ttctgtccag tttattcagc agcacctcct gccctcctc    3240 ccagctctgg tattgcagct tcctcctggc tgcaaacttt ctccacaatc taaatggaat    3300
gtcagtttcc tcctgttcct gtccatccgc acccactatc ttcatgttgt tgcagatgaa    3360
gcgcgcaaga ccgtctgaag ataccttcaa ccccgtgtat ccatatgaca cggaaaccgg    3420
tcctccaact gtgccttttc ttactcctcc ctttgtatcc cccaatgggt ttcaagagag    3480 tcccctggg gtactctctt tgcgcctatc cgaacctcta gttacctcca atggcatgct    3540
tgcgctcaaa atgggcaacg gcctctctct ggacgaggcc ggcaaccta cctcccaaaa    3600 tgtaaccact gtgagcccac ctctcaaaaa aaccaagtca aacataaacc tggaaatatc    3660
tgcacccctc acagttacct cagaagccct aactgtggct gccgccgcac tctaatggt    3720 cgcgggcaac acactcacca tgcaatcaca ggccccgcta accgtgcacg actccaaact    3780
tagcattgcc acccaaggac ccctcacagt gtcagaagga aagctagccc tgcaaacatc    3840
aggccccctc accaccaccg atagcagtac ccttactatc actgcctcac cccctctaac    3900
tactgccact ggtagcttgg gcattgactt gaaagagccc atttatacac aaaatggaaa    3960
actaggacta aagtacgggg ctcctttgca tgtaacagac gacctaaaca ctttgaccgt    4020
agcaactggt ccaggtgtga ctattaataa tacttccttg caaactaaag ttactggagc    4080
cttgggtttt gattcacaag gcaatatgca acttaatgta gcaggaggac taaggattga    4140
ttctcaaaac agacgcctta tacttgatgt tagttatccg tttgatgctc aaaaccaact    4200
aaatctaaga ctaggacagg cccctctttt tataaactca gcccacaact tggatattaa    4260
ctacaacaaa ggcctttact tgtttacagc ttcaaacaat tccaaaaagc ttgaggttaa    4320
cctaagcact gccaagggt tgatgtttga cgctacagcc atagccatta atgcaggaga    4380
tgggcttgaa tttggttcac ctaatgcacc aaacacaaat cccctcaaaa caaaaattgg    4440
ccatggccta gaatttgatt caaacaaggc tatggttcct aaactaggaa ctggccttag    4500
ttttgacagc acaggtgcca ttacagtagg aaacaaaaat aatgataagc taaccctatg    4560
gacaggtcca aaaccagaag ccaactgcat aattgaatac gggaaagaaa acccagatag    4620
caaactaact ttaatccttg taaaaaatgg aggaattgtt aatggatatg taacgctaat    4680
gggagcctca gactatgtta acaccttatt taaaaacaaa aatgtctcca ttaatgtaga    4740
attatacttt gatgccactg gtcatatatt accagactta tcttctctta aaacagatct    4800
agaactaaaa tacaagcaaa ccactcactt tagtgcaaga ggttttatgc caagtactac    4860
agcgtatcca tttgtccttc ctaatgcggg aacagataat gaaaattata ttttggtca    4920 atgctactac aaagcaagcg atggcgccct ttttccgttg gaagttactg ttacgcttaa    4980
taaacgcctg ccagatagtc gcacatccta tgttatgact ttttatggt ccttgaatgc    5040
```

-continued

```
tggtctagct ccagaaacta ctcaggcaac cctcataacc tccccattta ccttttccta      5100
tattagagaa gatgactgac ggtggaggcg gttcaggcgg aggtggctct ggcggtggcg      5160
gatcctgtga ctgccgcgga gactgtttct gctaataaac tctaaagaat cgtttgtgtt      5220
atgtttcaac gtgtttattt ttcaattgca gaaaatttca agtcattttt cattcagtag      5280
tatagcccca ccaccacata gcttatacag atcaccgtac cttaatcaaa ctcacagaac      5340
cctagtattc aacctgccac ctccctccca acacacagag tacacagtcc tttctccccg      5400
gctggcctta aaaagcatca tatcatgggt aacagacata ttcttaggtg ttatattcca      5460
cacggtttcc tgtcgagcca aacgctcatc agtgatatta ataaactccc cgggcagctc      5520
acttaagttc atgtcgctgt ccagctgctg agccacaggc tgctgtccaa cttgcggttg      5580
cttaacgggc ggcgaaggag aagtccacgc ctacatgggg gtagagtcat aatcgtgcat      5640
caggataggg cggtggtgct gcagcagcgc gcgaataaac tgctgccgcc gccgctccgt      5700
cctgcaggaa tacaacatgg cagtggtctc ctcagcgatg attcgcaccg cccgcagcat      5760
aaggcgcctt gtcctccggg cacagcagcg caccctgatc tcacttaaat cagcacagta      5820
actgcagcac agcaccacaa tattgttcaa aatcccacag tgcaaggcgc tgtatccaaa      5880
gctcatggcg gggaccacag aacccacgtg gccatcatac cacaagcgca ggtagattaa      5940
gtggcgaccc ctcataaaca cgctggacat aaacattacc tcttttggca tgttgtaatt      6000
caccacctcc cggtaccata taaacctctg attaaacatg cgccatcca ccaccatcct       6060
aaaccagctg gccaaaacct gcccgccggc tatacactgc agggaaccgg gactggaaca      6120
atgacagtgg agagcccagg actcgtaacc atggatcatc atgctcgtca tgatatcaat      6180
gttggcacaa cacaggcaca cgtgcataca cttcctcagg attacaagct cctcccgcgt      6240
tagaaccata tcccagggaa caacccattc ctgaatcagc gtaaatccca cactgcaggg      6300
aagacctcgc acgtaactca cgttgtgcat tgtcaaagtg ttacattcgg gcagcagcgg      6360
atgatcctcc agtatggtag cgcgggtttc tgtctcaaaa ggaggtagac gatccctact      6420
gtacggagtg cgccgagaca accgagatcg tgttggtcgt agtgtcatgc caaatggaac      6480
gccgacgta gtcatatttc ctgaagcaaa accaggtgcg ggcgtgacaa acagatctgc       6540
gtctccggtc tcgccgctta gatcgctctg tgtagtagtt gtagtatatc cactctctca      6600
aagcatccag gcgcccctg gcttcgggtt ctatgtaaac tccttcatgc gccgctgccc        6660
tgataacatc caccaccgca gaataagcca cacccagcca acctacacat tcgttctgcg      6720
agtcacacac gggaggagcg ggaagagctg gaagaaccat gttttttttt ttattccaaa      6780
agattatcca aaacctcaaa atgaagatct attaagtgaa cgcgctcccc tccggtggcg      6840
tggtcaaact ctacagccaa agaacagata atggcatttg taagatgttg cacaatggct      6900
tccaaaaggc aaacggccct cacgtccaag tggacgtaaa ggctaaaccc ttcagggtga      6960
atctcctcta taaacattcc agcaccttca accatgccca ataattctc atctcgccac       7020
cttctcaata tatctctaag caaatcccga atattaagtc cggccattgt aaaaatctgc      7080
tccagagcgc cctccacctt cagcctcaag cagcgaatca tgattgcaaa aattcaggtt      7140
cctcacagac ctgtataaga ttcaaaagcg gaacattaac aaaaataccg cgatcccgta      7200
ggtcccttcg cagggccagc tgaacataat cgtgcaggtc tgcacggacc agcgcggcca      7260
cttccccgcc aggaaccatg acaaaagaac ccacactgat tatgacacgc atactcggag      7320
ctatgctaac cagcgtagcc ccgatgtaag cttgttgcat gggcggcgat ataaaatgca      7380
aggtgctgct caaaaaatca ggcaaagcct cgcgcaaaaa agaaagcaca tcgtagtcat      7440
```

```
gctcatgcag ataaaggcag gtaagctccg gaaccaccac agaaaaagac accatttttc   7500
tctcaaacat gtctgcgggt ttctgcataa acacaaaata aaataacaaa aaaacattta   7560
aacattagaa gcctgtctta caacaggaaa aacaaccctt ataagcataa gacggactac   7620
ggccatgccg gcgtgaccgt aaaaaaactg gtcaccgtga ttaaaaagca ccaccgacag   7680
ctcctcggtc atgtccggag tcataatgta agactcggta aacacatcag gttgattcac   7740
atcggtcagt gctaaaaagc gaccgaaata gcccggggga atacataccc gcaggcgtag   7800
agacaacatt acagccccca taggaggtat aacaaaatta ataggagaga aaaacacata   7860
aacacctgaa aaaccctcct gcctaggcaa aatagcaccc tcccgctcca gaacaacata   7920
cagcgcttcc acagcggcag ccataacagt cagccttacc agtaaaaaag aaaacctatt   7980
aaaaaaacac cactcgacac ggcaccagct caatcagtca cagtgtaaaa aagggccaag   8040
tgcagagcga gtatatatag gactaaaaaa tgacgtaacg gttaaagtcc acaaaaaaca   8100
cccagaaaac cgcacgcgaa cctacgccca gaaacgaaag ccaaaaaacc cacaacttcc   8160
tcaaatcgtc acttccgttt tcccacgtta cgtcacttcc cattttaaga aaactacaat   8220
tcccaacaca tacaagttac tccgccctaa aacctacgtc acccgccccg ttcccacgcc   8280
ccgcgccacg tcacaaactc caccccctca ttatcatatt ggcttcaatc caaaataagg   8340
tatattattg atgatgttaa ttaagaattc ggatctgcga cgcgaggctg gatgccttc    8400 cccattatga ttcttctcgc ttccggcggc atcgggatgc ccgcgttgca ggccatgctg   8460
tccaggcagg tagatgacga ccatcaggga cagcttcacg gccagcaaaa ggccaggaac   8520
cgtaaaaagg ccgcgttgct ggcgtttttc cataggctcc gcccccctga cgagcatcac   8580
aaaaatcgac gctcaagtca gaggtggcga aacccgacag gactataaag ataccaggcg   8640
tttccccctg gaagctccct cgtgcgctct cctgttccga ccctgccgct taccggatac   8700
ctgtccgcct ttctcccttc gggaagcgtg gcgctttctc aatgctcacg ctgtaggtat   8760
ctcagttcgg tgtaggtcgt tcgctccaag ctgggctgtg tgcacgaacc ccccgttcag   8820
cccgaccgct gcgccttatc cggtaactat cgtcttgagt ccaacccggt aagacacgac   8880
ttatcgccac tggcagcagc cactggtaac aggattagca gagcgaggta tgtaggcggt   8940
gctacagagt tcttgaagtg gtggcctaac tacggctaca ctagaaggac agtatttggt   9000
atctgcgctc tgctgaagcc agttaccttc ggaaaaagag ttggtagctc ttgatccggc   9060
aaacaaacca ccgctggtag cggtggtttt tttgtttgca agcagcagat tacgcgcaga   9120
aaaaaaggat ctcaagaaga tcctttgatc ttttctacgg ggtctgacgc tcagtggaac   9180
gaaaactcac gttaagggat tttggtcatg agattatcaa aaaggatctt cacctagatc   9240
cttttaaatc aatctaaagt atatatgagt aaacttggtc tgacagttac caatgcttaa   9300
tcagtgaggc acctatctca gcgatctgtc tatttcgttc atccatagtt gcctgactcc   9360
ccgtcgtgta gataactacg atacgggagg gcttaccatc tggccccagt gctgcaatga   9420
taccgcgaga cccacgctca ccggctccag atttatcagc aataaaccag ccagccggaa   9480
gggccgagcg cagaagtggt cctgcaactt tatccgcctc catccagtct attaattgtt   9540
gccgggaagc tagagtaagt agttcgccag ttaatagttt gcgcaacgtt gttgccattg   9600
ntgcaggcat cgtggtgtca cgctcgtcgt ttggtatggc ttcattcagc tccggttccc   9660
aacgatcaag gcgagttaca tgatccccca tgttgtgcaa aaaagcggtt agctccttcg   9720
gtcctccgat cgttgtcaga agtaagttgg ccgcagtgtt atcactcatg gttatggcag   9780
```

```
cactgcataa ttctcttact gtcatgccat ccgtaagatg cttttctgtg actggtgagt    9840
actcaaccaa gtcattctga gaatagtgta tgcggcgacc gagttgctct tgcccggcgt    9900
caacacggga taataccgcg ccacatagca gaactttaaa agtgctcatc attggaaaac    9960
gttcttcggg gcgaaaactc tcaaggatct taccgctgtt gagatccagt tcgatgtaac   10020
ccactcgtgc acccaactga tcttcagcat cttttacttt caccagcgtt tctgggtgag   10080
caaaaacagg aaggcaaaat gccgcaaaaa agggaataag ggcgacacgg aaatgttgaa   10140
tactcatact cttcctttt caatattatt gaagcattta tcagggttat tgtctcatga   10200
gcggatacat atttgaatgt atttagaaaa ataaacaaat aggggttccg cgcacatttc   10260
cccgaaaagt gccacctgac g                                             10281
```